US011466279B2

(12) United States Patent
Romesberg et al.

(10) Patent No.: US 11,466,279 B2
(45) Date of Patent: Oct. 11, 2022

(54) IMPORT OF UNNATURAL OR MODIFIED NUCLEOSIDE TRIPHOSPHATES INTO CELLS VIA NUCLEIC ACID TRIPHOSPHATE TRANSPORTERS

(71) Applicant: The Scripps Research Institute, La Jolla, CA (US)

(72) Inventors: Floyd E. Romesberg, La Jolla, CA (US); Denis A. Malyshev, La Jolla, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 82 days.

(21) Appl. No.: 16/591,422

(22) Filed: Oct. 2, 2019

(65) Prior Publication Data

US 2020/0095591 A1 Mar. 26, 2020

Related U.S. Application Data

(62) Division of application No. 15/302,874, filed as application No. PCT/US2015/025175 on Apr. 9, 2015, now Pat. No. 10,513,706.

(60) Provisional application No. 61/977,439, filed on Apr. 9, 2014, provisional application No. 61/977,430, filed on Apr. 9, 2014.

(51) Int. Cl.

| | |
|---|---|
| ***C12N 15/70*** | (2006.01) |
| ***C12P 19/34*** | (2006.01) |
| ***C12N 15/82*** | (2006.01) |
| ***C07K 14/295*** | (2006.01) |
| ***C07K 14/405*** | (2006.01) |

(52) U.S. Cl.

CPC ............ *C12N 15/70* (2013.01); *C07K 14/295* (2013.01); *C07K 14/405* (2013.01); *C12N 15/8243* (2013.01); *C12P 19/34* (2013.01)

(58) Field of Classification Search

CPC ...... C12N 15/70; C12N 15/8243; A61P 19/34
USPC .... 435/6.1, 91.1, 91.31, 455, 459; 536/23.1, 536/24.6
See application file for complete search history.

(56) References Cited

U.S. PATENT DOCUMENTS

| | | | |
|---|---|---|---|
| 3,687,808 | A | 8/1972 | Merigan, Jr. et al. |
| 4,469,863 | A | 9/1984 | Ts et al. |
| 4,476,301 | A | 10/1984 | Imbach et al. |
| 4,587,044 | A | 5/1986 | Miller et al. |
| 4,605,735 | A | 8/1986 | Miyoshi et al. |
| 4,667,025 | A | 5/1987 | Miyoshi et al. |
| 4,683,195 | A | 7/1987 | Mullis et al. |
| 4,683,202 | A | 7/1987 | Mullis |
| 4,762,779 | A | 8/1988 | Snitman |
| 4,789,737 | A | 12/1988 | Miyoshi et al. |
| 4,824,941 | A | 4/1989 | Gordon et al. |
| 4,828,979 | A | 5/1989 | Klevan et al. |
| 4,835,263 | A | 5/1989 | Nguyen et al. |
| 4,845,205 | A | 7/1989 | Huynh et al. |
| 4,849,513 | A | 7/1989 | Smith et al. |
| 4,876,335 | A | 10/1989 | Yamane et al. |
| 4,904,582 | A | 2/1990 | Tullis |
| 4,910,300 | A | 3/1990 | Urdea et al. |
| 4,948,882 | A | 8/1990 | Ruth |
| 4,958,013 | A | 9/1990 | Letsinger |
| 4,965,188 | A | 10/1990 | Mullis et al. |
| 4,981,957 | A | 1/1991 | Lebleu et al. |
| 5,015,733 | A | 5/1991 | Smith et al. |
| 5,023,243 | A | 6/1991 | Tullis |
| 5,034,506 | A | 7/1991 | Summerton et al. |
| 5,082,830 | A | 1/1992 | Brakel et al. |
| 5,093,232 | A | 3/1992 | Urdea et al. |
| 5,109,124 | A | 4/1992 | Ramachandran et al. |
| 5,112,963 | A | 5/1992 | Pieles et al. |
| 5,118,800 | A | 6/1992 | Smith et al. |
| 5,118,802 | A | 6/1992 | Smith et al. |
| 5,130,302 | A | 7/1992 | Spielvogel et al. |
| 5,134,066 | A | 7/1992 | Rogers et al. |
| 5,138,045 | A | 8/1992 | Cook et al. |
| 5,166,315 | A | 11/1992 | Summerton et al. |
| 5,175,273 | A | 12/1992 | Bischofberger et al. |
| 5,177,196 | A | 1/1993 | Meyer, Jr. et al. |
| 5,185,444 | A | 2/1993 | Summerton et al. |
| 5,188,897 | A | 2/1993 | Suhadolnik et al. |
| 5,214,134 | A | 5/1993 | Weis et al. |
| 5,214,136 | A | 5/1993 | Lin et al. |
| 5,216,141 | A | 6/1993 | Benner |
| 5,218,105 | A | 6/1993 | Cook et al. |
| 5,232,841 | A | 8/1993 | Hashimoto et al. |
| 5,235,033 | A | 8/1993 | Summerton et al. |
| 5,245,022 | A | 9/1993 | Weis et al. |

(Continued)

FOREIGN PATENT DOCUMENTS

| | | | |
|---|---|---|---|
| EP | 0614907 | A1 | 9/1994 |
| EP | 0629633 | A2 | 12/1994 |

(Continued)

OTHER PUBLICATIONS

Acimovic et al. Molecular Evolution of the Equilibrative Nucleoside Transporter Family: Identification of Novel Family Members in Prokaryotes and Eukaryotes. Mol Biol Evol 12:2199-2210 (2002).

(Continued)

*Primary Examiner* — Jane J Zara
(74) *Attorney, Agent, or Firm* — Wilson Sonsini Goodrich & Rosati

(57) ABSTRACT

A recombinantly expressed nucleotide triphosphate transporter efficiently imports the triphosphates of unnatural nucleotides into cells, and the endogenous cellular machinery incorporates those nucleotides into cellular nucleic acids. UBPs can therefore form within the cell's nucleic acids. Moreover, neither the presence of the unnatural triphosphates nor the replication of the UBP represents a significant growth burden. The UBP is not efficiently excised by nucleic acid repair pathways, and therefore can be retained as long as the unnatural triphosphates are available in the growth medium. Thus, the resulting cell is the first organism to stably propagate an expanded genetic alphabet.

18 Claims, 28 Drawing Sheets

Specification includes a Sequence Listing.

(56) References Cited

U.S. PATENT DOCUMENTS

| | | | |
|---|---|---|---|
| 5,254,469 | A | 10/1993 | Warren, III et al. |
| 5,258,506 | A | 11/1993 | Urdea et al. |
| 5,262,536 | A | 11/1993 | Hobbs, Jr. |
| 5,264,423 | A | 11/1993 | Cohen et al. |
| 5,264,562 | A | 11/1993 | Matteucci |
| 5,264,564 | A | 11/1993 | Matteucci |
| 5,268,273 | A | 12/1993 | Buckholz |
| 5,272,250 | A | 12/1993 | Spielvogel et al. |
| 5,276,019 | A | 1/1994 | Cohen et al. |
| 5,278,302 | A | 1/1994 | Caruthers et al. |
| 5,286,717 | A | 2/1994 | Cohen et al. |
| 5,292,873 | A | 3/1994 | Rokita et al. |
| 5,317,098 | A | 5/1994 | Shizuya et al. |
| 5,319,080 | A | 6/1994 | Leumann |
| 5,321,131 | A | 6/1994 | Agrawal et al. |
| 5,359,044 | A | 10/1994 | Cook et al. |
| 5,367,066 | A | 11/1994 | Urdea et al. |
| 5,371,241 | A | 12/1994 | Brush |
| 5,389,529 | A | 2/1995 | Panayotatos et al. |
| 5,391,723 | A | 2/1995 | Priest |
| 5,393,878 | A | 2/1995 | Leumann |
| 5,399,676 | A | 3/1995 | Froehler |
| 5,405,938 | A | 4/1995 | Summerton et al. |
| 5,405,939 | A | 4/1995 | Suhadolnik et al. |
| 5,414,077 | A | 5/1995 | Lin et al. |
| 5,416,203 | A | 5/1995 | Letsinger |
| 5,432,272 | A | 7/1995 | Benner |
| 5,434,257 | A | 7/1995 | Matteucci et al. |
| 5,446,137 | A | 8/1995 | Maag et al. |
| 5,451,463 | A | 9/1995 | Nelson et al. |
| 5,453,496 | A | 9/1995 | Caruthers et al. |
| 5,455,233 | A | 10/1995 | Spielvogel et al. |
| 5,457,187 | A | 10/1995 | Gmeiner et al. |
| 5,459,255 | A | 10/1995 | Cook et al. |
| 5,466,677 | A | 11/1995 | Baxter et al. |
| 5,466,786 | A | 11/1995 | Buhr et al. |
| 5,470,719 | A | 11/1995 | Meng et al. |
| 5,470,967 | A | 11/1995 | Huie et al. |
| 5,476,925 | A | 12/1995 | Letsinger et al. |
| 5,484,908 | A | 1/1996 | Froehler et al. |
| 5,486,603 | A | 1/1996 | Buhr |
| 5,489,677 | A | 2/1996 | Sanghvi et al. |
| 5,502,177 | A | 3/1996 | Matteucci et al. |
| 5,510,475 | A | 4/1996 | Agrawal et al. |
| 5,512,439 | A | 4/1996 | Hornes et al. |
| 5,512,667 | A | 4/1996 | Reed et al. |
| 5,514,785 | A | 5/1996 | Van Ness et al. |
| 5,519,126 | A | 5/1996 | Hecht |
| 5,519,134 | A | 5/1996 | Acevedo et al. |
| 5,525,465 | A | 6/1996 | Haralambidis et al. |
| 5,525,711 | A | 6/1996 | Hawkins et al. |
| 5,536,821 | A | 7/1996 | Agrawal et al. |
| 5,539,082 | A | 7/1996 | Nielsen et al. |
| 5,541,306 | A | 7/1996 | Agrawal et al. |
| 5,541,307 | A | 7/1996 | Cook et al. |
| 5,541,313 | A | 7/1996 | Ruth |
| 5,545,730 | A | 8/1996 | Urdea et al. |
| 5,550,111 | A | 8/1996 | Suhadolnik et al. |
| 5,552,538 | A | 9/1996 | Urdea et al. |
| 5,552,540 | A | 9/1996 | Haralambidis |
| 5,561,225 | A | 10/1996 | Maddry et al. |
| 5,563,253 | A | 10/1996 | Agrawal et al. |
| 5,565,552 | A | 10/1996 | Magda et al. |
| 5,567,810 | A | 10/1996 | Weis et al. |
| 5,567,811 | A | 10/1996 | Misiura et al. |
| 5,571,799 | A | 11/1996 | Tkachuk et al. |
| 5,574,142 | A | 11/1996 | Meyer, Jr. et al. |
| 5,576,427 | A | 11/1996 | Cook et al. |
| 5,578,717 | A | 11/1996 | Urdea et al. |
| 5,578,718 | A | 11/1996 | Cook et al. |
| 5,580,731 | A | 12/1996 | Chang et al. |
| 5,585,481 | A | 12/1996 | Arnold, Jr. et al. |
| 5,587,361 | A | 12/1996 | Cook et al. |
| 5,587,371 | A | 12/1996 | Sessler et al. |
| 5,587,469 | A | 12/1996 | Cook et al. |
| 5,591,584 | A | 1/1997 | Chang et al. |
| 5,591,722 | A | 1/1997 | Montgomery et al. |
| 5,594,121 | A | 1/1997 | Froehler et al. |
| 5,595,726 | A | 1/1997 | Magda et al. |
| 5,595,899 | A | 1/1997 | Sato et al. |
| 5,596,086 | A | 1/1997 | Matteucci et al. |
| 5,596,091 | A | 1/1997 | Switzer |
| 5,597,696 | A | 1/1997 | Linn et al. |
| 5,597,909 | A | 1/1997 | Urdea et al. |
| 5,599,923 | A | 2/1997 | Sessler et al. |
| 5,599,928 | A | 2/1997 | Hemmi et al. |
| 5,602,240 | A | 2/1997 | Mesmaeker et al. |
| 5,608,046 | A | 3/1997 | Cook et al. |
| 5,610,289 | A | 3/1997 | Cook et al. |
| 5,610,300 | A | 3/1997 | Altmann et al. |
| 5,612,199 | A | 3/1997 | Western et al. |
| 5,614,617 | A | 3/1997 | Cook et al. |
| 5,618,704 | A | 4/1997 | Sanghvi et al. |
| 5,623,070 | A | 4/1997 | Cook et al. |
| 5,625,050 | A | 4/1997 | Beaton et al. |
| 5,627,053 | A | 5/1997 | Usman et al. |
| 5,633,360 | A | 5/1997 | Bischofberger et al. |
| 5,639,873 | A | 6/1997 | Barascut et al. |
| 5,645,985 | A | 7/1997 | Froehler et al. |
| 5,646,265 | A | 7/1997 | McGee |
| 5,648,247 | A | 7/1997 | Picataggio et al. |
| 5,656,493 | A | 8/1997 | Mullis et al. |
| 5,658,873 | A | 8/1997 | Bertsch-Frank et al. |
| 5,663,312 | A | 9/1997 | Chaturvedula |
| 5,670,633 | A | 9/1997 | Cook et al. |
| 5,677,437 | A | 10/1997 | Teng et al. |
| 5,677,439 | A | 10/1997 | Weis et al. |
| 5,681,941 | A | 10/1997 | Cook et al. |
| 5,688,941 | A | 11/1997 | Cook et al. |
| 5,700,920 | A | 12/1997 | Altmann et al. |
| 5,712,114 | A | 1/1998 | Mankovich et al. |
| 5,714,331 | A | 2/1998 | Buchardt et al. |
| 5,719,262 | A | 2/1998 | Buchardt et al. |
| 5,750,692 | A | 5/1998 | Cook et al. |
| 5,763,588 | A | 6/1998 | Matteucci et al. |
| 5,830,653 | A | 11/1998 | Froehler et al. |
| 5,846,818 | A | 12/1998 | Robinson et al. |
| 5,888,732 | A | 3/1999 | Hartley et al. |
| 5,932,474 | A | 8/1999 | Tsien et al. |
| 6,005,096 | A | 12/1999 | Matteucci et al. |
| 6,008,378 | A | 12/1999 | Tsien et al. |
| 6,054,271 | A | 4/2000 | Tsien et al. |
| 6,124,090 | A | 9/2000 | Rose et al. |
| 6,143,557 | A | 11/2000 | Hartley et al. |
| 6,171,861 | B1 | 1/2001 | Hartley et al. |
| 6,261,797 | B1 | 7/2001 | Sorge et al. |
| 6,268,490 | B1 | 7/2001 | Imanishi et al. |
| 6,270,969 | B1 | 8/2001 | Hartley et al. |
| 6,277,608 | B1 | 8/2001 | Hartley et al. |
| 6,288,302 | B1 | 9/2001 | Yu et al. |
| 6,294,323 | B1 | 9/2001 | Ullman et al. |
| 6,365,375 | B1 | 4/2002 | Dietmaier et al. |
| 6,391,544 | B1 | 5/2002 | Salituro et al. |
| 6,451,569 | B1 | 9/2002 | Tsien et al. |
| 6,525,191 | B1 | 2/2003 | Ramasamy |
| 6,670,461 | B1 | 12/2003 | Wengel et al. |
| 6,720,140 | B1 | 4/2004 | Hartley et al. |
| 6,770,748 | B2 | 8/2004 | Imanishi et al. |
| 6,794,499 | B2 | 9/2004 | Wengel et al. |
| 6,955,807 | B1 | 10/2005 | Shanafelt et al. |
| 7,034,133 | B2 | 4/2006 | Wengel et al. |
| 7,053,207 | B2 | 5/2006 | Wengel |
| 7,393,632 | B2 | 7/2008 | Cheo et al. |
| 7,399,845 | B2 | 7/2008 | Seth et al. |
| 7,427,672 | B2 | 9/2008 | Imanishi et al. |
| 7,670,823 | B1 | 3/2010 | Hartley et al. |
| 8,501,805 | B2 | 8/2013 | Seth et al. |
| 8,546,556 | B2 | 10/2013 | Seth et al. |
| 10,513,706 | B2 * | 12/2019 | Romesberg .......... C07K 14/405 |
| 10,626,138 | B2 | 4/2020 | Romesberg et al. |
| 10,696,719 | B2 | 6/2020 | Romesberg et al. |
| 10,696,720 | B2 | 6/2020 | Romesberg et al. |
| 2002/0007051 | A1 | 1/2002 | Cheo et al. |
| 2003/0083373 | A1 | 5/2003 | Tsien et al. |

(56) References Cited

U.S. PATENT DOCUMENTS

| | | | |
|---|---|---|---|
| 2004/0171570 | A1 | 9/2004 | Allerson et al. |
| 2005/0112590 | A1 | 5/2005 | Boom et al. |
| 2005/0130923 | A1 | 6/2005 | Bhat et al. |
| 2006/0035254 | A1 | 2/2006 | Manoharan et al. |
| 2006/0074035 | A1 | 4/2006 | Hong et al. |
| 2006/0084136 | A1 | 4/2006 | Kudlicki et al. |
| 2006/0263771 | A1 | 11/2006 | Hirao et al. |
| 2007/0287831 | A1 | 12/2007 | Seth et al. |
| 2008/0039618 | A1 | 2/2008 | Allerson et al. |
| 2008/0300163 | A1 | 12/2008 | Cho et al. |
| 2012/0022013 | A1 | 1/2012 | Sinclair et al. |
| 2012/0077252 | A1 | 3/2012 | Picataggio et al. |
| 2012/0244112 | A1 | 9/2012 | Ast et al. |
| 2013/0333068 | A1 | 12/2013 | Coffin |
| 2014/0328791 | A1 | 11/2014 | Bossard et al. |
| 2017/0029829 | A1 | 2/2017 | Romesberg et al. |
| 2017/0369871 | A1 | 12/2017 | Ptacin et al. |
| 2019/0218257 | A1 | 7/2019 | Romesberg et al. |
| 2019/0376054 | A1 | 12/2019 | Ptacin et al. |
| 2020/0024597 | A1 | 1/2020 | Ptacin et al. |
| 2020/0131555 | A1 | 4/2020 | Ptacin et al. |
| 2020/0224234 | A1 | 7/2020 | Romesberg et al. |
| 2020/0277342 | A1 | 9/2020 | Romesberg et al. |
| 2020/0318122 | A1 | 10/2020 | Romesberg et al. |
| 2020/0377877 | A1 | 12/2020 | Romesberg et al. |
| 2020/0392550 | A1 | 12/2020 | Romesberg et al. |
| 2021/0222147 | A1 | 7/2021 | Ptacin et al. |

FOREIGN PATENT DOCUMENTS

| | | | |
|---|---|---|---|
| WO | WO-9213869 | A1 | 8/1992 |
| WO | WO-9422890 | A1 | 10/1994 |
| WO | WO-9735869 | A1 | 10/1997 |
| WO | WO-9914226 | A2 | 3/1999 |
| WO | WO-9921013 | A1 | 4/1999 |
| WO | WO-9962923 | A2 | 12/1999 |
| WO | WO-0105801 | A1 | 1/2001 |
| WO | WO-0132887 | A1 | 5/2001 |
| WO | WO-02070533 | A2 | 9/2002 |
| WO | WO-03070918 | A2 | 8/2003 |
| WO | WO-2004007713 | A1 | 1/2004 |
| WO | WO-2004106356 | A1 | 12/2004 |
| WO | WO-2005021570 | A1 | 3/2005 |
| WO | WO-2005026187 | A1 | 3/2005 |
| WO | WO-2005045015 | A2 | 5/2005 |
| WO | WO-2006049297 | A1 | 5/2006 |
| WO | WO-2007015557 | A1 | 2/2007 |
| WO | WO-2007066737 | A1 | 6/2007 |
| WO | WO-2007090071 | A2 | 8/2007 |
| WO | WO-2007134181 | A2 | 11/2007 |
| WO | WO-2008101157 | A1 | 8/2008 |
| WO | WO-2008150729 | A2 | 12/2008 |
| WO | WO-2008154401 | A2 | 12/2008 |
| WO | WO-2009006478 | A2 | 1/2009 |
| WO | WO-2009123216 | A1 | 10/2009 |
| WO | WO-2011043385 | A1 | 4/2011 |
| WO | WO-2011139699 | A2 | 11/2011 |
| WO | WO-2015021432 | A1 | 2/2015 |
| WO | WO-2015157555 | A2 | 10/2015 |
| WO | WO-2016115168 | A1 | 7/2016 |
| WO | WO-2017106767 | A1 | 6/2017 |
| WO | WO-2017223528 | A1 | 12/2017 |
| WO | WO-2019014262 | A1 | 1/2019 |
| WO | WO-2019014267 | A1 | 1/2019 |
| WO | WO-2019133883 | A1 | 7/2019 |

OTHER PUBLICATIONS

Acsadi et al. Human Dystrophin Expression in mdx Mice After Intramuscular Injection of DNA Constructs. Nature 352:815-818 (1991).

Adhikary et al. Adaptive Mutations Alter Antibody Structure and Dynamics During Affinity Maturation. Biochemistry 54(11):2085-93 (2015).

Akbergenov et al. ARC-1, a sequence element complementary to an internal 18S rRNA segment, enhances translation efficiency in plants when present in the leader or intercistronic region of mRNAs. Nucleic Acids Res 32(1):239-247 (2004).

Allen et al. Roles of DNA polymerase I in leading and lagging-strand replication defined by a high-resolution mutation footprint of ColE1 plasmid replication. Nucleic Acids Res. 39:7020-7033 (2011).

Alpert et al. ABRF 2003: Precipitation of Large, High-Abundance Proteins from Serum With Organic Solvents. Poster No. P111-W (10 pgs) (2003).

Ambrogelly et al. Pyrrolysine is not hardwired fro cotranslational insertion at UAG condons. PNAS 104(9):3141-3146 (2007).

Amiri et al. Deep origin of plastid/parasite ATP/ADP translocases. J. Mol. Evol. 56:137-150 (2003).

Arie et al. Phylogenetic identification of n-alkane assimilating Candida yeasts based on nucleotide divergence in the 59 end of LSU rDNA gene. J Gen Appl Microbiol. 46(5):257-262 (2000).

Ast et al. Diatom plastids depend on nucleotide import from the cytosol. PNAS USA 106:3621-3626 (2009).

Audia et al. Study of the five Rickettsia prowazekii proteins annotated as ATP/ADP translocases (Tlc): Only Tlc1 transports ATP/ADP, while Tlc4 and T1c5 transport other ribonucleotides. J. Bacteriol. 188:6261-6268 (2006).

Baba et al. Construction of Escherichia coli K-12 in-frame, single-gene knockout mutants: the Keio collection. Mol Syst Biol 2006. 0008 (2006).

Beigelman et al. Synthesis of 5'-C-Methyl-D-allo- & L-Talo-ribonucleoside 3' -O-Phosphoramidites & Their Incorporation into Hammerhead Ribozymes. Nucleosides and Nucleotides 14(3-5):901-905 (1995).

Berger et al. Stability and selectivity of unnatural DNA with five-membered-ring nucleobase analogues. J Am Chem Soc 124(7):1222-6 (2002).

Berger et al. Stable and selective hybridization of oligonucleotides with unnatural hydrophobic bases. Angew Chem Int Ed Engl 39:2940-2942 (2000).

Berger et al. Universal bases for hybridization, replication and chain termination. Nucleic Acids Res 28(15):2911-2914 (2000).

Betz et al. KlenTaq polymerase replicates unnatural base pairs by inducing a Watson-Crick geometry. Nat Chem Biol 8:612-614 (2012).

Betz et al. Structural insights into DNA replication without hydrogen bonds. J Am Chem Soc 135:18637-18643 (2013).

Bohringer et al. Synthesis of 5'-deoxy-5'-methylphosphonate linked thymidine oligonucleotides. Tet Lett 34:2723-2726 (1993).

Bordo et al. Suggestions for “safe” residue substitutions in site-directed mutagenesis. J Mol Biol 217:721-729 (1991).

Braasch et al. Locked nucleic acid (LNA): fine-tuning the recognition of DNA and RNA. Chem Bio 8:1-7 (2001).

Brauns et al. Studies on Lignin and Related Compounds: XII. Methanol Lignin. Canadian Journal of Research 13b(1):28-34 (1935).

Cann et al. A heterodimeric DNA polymerase: Evidence that members of Euryarchaeota possess a distinct DNA polymerase. PNAS USA 95:14250 (1998).

Capone et al. Amber, ochre and opal suppressor tRNA genes derived from a human serine tRNAgene. EMBO J 4(1): 213-221 (1985).

Cariello et al. Fidelity of Thermococcus litoralis DNA polymerase (VentTM) in PCR determined by denaturing gradient gel electrophoresis Nucl Acid Res 19:4193-4198 (1991).

Charych et al. Modeling the receptor pharmacology, pharmacokinetis, and pharmacodynamics of NKTR-214, a kinetically-controlled interleukin-2 (IL2) receptor agonist for cancer immunotherapy. PLoS One 12(7):e0179431 (2017).

Charych et al. NKTR-214, an Engineered Cytokine with Biased IL2 Receptor Binding, Increased Tumor Exposure, and Marked Efficacy in Mouse Tumor Models. Clin Cancer Res 22(3):680-690 (2016) (w/Supplemental Figures).

Chatterjee et al. A Versatile Platform for Single- and Multiple-Unnatural Amino Acid Mutagenesis in *Escherichia coli*. Biochemistry 52(10):1828-1837 (2013).

(56) References Cited

OTHER PUBLICATIONS

Chaturvedi et al. Stabilization of triple-stranded oligonucleotide complexes: use of probes containing alternating phosphodiester and stereo-uniform cationic phosphoramidate linkages. Nucleic Acids Res. 24:2318-2323 (1996).
Chatzkel et al. Coordinated pembrolizumab and high dose IL-2 (5-in-a-row schedule) for therapy of metastatic clear cell renal cancer: a single-center, single-arm trial. Poster Abstract No. 244333 (2010).
Chen et al. Phosphonate Analogues of Cytosine Arabinoside Monophosphate. Phosphorus, Sulfur and Silicon 177:1783-1786 (2002).
Chen et al. The expanding world of DNA and RNA. Curr Opin Chem Biol 34:80-87 (2016).
Cleary et al. Production of complex nucleic acid libraries using highly parallel in situ oligonucleotide synthesis. Nat Methods 1(3):241-248 (2004).
Collingwood et al. The Synthesis and Incorporation in Oligonucleotides of a Thymidine Dimer Containing an Internucleoside Phosphinate Linkage. Synlett 7:703-705 (1995).
Co-pending U.S. Appl. No. 16/518,715, filed Jul. 22, 2019.
Co-pending U.S. Appl. No. 16/535,992, filed Aug. 8, 2019.
Crooke et al. Pharmacokinetic properties of several novel oligonucleotide analogs in mice. J Pharmacol Exp Ther 277:923-937 (1996).
De Mesmaeker et al. Amide-Modified Oligonucleotides with Preorganized Backbone and Furanose Rings: Highly Increased Thermodynamic Stability of the Duplexes Formed with their RNA and DNA Complements. Synlett 1997(11)1287-1290 (1997).
Dien et al. Eight-Letter DNA. Biochemistry 58:2581-2583 (2019).
Dien et al. Expansion of the genetic code via expansion of the genetic alphabet. Curr Opin Chem Biol 46:196-202 (2018).
Dien et al. Progress Toward a Semi-Synthetic Organism with an Unrestricted Expanded Genetic Alphabet. J Am Chem Soc. 140:16115-16123 (2018).
Dufour. THOR-707, an engineered not-alpha IL-2, for the treatment of solid tumors induces strong immunological responses in vivo. CSCO Immunotherapy Seminar Mar. 22-23, 2019 Shanghi, China (12 pgs).
Dupradeau et al. Differential solvation and tautomer stability of a model base pair within the minor and major grooves of DNA. J Am Chem Soc 127(44):15612-7 (2005).
Eggertsson et al. Transfer ribonucleic acid-mediated suppression of termination codons in *Escherichia coli*. Microbiol Rev 52(3):354-374 (1988).
Engleerg-Kukla et al. Chapter 60: Suppression of Termination Codons. *Escherichia coli* and *Salmonella* Cellular and Molecular Biology (pp. 909-921) (1996).
Englisch et al. Chemically Modified Oligonucleotides as Probes and Inhibitors. Angew. Chem. Int. Ed. Eng. 30:613-629 (1991).
Eppacher et al. Synthesis and Incorporation of C(5')-Ethynylated Uracil-Derived Phosphoramidites into RNA. Helvetica Chimica Acta 87:3004-3020 (2004).
Fa et al. Expanding the substrate repertoire of a DNA polymerase by directed evolution. J Am Chem Soc 126(6):1748-54 (2004).
Fairhurst et al. Synthesis and Hybridisation Properties of Phosphonamidate Ester Modified Nucleic Acid. Synlett 4:467-472 (2001).
Fan et al. Rationally evolving tRNAPyl for efficient incorporation of noncanonical amino acids. Nucleic Acids Res 43(22):e156 (2015).
Feldman et al. A Tool for the Import of Natural and Unnatural Nucleoside Triphosphates into Bacteria. J Am Chem Soc 140(4):1447-1454 (2018).
Feldman et al. Chemical Stabilization of Unnatural Nucleotide Triphosphates for the in Vivo Expansion of the Genetic Alphabet. J Am Chem Soc 139(6):2464-2467 (2017).
Feldman et al. In Vivo Structure-Activity Relationships and Optimization of an Unnatural Base Pair for Replication in a Semi-Synthetic Organism. J Am Chem Soc 139:11427-11433 (2017).
Feldman et al. Optimization of Replication, Transcription, and Translation in a Semi-Synthetic Organism. J Am Chem Soc 141:10644-10653 (2019).
Feldman. Expansion of the Genetic Alphabet: A Chemist's Approach to Synthetic Biology. Acc Chem Res 51(2):394-403 (2018).
Fersht. Enzyme Structure and Mechanism, 2nd ed., W. H. Freeman & Co., New York (pp. 350-351) (1985).
Fisher et al. Chlamydia trachomatis Transports NAD via the Npt1 ATP/ADP Translocase. Journal of Bacteriology 195(15):3381-3386 (2013).
Friedhoff et al. Quantitative polymerase chain reaction with oligodeoxynucleotide ligation assay/enzyme-linked immunosorbent assay detection. Anal Biochem 215(1):9-16 (1993).
Gallie et al. The 5'-leader sequence of tobacco mosaic virus RNA enhances the expression of foreign gene transcripts in vitro and in vivo. Nucleic Acids Res. 15(8):3257-3273 (1987).
Gallie. The 5'-leader of tobacco mosaic virus promotes translation through enhanced recruitment of elF4F. Nucleic Acids Res 30(15):3401-3411 (2002).
Gallier et al. Ex-Chiral-Pool Synthesis of β-Hydroxyphosphonate Nucleoside Analogues. Eur J Org Chem 6:925-933 (2007).
Geze et al. Synthesis of sinefungin and its C-6' epimer. J Am Chem Soc 105(26):7638-7640 (1983).
Goodman. Error-prone repair DNA polymerases in prokaryotes and eukaryotes. Annu. Rev. Biochem. 71:17-50 (2002).
Guatelli et al. Isothermal, in vitro amplification of nucleic acids by a multienzyme reaction modeled after retroviral replication. PNAS USA 87(5):1874-1878 (1990).
Haferkamp et al. Functional expression and characterisation of membrane transport proteins. Plant Biol. 14:675-690 (2012).
Haferkamp et al. Tapping the nucleotide pool of the host: novel nucleotide carrier proteins of Protochlamydia amoebophila. Mol. Microbiol. 60:1534-1545 (2006).
Hampton et al. Design of substrate-site-directed inhibitors of adenylate kinase and hexokinase. Effect of substrate substituents on affinity on affinity for the adenine nucleotide sites. J Med Chem 19:1371-1377 (1976).
Hampton et al. Design of substrate-site-directed irreversible inhibitors of adenosine 5'-phosphate aminohydrolase. Effect of substrate substituents on affinity for the substrate site. J Med Chem 19(8):1029-1033 (1976).
Hampton et al. Synthesis of 6'-cyano-6'-deoxyhomoadenosine-6'-phosphonic acid and its phosphoryl and pyrophosphoryl anhydrides and studies of their interactions with adenine nucleotide utilizing enzymes. J Am Chem Soc 95(13):4404-4414 (1973).
Hancock et al. Expanding the Genetic Code of Yeast for Incorporation of Diverse Unnatural Amino Acids via a Pyrrolysyl-tRNA Synthetase/tRNA Pair. JACS 132:14819-14824 (2010).
Hari et al. Optimization of the pyridyl nucleobase scaffold for polymerase recognition and unnatural base pair replication. Chembiochem 9(17):2796-2799 (2008).
Hatch et al. Adenine nucleotide and lysine transport in Chlamydia psittaci. J. Bacteriol. 150:662-670 (1982).
Henry et al. Beyond A, C, G and T: augmenting nature's alphabet. Curr Opin Chem Biol 7(6):727-33 (2003).
Henry et al. Determinants of unnatural nucleobase stability and polymerase recognition. J Am Chem Soc 125(32):9638-9646 (2003).
Henry et al. Efforts to expand the genetic alphabet: identification of a replicable unnatural DNA self-pair. J Am Chem Soc 126(22):6923-31 (2004).
Hinnisdaels et al. Direct cloning of PCR products amplified with Pwo DNA polymerase. Biotechniques 20:186-188 (1996).
Hirao et al. An unnatural base pair between imidazolin-2-one and 2-amino-6-(2-thienyl)purine in replication and transcription. Nucleic Acids Res Suppl. 2(1):37-38 (2002).
Hirao et al., Unnatural base pair systems toward the expansion of the genetic alphabet in the central dogma.Proceedings of the Japan Academy, Series B, Phys Biol Sci. 88:345-367 (2012).
Horn et al. Bacterial endosymbionts of free-living amoebae. J. Eukaryot. Microbiol. 5:509-514 (2004).
Hwang et al. Polymerase recognition and stability of fluoro-substituted pyridone nucleobase analogues. Chembiochem 8:1606-1611 (2007).

(56) References Cited

OTHER PUBLICATIONS

Hwang et al. Substituent effects on the pairing and polymerase recognition of simple unnatural base pairs. Nucleic Acids Res 34(7):2037-45 (2006).
Hwang et al. The effects of unnatural base pairs and mispairs on DNA duplex stability and solvation. Nucleic Acids Res 37(14):4757-4763 (2009).
Hwang et al. Unnatural substrate repertoire of A, B, and X family DNA polymerases. J Am Chem Soc 130(44):14872-14882 (2008).
Jager et al. Oligonucleotide N-alkylphosphoramidates: synthesis and binding to polynucleotides. Biochemistry 27:7247-7246 (1988).
Johansson et al. The solution structures of mutant calbindin D9k's, as determined by NMR, show that the calcium-binding site can adopt different folds. Biochemistry 35(25):8429-8438 (1996).
Joseph et al. THOR-707, A novel not-alpha IL-2, elicits durable pharmacodynamic responses in non-human primates and, efficacy as single agent and in combination with anti PD-1 in multiple syngeneic mouse models. American Association of Cancer Research (AACR) Annual Meeting 2019 Poster (Apr. 2, 2019).
Juncosa-Ginesta et al. Improved efficiency in site-directed mutagenesis by PCR using a *Pyrococcus* sp. GB-D polymerase. Biotechniques 16:820-823 (1994).
Jung et al. Synthesis of phosphonate derivatives of uridine, cytidine, and cytosine arabinoside. Bioorg Med Chem 8:2501-2509 (2000).
Kabanov et al. A new class of antivirals: antisense oligonucleotides combined with a hydrophobic substituent effectively inhibit influenza virus reproduction and synthesis of virus-specific proteins in MDCK cells. FEBS Lett 259:327-330 (1990).
Kandimalla et al. Effect of chemical modifications of cytosine and guanine in a CpG-motif of oligonucleotides: structure-immunostimulatory activity relationships. Bioorg. Med. Chem. 9:807-813 (2001).
Kappler et al. Isozyme-specific enzyme inhibitors. 11. L-homocysteine-ATP S-C5' covalent adducts as inhibitors of rat methionine adenosyltransferases. J Med Chem 29:1030-1038 (1986).
Kappler et al. Species- or isozyme-specific enzyme inhibitors. 8. Synthesis of disubstituted two-substrate condensation products as inhibitors of rat adenylate kinases. J Med Chem 25:1179-1184 (1982).
Kim et al. Stability and polymerase recognition of pyridine nucleobase analogues: role of minor-groove H-bond acceptors. Angew Chem Int Ed Engl 45(46):7809-12 (2006).
Kimoto et al. Generation of high-affinity DNA aptamers using an expanded genetic alphabet. Nat. Biotech. 31(5):453-458 (2013).
Knab et al. Nucleotide parasitism by Simkania negevensis (Chlamydiac). J. Bacteriol. 193:225-235 (2011).
Koshkin et al. LNA (locked nucleic acids): synthesis of the adenine, cytosine, guanine 5-methylcytosine, thymine and uracil bicyclonucleoside monomers, oligomerisation, and unprecedented nucleic acid recognition. Tetrahedron 54(14):3607-3630 (1998).
Kroschwitz. The Concise Encyclopedia of Polymer Science and Engineering, (pp. 858-859) (1990).
Kumar et al. The First Analogues of LNA (Locked Nucleic Acids): Phosphorothioate LNA and 2'-Thio-LNA. Bioorg Med Chem Lett 8:2219-2222 (1998).
Kutyavin. Use of base-modified duplex-stabilizing deoxynucleoside 5'-triphosphates to enhance the hybridization properties of primers and probes in detection polymerase chain reaction. Biochemistry 47(51):13666-13673 (2008).
Kwoh et al. Transcription-based amplification system and detection of amplified human immunodeficiency virus type 1 with a bead-based sandwich hybridization format. PNAS USA 86:1173-1177 (1989).
Landy. Mechanistic and structural complexity in the site-specific recombination pathways of Int and FLP. CurrOpin Genet Dev. 3(5):699-707 (1993).
Lavergne et al. Expanding the scope of replicable unnatural DNA: Stepwise optimization of a predominantly hydrophobic base pair. JACS 135:5408-5419 (2013).
Lavergne et al. FRET Characterization of Complex Conformational Changes in a Large 16S Ribosomal RNA Fragment Site-Specifically Labeled Using Unnatural Base Pairs. ACS Chem Biol 11(5):1347-53 (2016).
Lavergne et al. Major groove substituents and polymerase recognition of a class of predominantly hydrophobic unnatural base pairs. Chem. Eur. J. 18:1231-1239 (2012).
Leconte et al. Amplify this! DNA and RNA get a third base pair. Nat Meth 3:667-668 (2006).
Leconte et al. An efficiently extended class of unnatural base pairs. J Am Chem Soc 128(21):6780-1 (2006).
Leconte et al. Chemical biology: a broader take on DNA. Nature 444:553-555 (2006).
Leconte et al. Directed Evolution of DNA Polymerases for Next-Generation Sequencing. Angew Chem Int Ed Engl 49(34):5921-5924 (2010).
Leconte et al. Discovery, characterization, and optimization of an unnatural base pair for expansion of the genetic alphabet. J Am Chem Soc 130(7):2336-2343 (2008).
Leconte et al. Efforts towards expansion of the genetic alphabet: pyridone and methyl pyridone nucleobases. Angew Chem Int Ed Engl 45(26):4326-9 (2006).
Leconte et al. Polymerase evolution: efforts toward expansion of the genetic code. J Am Chem Soc 127(36):12470-1 (2005).
Ledbetter et al. Editorial overview: Expanding the genetic alphabet and code. Curr Opin Chem Biol 46:A1-A2 (2018).
Ledbetter et al. Reprograming the Replisome of a Semisynthetic Organism for the Expansion of the Genetic Alphabet. J Am Chem Soc. 140:758-765 (2018).
Ledbetter et al. Site-Specific Labeling of DNA via PCR with an Expanded Genetic Alphabet. Methods Mol Biol 1973:193-212 (2019).
Letsinger et al. Cholesteryl-conjugated oligonucleotides: Synthesis, properties, and activity as inhibitors of replication of human immunodeficiency virus in cell culture. PNAS 86:6553-6556 (1989).
Li et al. Improved Inhibition of Tumor Growth by Diabody-Drug Conjugates via Half-Life Extension. Bioconjugate Chem 30:1232-1243 (2019).
Li et al. Natural-like Replication of an Unnatural Base Pair for the Expansion of the Genetic Alphabet and Biotechnology Applications. J Am Chem Soc 136:826-829 (2014).
Li et al. Site-Specifically Arraying Small Molecules or Proteins on DNA Using an Expanded Genetic Alphabet. Chem Eur J 19:14205-14209 (2013).
Lizardi et al. Exponential amplification of recombinant-RNA hybridization probes. Nature Biotechnology 6:1197-1202 (1988).
Lotze et al. In vivo administration of purified human interleukin 2. II. Half life, immunologic effects, and expansion of peripheral lymphoid cells in vivo with recombinant IL 2. J Immunol 135:2865-2875 (1985).
Ludwig et al. Rapid and efficient synthesis of nucleoside 5'-0-(1-thiotriphosphates), 5'-triphosphates and 2',3'-cyclophosphorothioates using 2-chloro-4H-1,3,2-benzodioxaphosphorin-4-one. J. Org. Chem. 54:631-635 (1989).
Lundberg et al. High-fidelity amplification using a thermostable DNA polymerase isolated from Pyrococcus furiosus. Gene 108:1-6 (1991).
Malyshev et al. A semi-synthetic organism with an expanded genetic alphabet. Nature 509(7500):385-388 (2014).
Malyshev et al. Efficient and sequence-independent replication of DNA containing a third base pair establishes a functional six-letter genetic alphabet. PNAS USA 109:12005-12010 (2012).
Malyshev et al. PCR with an Expanded Genetic Alphabet. JACS 131(41):14620-14621 (2009).
Malyshev et al. Solution structure, mechanism of replication, and optimization of an unnatural base pair. Chem Eur J 16:12650-12659 (2010).
Manoharan et al. Chemical Modifications to Improve Uptake and Bioavailability of Antisense Oligonucleotides. Ann. N.Y. Acad. Scie 660:306-309 (1992).
Manoharan et al. Cholic Acid-Oligonucleotide Conjugates for Antisense Applications. Bioorg. Med. Chem. Let 4:1053-1060 (1994).

(56) References Cited

OTHER PUBLICATIONS

Manoharan et al. Introduction of a Lipophilic Thioether in the Minor Groove of Nucleic Acids for Antisense Applications. Bioorg. Med. Chem. Let 3:2765-2770 (1993).
Manoharan et al. Lipidic Nucleic Acids. Tetrahedron Lett 36:3651-3654 (1995).
Manoharan et al. Oligonucleotide Conjugates: Alteration of the Pharmacokinetic Properties of Antisense Agents. Nucleosides & Nucleotides 14:969-973 (1995).
Matsuda et al. Efforts toward expansion of the genetic alphabet: structure and replication of unnatural base pairs. J Am Chem Soc 129(34):10466-73 (2007).
Matsuda et al. Minor groove hydrogen bonds and the replication of unnatural base pairs. J Am Chem Soc 129(17):5551-7 (2007).
Matsuda et al. Optimization of interstrand hydrophobic packing interactions within unnatural DNA base pairs. J Am Chem Soc 126(44):14419-27 (2004).
Matsuda et al. Optimization of unnatural base pair packing for polymerase recognition. J Am Chem Soc 128(19):6369-75 (2006).
Matsuda et al. The effect of minor-groove hydrogen-bond acceptors and donors on the stability and replication of four unnatural base pairs. J Am Chem Soc 125(20):6134-9 (2003).
McMinn et al. Efforts toward Expansion of the Genetic Alphabet: DNA Polymerase Recognition of a Highly Stable, Self-Pairing Hydrophobic Base. J. Am. Chem. Soc. 121:11585-11586 (1999).
Meggers et al. A Novel Copper-Mediated DNA Base Pair. J. Am. Chem. Soc.122:10714-10715 (2000).
Melero et al. Clinical activity safety, and PK/PD from a Phase 1 study of RO6874281, a fibroblast activation protein (FAP) targeted interleukin-2 variant (IL-cv). ESMO 2018 Congress Poster (Oct. 20, 2018).
Meyers et al. Optimal alignments in linear space. CABIOS 4:11-17 (1989).
Micklefield. Backbone Modification of Nucleic Acids: Synthesis, Structure and Therapeutic Applications. Current Medicinal Chemistry 8:1157-1179 (2001).
Mignone et al. Untranslated regions of mRNAs. Genome Biol. 3(3):REVIEWS0004 (2002).
Mignone et al. UTRdb and UTRsite: a collection of sequences and regulatory motifs of the untranslated regions of eukaryotic mRNAs. Nucleic Acids Res 33(Database issue):D141-D146 (2005).
Mikhailov et al. Substrate Properties of C'-Methylnucleoside and C'-Methyl-2'-deoxynucleoside 5'-Triphosphates in RNA and DNA Synthesis Reactions Catalysed by RNA and DNA Polymerases Nucleosides & Nucleotides 10(1-3):339-343 (1991).
Milla et al. THOR-707: An engineered IL-2 for the treatment of solid tumors with superior pre-clinical efficacy and safety evidence. 2018 Society for Immunotherapy of Cancer (SITC) 33rd Annual Meeting Poster (Nov. 9, 2018).
Milla et al. THOR-707: Using Synthetic Biology to Reprogram the Therapeutic Activity of Interleukin-2 (IL-2). 2019 American Society of Clinical Oncology (ASCO) Annual Meeting Poster (May 15, 2019).
Miller et al. Conformation and interaction of dinucleoside mono-and diphosphates. V. Syntheses and properties of adenine and thymine nucleoside alkyl phosphotriesters, the neutral analogs of dinucleoside monophosphates. JACS 93:6657-6665 (1971).
Miroux et al. Over-production of proteins in *Escherichia coli*: mutant hosts that allow synthesis of some membrane proteins and globular proteins at high levels. J Mol Biol 260:289-298 (1996).
Mishra et al. Improved leishmanicidal effect of phosphorotioate antisense oligonucleotides by LDL-mediated delivery. Biochem Biophys Acta 1264:229-237 (1995).
Morris et al. Synthetic Biology Parts for the Storage of Increased Genetic Information in Cells. ACS Synth Biol 6(10):1834-1840 (2017).
Mulligan et al. Expression of a bacterial gene in mammalian cells. Science 209:1422-1427 (1980).
Mullis et al. Specific enzymatic amplification of DNA in vitro the polymerase chain reaction. Cold Spring Harbor Symp. Quant. Biol. 51:263 (1986).
Myers et al. Reverse transcription and DNA amplification by a Thermus thermophilus DNA polymerase. Biochemistry 30:7661-7666 (1991).
Nakazawa et al. UV and skin cancer: specific p53 gene mutation in normal skin as a biologically relevant exposure measurement. PNAS USA 91(1):360-364 (1994).
Nawrot et al. A novel class of DNA analogs bearing 5'-C-phosphonothymidine units: synthesis and physicochemical and biochemical properties. Oligonucleotides16(1):68-82 (2006).
Needleman et al. A general method applicable to the search for similarities in the amino acid sequence of two proteins. J. Mol. Biol. 48:443-453 (1970).
Nelson et al. N3'-->P5' Oligodeoxyribonucleotide Phosphoramidates: A New Method of Synthesis Based on a Phosphoramidite Amine-Exchange Reaction. J Org Chem 62:7278-7287 (1997).
Nguyen et al. Genetic Encoding and Labeling of Aliphatic Azides and Alkynes in Recombinant Proteins via a Pyrrolysyl-tRNA Synthetase/tRNACUA Pair and Click Chemistry. JACS 131:8720-8721 (2009).
Nielsen et al. Sequence-selective recognition of DNA by strand displacement with a thymine-substituted polyamide. Science 254:1497-1500 (1991).
Oberhauser et al. Effective incorporation of 2'-O-methyl-oligoribonucleotides into liposomes and enhanced cell association through modification with thiocholesterol. Nucl. Acids Res. 20:533-538 (1992).
Ogawa et al. Efforts toward the Expansion of the Genetic Alphabet: Information Storage and Replication with Unnatural Hydrophobic Base Pairs. J. Am. Chem. Soc. 122:3274-3278 (2000).
Ogawa et al. Rational Design of an Unnatural base Pair with Increased Kinetic Selectivity. J. Am. Chem. Soc. 122:8803-8804 (2000).
Ohtsuki et al. Unnatural base pairs for specific transcription. PNAS USA 98(9):4922-4925 (2001).
Orum et al. Locked nucleic acids: a promising molecular family for gene-function analysis and antisense drug development. Curr Opinion Mol Ther 3:239-243 (2001).
Parel et al. Triple-helix formation in the antiparallel binding motif of oligodeoxynucleotides containing N(9)- and N(7)-2-aminopurine deoxynucleosides. Nucleic Acids Res. 29(11):2260-2267 (2001).
Parrish et al. Functional anatomy of a dsRNA trigger: differential requirement for the two trigger strands in RNA interference. Mol Cell 6(5):1077-1087 (2000).
Paulous et al. Comparison of the capacity of different viral internal ribosome entry segments to direct translation initiation in poly(A)-dependent reticulocyte lysates. Nucleic Acids Res. 31(2):722-733 (2003).
PCT/US2015/025175 International Reporton Patentability dated Oct. 20, 2016.
PCT/US2015/025175 International Search Report and Written Opinion dated Oct. 13, 2015.
PCT/US2018/041503 International Search Report and Written Opinion dated Nov. 7, 2018.
PCT/US2018/045257 International Search Report and Written Opinion dated Nov. 21, 2018.
Piccirilli et al. A C-nucleotide base pair: methylpseudouridine-directed incorporation of formycin triphosphate into RNA catalyzed by T7 RNA polymerase. Biochemistry 30(42):10350-10356 (1991).
Piccirilli et al. Enzymatic incorporation of a new base pair into DNA and RNA extends the genetic alphabet. Nature 343:33-37 (1990).
Quan et al. Circular polymerase extension cloning for high-throughput cloning of complex and combinatorial DNA libraries. Nat Protoc 6(2):242-251 (2011).
Romesberg et al. Development of a universal nucleobase and modified nucleobases for expanding the genetic code. Curr Prot Nucleic Acid Chem Chapter 1:Unit 1.5 (2002).
Saha et al. 5'-Methyl-DNA-A New Oligonucleotide Analog: Synthesis and Biochemical Properties J Org Chem 60:788-789 (1995).

(56) References Cited

OTHER PUBLICATIONS

Saison-Behmoaras et al. Short modified antisense oligonucleotides directed against Ha-ras point mutation induce selective cleavage of the mRNA and inhibit T24 cells proliferation. EMBO J. 10:1111-1118 (1991).
Sanghvi. Chapter 15: Heterocyclic Base Modifications in Nucleic Acids and Their Applications in Antisense Oligonucleotides. Antisense Research and Applications, Crookeand Lebleu Eds., CRC Press (pp. 273-288) (1993).
Sauer. Site-specific recombination: developments and applications. Curr Opin Biotechnol 5(5):521-527 (1994).
Schmied et al. Efficient Multisite Unnatural Amino Acid Incorporation in Mammalian Cells via Optimized Pyrrolysyl tRNA Synthetase/tRNA Expression and Engineered eRF1. JACS 136:15577-15583 (2014).
Seo et al. Major groove derivatization of an unnatural base pair. Chembiochem 10(14):2394-2400 (2009).
Seo et al. Optimization of an unnatural base pair toward natural-like replication. J Am Chem Soc 131:3246-3252 (2009).
Seo et al. Site-specific labeling of DNA and RNA using an efficiently replicated and transcribed class of unnatural base pairs. J Am Chem Soc 133:19878-19888 (2011).
Seo et al. Transcription of an Expanded Genetic Alphabet. JACS 131(14):5046-5047 (2009).
Shaloiko et al. Effective non-viral leader for cap-independent translation in a eukaryotic cell-free system. Biotechnology and Bioengineering 88(6):730-739 (2004).
Shea et al. Synthesis, hybridization properties and antiviral activity of lipid-oligodeoxynucleotide conjugates. Nucl. Acids Res 18:3777-3783 (1990).
Singh et al. LNA (locked nucleic acids): synthesis and high-affinity nucleic acid recognition. Chem Commun 4:455-456 (1998).
Singh et al. Synthesis of 2'-amino-LNA: A novel conformationally restricted high-affinity oligonucleotide analogues with a handle. J Bio Chem 63:10035-10039 (1998).
Southern et al. Transformation of mammalian cells to antibiotic resistance with a bacterial gene under control of the SV40 early region promoter. J Mol Appl Genet 1:327-341 (1982).
Stenesh et al. DNA polymerase from mesophilic and thermophilic bacteria. III. Lack of fidelity in the replication of synthetic polydeoxyribonucleotides by DNA polymerase from Bacillus licheniformis and Bacillus stearothermophilus. Biochim Biophys Acta 475:32-41 (1977).
Svinarchuk et al. Inhibition of HIV proliferation in MT-4 cells by antisense oligonucleotide conjugated to lipophilic groups. Biochimie 75:49-54 (1993).
Switzer et al. Enzymatic recognition of the base pair between isocytidine and isoguanosine. Biochemistry 32(39):10489-10496 (1993).
Synthorx, Inc. Commission File No. 001-38756. Form 10-K Annual Report Pursuant to Section 13 or 15(d) of the Securities Exchange Act of 1934 for Fiscal Year End dated Dec. 31, 2018 (144 pgs).
Synthorx, Inc. Commission File No. 001-38756. Form 10-Q Quarterly Report Pursuant to Section 13 or 15(d) of the Securities Exchange Act of 1934 for Quarterly Period Ended Mar. 31, 2019.
Synthorx, Inc. Commission File No. 001-38756. Form 8-K Current Report Pursuant to Section 13 or 15(d) of the Securities Exchange Act of 1934 dated Apr. 2, 2019 (8 pgs).
Synthorx, Inc. Commission File No. 001-38756. Form 8-K Current Report Pursuant to Section 13 or 15(d) of the Securities Exchange Act of 1934 dated May 31, 2019 (15 pgs).
Synthorx, Inc. Registration No. 333-228355. Amendment No. 1 to Form S-1 Registration Statement Under the Securities Act of 1933 filed Nov. 27, 2018 (355 pgs.).
Tae et al. Efforts toward expansion of the genetic alphabet: replication of DNA with three base pairs. J. Am. Chem. Soc. 123:7439-7440 (2001).
Takagi et al. Characterization of DNA polymerase from *Pyrococcus* sp. strain KOD1 and its application to PCR. Appl Environ Microbiol 63(11):4504-4510 (1997).
Tjalsma et al. Signal peptide-dependent protein transport in Bacillus subtilis: a genome-based survey of the secretome. Microbiol Mol Biol Rev 64(3):515-547 (2000).
Tomizawa et al. Initiation of DNA synthesis in *Escherichia coli*. Annu. Rev. Biochem. 48:999-1034 (1979).
U.S. Appl. No. 15/302,874 Office Action dated Jan. 28, 2019.
U.S. Appl. No. 15/302,874 Office Action dated Jul. 27, 2018.
U.S. Appl. No. 15/302,874 Office Action dated Jun. 19, 2019.
U.S. Appl. No. 15/302,874 Office Action dated Mar. 13, 2018.
Van Gool et al. Interleukin-5-producing group 2 innate lymphoid cells control eosinophilia induced by interleukin-2 therapy. Blood 124(24):3572-3576 (2014).
Van Haelst Pinsani et al. Administration of Interleukin-2 (IL-2) Results in Increased Plasma Concentrations of IL-5 and Eosinophilia in Patients with Cancer. Blood 78:1538-1544 (1991).
VanBrunt et al. Genetically Encoded Azide Containing Amino Acid in Mammalian Cells Enables Site-Specific Antibody-Drug Conjugates Using Click Cycloaddition Chemistry. Bioconjug Chem. 26(11):2249-60 (2015).
Verma. The reverse transcriptase. Biochim Biophys Acta. 473:1-38 (1977).
Vrudhula et al. Isozyme-specific enzyme inhibitors. 13. S-[5'(R)-[(N-triphosphoamino)methyl]adenosyl]-L-homocysteine, a potent inhibitor of rat methionine adenosyltransferases. J Med Chem 30:888-894 (1987).
Wahlestedt et al. Potent and nontoxic antisense oligonucleotides containing locked nucleic acids. PNAS USA 97:5633-5638 (2000).
Wandry et al. Probing unnatural amino acid integration into enhanced green fluorescent protein by genetic code expansion with a high-throughput screening platform. J Biol Eng. 10:11 (2016).
Wang et al. Biophysical and biochemical properties of oligodeoxynucleotides containing 4'-C-and 5'-C-substituted thymidines. Bioorg Med Chem Lett 9:885-890 (1999).
Wang et al. Synthesis of Azole Nucleoside 5'-Monophosphate Mimics (P1Ms) and Their Inhibitory Properties of IMP Dehydrogenases. Nucleosides Nucleotides & Nucleic Acids 23(1 & 2):317-337 (2004).
Winkler et al. Non-mitochondrial ATP transport. Trends Biochem. Sci. 24:64-68 (1999).
Winkler. Rickettsial permeability: an ADP-ATP transport system. J Biol Chem 251:389-396 (1976).
Wolff et al. Direct gene transfer into mouse muscle in vivo. Science 247:1465-1468 (1990).
Wu et al. Efforts toward expansion of the genetic alphabet: Optimization of interbase hydrophobic interactions. J Am Chem Soc 122:7621-7632 (2000).
Wu et al. Enzymatic phosphorylation of unnatural nucleosides. J Am Chem Soc 124:14626-14630 (2002).
Wu et al. Functionalization of the sugar moiety of oligoribonucleotides on solid support. Bioconjugate Chem 10:921-924 (1999).
Wu et al. Reverse transcriptase. CRC Crit Rev Biochem 3:289-347 (1975).
Wu et al. Synthesis of 5'-C- and 2'-O-(Bromoalkyl)-Substituted Ribonucleoside Phosphoramidites for the Post-synthetic Functionalization of Oligonucleotides on Solid Support. Helvetica Chimica Acta 83:1127-1143 (2000).
Wu et al. Synthesis of Site-Specific Radiolabeled Antibodies for Radioimmunotherapy via Genetic Code Expansion. Bioconjugate Chem. 27:2460-2468 (2016).
Xia et al. Directed evolution of novel polymerase activities: mutation of a DNA polymerase into an efficient RNA polymerase. PNAS USA 99(10):6597-602 (2002).
Yan et al. Nucleoside monophosphate kinases: structure, mechanism, and substrate specificity. Adv. Enzymol. Relat. Areas Mol. Biol. 73:103-134 (1999).
Yu et al. Polymerase recognition of unnatural base pairs. Angew Chem Int Ed Engl 41(20):3841-4 (2002).
Zhang et al. A semisynthetic organism engineered for the stable expansion of the genetic alphabet. PNAS USA 114(6):1317-1322 (2017).
Zhang et al. A Semi-Synthetic Organism that Stores and Retrieves Increased Genetic Information. Nature 551(7682):644-647 (2017).

(56) References Cited

OTHER PUBLICATIONS

Zhang et al. Semisynthetic Organisms with Expanded Genetic Codes. Biochemistry 57:2177-2178 (20180.
Zhang et al. Studies of nucleoside transporters using novel autofluorescent nucleoside probes. Biochemistry 45(4):1087-1098 (2006).
Zhou et al. Fine tuning of electrostatics around the internucleotidic phosphate through incorporation of modified 2',4'-carbocyclic-LNAs and -ENAs leads to significant modulation of antisense properties. J Org Chem 74:118-134 (2009).
Zon. Chapter 8: Oligonucleotide Phosphorothioates in Protocols for Oligonucleotides and Analogs, Synthesis and Properties. Humana Press (pp. 165-190) (1993).
Arenas-Ramirez et al. Improved cancer immunotherapy by a CD25-mimobody conferring selectivity to human interleukin-2. Sci Transl Med 8:367ra166 (Nov. 30, 2016). 13 pages.
Charych et al. Combining Complementary Mechanisms of Immune Activation: NKTR-214, a biased IL-2 Pathway Agonist and Immune Checkpoint Antagonists. Poster Abstract 3018. ESMO Annual Meeting (Oct. 9, 2016, Copenhagen, Denmark).
Chastgner et al. Lack of intermediate-affinity interleukin-2 receptor in mice leads to dependence on interkeukin-2 receptor α,β and γ chain expression for T cell growth. Eur J Immunol 26:201-206 (1996).
Chen et al. A novel human IL-2 mutein with minimal systemic toxicity exerts greater antitumor efficacy than wild-type IL-2. Cell Death& Disease 9:989 (2018).
Diab et al. NKTR-214 (CD-122-biased agonist) plus nivolumab in patients with advanced solid tumors: Preliminary phase 1/2 results of PIVOT. Powerpoint presentation. ClinicalTrials.gov NCT02983045. 2018 ASCO Annual Meeting (2018).
Diab et al. Pivot-02: Preliminary safety, efficacy and biomarker results from dose escalation of the Phase 1/2 study of CD-122-biased agonist NKTR-214 plus nivolumab in patients with locally advanced/metastatic melanoma, renal cell carcinoma and non-small cell lung cancer. ClinicalTrials.gov Identifier: NCT02983045 PowerPoint presentation. SITC 2017 (Nov. 2017).
Dranoff. Cytokines in cancer pathogenesis and cancer therapy. Nature Reviews Cancer 4:11-22 (2004).
Floros et al. Anticancer Cytokines: Biology and Clinical Effects of Interferon-α2, Interleukin (IL)-2, IL-15, IL-21, and IL-12. Semin Oncol 42(4):539-548 (2015).
Gillies et al. A Low-Toxicity IL-2-based Immunocytokine Retains Antitumor Activity Despite Its High Degree of IL-2 receptor Selectivity. Clin Cancer Res 17(11):3673-3686 (2011).
Heaton et al. Characterization of lymphokine-activated killing by human peripheral blood mononuclear cells stimulated with interleukin 2 (IL-2) analogs specific for the intermediate affinity IL-2 receptor. Cell Immunol 147:167-179 (1993).
Heaton et al. Human interleukin 2 analogues that preferentially bind the intermediate-affinity interleukin 2 receptor lead to reduced secondary cytokine secretion: implications for the use of these interleukin 2 analogues in cancer immunotherapy. Cancer Res 53:2597-2602 (1993).
Hu et al. The Generation of Low Toxicity Interleukin-2 Fusion Proteins Devoid of Vasopermeability Activity. Blood 101(12):4853-61 (2003).
Hurwitz et al. A Novel Immune Agonist, NKTR-214, Increases the Number of Activity of CD8+ Tumor Infiltrating Lymphocytes in Patients with Advance Renal Cell Carcinoma. Poster Abstract #454. Poster Session C. ASCO Feb. 18, 2017 (ASCO 2017).
Insight-Esprit Study Group et al. Interleukin-2 Therapy in Patients with HIV Infection. N Engl J Med. 361(16):1548-59 (2009).
Jones et al. A Subset of Latency-Reversing Agents Expose HIV-Infected Resting CD4+ T-Cells to Recognition by Cytotoxic T-Lymphocytes. PLoS Pathogens 12(4):e1005545 (2016).
Khalili et al. Mechanistic modeling of a new kinetically-controlled CD122 agonist for cancer immunotherapy: NKTR-214 pharmacokinetics, pharmacodynamics, and receptor pharmacology. Poster Abstract 1614. AACR Annual Meeting, Apr. 2017 (AACR 2017).
Kivimae et al. Comprehensive Antitumor Immune Activation by a Novel TLR 7/8 Targeting Agent NKTR-262 Combined With CD122-Biased Immunostimulary Cytokine NKTR-214. Poster #3755 (AACR Apr. 14-18, 2018).
Kivimäe et al. Harnessing the innate and adaptive immune system to eradicate treated and distant untreated solid tumors. Poster #P275. Immunotherapy of Cancer 2017 Annual Meeting (2017).
Klein et al. Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines. Oncoimmunology 6(3):e1277306 (2017).
Krieg et al. Improved IL-2 immunotherapy by selective stimulation of IL-2 receptors on lymphocytes and endothelial cells. PNAS USA 107(26):11906-11911 (Jun. 29, 2010).
Langowski et al. The CD122-biased immunostimulatory cytokine NKTR-214 combined with checkpoint blockade leads to mobilization of anti-tumor immunity and synergistic activity. Poster Abstract 311.2016 CR-CIMT-EATIR-AACR Cancer Immunotherapy Conference (2016).
Lazear et al. Targeting of IL-2 to cytotoxic lymphocytes as an improved method of cytokine-driven immunotherapy. Oncoimmunology 6(2):e1265721 (2017).
Letourneau et al. IL-2/anti-IL-2 antibody complexes show strong biological activity by avoiding interaction with IL-2 receptor alpha subunit CD25. PNAS USA 107:2171-2176 (2010).
Lopes et al. Characterization of the Pharmacodynamic Immune Response to a Novel Immunotherapeutic Agent, ALKS 4230, in Mice and Non-Human Primates. Poster 22 (Abstract #2663) (AACR2017).
Lopes et al. Ex Vivo Expansion and Activation of Human Lymphocytes With a Selective Activator of Effector Cells. Abstract #3158 Poster (AACR 2015).
Losey et al. Abstract #4280: Utilizing a Selective Agonist of the Intermediate-Affinity IL-2 Receptor With an Improved Pharmacokinetic Profile Leads to an Enhanced Immunostimulatory Response With Reduced Toxicity in Mice. Proceedings: AACR 106th Annual Meeting 2015 (Apr. 18-22, 2015, Philadelphia, PA).
Losey et al. Efficacy of ALKS 4230, a Novel Immunotherapeutic Agent, in Murine Syngeneic Tumor Models Alone and in Combination with Immune checkpoint Inhibitors. Poster 25 (Abstract #591) (AACR 2017).
Losey et al. Utilizing a Selective Agonist of the Intermediate-Affinity IL-2 Receptor With an Improved Pharmacokinetic Profile Leads to an Enhanced Immunostimulatory Response With Reduced Toxicity in Mice. Poster for Abstract #4280 (AACR 2015).
Lou et al. Fixing vascular leak in IL-2 immunotherapy. SciBX 3(27):2 pgs (2010).
Meghnem et al. Cutting Edge: Differential Fine-Tuning of IL-2- and IL-15-Dependent Functions by Targeting Their Common IL-2/15Rβ/γc Receptor. J Immunol 198(12):4563-4568 (May 2017).
Merchant et al. Preclinical characterization of IL-2 Superkines engineered with biased CD8+ T cell stimulating properties. Poster (SITC 2018).
Nektak Therapeutics Presents New Clinical Data from Ongoing Phase 1 Dose-Escalation Study of NKTR-214 at the Society for Immunotherapy of Cancer (SITC) 2016 Annual Meeting. PRNewswire Nov. 9, 2016.
Nektar Therapeutics. Investor Meeting presentation Jun. 3, 2017.
Nicolini et al. The FAP-IL2v Immunocytokine is a Versatile Combination Partner for Cancer Immunotherapy. Poster (SITC 2018).
Parisi et al. Enhanced expansion and tumor targeting of adoptively transferred T cells with NKTR-214. Poster Abstract #3566. (AACR Apr. 17, 2018).
Pfannenstiel et al. A Novel, Individualized Xenograft Model of Cancer Immunotherapy and Tumor Growth Inhibition by ALKS 4230. Poster #P351 (SITC 2017).
Pieper et al. NKTR-214 in combination with radiation produces a potent in situ vaccine in the syngeneic B78 melanoma model. Poster (STIC 2018).

(56) References Cited

OTHER PUBLICATIONS

Plieth. Cytokine therapy focus—interleukin-2 claims the early lead. EP Vantage. Evaluate Feb. 27, 2018 (Available at https://www.evaluate.com/vantage/articles/analysis/cytokine-therapy-focus-interleukin-2-claims-early-lead).
Roessler et al. Cooperative interactions between the interleukin 2 receptor α and β chains later the interleukin 2-binding affinity of the receptor subunits. PNAS USA 91:3344-3347 (1994).
Rosentrater et al. Determination of the Relative potency of a Selective Agonist of the Intermediate-Affinity IL-2 Receptor on Lymphocytes from Human, Cynomolgus Monkey and Mouse. Poster for Abstract #4281 (No date available).
Sharma et al. NKTR-214 enhances anti-tumor T cell immune responses induced by checkpoint blockade or vaccination. Poster (SITC 2017).
Siegel et al. Interleukin-2 Toxicity. J Clin Oncol 9(4):694-704 (1991).
Sim et al. IL2 Variant Circumvents ICOS+ Regulatory T-cell Expansion and Promotes NK Cell Activation. Cancer Immunol Res. 4(11):983-995 (Nov. 2016).
Sivakumar et al. Comparison of Vascular Leak Syndrome in Mice treated with IL21 or IL2. Comparative Medicine 63(1):13-21 (2013).
Spangler et al. Antibodies to Interleukin-2 Elicit Selective T Cell Subset Potentiation through Distinct Conformational Mechanism. Immunity 42:815-825 (2015).
Stauber et al. Crystal Structure of the IL-2 signaling complex: Paradigm for a heterotrimeric cytokine receptor. PNAS 103(8):2788-2793 (2006).
Sun et al. First-In-Human dose Selection of ALKS 4230, an Investigational Immunotherapeutic Agent. Poster 4088 (AACR 2017).
Sun et al. Pharmacokinetics and Pharmacodynamic Effects of ALKS 4230, an Investigational Immunotherapeutic Agent, in Cynomolgus Monkeys After Intravenous and Subcutaneous Administration. Poster (SITC 2018).
U.S. Appl. No. 15/543,217 Office Action dated Apr. 3, 2020.
U.S. Appl. No. 15/543,217 Office Action dated Aug. 7, 2019.
U.S. Appl. No. 15/543,217 Office Action dated Feb. 7, 2019.
U.S. Appl. No. 15/543,217 Office Action dated Nov. 18, 2019.
U.S. Appl. No. 15/543,217 Office Action dated Sep. 24, 2018.
U.S. Appl. No. 16/413,209, filed May 15, 2019.
U.S. Appl. No. 16/413,219, filed May 15, 2019.
U.S. Appl. No. 16/434,999, filed Jun. 7, 2019.
U.S. Appl. No. 16/530,742, filed Aug. 2, 2019.
U.S. Appl. No. 16/535,992, filed Aug. 8, 2019.
U.S. Appl. No. 16/546,097, filed Aug. 20, 2019.
U.S. Appl. No. 16/546,100, filed Aug. 20, 2019.
U.S. Appl. No. 16/577,347, filed Sep. 9, 2020.
U.S. Appl. No. 16/839,741, filed Apr. 3, 2020.
U.S. Appl. No. 16/900,154, filed Jun. 12, 2020.
Vaishampayan et al. A Phase 1 Trial of ALKS 4230, an Engineered Cytokine Activator of NK and Effector T Cells, in Patients with Advanced Solid Tumors. Poster for Abstract #TPS3111 (ASCO 2017).
Vaishampayan et al. Safety, pharmacokinetics and pharmacodynamic effects of ALKS 4230 in patients with advanced solid tumors from the ongoing dose escalation portion of a first in human (FIH) study. Poster (SITC 2018).
Vazquez-Lombardi et al. Potent antitumour activity of the interleukin-2-Fc fusion proteins requires Fc-mediated depletion of regulatory T-cells. Nat Comm 8:15373 (2017).
Waldmann et al. The Shared and Contrasting Roles of IL2 and IL15 in the Life and Death of Normal and Neoplastic Lymphocytes: Implications for Cancer Therapy. Cancer Immunol Res 3(3):219-227 (2015).
Walker et al. Combination of NKTR-214 and Radiotherapy (RT) to reverse anergy and expand specific CD8 T cells. Poster (SITC 2017).
Wang et al. Enhanced Anti-tumor Activity of the Combination of Entinostat and NKTR-214 in Renal and Colon Cancer Tumor Models. Poster. AACR Annual Meeting 2018 (AACR 2018).
Wang et al. Structure of the Quaternary Complex of Interleukin-2 with Its α, ß, and γc Receptors. Science 310:1159-63 (2005).
Webster et al. In vivo expansion of T reg cells with IL-2-mAb complexes: induction of resistance to EAE and long-term acceptance of islet allografts without immunosuppression. J Med Chem 206(4):751-760 (2009).
Yamaguchi et al. Role of IL-5 in IL-2-induced eosinophilia. In vivo and in vitro expression of IL-5 mRNA by IL-2. J Immunol 145:873-877 (1990).
Zalevsky. Jefferies 2016 Global Healthcare Conference. PowerPoint presentation (Nov. 16, 2016).
Database accession No. B7FWL8. Database UniProt [Online] Feb. 10, 2009 (Feb. 10, 2009), "RecName:Full=ADP,ATP carrier protein {ECO:0000256lRuleBase:RU363121};",XP055864093, retrieved from EBI accession No. UNIPROT:B7FWL8.

* cited by examiner d5SICS dNaM dC dG (Part of SEQ ID NOS: 26 and 27)

32(h)

146(h)

IMPORT OF UNNATURAL OR MODIFIED NUCLEOSIDE TRIPHOSPHATES INTO CELLS VIA NUCLEIC ACID TRIPHOSPHATE TRANSPORTERS

CROSS-REFERENCE

This application is a divisional of U.S. application Ser. No. 15/302,874, filed on Oct. 7, 2016, now U.S. Pat. No. 10,513,706, which is the U.S. National Stage entry of International Application No. PCT/US2015/025175, filed on Apr. 9, 2015, which claims the benefit of U.S. provisional Application No. 61/977,439, filed Apr. 9, 2014, and U.S. provisional Application No. 61/977,430, filed Apr. 9, 2014, all of which are incorporated herein by reference in their entireties.

STATEMENT AS TO FEDERALLY SPONSORED RESEARCH

This invention was made with government support under GM060005 awarded by National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Apr. 9, 2015, is named 46085701301_SL.txt and is 98,283 bytes in size.

BACKGROUND OF THE INVENTION

Large amounts of genetic information essential for vital activities of living organisms are recorded as sequences comprised of nucleic acid nucleobases. Unlike proteins which are composed of 20 types of amino acids, the chemical and physical diversity of nucleic acids is limited by only 4 bases (2 base pairs) in natural nucleic acids. Such nucleic acids allow self-replication using itself as a template and transmission of genetic information from DNA to DNA, from DNA to RNA, and/or from RNA to protein. Natural nucleotides pair through two or three hydrogen bonds (A:T/U, G:C) and this pairing enables replication and transmission of the genetic information. In vitro, the natural two-letter genetic alphabet has been expanded with chemically synthetized unnatural nucleotides that form unnatural base pairs (UBPs).

To create an organism with an expanded genetic alphabet, the unnatural nucleoside triphosphates must first be available inside the cell. It has been suggested that this might be accomplished by passive diffusion of free nucleosides into the cytoplasm followed by their conversion to the corresponding triphosphate via the nucleoside salvage pathway. Some unnatural nucleic acids are phosphorylated by the nucleoside kinase from *D. melanogaster*, and monophosphate kinases appear to be more specific. However, *E. coli* over-expression of endogenous nucleoside diphosphate kinase results in poor cellular growth.

Benner et al. have designed novel base pairs based on different hydrogen-bonding combinations from natural base pairs, e.g., isoG:isoC and κ:X base pairs (Piccirilli et al., 1990; Piccirilli et al., 1991; Switzer et al., 1993). However, isoG forms a base pair with T through keto-enol tautomerism between 1- and 2-positions; isoC and K are not substrates of polymerases due to an amino group substitution at the 2-position; and nucleoside derivatives of isoC are chemically unstable.

Base pairs that have hydrogen-bonding patterns different from those of natural base pairing and that are capable of eliminating base pairing with natural bases by steric hindrance have also been developed. For example, Ohtsuki et al. (2001) and Hirao et al. (2002) designed 2-amino-6-dimethylaminopurine (X), 2-amino-6-thienylpurine (S), and pyridin-2-one (Y). However, the incorporation of Y opposite X showed low selectivity.

Kool et al. synthesized A and T derivatives (4-methylbenzimidazole (Z) and 9-methyl-1-H-imidazo[(4,5)-b]pyridine (Q), respectively) lacking hydrogen bonding. These base pairs were found to be incorporated into DNA in a complementary manner by the Klenow fragment of *E. coli*-derived DNA polymerase I. Other base pairs including A:F, Q:T and Z:T are also shown to be incorporated [Morales & Kool, 1999]. Other examples include 7-(2-thienyl)-imidazo[4,5-b]pyridine (Ds) and pyrrole-2-carbaldehyde (Pa).

In an effort to develop an orthogonal third base pair, over 100 hydrophobic bases have been designed, synthesized as the triphosphate and phosphoramidite, and characterized in Floyd Romesberg's laboratory. A large number of hydrophobic base pairs have also been generated, including pyrrolopyridine (PP) and C3-methylisocarbostyryl (MICS) (Wu et al., 2000). However, these bases paired with each other independently of shape fitting, resulting in PP:PP and MICS:MICS incorporation into DNA; and elongation did not substantially proceed after incorporation of such base combinations formed without any shape fitting. Neither H-bonding nor a large aromatic surface area was found to be required for base pair stability in duplex DNA or polymerase mediated replication for some UBPs, e.g., a 3-fluorobenzene (3FB) self-pair.

The development of a third, unnatural DNA base pair, and an expanded genetic alphabet, is a central goal of synthetic and chemical biology and would increase the functional diversity of nucleic acids, provide tools for their site-specific labeling, increase the information potential of DNA, and lay the foundation of a semi-synthetic organism. Described herein is a newly developed class of UBPs that is formed between nucleotides bearing hydrophobic nucleobases (exemplified by the pair formed between d5SICS and dNaM (d5SICS-dNaM)), which is efficiently PCR amplified and transcribed, and whose unique mechanism of replication has been thoroughly characterized through kinetic (Lavergne et al., Chem. Eur. J. (2012) 18:1231-1239; Seo et al., J. Am. Chem. Soc. (2009) 131:3246-3252) and structural studies (Betz et al., J. Am. Chem. Soc. (2013) 135:18637-18643; Malyshev et al., Proc. Natl. Acad. Sci. USA (2012) 109: 12005-12010). Until now, no living organisms capable of incorporation and propagation of unnatural information existed.

The limitation of having only four different base components (nucleotides) in standard nucleic acids restricts their functions and potential, as compared to the 20 different amino acids in natural proteins. The UBPs and cells stably incorporating the UBPs described herein offer numerous advantages and can be applied to a broad range of biotechnologies. Having a third base pair that replicates in the ranges of natural ones could significantly increase the information density in the same length of DNA and make DNA a more attractive alternative for information storage. More importantly, a third UBP could expand coding of DNA for unnatural amino acids, providing access to proteins (including protein therapeutics) with unique properties not available using the 20 natural ones.

SUMMARY OF THE INVENTION

Provided herein, is a cell comprising a first unnatural nucleic acid, wherein the first unnatural nucleic acid is an imported unnatural nucleic acid.

In some embodiments, the cell further comprises an unnatural base pair (UBP), wherein the UBP is formed within the cell.

In some embodiments, the UBP comprises the first unnatural nucleic acid.

In some embodiments, the cell comprises an expanded genetic alphabet.

In some embodiments, the expanded genetic alphabet comprises the UBP.

In some embodiments, the UBP is incorporated into a nucleic acid of the cell.

In some embodiments, the UBP is stably incorporated into a nucleic acid of the cell.

In some embodiments, the UBP is not efficiently recognized by a DNA repair pathway of the cell.

In some embodiments, the UBP comprises the first unnatural nucleic acid.

In some embodiments, the cell further comprises a heterologous nucleic acid.

In some embodiments, the heterologous nucleic acid encodes for a nucleotide triphosphate transporter (NTT), a polymerase, or a combination thereof.

In some embodiments, the heterologous nucleic acid encodes for an NTT.

In some embodiments, the cell further comprises at least one template UBP comprising a first unnatural template nucleic acid.

In some embodiments, the first unnatural template nucleic acid is capable of base pairing with the first unnatural nucleic acid.

In some embodiments, the base pairing comprises hydrophobic base pairing.

In some embodiments, the base pairing does not comprise hydrogen bonding.

In some embodiments, the cell imports the first unnatural nucleic acid.

In some embodiments, the heterologous NTT transports the first unnatural nucleic acid into the cell.

In some embodiments, the cell comprises enhanced import of an unnatural nucleotide, enhanced incorporation of an unnatural nucleotide into a nucleic acid of the cell, or decreased degradation of an unnatural nucleic acid in comparison to a respective wild type cell.

In some embodiments, the cell comprises enhanced import of the first unnatural nucleic acid in comparison to a cell without the heterologous NTT.

In some embodiments, the heterologous NTT is bound to the first unnatural nucleic acid In some embodiments, the cell further comprises a second unnatural nucleic acid.

In some embodiments, the cell imports the second unnatural nucleic acid.

In some embodiments, the heterologous NTT transports the second unnatural nucleic acid into the cell.

In some embodiments, the at least one template UBP further comprises a second unnatural template nucleic acid.

In some embodiments, the second unnatural template nucleic acid is capable of base pairing with the second unnatural nucleic acid.

In some embodiments, the first unnatural template nucleic acid is capable of base pairing with the second unnatural template nucleic acid.

In some embodiments, the first unnatural nucleic acid is capable of base pairing with the second unnatural nucleic acid.

In some embodiments, the first unnatural nucleic acid is different from the second unnatural nucleic acid.

In some embodiments, the first unnatural nucleic acid is the same as the second unnatural nucleic acid.

In some embodiments, the at least one template UBP comprises at least about 2, 3, 4, 5, 6, 7, 8, 9, 10, 20, 30, 40, 50, 60, 70, 80, 90, 100, 200, 300, 400, 500, 600, 700, 800, 900, or 1000 template UBPs.

In some embodiments, the at least one template UBP is present in at least one heterologous nucleic acid.

In some embodiments, the at least one heterologous nucleic acid comprises at least about 2, 3, 4, 5, 6, 7, 8, 9, 10, 20, 30, 40, 50, 60, 70, 80, 90, 100, 200, 300, 400, 500, 600, 700, 800, 900, or 1000 heterologous nucleic acids.

In some embodiments, the at least one template UBP is introduced into the cell by transfection, lipofection, injection, viral vector, or electroporation.

In some embodiments, the UBP comprises the first unnatural template nucleic acid.

In some embodiments, the UBP comprises the second unnatural nucleic acid.

In some embodiments, the UBP comprising the second unnatural nucleic acid comprises the second unnatural template nucleic acid.

In some embodiments, the UBP comprises at least 2 UBPs.

In some embodiments, the at least 2 UBPs comprise at least 3, 4, 5, 6, 7, 8, 9, 10, 20, 30, 40, 50, 60, 70, 80, 90, 100, 200, 300, 400, 500, 600, 700, 800, 900, or 1000 UBPs.

In some embodiments, the at least 2 UBPs comprise a first UBP and a second UBP, wherein the first UBP comprises: the first unnatural nucleic acid and the first unnatural template nucleic acid or the first unnatural nucleic acid and the second unnatural template nucleic acid; and wherein the second UBP comprises: the second unnatural nucleic acid and the second unnatural template nucleic acid, or the second unnatural nucleic acid and the first unnatural template nucleic acid; or any combination thereof.

In some embodiments, the at least one template UBP is formed outside of the cell.

In some embodiments, the first or second unnatural nucleic acid is a deoxyribonucleoside.

In some embodiments, the first or second unnatural nucleic acid is a ribonucleoside.

In some embodiments, the first or second unnatural nucleic acid is a nucleoside triphosphate.

In some embodiments, the first or second unnatural nucleic acid comprises a modified sugar group In some embodiments, the first or second unnatural nucleic acid is selected from the group consisting of any one of those listed in Appendix A, and any combination thereof.

In some embodiments, the cell comprises at least one genetic modification.

In some embodiments, the at least one genetic modification comprises a heterologous polymerase, a mutant polymerase, a disruption in a nucleotidase of the cell, a disruption of a phosphatase of the cell, or a combination thereof.

In some embodiments, the cell is in contact with a phosphatase inhibitor or a nucleotidase inhibitor.

In some embodiments, the cell is a prokaryotic cell.

In some embodiments, the cell is from *Phaeodactylum tricornutum, Thalassiosira pseudonana* or *Protochlamydia amoebophila.*

In some embodiments, the cell is a eukaryotic cell.

In some embodiments, the cell is *E. coli.*

In some embodiments, the heterologous NTT is from *Phaeodactylum tricornutum* (Pt) NTT2, *Thalassiosira pseudonana* (Tp) NTT2, *Protochlamydia amoebophila* (Pam) NTT2, *Protochlamydia amoebophila* (Pam) NTT5, or a combination thereof.

In some embodiments, the heterologous NTT is a nucleotide transporter 1 (NTT1), nucleotide transporter 2 (NTT2), nucleotide transporter 3 (NTT3), nucleotide transporter 4 (NTT4), nucleotide transporter 5 (NTT5), nucleotide transporter 6 (NTT6), nucleotide transporter 7 (NTT7), nucleotide transporter 8 (NTT8), or a combination thereof.

In some embodiments, the UBP is not efficiently removed by the cell.

In some embodiments, the removal comprises 3'-5' nuclease activity.

In some embodiments, the removal comprises nucleotide excision by the cell.

In some embodiments, the UBP is not efficiently removed from the cell after growth for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 50 or more duplications.

In some embodiments, the UBP is not efficiently removed from the cell after growth for about 1, 2, 3, 4, 5, 6, 7, 8, 9, 10, 11, 12, 13, 14, 15, 16, 17, 18, 19, 20, 21, 22, 23, or 24 hours; 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days; 2, 3, 4, 5, 6, 7, 8, 9, 10, 11, or 12 months; or 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50 years of growth.

In some embodiments, the first or second unnatural nucleic acid comprises an unnatural base.

In some embodiments, the unnatural base is selected from the group consisting of 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-amino-adenine, 2-amino-propyl-adenine, 2-aminopyridine, 2-pyridone, 2'-deoxyuridine, 2-amino-2'-deoxyadenosine 3-deazaguanine, 3-deazaadenine, 4-thio-uracil, 4-thio-thymine, uracil-5-yl, hypoxanthin-9-yl (I), 5-methyl-cytosine, 5-hydroxymethyl cytosine, xanthine, hypoxanthine, 5-bromo, and 5-trifluoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azo cytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, 0-6 substituted purines, those that increase the stability of duplex formation, universal nucleic acids, hydrophobic nucleic acids, promiscuous nucleic acids, size-expanded nucleic acids, fluorinated nucleic acids, tricyclic pyrimidines, phenoxazine cytidine([5,4-b][1,4]benzoxazin-2(3H)-one), phenothiazine cytidine (1H-pyrimido [5,4-b][1,4]benzothiazin-2(3H)-one), G-clamps, phenoxazine cytidine (9-(2-aminoethoxy)-H-pyrimido[5,4-b][1,4]benzoxazin-2(3H)-one), carbazole cytidine (2H-pyrimido [4,5-b]indol-2-one), pyridoindole cytidine (H-pyrido [3',2':4,5]pyrrolo [2,3-d]pyrimidin-2-one), 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methyl aminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine and those in which the purine or pyrimidine base is replaced with a heterocycle.

In some embodiments, the unnatural base is selected from the group consisting of

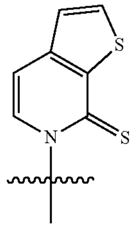
(d)TPT3

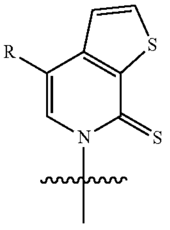
(d)TPT3pa

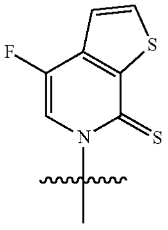
(d)FTPT3

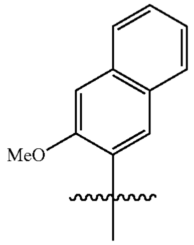
(d)NaM

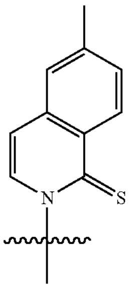
(d)5SICS

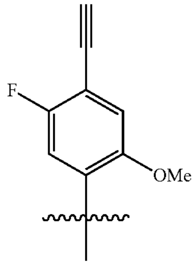
(d)FEMO

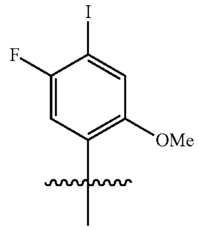
(d)FIMO

-continued

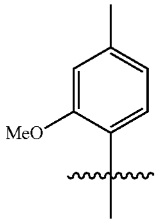

(d)MMO2 wherein R is a functional group.

In some embodiments, the functional group is selected from the group consisting of an affinity tag such as biotin, fluorophore, alkyl, alkenyl, alkynyl, phenyl, benyl, halo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, orthoester, methylenedioxy, orthocasrbonate ester, carboxamide, primary amine, secondary amine, tertiary amine, primary ketamine, secondary ketamine, primary aldimine, secondary aldimine, imide, azide, azo, cyanate, isocyanate, nitrate, nitrile, isonitrile, nitrosooxy, nitro, nitroso, pyridyl, sulfhydryl, sulfide, disulfide, sulfinyl, sulfino, sulfo, thiocyanate, isothiocyanante, carbonothioyl, phoshino, phosphono, phosphate, borono, boronate, borino, borinate, and combinations thereof.

In some embodiments, the first or second unnatural nucleic acid comprises an unnatural sugar moeity.

In some embodiments, the unnatural sugar moeity is selected from the group consisting of a modification at the 2' position: OH; substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2F$; O-alkyl, S-alkyl, N-alkyl; O-alkenyl, S-alkenyl, N-alkenyl; O-alkynyl, S-alkynyl, N-alkynyl; O-alkyl-O-alkyl, 2'-F, 2'-$OCH_3$, 2'-$O(CH_2)_2OCH_3$ wherein the alkyl, alkenyl and alkynyl may be substituted or unsubstituted $C_1$-$C_{10}$, alkyl, $C_2$-$C_{10}$ alkenyl, $C_2$-$C_{10}$ alkynyl, —$O[(CH_2)n\ O]mCH_3$, —$O(CH_2)nOCH_3$, —$O(CH_2)n\ NH_2$, —$O(CH_2)n\ CH_3$, —$O(CH_2)n$-$ONH_2$, and —$O(CH_2)nON[(CH_2)n\ CH_3)]_2$, where n and m are from 1 to about 10; and/or a modification at the 5' position: 5'-vinyl, 5'-methyl (R or S), a modification at the 4' position, 4'-S, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and any combination thereof.

In some embodiments, the unnatural nucleic acid comprises an unnatural backbone.

In some embodiments, the unnatural backbone is selected from the group consisting of a phosphorothioate, chiral phosphorothioate, phosphorodithioate, phosphotriester, aminoalkylphosphotriester, phosphonates, 3'-alkylene phosphonate, chiral phosphonates, phosphinates, phosphoramidates, 3'-amino phosphoramidate, aminoalkylphosphoramidates, thionophosphoramidates, thionoalkylphosphonates, thionoalkylphosphotriesters, and boranophosphates.

In some embodiments, the cell is in contact with a natural nucleic acid.

In some embodiments, the natural nucleic acid is selected from the group consisting of ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, dGMP, dATP, dTTP, dCTP, dGTP, dADP, dTDP, dCDP, dGDP, dAMP, dTMP, dCMP, dGMP, and any combination thereof.

In some embodiments, the natural nucleic acid is selected from the group consisting of ATP, UTP, CTP, GTP, and any combination thereof.

In some embodiments, the NTT is from a bacterium.

In some embodiments, the bacterium is *Phaeodactylum tricornutum, Thalassiosira pseudonana*, or *Protochlamydia amoebophila.*

In some embodiments, the NTT comprises an amino acid sequence with at least about 60% identity to any one of SEQ ID NOs: 1, 3, 5, 7, 9, 11, 13, 14, 16, 18, 19, 20, 22, or 24.

In some embodiments, the NTT is encoded by a nucleic acid encoding an amino acid sequence with at least about 60% identity to any one of SEQ ID NOs: 1, 3, 5, 7, 9, 11, 13, 14, 16, 18, 19, 20, 22, or 24.

In some embodiments, the NTT is encoded by a nucleic acid sequence with at least about 60% identical to any one of SEQ ID NOs: 2, 4, 6, 8, 10, 12, 15, 17, 19, 21, 23, 25, or 28.

In some embodiments, the cell comprises a vector comprising the heterologous nucleic acid.

In some embodiments, the heterologous nucleic acid is incorporated into the genome of the cell.

In some embodiments, the heterologous nucleic acid encodes for a polymerase.

In some embodiments, the polymerase is a mesophilic polymerase or a thermophilic polymerase.

In some embodiments, the polymerase is altered.

In some embodiments, the polymerase is 3'-5' exonuclease-deficient.

In some embodiments, the polymerase is selected from the group consisting DNA polymerase, RNA polymerase, and reverse transcriptase.

In some embodiments, the polymerase is selected from the group consisting of Φ29, B103, GA-1, PZA, Φ15, BS32, M2Y, Nf, G1, Cp-1, PRD1, PZE, SF5, Cp-5, Cp-7, PR4, PR5, PR722, L17, ThermoSequenase®, 9° Nm™, Therminator™, Tne, Tma, Tfl, Tth, Tli, Stoffel fragment, Vent™ and Deep Vent™ DNA polymerase, KOD DNA polymerase, Tgo, JDF-3, Pfu, Taq, T7 DNA polymerase, PGB-D, UlTma DNA polymerase, *E. coli* DNA polymerase I, archaeal DP1I/DP2 DNA polymerase II, 9° N DNA Polymerase, Taq DNA polymerase, Phusion® DNA polymerase, Pfu DNA polymerase, and RB69 DNA polymerase.

In some embodiments, the polymerase is a reverse transcriptase from a retrovirus.

In some embodiments, the retrovirus is from HIV, HTLV-I, HTLV-II, FeLV, FIV, SIV, AMV, MMTV, or MoMuLV.

In some embodiments, the alteration comprises an alteration arising from directed evolution.

In some embodiments, the cell further comprises an alteration in a homologous nucleic acid.

In some embodiments, the homologous nucleic acid encodes for a nucleotidase, a nucleotide phosphatase, or a combination thereof.

In some embodiments, the homologous nucleic acid comprises a gene that encodes for a nucleotide phosphatase, and wherein the nucleotide phosphatase is selected from the group consisting of: polynucleotide phosphatase; nucleotide phosphatase activity, acting on free nucleotides; nucleotide triphosphatase apyrase; ATP-diphosphatase; adenosine diphosphatase; ADPase; ATP diphosphohydrolase nucleoside diphosphate phosphatase; nucleoside-diphosphatase; thiaminpyrophosphatase; UDPase; inosine diphosphatase; adenosine diphosphatase; IDPase; ADPase; adenosinepyrophosphatase; guanosine diphosphatase; guanosine 5'-diphosphatase; inosine 5'-diphosphatase; uridine diphosphatase; uridine 5'-diphosphatase; type B nucleoside diphosphatase; GDPase; CDPase; nucleoside 5'-diphosphatase; type L nucleoside diphosphatase; NDPase; nucleoside diphosphate phosphohydrolase; and any combination thereof.

In some embodiments, the homologous nucleic acid encodes for a nucleotide phosphatase, and wherein the nucleotide phosphatase is selected from the group consisting of any of those listed in Table 4 or 5.

In some embodiments, the homologous nucleic acid encodes for a nucleotidase, and wherein the nucleotidase, is selected from the group consisting of a 5'-nucleotidase, 3'-nucleotidase, or a combination thereof.

In some embodiments, the homologous nucleic acid encodes for a nucleotidase, and wherein the nucleotidase, is selected from the group consisting of any of those listed in Table 2 or 3.

In some embodiments, the alteration comprises a loss or decrease of function of a gene encoded by the homologous nucleic acid.

In some embodiments, the alteration comprises an alteration arising from directed evolution.

In some embodiments, the cell is in contact with a phosphatase or a nucleotidase inhibitor.

In some embodiments, the phosphatase or nucleotidase inhibitor is selected from the group consisting of Sodium Fluoride, Sodium Orthovanadate, beta-Glycerophosphate, pyrophosphate and salts thereof, potassium phosphate (KPi), Phosphate (Pi), Oligomycin, pyrophosphate (PPi) anions, ammonium ions inositol hexaphosphate, and combinations thereof.

In some embodiments, the phosphatase or nucleotidase inhibitor is present at a concentration of from 0.1 μM to 500 mM, 0.1 mM to 500 mM, 0.2 mM to 250 mM, 0.25 mM to 200 mM, 1.0 mM to 150 mM, 2.5 mM to 125 mM, 5 mM to 100 mM, 25 mM to 75 mM, or 40 mM to 60 mM.

In some aspects, provided herein is a method for producing a genetically modified cell comprising: providing a cell exhibiting a wild type level of import of a first unnatural nucleotide; and introducing a heterologous NTT into the cell, thereby enhancing the level of import of the first unnatural nucleotide in comparison the level of import of the first unnatural nucleotide into the cell that exhibits a wild type level of import of the first unnatural nucleotide.

In some embodiments, the cell that exhibits a wild type level of import of the first unnatural nucleotide does not comprise the heterologous NTT.

In some embodiments, the method further comprises contacting the cell comprising a heterologous NTT with the first unnatural nucleotide.

In some aspects, provided herein is a method incorporating an unnatural nucleic acid into a cell, comprising contacting a cell comprising a heterologous NTT with a first unnatural nucleic acid; and cultivating the cell for a period of time; wherein the heterologous NTT transports the first unnatural nucleic acid into the cell In some aspects, provided herein is a method for genetically engineering a cell comprising: contacting a cell comprising a heterologous NTT with a liquid, the liquid comprising a concentration of an unnatural nucleic acid, and a concentration of a natural nucleic acid; cultivating the cell for a period of time; increasing the ratio of the concentration of the unnatural nucleic acid to the concentration of the natural nucleic acid; and repeating (b) and (c) one or more times.

In some embodiments, after one or more repeats of (b) and (c), the cell comprises enhanced import of an unnatural nucleotide, enhanced incorporation of an unnatural nucleotide into a nucleic acid of the cell, or decreased degradation of an unnatural nucleic acid in comparison to the respective wild type cell.

In some embodiments, the cell comprising the heterologous NTT further comprises at least one template UBP comprising a first unnatural template nucleic acid.

In some embodiments, the first unnatural template nucleic acid is capable of base pairing with the first unnatural nucleic acid.

In some aspects, provided herein is a method of making a cell with an expanded genetic alphabet, comprising: contacting a first unnatural nucleic acid to a cell, the cell comprising a heterologous NTT, and at least one template UBP comprising an unnatural template nucleic acid; and cultivating the cell for a period of time, wherein the unnatural template nucleic acid base is capable of base pairing with the first unnatural nucleic acid.

In some embodiments, the cell comprising the heterologous NTT comprises enhanced import of the first unnatural nucleic acid in comparison to a cell without the heterologous NTT.

In some embodiments, a UBP is formed within the cell comprising the heterologous NTT.

In some embodiments, the UBP formed within the cell comprises the imported first unnatural nucleic acid.

In some embodiments, the method further comprises determining the presense of the UBP comprising the imported first unnatural nucleic acid.

In some embodiments, the method further comprises isolating the UBP comprising the first unnatural nucleic acid from the cell.

In some embodiments, the method further comprises determining the amount of the first unnatural nucleic acid present inside the cell.

In some embodiments, the method further comprises comparing the amount of the first unnatural nucleic acid present inside the cell to the amount of the first unnatural nucleic acid present inside a corresponding wild type cell.

In some embodiments, the contacting comprises contacting a liquid containing the first unnatural nucleic acid to the cell and wherein the method further comprises determining the amount of the first unnatural nucleic acid present in the liquid after the period of time in comparison to the respective wild type.

In some embodiments, the period of time is 1 hour or more.

In some embodiments, the cell comprises at least one genetic modification.

In some embodiments, the at least one genetic modification comprises a heterologous polymerase, a mutant polymerase, a disruption in a nucleotidase of the cell, a disruption of a phosphatase of the cell, or a combination thereof.

In some embodiments, the method further comprises adding a phosphatase or a nucleotidase inhibitor.

In some embodiments, the cell is a prokaryotic cell.

In some embodiments, the cell is from *Phaeodactylum tricornutum, Thalassiosira pseudonana* or *Protochlamydia amoebophila.*

In some embodiments, the cell is a eukaryotic cell.

In some embodiments, the cell is *E. coli.*

In some embodiments, the heterologous NTT is from *Phaeodactylum tricornutum* (Pt) NTT2, *Thalassiosira*

*pseudonana* (Tp) NTT2, *Protochlamydia amoebophila* (Pam) NTT2, *Protochlamydia amoebophila* (Pam) NTT5, or a combination thereof.

In some embodiments, the heterologous NTT is a nucleotide transporter 1 (NTT1), nucleotide transporter 2 (NTT2), nucleotide transporter 3 (NTT3), nucleotide transporter 4 (NTT4), nucleotide transporter 5 (NTT5), nucleotide transporter 6 (NTT6), nucleotide transporter 7 (NTT7), nucleotide transporter 8 (NTT8), or a combination thereof.

In some embodiments, the method further comprises contacting the cell with a second unnatural nucleic acid.

In some embodiments, the heterologous NTT transports the second unnatural nucleic acid into the cell.

In some embodiments, the at least one template UBP further comprises a second unnatural template nucleic acid.

In some embodiments, the first unnatural template nucleic acid is capable of base pairing with the second unnatural template nucleic acid.

In some embodiments, the second unnatural template nucleic acid is capable of base pairing with the second unnatural nucleic acid.

In some embodiments, the first unnatural nucleic acid is capable of base pairing with the second unnatural nucleic acid.

In some embodiments, the first unnatural nucleic acid is different from the second unnatural nucleic acid.

In some embodiments, the first unnatural nucleic acid is the same as the second unnatural nucleic acid.

In some embodiments, the at least one template UBP comprises at least 2, 3, 4, 5, 6, 7, 8, 9, 10, 20, 30, 40, 50, 60, 70, 80, 90, 100, 200, 300, 400, 500, 600, 700, 800, 900, or 1000 template UBPs.

In some embodiments, the at least one template UBP is present in the cell prior to the contacting with the first or second unnatural nucleic acid.

In some embodiments, the at least one template UBP is present in at least one heterologous nucleic acid.

In some embodiments, the at least one heterologous nucleic acid comprises at least 2, 3, 4, 5, 6, 7, 8, 9, 10, 20, 30, 40, 50, 60, 70, 80, 90, 100, 200, 300, 400, 500, 600, 700, 800, 900, or 1000 heterologous nucleic acids.

In some embodiments, the at least one template UBP is introduced into the cell by transfection, lipofection, injection, viral vector, or electroporation.

In some embodiments, the cell forms a UBP comprising the imported first unnatural nucleic acid.

In some embodiments, the UBP comprising the imported second unnatural nucleic acid further comprises the first unnatural template nucleic acid.

In some embodiments, the cell forms a UBP comprising the imported second unnatural nucleic acid.

In some embodiments, the UBP comprising the imported second unnatural nucleic acid further comprises the second unnatural template nucleic acid.

In some embodiments, the cell forms a UBP comprising the imported first unnatural nucleic acid and the imported second unnatural nucleic acid.

In some embodiments, the UBP is formed within the cell.

In some embodiments, the first or second unnatural nucleic acid is a deoxyribonucleoside.

In some embodiments, the first or second unnatural nucleic acid is a ribonucleoside.

In some embodiments, the first or second unnatural nucleic acid is a nucleoside triphosphate.

In some embodiments, the first or second unnatural nucleic acid comprises a modified sugar group.

In some embodiments, the unnatural sugar moeity is selected from the group consisting of a modification at the 2' position: OH; substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2F$; O-alkyl, S-alkyl, N-alkyl; O-alkenyl, S-alkenyl, N-alkenyl; O-alkynyl, S-alkynyl, N-alkynyl; 2'-F, 2'-$OCH_3$, 2'-$O(CH_2)_2OCH_3$ wherein the alkyl, alkenyl and alkynyl may be substituted or unsubstituted C alkyl, $C_2$-$C_{10}$ alkenyl, $C_2$-$C_{10}$ alkynyl, —$O[(CH_2)n\ O]mCH_3$, —$O(CH_2)nOCH_3$, —$O(CH_2)n\ NH_2$, —$O(CH_2)n\ CH_3$, —$O(CH_2)n$-$ONH_2$, and —$O(CH_2)nON[(CH_2)n\ CH_3)]_2$, where n and m are from 1 to about 10; and/or a modification at the 5' position: 5'-vinyl, 5'-methyl (R or S), a modification at the 4' position, 4'-S, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and any combination thereof.

In some embodiments, the first or second unnatural nucleic acid comprises a modified base group.

In some embodiments, the modified base group is selected from the group consisting of

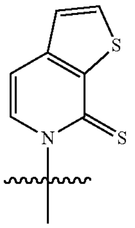
(d)TPT3

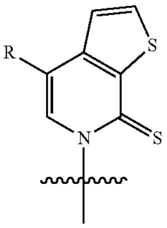
(d)TPT3pa

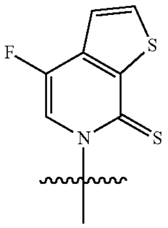
(d)FTPT3

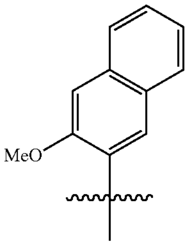
(d)NaM

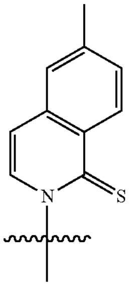
(d)5SICS

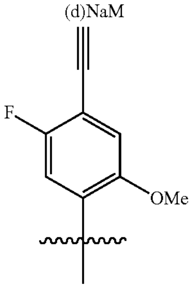
(d)FEMO

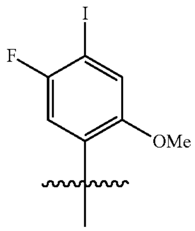
(d)FIMO

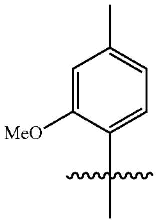
(d)MMO2 wherein R is a functional group.

In some embodiments, the functional group is selected from the group consisting of an affinity tag such as biotin, fluorophore, alkyl, alkenyl, alkynyl, phenyl, benyl, halo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, orthoester, methylenedioxy, orthocasrbonate ester, carboxamide, primary amine, secondary amine, tertiary amine, primary ketamine, secondary ketamine, primary aldimine, secondary aldimine, imide, azide, azo, cyanate, isocyanate, nitrate, nitrile, isonitrile, nitrosooxy, nitro, nitroso, pyridyl, sulfhydryl, sulfide, disulfide, sulfinyl, sulfino, sulfo, thiocyanate, isothiocyanante, carbonothioyl, phoshino, phosphono, phosphate, borono, boronate, borino, borinate, and combinations thereof.

In some embodiments, the first or second unnatural nucleic acid comprises an unnatural backbone.

In some embodiments, the unnatural backbone is selected from the group consisting of a phosphorothioate, chiral phosphorothioate, phosphorodithioate, phosphotriester, aminoalkylphosphotriester, phosphonates, 3'-alkylene phosphonate, chiral phosphonates, phosphinates, phosphoramidates, 3'-amino phosphoramidate, aminoalkylphosphoramidates, thionophosphoramidates, thionoalkylphosphonates, thionoalkylphosphotriesters, and boranophosphates.

In some embodiments, the method further comprises contacting the cell with one or more natural nucleotide triphosphates.

In some embodiments, the one or more natural nucleotide triphosphates comprise dATP, dTTP, ATP, TTP, UTP, or any mixture thereof.

In some embodiments, the first or second unnatural nucleic acid is selected from the group consisting of any one of those listed in Appendix A, and any combination thereof.

In some aspects, provided herein is an isolated nucleic acid comprising a UBP, wherein the UBP was formed within a cell.

In some embodiments, the UBP is selected from the group consisting of any one of those listed in Appendix A, and any combination thereof.

In some aspects, provided herein is an isolated heterologous NTT protein comprising an unnatural nucleic acid bound thereto.

In some embodiments, the unnatural nucleic acid bound thereto is selected from the group consisting of any one of those listed in Appendix A.

The details of one or more inventive embodiments are set forth in the accompanying drawings, the claims, and in the description herein. Other features, objects, and advantages of inventive embodiments disclosed and contemplated herein will be apparent from the description and drawings, and from the claims.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Figure 1:
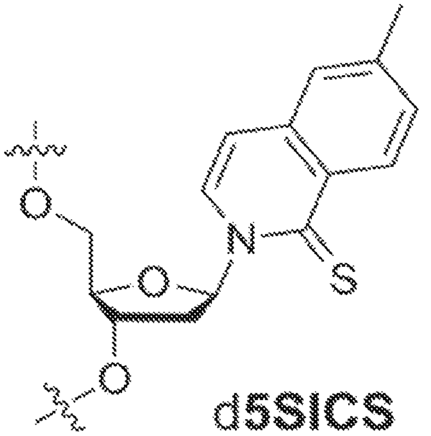
FIG. 1 shows the structure of d5SICS-dNaM with a natural (dC-dG) base pair shown for comparison.
Figure 1:
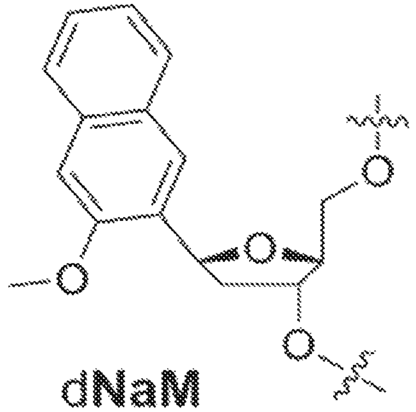
Figure 1:
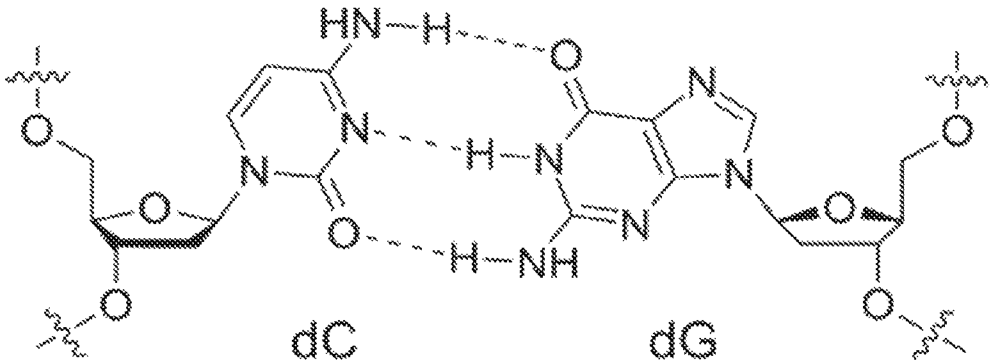
Figure 2:
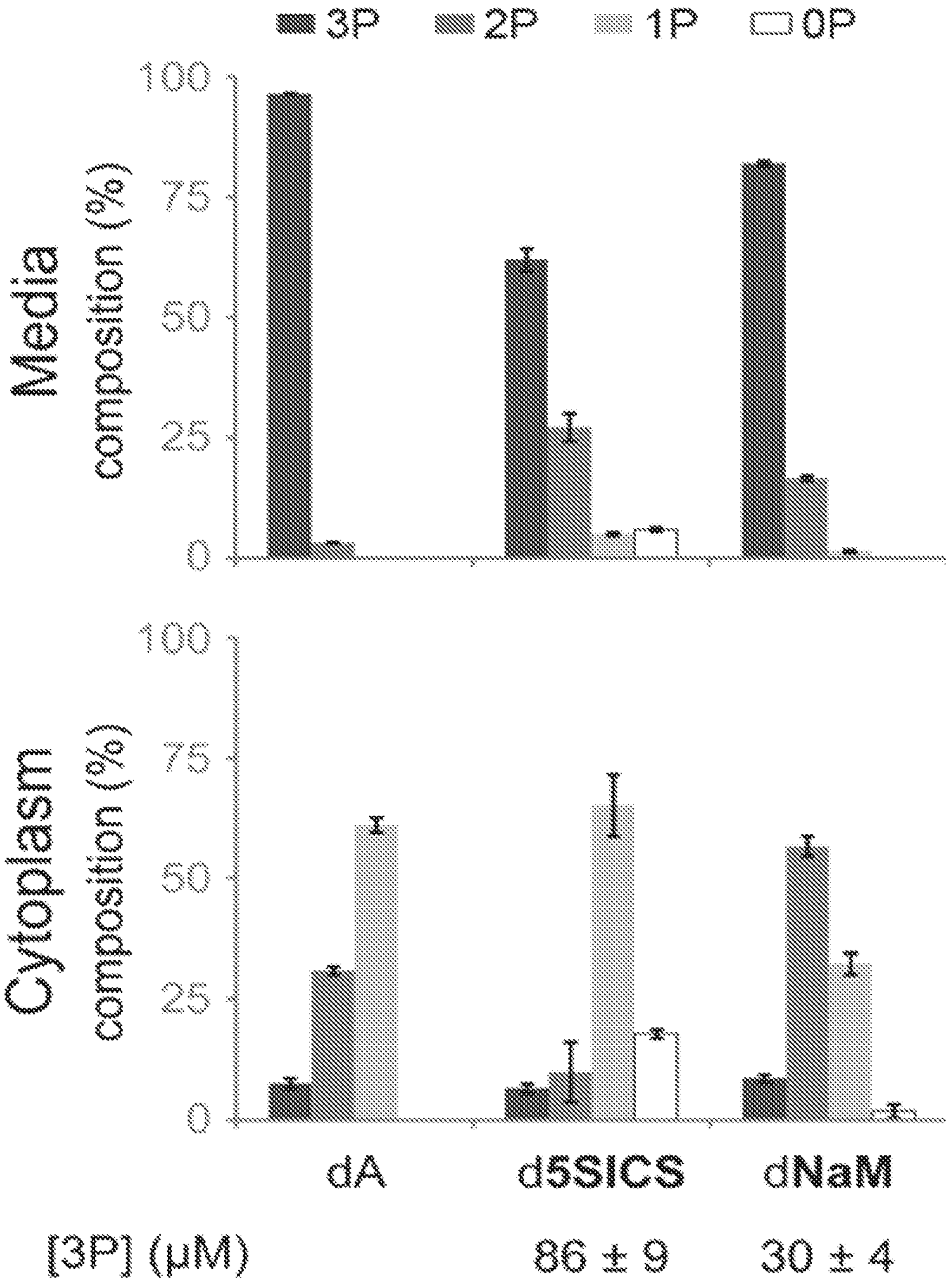
FIG. 2 depicts data relating to nucleoside triphosphate stability and import; and a composition analysis of d5SICS, and dNaM nucleotides in the media and cytoplasmic fractions of cells expressing PtNTT2. 3P, 2P, 1P and 0P correspond to triphosphate, diphosphate, monophosphate and nucleoside, respectively. [3P]=the total intracellular concentration of triphosphate.

As illustrated herein, d5SICSTP and dNaMTP can be efficiently imported into *E. coli* by the transporter 2 from *Phaeodactylum tricornutum* (PtNTT2), and *E. coli* replication machinery can efficiently incorporate these unnatural triphosphates into DNA within the cellular environment to form unnatural DNA base pairs.

The present invention is based, in part, on the discovery that particular unnatural base bairs (UBPs) including but not limited to (d)5SICS-(d)NaM and (d)TPT3-(d)NaM can be amplified with natural base pair-like efficiency and fidelity (Malyshev et al., Proc. Natl. Acad. Sci. USA (2012) 109: 12005-12010; Li et al., J. Am. Chem. Soc. (2014) 136:826-829). Thus, provided herein are methods, compositions, and kits, for increasing the genetic alphabet of cell or an organism. Also, provided herein are compositions, e.g., cells, comprising an expanded genetic alphabet, e.g., cells that stably propagate an expanded genetic alphabet. Also, provided herein are compositions, e.g., cells, comprising an expanded genetic alphabet, wherein neither the presence of unnatural triphosphates nor the replication of the UBP represents a significant growth burden on the cells.

In addition, the present invention relates to genetic constructs, modified cells and methods of importing and incorporating natural and unnatural nucleotides into nucleic acids of a living cell. Aspects of the invention facilitate labeling and modification of living cells. Unnatural nucleotides imported into cells by the modified cells and methods described herein can form UBPs in vivo and these UBPs can be replicated through one or more replication cycles of the cell. For the first time, a cell that stably incorporates within its cellular nucleic acids, nucleotides other than A, G, T, and C, e.g., (d)5SICS and (d)NaM, is described. Also provided herein are methods of incorporating an unnatural nucleotide into a nucleic acid by using, as a template, a nucleic acid containing a first unnatural nucleotide so that a second unnatural nucleic acid is incorporated at a site complementary to the first unnatural nucleotide. For example, such methods of incorporating an unnatural nucleotide into a nucleic acid can comprise effecting transcription, replication, reverse transcription or translation of unnatural nucleotides into unnatural amino acids.

Also, provided herein are compositions, e.g., cells, that retain a UBP, e.g., when unnatural triphosphates are available in a growth medium of the cells. The methods, compositions, and kits, can utilize enhanced cellular uptake of nucleic acids, e.g., via enhanced cellular import of nucleic acids. The nucleic acids undergoing enhanced cellular uptake can be one or more unnatural nucleotides. In some embodiments, nucleic acids undergoing enhanced cellular uptake can be one or more unnatural nucleotides, and not a natural nucleic acid. In some embodiments, nucleic acids undergoing enhanced cellular uptake can be one or more unnatural nucleotide and one or more natural nucleotides. In some embodiments, nucleic acids undergoing enhanced cellular uptake can be one or more unnatural nucleotide and one or more first natural nucleotides, but not one or more second natural nucleotides. In some embodiments, nucleic acids undergoing enhanced cellular uptake can be one or more first unnatural nucleotide and one or more natural nucleotides, but not one or more second unnatural nucleotides.

The methods, compositions, and kits, can utilize one or more endogenous or exogenous enzymes to stably integrate unnatural nucleic acids, e.g., unnatural nucleoside triphosphates. The methods, compositions, and kits, can utilize one or more endogenous or exogenous enzymes to copy a homologous nucleic acid to form a nucleic acid comprising an unnatural nucleic acid. For example, endogenous or exogenous enzymes, e.g., endogenous or exogenous polymerases, can be utilized to replicate genomic DNA to form a containing a UBP within a cell. The methods, compositions, and kits, can utilize one or more endogenous or exogenous enzymes to copy a cellular nucleic acid comprising a UBP to form a nucleic acid copy comprising an unnatural nucleic acid. For example, endogenous or exogenous polymerases can be utilized to replicate genomic DNA containing a UBP within a cell. The methods, compositions, and kits, can also utilize a UBP that is not efficiently excised by DNA repair pathways.

Nucleic Acids

A nucleic acid (e.g., also referred to herein as target nucleic acid, target nucleotide sequence, nucleic acid sequence of interest or nucleic acid region of interest) can be from any source or composition, such as DNA, cDNA, gDNA (genomic DNA), RNA, siRNA (short inhibitory RNA), RNAi, tRNA or mRNA, for example, and can be in any form (e.g., linear, circular, supercoiled, single-stranded, double-stranded, and the like). Nucleic acids can comprise nucleotides, nucleosides, or polynucleotides. Nucleic acids can comprise natural and unnatural nucleic acids. A nucleic acid can also comprise unnatural nucleic acids, such as DNA or RNA analogs (e.g., containing base analogs, sugar analogs and/or a non-native backbone and the like). It is understood that the term “nucleic acid” does not refer to or infer a specific length of the polynucleotide chain, thus polynucleotides and oligonucleotides are also included in the definition. Exemplary natural nucleotides include, without limitation, ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP. Exemplary natural deoxyribonucleotides include dATP, dTTP, dCTP, dGTP, dADP, dTDP, dCDP, dGDP, dAMP, dTMP, dCMP, and dGMP. Exemplary natural ribonucleotides include ATP, UTP, CTP, GTP, ADP, UDP, CDP, GDP, AMP, UMP, CMP, and GMP. For RNA, the uracil base is uridine. A nucleic acid sometimes is a vector, plasmid, phage, autonomously replicating sequence (ARS), centromere, artificial chromosome, yeast artificial chromosome (e.g., YAC) or other nucleic acid able to replicate or be replicated in a host cell. An unnatural nucleic acid can be a nucleic acid analogue. An unnatural nucleic acid can be from an extracellular source. An unnatural nucleic acid can be available to the intracellular space of an organism provided herein, e.g., a genetically modified organism.

Unnatural Nucleic Acids

A nucleotide analog, or unnatural nucleotide, comprises a nucleotide which contains some type of modification to either the base, sugar, or phosphate moieties. A modification can comprise a chemical modification. Modifications may be, for example, of the 3'OH or 5'OH group, of the backbone, of the sugar component, or of the nucleotide base. Modifications may include addition of non-naturally occurring linker molecules and/or of interstrand or intrastrand cross links. In one aspect, the modified nucleic acid comprises modification of one or more of the 3'OH or 5'OH group, the backbone, the sugar component, or the nucleotide base, and/or addition of non-naturally occurring linker molecules. In one aspect a modified backbone comprises a backbone other than a phosphodiester backbone. In one aspect a modified sugar comprises a sugar other than deoxyribose (in modified DNA) or other than ribose (modified RNA). In one aspect a modified base comprises a base other than adenine, guanine, cytosine or thymine (in modified DNA) or a base other than adenine, guanine, cytosine or uracil (in modified RNA).

The nucleic acid may comprise at least one modified base. Modifications to the base moiety would include natural and synthetic modifications of A, C, G, and T/U as well as different purine or pyrimidine bases. In some embodiments, a modification is to a modified form of adenine, guanine cytosine or thymine (in modified DNA) or a modified form of adenine, guanine cytosine or uracil (modified RNA).

A modified base of a unnatural nucleic acid includes but is not limited to uracil-5-yl, hypoxanthin-9-yl (I), 2-aminoadenin-9-yl, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Certain unnatural nucleic acids, such as 5-substituted pyrimidines, 6-azapyrimidines and N-2 substituted purines, N-6 substituted purines, 0-6 substituted purines, 2-aminopropyladenine, 5-propynyluracil, 5-propynylcytosine, 5-methylcytosine, those that increase the stability of duplex formation, universal nucleic acids, hydrophobic nucleic acids, promiscuous nucleic acids, size-expanded nucleic acids, fluorinated nucleic acids, 5-substituted pyrimidines, 6-azapyrimidines and N-2, N-6 and 0-6 substituted purines, including 2-aminopropyladenine, 5-propynyluracil and 5-propynylcytosine. 5-methylcytosine (5-me-C), 5-hydroxymethyl cytosine, xanthine, hypoxanthine, 2-aminoadenine, 6-methyl, other alkyl derivatives of adenine and guanine, 2-propyl and other alkyl derivatives of adenine and guanine, 2-thiouracil, 2-thiothymine and 2-thiocytosine, 5-halouracil, 5-halocytosine, 5-propynyl (—C≡C-CI¼) uracil, 5-propynyl cytosine, other alkynyl derivatives of pyrimidine nucleic acids, 6-azo uracil, 6-azo cytosine, 6-azo thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl, other 5-substituted uracils and cytosines, 7-methylguanine, 7-methyl adenine, 2-F-adenine, 2-aminoadenine, 8-azaguanine, 8-azaadenine, 7-deazaguanine, 7-deazaadenine, 3-deazaguanine, 3-deazaadenine, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one), those in which the purine or pyrimidine base is replaced with other heterocycles, 7-deaza-adenine, 7-deazaguanosine, 2-aminopyridine, 2-pyridone, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 2-amino-adenine, 6-thioguanine, 2-thio-thymine, 4-thio-thymine, 5-propynyl-uracil, 4-thio-uracil, N4-ethylcytosine, 7-deazaguanine, 7-deaza-8-azaguanine, 5-hydroxycytosine, 2'-deoxyuridine, 2-amino-2'-deoxyadenosine, and those described in U.S. Pat. Nos. 3,687,808; 4,845,205; 4,910,300; 4,948,882; 5,093,232; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096; WO 99/62923; Kandimalla et al., (2001) Bioorg. Med. Chem. 9:807-813; The Concise Encyclopedia of Polymer Science and Engineering, Kroschwitz, J. I., Ed., John Wiley & Sons, 1990, 858-859; Englisch et al., Angewandte Chemie, International Edition, 1991, 30, 613; and Sanghvi, Chapter 15, Antisense Research and Applications, Crooke and Lebleu Eds., CRC Press, 1993, 273-288. Additional base modifications can be found, for example, in U.S. Pat. No. 3,687,808; Englisch et al., Angewandte Chemie, International Edition, 1991, 30, 613; and Sanghvi, Chapter 15, Antisense Research and Applications, pages 289-302, Crooke and Lebleu ed., CRC Press, 1993.

Unnatural nucleic acids comprising various heterocyclic bases and various sugar moieties (and sugar analogs) are available in the art, and the nucleic acid can include one or several heterocyclic bases other than the principal five base components of naturally-occurring nucleic acids. For example, the heterocyclic base may include uracil-5-yl, cytosin-5-yl, adenin-7-yl, adenin-8-yl, guanin-7-yl, guanin-8-yl, 4-aminopyrrolo [2.3-d] pyrimidin-5-yl, 2-amino-4-oxopyrolo [2, 3-d] pyrimidin-5-yl, 2-amino-4-oxopyrrolo [2.3-d] pyrimidin-3-yl groups, where the purines are attached to the sugar moiety of the nucleic acid via the 9-position, the pyrimidines via the 1-position, the pyrrolopyrimidines via the 7-position and the pyrazolopyrimidines via the 1-position.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Unnatural nucleic acids can include 2',3'-dideoxy-2',3'-didehydro-nucleosides (PCT/US2002/006460), 5'-substituted DNA and RNA derivatives (PCT/US2011/033961; Saha et al., J. Org Chem., 1995, 60, 788-789; Wang et al., Bioorganic & Medicinal Chemistry Letters, 1999, 9, 885-890; and Mikhailov et al., Nucleosides & Nucleotides, 1991, 10(1-3), 339-343; Leonid et al., 1995, 14(3-5), 901-905; and Eppacher et al., Helvetica Chimica Acta, 2004, 87, 3004-3020; PCT/JP2000/004720; PCT/JP2003/002342; PCT/JP2004/013216; PCT/JP2005/020435; PCT/JP2006/315479; PCT/JP2006/324484; PCT/JP2009/056718; PCT/JP2010/067560), or 5'-substituted monomers made as the monophosphate with modified bases (Wang et al., Nucleosides Nucleotides & Nucleic Acids, 2004, 23 (1 & 2), 317-337).

Unnatural nucleic acids can include modifications at the 5'-position and the 2'-position of the sugar ring (PCT/US94/02993), such as 5'-$CH_2$-substituted 2'-O-protected nucleosides (Wu et al., Helvetica Chimica Acta, 2000, 83, 1127-1143 and Wu et al., Bioconjugate Chem. 1999, 10, 921-924). Unnatural nucleic acids can include amide linked nucleoside dimers have been prepared for incorporation into oligonucleotides wherein the 3' linked nucleoside in the dimer (5' to 3') comprises a 2'-$OCH_3$ and a 5'-(S)—$CH_3$ (Mesmaeker et al., Synlett, 1997, 1287-1290). Unnatural nucleic acids can include 2'-substituted 5'-$CH_2$ (or O) modified nucleosides (PCT/US92/01020). Unnatural nucleic acids can include 5'-methylenephosphonate DNA and RNA monomers, and dimers (Bohringer et al., Tet. Lett., 1993, 34, 2723-2726; Collingwood et al., Synlett, 1995, 7, 703-705; and Hutter et al., Helvetica Chimica Acta, 2002, 85, 2777-2806). Unnatural nucleic acids can include 5'-phosphonate monomers having a 2'-substitution (US2006/0074035) and other modified 5'-phosphonate monomers (WO1997/35869). Unnatural nucleic acids can include 5'-modified methylenephosphonate monomers (EP614907 and EP629633). Unnatural nucleic acids can include analogs of 5' or 6'-phosphonate ribonucleosides comprising a hydroxyl group at the 5' and/or 6'-position (Chen et al., Phosphorus, Sulfur and Silicon, 2002, 777, 1783-1786; Jung et al., Bioorg. Med. Chem., 2000, 8, 2501-2509; Gallier et al., Eur. J. Org. Chem., 2007, 925-933; and Hampton et al., J. Med. Chem., 1976, 19(8), 1029-1033). Unnatural nucleic acids can include 5'-phosphonate deoxyribonucleoside monomers and dimers having a 5'-phosphate group (Nawrot et al., Oligonucleotides, 2006, 16(1), 68-82). Unnatural nucleic acids can include nucleosides having a 6'-phosphonate group wherein the 5' or/and 6'-position is unsubstituted or substituted with a thio-tert-butyl group ($SC(CH_3)_3$) (and analogs thereof); a methyleneamino group ($CH_2NH_2$) (and analogs thereof) or a cyano group (CN) (and analogs thereof) (Fairhurst et al., Synlett, 2001, 4, 467-472; Kappler et al., J. Med. Chem., 1986, 29, 1030-1038; Kappler et al., J. Med. Chem., 1982, 25, 1179-1184; Vrudhula et al., J. Med. Chem., 1987, 30, 888-894; Hampton et al., J. Med. Chem., 1976, 19, 1371-1377; Geze et al., J. Am. Chem. Soc, 1983, 105(26), 7638-7640; and Hampton et al., J. Am. Chem. Soc, 1973, 95(13), 4404-4414).

Unnatural nucleic acids can also include modifications of the sugar moiety. Nucleic acids of the invention can optionally contain one or more nucleosides wherein the sugar group has been modified. Such sugar modified nucleosides may impart enhanced nuclease stability, increased binding affinity, or some other beneficial biological property. In certain embodiments, nucleic acids comprise a chemically modified ribofuranose ring moiety. Examples of chemically modified ribofuranose rings include, without limitation, addition of substitutent groups (including 5' and/or 2' substituent groups; bridging of two ring atoms to form bicyclic nucleic acids (BNA); replacement of the ribosyl ring oxygen atom with S, N(R), or C(Ri)($R_2$) (R═H, $C_1$-$C_{12}$ alkyl or a protecting group); and combinations thereof. Examples of chemically modified sugars can be found in WO2008/101157, US2005/0130923, and WO2007/134181.

A modified nucleic acid may comprise modified sugars or sugar analogs. Thus, in addition to ribose and deoxyribose, the sugar moiety can be pentose, deoxypentose, hexose, deoxyhexose, glucose, arabinose, xylose, lyxose, or a sugar "analog" cyclopentyl group. The sugar can be in a pyranosyl or furanosyl form. The sugar moiety may be the furanoside of ribose, deoxyribose, arabinose or 2'-O-alkylribose, and the sugar can be attached to the respective heterocyclic bases either in [alpha] or [beta] anomeric configuration. Sugar modifications include, but are not limited to, 2'-alkoxy-RNA analogs, 2'-amino-RNA analogs, 2'-fluoro-DNA, and 2'-alkoxy- or amino-RNA/DNA chimeras. For example, a sugar modification may include 2'-O-methyl-uridine or 2'-O-methyl-cytidine. Sugar modifications include 2'-O-alkyl-substituted deoxyribonucleosides and 2'-O-ethyleneglycol like ribonucleosides. The preparation of these sugars or sugar analogs and the respective "nucleosides" wherein such sugars or analogs are attached to a heterocyclic base (nucleic acid base) is known. Sugar modifications may also be made and combined with other modifications.

Modifications to the sugar moiety include natural modifications of the ribose and deoxy ribose as well as unnatural modifications. Sugar modifications include but are not limited to the following modifications at the 2' position: OH; F;

O-, S-, or N-alkyl; O-, S-, or N-alkenyl; O—, S- or N-alkynyl; or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to $—O[(CH_2)_nO]_mCH_3$, $—O(CH_2)_nOCH_3$, $—O(CH_2)_nNH_2$, $—O(CH_2)_nCH_3$, $—O(CH_2)_nONH_2$, and $—O(CH_2)_nON[(CH_2)_nCH_3)]_2$, where n and m are from 1 to about 10.

Other modifications at the 2' position include but are not limited to: $C_1$ to $C_{10}$ lower alkyl, substituted lower alkyl, alkaryl, aralkyl, O-alkaryl, O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of the 5' terminal nucleotide. Modified sugars also include those that contain modifications at the bridging ring oxygen, such as $CH_2$ and S. Nucleotide sugar analogs may also have sugar mimetics such as cyclobutyl moieties in place of the pentofuranosyl sugar. There are numerous United States patents that teach the preparation of such modified sugar structures and which detail and describe a range of base modifications, such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,700,920, each of which is herein incorporated by reference in its entirety.

Examples of nucleic acids having modified sugar moieties include, without limitation, nucleic acids comprising 5'-vinyl, 5'-methyl (R or S), 4'-S, 2'-F, 2'-$OCH_3$, and 2'-O $(CH_2)_2OCH_3$ substituent groups. The substituent at the 2' position can also be selected from allyl, amino, azido, thio, O-allyl, O—($C_1$-$C_{10}$ alkyl), $OCF_3$, $O(CH_2)_2SCH_3$, $O(CH_2)_2—O—N(R_m)(R_n)$, and $O—CH_2—C(=O)—N(R_m)(R_n)$, where each $R_m$ and $R_n$ is, independently, H or substituted or unsubstituted $C_1$-$C_{10}$ alkyl.

In certain embodiments, nucleic acids of the present invention include one or more bicyclic nucleic acids. In certain such embodiments, the bicyclic nucleic acid comprises a bridge between the 4' and the 2' ribosyl ring atoms. In certain embodiments, nucleic acids provided herein include one or more bicyclic nucleic acids wherein the bridge comprises a 4' to 2' bicyclic nucleic acid. Examples of such 4' to 2' bicyclic nucleic acids include, but are not limited to, one of the formulae: 4'-($CH_2$)—O-2' (LNA); 4'-($CH_2$)—S-2'; 4'-$(CH_2)_2$—O-2' (ENA); 4'-CH($CH_3$)—O-2' and 4'-CH($CH_2OCH_3$)—O-2', and analogs thereof (see, U.S. Pat. No. 7,399,845); 4'-C($CH_3$)($CH_3$)—O-2' and analogs thereof, (see WO2009/006478, WO2008/150729, US2004/0171570, U.S. Pat. No. 7,427,672, Chattopadhyaya et al., J. Org. Chem., 209, 74, 118-134, and WO2008/154401). Also see, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 2007, 129(26) 8362-8379; Elayadi et al., Curr. Opinion Invens. Drugs, 2001, 2, 558-561; Braasch et al., Chem. Biol, 2001, 8, 1-7; Oram et al., Curr. Opinion Mol. Ther., 2001, 3, 239-243; U.S. Pat. Nos. 4,849,513; 5,015,733; 5,118,800; 5,118,802; 7,053,207; 6,268,490; 6,770,748; 6,794,499; 7,034,133; 6,525,191; 6,670,461; and 7,399,845; International Publication Nos. WO2004/106356, WO1994/14226, WO2005/021570, WO2007/090071, and WO2007/134181; U.S. Patent Publication Nos. US2004/0171570, US2007/0287831, and US2008/0039618; U.S. Provisional Application Nos. 60/989,574, 61/026,995, 61/026,998, 61/056,564, 61/086,231, 61/097,787, and 61/099,844; and International Applications Nos. PCT/US2008/064591, PCT US2008/066154, PCT US2008/068922, and PCT/DK98/00393.

In certain embodiments, nucleic acids can comprise linked nucleic acids. Nucleic acids can be linked together using any inter nucleic acid linkage. The two main classes of inter nucleic acid linking groups are defined by the presence or absence of a phosphorus atom. Representative phosphorus containing inter nucleic acid linkages include, but are not limited to, phosphodiesters, phosphotriesters, methylphosphonates, phosphoramidate, and phosphorothioates (P=S). Representative non-phosphorus containing inter nucleic acid linking groups include, but are not limited to, methylenemethylimino ($—CH_2—N(CH_3)—O—CH_2—$), thiodiester (—O—C(O)—S—), thionocarbamate (—O—C(O)(NH)—S—); siloxane ($—O—Si(H)_2—O—$); and N,N*-dimethylhydrazine ($—CH_2—N(CH_3)—N(CH_3)$)). In certain embodiments, inter nucleic acids linkages having a chiral atom can be prepared as a racemic mixture, as separate enantiomers, e.g., alkylphosphonates and phosphorothioates. Unnatural nucleic acids can contain a single modification. Unnatural nucleic acids can contain multiple modifications within one of the moieties or between different moieties.

Backbone phosphate modifications to nucleic acid include, but are not limited to, methyl phosphonate, phosphorothioate, phosphoramidate (bridging or non-bridging), phosphotriester, phosphorodithioate, phosphodithioate, and boranophosphate, and may be used in any combination. Other non-phosphate linkages may also be used.

In some embodiments, backbone modifications (e.g., methylphosphonate, phosphorothioate, phosphoroamidate and phosphorodithioate internucleotide linkages) can confer immunomodulatory activity on the modified nucleic acid and/or enhance their stability in vivo.

A phosphorous derivative (or modified phosphate group) can be attached to the sugar or sugar analog moiety in and can be a monophosphate, diphosphate, triphosphate, alkylphosphonate, phosphorothioate, phosphorodithioate, phosphoramidate or the like. Exemplary polynucleotides containing modified phosphate linkages or non-phosphate linkages can be found in Peyrottes et al., 1996, Nucleic Acids Res. 24: 1841-1848; Chaturvedi et al., 1996, Nucleic Acids Res. 24:2318-2323; and Schultz et al., (1996) Nucleic Acids Res. 24:2966-2973; Matteucci, 1997, "Oligonucleotide Analogs: an Overview" in Oligonucleotides as Therapeutic Agents, (Chadwick and Cardew, ed.) John Wiley and Sons, New York,N.Y.; Zon, 1993, "Oligonucleoside Phosphorothioates" in Protocols for Oligonucleotides and Analogs, Synthesis and Properties, Humana Press, pp. 165-190; Miller et al., 1971, JACS 93:6657-6665; Jager et al., 1988, Biochem. 27:7247-7246; Nelson et al., 1997, JOC 62:7278-7287; U.S. Pat. No. 5,453,496; and Micklefield, 2001, Curr. Med. Chem. 8: 1157-1179.

Backbone modification may comprise replacing the phosphodiester linkage with an alternative moiety such as an anionic, neutral or cationic group. Examples of such modifications include: anionic internucleoside linkage; N3' to P5' phosphoramidate modification; boranophosphate DNA; prooligonucleotides; neutral internucleoside linkages such as methylphosphonates; amide linked DNA; methylene(methylimino) linkages; formacetal and thioformacetal linkages; backbones containing sulfonyl groups; morpholino oligos; peptide nucleic acids (PNA); and positively charged deoxyribonucleic guanidine (DNG) oligos (Micklefield, 2001, Current Medicinal Chemistry 8: 1157-1179). A modified nucleic acid may comprise a chimeric or mixed backbone comprising one or more modifications, e.g. a combination of phosphate linkages such as a combination of phosphodiester and phosphorothioate linkages.

Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference. It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. See also Nielsen et al., Science, 1991, 254, 1497-1500. It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. KY. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EM5OJ, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1-di-O-hexadecyl-rac-glycero-S—H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochem. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937). Numerous United States patents teach the preparation of such conjugates and include, but are not limited to U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

Nucleic Acids for Cellular Import

In some embodiments, the nucleic acids undergoing enhanced cellular uptake comprise nucleotide triphosphates. In some embodiments, the nucleic acids undergoing enhanced cellular uptake comprise nucleotide diphosphates. In some embodiments, the nucleic acids undergoing enhanced cellular uptake comprise nucleotide monophosphates. In some embodiments, the nucleic acids undergoing enhanced cellular uptake comprise nucleosides. In some embodiments, the nucleic acids undergoing enhanced cellular uptake do not comprise nucleotide diphosphates. In some embodiments, the nucleic acids undergoing enhanced cellular uptake do not comprise nucleotide monophosphates. In some embodiments, the nucleic acids undergoing enhanced cellular uptake do not comprise nucleosides.

In some embodiments, the nucleic acids undergoing enhanced cellular uptake comprise nucleic acid analogs e.g., unnatural nucleic acids. In some embodiments enhanced uptake of active transport of nucleic acids utilizes nucleotide triphosphate transporters (NTTs), e.g., from obligate intracellular bacteria or algal plastids. In some embodiments, the methods, compositions, and kits incorporate natural and/or unnatural nucleotides into an organism or cell.

A variety of natural and unnatural nucleotides can be imported into cells. One example of a pair of unnatural nucleotide triphosphates that can be transported into cells and that can base pair to form an UBP when incorporated into nucleic acids with the cells, includes a triphosphate of (d)5SICS ((d)5SICSTP) and a triphosphate of (d)NaM ((d) NaMTP). One example of a pair of unnatural nucleotide triphosphates that can be transported into cells and that can base pair to form an UBP when incorporated into nucleic acids with the cells, includes a triphosphate of (d)TPT3 ((d)TPT3TP) and a triphosphate of (d)NaM ((d)NaMTP), which can be PCR amplified with a natural base pair-like efficiency and fidelity. In some embodiments, (d)TPT3 comprises a propargyl amine linker ($TPT3^{PA}$). One example of a pair of unnatural nucleotide triphosphates that can be transported into cells and that can base pair to form an UBP when incorporated into nucleic acids with the cells, includes a triphosphate of $(d)TPT3^{PA}$ and a triphosphate of $NaM^{A}$-dNaM pair which can be PCR amplified with a natural base pair-like efficiency and fidelity. Such unnatural nucleotides can have a ribose or deoxyribose sugar moiety. The structures of 5SICS, d5SICS, NAM, and dNaM, unnatural nucleotides are shown below.

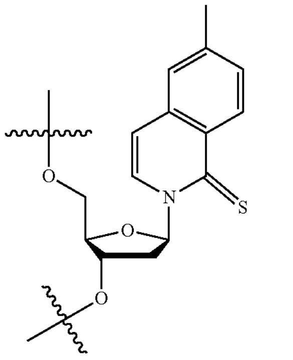

d5SICS

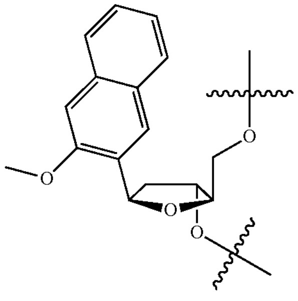

dNAM

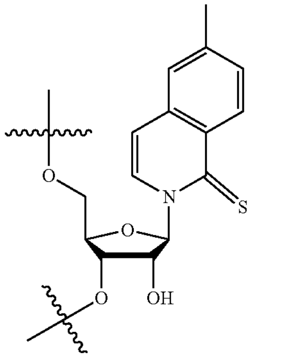

5SICS

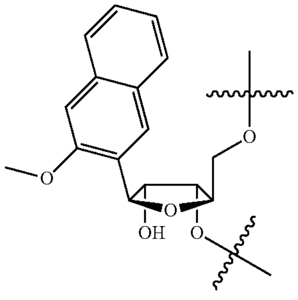

NAM

Other types of unnatural nucleotides can be imported into the cells by the nucleotide triphosphate transporter, such as (d)TPT3, (d)TPT3$^{PA}$, (d)FTPT3, (d)NaM, (d)5SICS, (d)FEMO, (d)FIMO, (d)MMO2 and combinations thereof, wherein (d) means that the nucleobase can be attached to a deoxyribose or a ribose. The structures of the nucleobases of these unnatural nucleotide triphosphates are shown below.

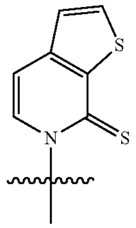

(d)TPT3

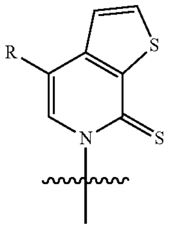

(d)TPT3pa

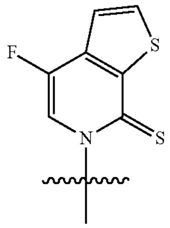

(d)FTPT3

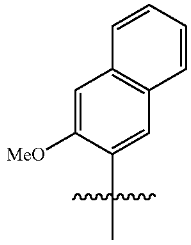

(d)NaM

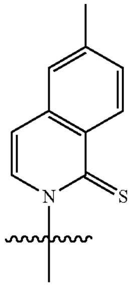

(d)5SICS

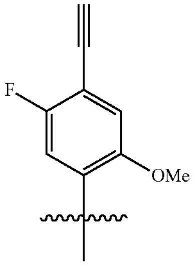

(d)FEMO

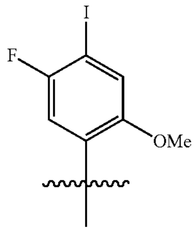

(d)FIMO

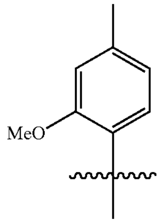

(d)MMO2 wherein the wavy line identifies a point of attachment to the (deoxy)ribose or ribose sugar and R indicates a propargyl amine linker. The sugar can be phosphorylated (i.e., to form a nucleotide triphosphate).

A variety of naturally-occurring nucleotide triphosphates can also be transported by the methods described herein. Naturally-occurring nucleotide triphosphates include the ribose or deoxyribose nucleotide triphosphates having adenosine, guanine, cytosine, thymine or uracil.

Examples of other types of modified or unnatural nucleotide triphosphates that can also be transported into cells include those with 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methyl aminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine.

The structures of TPT3, dTPT3, NAM, and dNaM, unnatural nucleotides are shown below.

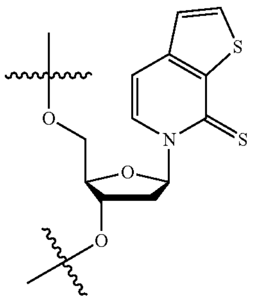

dTPT3

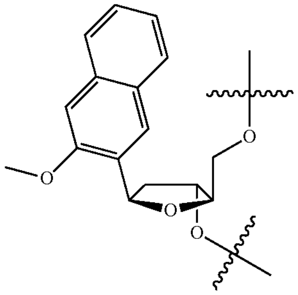

dNAM

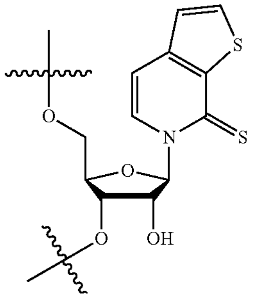

TPT3

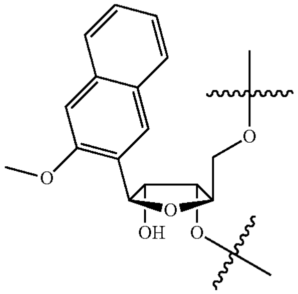

NAM

Exemplary nucleic acids (or UDPs) that can be used, e.g., for importation into cells, can also include any one or more of the nucleic acid structures depicted in Appendix A, wherein the wavy line identifies a point of attachment to the sugar moeity, such as a (deoxy)ribose or ribose.

A variety of naturally-occurring nucleotides as well other modified or unnatural nucleotides can also be transported into cells via the methods described herein.

In some embodiments, the imported nucleic acids may locate within a region of a cell or a cellular compartment. In some embodiments, the region or compartment of a cell may include a membrane, an organelle and/or the cytosol. For example, the membranes may include, but are not limited to, nuclear membrane, plasma membrane, endoplasmic reticulum membrane, cell wall, cell membrane and/or mitochondrial membrane. In some embodiments, the membranes may include a complete membrane or a fragment of a membrane. For example, the organelles may include, but are not limited to, the nucleolus, nucleus, chloroplast, plastid, endoplasmic reticulum, rough endoplasmic reticulum, smooth endoplasmic reticulum, centrosome, golgi apparatus, mitochondria, vacuole, acrosome, autophagosome, centriole, cilium, eyespot apparatus, glycosome, glyoxysome, hydrogenosome, lysosome, melanosome, mitosome, myofibril, parenthesome, peroxisome, proteasome, ribosome, vesicle, carboxysome, chlorosome, flagellum, magenetosome, nucleoid, plasmid, thylakoid, mesosomes, cytoskeleton, and/or vesicles. In some embodiments, the organelles may include a complete membrane or a fragment of a membrane. For example, the cytosol may be encapsulated by the plasma membrane, cell membrane and/or the cell wall.

Nucleic Acid Base Pairing Properties

An unnatural nucleic acid can form a base pair with another nucleic acid. In some embodiments, a stably integrated unnatural nucleic acid is an unnatural nucleic acid that can form a base pair with another nucleic acid, e.g., a natural or unnatural nucleic acid. In some embodiments, a stably integrated unnatural nucleic acid is an unnatural nucleic acid that can form a base pair with another unnatural nucleic acid (unnatural nucleic acid base pair (UBP)). For example, a first unnatural nucleic acid can form a base pair with a second unnatural nucleic acid. For example, one pair of unnatural nucleotide triphosphates that can base pair when incorporated into nucleic acids include a triphosphate of (d)5SICS ((d)5SICSTP) and a triphosphate of (d)NaM ((d)NaMTP). For example, one pair of unnatural nucleotide triphosphates that can base pair when incorporated into nucleic acids include a triphosphate of (d)TPT3 ((d) TPT3TP) and a triphosphate of (d)NaM ((d)NaMTP). Such unnatural nucleotides can have a ribose or deoxyribose sugar moiety. In some embodiments, an unnatural nucleic acid does not substantially form a base pair with a natural nucleic acid (A, T, G, C). In some embodiments, a stably integrated unnatural nucleic acid can form a base pair with a natural nucleic acid.

In some embodiments, a stably integrated unnatural nucleic acid is an unnatural nucleic acid that can form a UBP, but does not substantially form a base pair with each of the four natural nucleic acids. In some embodiments, a stably integrated unnatural nucleic acid is an unnatural nucleic acid that can form a UBP, but does not substantially form a base pair with one or more natural nucleic acids. For example, a stably integrated unnatural nucleic acid may not substantially form a base pair with A, T, and, C, but can form a base pair with G. For example, a stably integrated unnatural nucleic acid may not substantially form a base pair with A, T, and, G, but can form a base pair with C. For example, a stably integrated unnatural nucleic acid may not substantially form a base pair with C, G, and, A, but can form a base pair with T. For example, a stably integrated unnatural nucleic acid may not substantially form a base pair with C, G, and, T, but can form a base pair with A. For example, a stably integrated unnatural nucleic acid may not substantially form a base pair with A and T, but can form a base pair with C and G. For example, a stably integrated unnatural nucleic acid may not substantially form a base pair with A and C, but can form a base pair with T and G. For example, a stably integrated unnatural nucleic acid may not substantially form a base pair with A and G, but can form a base pair with C and T. For example, a stably integrated unnatural nucleic acid may not substantially form a base pair with C and T, but can form a base pair with A and G. For example, a stably integrated unnatural nucleic acid may not substantially form a base pair with C and G, but can form a base pair with T and G. For example, a stably integrated unnatural nucleic acid may not substantially form a base pair with T and G, but can form a base pair with A and G. For example, a stably integrated unnatural nucleic acid may not substantially form a base pair with, G, but can form a base pair with A, T, and, C. For example, a stably integrated unnatural nucleic acid may not substantially form a base pair with, A, but can form a base pair with G, T, and, C. For example, a stably integrated unnatural nucleic acid may not substantially form a base pair with, T, but can form a base pair with G, A, and, C. For example, a stably integrated unnatural nucleic acid may not substantially form a base pair with, C, but can form a base pair with G, T, and, A.

Exemplary, unnatural nucleotides capable of forming an unnatural DNA or RNA base pair (UBP) under conditions in vivo can include 5SICS, d5SICS, NAM, dNaM, and combinations thereof.

Target Sequences/Activities

A nucleotide reagent sometimes can comprise a target nucleotide sequence. A "target nucleic acid" sequence as used herein encodes a nucleic acid, peptide, polypeptide or protein of interest, and may be a ribonucleotide sequence or a deoxyribonucleotide sequence. A target nucleic acid sometimes is an untranslated ribonucleic acid and sometimes is a translated ribonucleic acid. An untranslated ribonucleic acid may include, but is not limited to, a small interfering ribonucleic acid (siRNA), a short hairpin ribonucleic acid (shRNA), other ribonucleic acid capable of RNA interference (RNAi), an antisense ribonucleic acid, or a ribozyme. A translatable target nucleotide sequence (e.g., a target ribonucleotide sequence) sometimes encodes a peptide, polypeptide or protein, which are sometimes referred to herein as "target peptides," "target polypeptides" or "target proteins."

A translatable nucleotide sequence generally is located between a start codon (AUG in ribonucleic acids and ATG in deoxyribonucleic acids) and a stop codon (e.g., UAA (ochre), UAG (amber) or UGA (opal) in ribonucleic acids and TAA, TAG or TGA in deoxyribonucleic acids), and sometimes is referred to herein as an "open reading frame" (ORF). A translatable nucleotide sequence (e.g., ORF) sometimes is encoded differently in one organism (e.g., most organisms encode CTG as leucine) than in another organism (e.g., *C. tropicalis* encodes CTG as serine). In some embodiments, a translatable nucleotide sequence is altered to correct alternate genetic code (e.g., codon usage) differences between a nucleotide donor organism and a nucleotide recipient organism (e.g., engineered organism). In certain embodiments, a translatable nucleotide sequence is altered to improve; (i) codon usage, (ii) transcriptional efficiency, (iii) translational efficiency, (iv) the like, and combinations thereof.

Any peptides, polypeptides or proteins, or an activity catalyzed by one or more peptides, polypeptides or proteins may be encoded by a target nucleotide sequence and may be selected by a user. Representative proteins include transporters (e.g., nucleotide triphosphate transporters), enzymes (e.g., polymerases, replication machinery, and the like, for example) and membrane bound proteins, and include both naturally occurring and exogenously expressed polypeptides.

Representative activities (e.g., enzymes or combinations of enzymes which are functionally associated to provide an activity) include nucleotide triphosphate transporter activity and polymerase activity, Specific polypeptides (e.g., enzymes) useful for embodiments described herein are listed herein. A protein or polypeptide sometimes is of intracellular origin (e.g., located in the nucleus, cytosol, or interstitial space of host cells in vivo) and sometimes is a cell membrane protein in vivo. In some embodiments (described above, and in further detail hereafter), a genetic modification can result in a modification (e.g., increase, substantially increase, decrease or substantially decrease) of a target activity.

Nucleotide Triphosphate Transporter Activity

Chloroplasts are characteristic organelles of plants, possess an envelope of two membranes and arose by a primary endosymbiosis between a protozoan host and a cyanobacterium (higher plant, green algae, red algae and glaucophyta). However, the engulfment of a red or a green alga by a non-photosynthetic host through a process called secondary endosymbiosis gave rise to further groups of complex chimeric eukaryotes (chloraracheans, chromalveolates). The resulting photosynthetic organelle accordingly exhibits four bounding membranes. Until now the knowledge on metabolic fluxes across the membranes of complex plastids is limited. Biochemical characterization of plastidial carrier proteins involved in energy provision (nucleotide transporters, NTTs) and in the transport of intermediates of starch metabolism provided insights into the cellular communication across the envelope membranes of primary and complex plastids.

Apart from plastidial nucleotide transporters (NTTs), which mediate the transport of ATP in counter exchange with ADP and other deoxyribonucleotides and ribonucleotides, structurally related proteins are also present in some intracellular living bacterial species. The different biochemical characteristics of specialized NTTs enable these intracellular bacteria to exploit metabolic intermediates of the host cell. The endosymbiotic bacterium *Protochlamydia amoebophila* for example possesses five NTTs essential not only for energy provision by ATP/ADP counter exchange, but also for uptake of DNA and RNA components and nucleotide derivatives from the host cell. Furthermore, in *Protochlamydia amoebophila* corresponding biosynthetic pathways were eliminated during evolution.

A cell can contain, or can be modified to contain, a nucleotide triphosphate transporter that facilitates transport of the unnatural nucleotides through cellular and other membranes so that the unnatural nucleotides are available to the cellular machinery for incorporation into the cell's nucleic acids. UBPs can therefore form within the cell's nucleic acids. Moreover, neither the presence of the unnatural triphosphates nor the replication of the UBP represents a significant growth burden. The UBPs are not efficiently excised by nucleic acid repair pathways, and therefore can be retained as long as the unnatural triphosphates are available in the growth medium. Thus, the resulting cell is the first organism to stably propagate an expanded genetic alphabet.

Certain types of nucleotide triphosphate transporters are more effective than others. For example, nucleotide triphosphate transporters from some types or diatoms or algae are useful for transporting natural and/or unnatural nucleotide triphosphates into cells without degradation or loss of the nucleotide triphosphates, particularly when the cells and nucleotide triphosphates are maintained in the presence of potassium phosphate.

The unnatural nucleotides are transported into cells by a nucleotide triphosphate transporter. As illustrated herein, a variety of nucleotide triphosphate transporters can be employed to transport the unnatural nucleotides into cells.

Examples of nucleotide triphosphate transporters that can be employed include those from diatoms such as *Phaeodactylum tricornutum, Thalassiosira pseudonana* and/or *Protochlamydia amoebophila.*

Diatom plastids rely on nucleotide uptake by a specialized import system in their membranes that interconnects cytosolic nucleotide formation and nucleotide consumption in the organelle. Because diatom plastids are surrounded by four membranes, whereas primary plastids possess only two, diatoms have extra transporters in the additional membranes.

Examples of nucleotide triphosphate transporters that can be employed include those from *Phaeodactylum tricornutum* with NCBI accession numbers EEC44449.1 (GI:217404502, protein NTT1, PHATRDRAFT_49533); EEC49227.1 (GI:217409295, protein NTT2, PHATRDRAFT_45145); EEC43534.1 (GI:217403582, protein NTT3, PHATRDRAFT_50189); ACI65362.1 (GI:209582741, protein NTT4, PHATR_46794); EEC50831.1 (GI:217410902, protein NTT5, PHATRDRAFT_54110); XP 002182967.1 (GI:219125393, protein NTT6, PHATRDRAFT_54907).

A nucleotide triphosphate transporter 2 from *Phaeodactylum tricornutum* (PtNTT2; EEC49227.1, GI:217409295) that has the following sequence SEQ ID NO: 1

```
  1 MRPYPTIALI SVFLSAATRI SATSSHQASA LPVKKGTHVP
 41 DSPKLSKLYI MAKTKSVSSS FDPPRGGSTV APTTPLATGG
 81 ALRKVRQAVF PIYGNQEVTK FLLIGSIKFF IILALTLTRD
121 TKDTLIVTQC GAEAIAFLKI YGVLPAATAF IALYSKMSNA
161 MGKKMLFYST CIPFFTFFGL FDVFIYPNAE RLHPSLEAVQ
201 AILPGGAASG GMAVLAKIAT HWTSALFYVM AEIYSSVSVG
241 LLFWQFANDV VNVDQAKRFY PLFAQMSGLA PVLAGQYVVR
281 FASKAVNFEA SMHRLTAAVT FAGIMICIFY QLSSSYVERT
321 ESAKPAADNE QSIKPKKKKP KMSMVESGKF LASSQYLRLI
361 AMLVLGYGLS INFTEIMWKS LVKKQYPDPL DYQRFMGNFS
401 SAVGLSTCIV IFFGVHVIRL LGWKVGALAT PGIMAILALP
441 FFACILLGLD SPARLEIAVI FGTIQSLLSK TSKYALFDPT
481 TQMAYIPLDD ESKVKGKAAI DVLGSRIGKS GGSLIQQGLV
521 FVFGNIINAA PVVGVVYYSV LVAWMSAAGR LSGLFQAQTE
561 MDKADKMEAK TNKEK
```

A nucleotide triphosphate transporter 2 from *Phaeodactylum tricornutum* with SEQ ID NO:1 is encoded by a nucleic acid with the following cDNA sequence SEQ ID NO:2

```
   1 ATGAGACCAT ATCCGACGAT TGCCTTGATT TCGGTTTTTC
  41 TTTCGGCGGC GACTCGTATT TCGGCCACTT CCTCTCATCA
  81 AGCAAGTGCA CTTCCTGTCA AAAAGGGAAC GCATGTCCCG
 121 GACTCTCCGA AGTTGTCAAA GCTATATATC ATGGCCAAAA
 161 CCAAGAGTGT ATCCTCGTCC TTCGACCCCC CTCGGGGAGG
 201 CAGTACTGTT GCGCCAACTA CACCGTTGGC AACCGGCGGT
```

-continued

```
 241 GCGCTCCGCA AAGTGCGACA AGCCGTCTTT CCCATCTACG
 281 GAAACCAAGA AGTCACCAAA TTTCTGCTCA TCGGATCCAT
 321 TAAATTCTTT ATAATCTTGG CACTCACGCT CACGCGTGAT
 361 ACCAAGGACA CGTTGATTGT CACGCAATGT GGTGCCGAAG
 401 CGATTGCCTT TCTCAAAATA TACGGGGTGC TACCCGCAGC
 441 GACCGCATTT ATCGCGCTCT ATTCCAAAAT GTCCAACGCC
 481 ATGGGCAAAA AAATGCTATT TTATTCCACT TGCATTCCTT
 521 TCTTTACCTT TTTCGGGCTG TTTGATGTTT TCATTTACCC
 561 GAACGCGGAG CGACTGCACC CTAGTTTGGA AGCCGTGCAG
 601 GCAATTCTCC CGGGCGGTGC CGCATCTGGC GGCATGGCGG
 641 TTCTGGCCAA GATTGCGACA CACTGGACAT CCGCCTTATT
 681 TTACGTCATG GCGGAAATAT ATTCTTCCGT ATCGGTGGGG
 721 CTATTGTTTT GGCAGTTTGC GAACGACGTC GTCAACGTGG
 761 ATCAGGCCAA GCGCTTTTAT CCATTATTTG CTCAAATGAG
 801 TGGCCTCGCT CCAGTTTTAG CGGGCCAGTA TGTGGTACGG
 841 TTTGCCAGCA AAGCGGTCAA CTTTGAGGCA TCCATGCATC
 881 GACTCACGGC GGCCGTAACA TTTGCTGGTA TTATGATTTG
 921 CATCTTTTAC CAACTCAGTT CGTCATATGT GGAGCGAACG
 961 GAATCAGCAA AGCCAGCGGC AGATAACGAG CAGTCTATCA
1001 AACCGAAAAA GAAGAAACCC AAAATGTCCA TGGTTGAATC
1041 GGGGAAATTT CTCGCGTCAA GTCAGTACCT GCGTCTAATT
1081 GCCATGCTGG TGCTGGGATA CGGCCTCAGT ATTAACTTTA
1121 CCGAAATCAT GTGGAAAAGC TTGGTGAAGA AACAATATCC
1161 AGACCCGCTA GATTATCAAC GATTTATGGG TAACTTCTCG
1201 TCAGCGGTTG GTTTGAGCAC ATGCATTGTT ATTTTCTTCG
1241 GTGTGCACGT GATCCGTTTG TTGGGGTGGA AAGTCGGAGC
1281 GTTGGCTACA CCTGGGATCA TGGCCATTCT AGCGTTACCC
1321 TTTTTTGCTT GCATTTTGTT GGGTTTGGAT AGTCCAGCAC
1361 GATTGGAGAT CGCCGTAATC TTTGGAACAA TTCAGAGTTT
1401 GCTGAGCAAA ACCTCCAAGT ATGCCCTTTT CGACCCTACC
1441 ACACAAATGG CTTATATTCC TCTGGACGAC GAATCAAAGG
1481 TCAAAGGAAA AGCGGCAATT GATGTTTTGG GATCGCGGAT
1521 TGGAAAGAGT GGAGGCTCAC TGATCCAGCA GGGCTTGGTC
1561 TTTGTTTTTG GAAATATCAT TAATGCCGCA CCTGTAGTAG
1601 GGGTTGTCTA CTACAGTGTC CTTGTTGCGT GGATGAGCGC
1641 AGCTGGCCGA CTAAGTGGGC TTTTTCAAGC ACAAACAGAA
1681 ATGGATAAGG CCGACAAAAT GGAGGCAAAG ACCAACAAAG
1721 AAAAGTAG
```

A nucleotide triphosphate transporter 2 from *Protochlamydia amoebophila* (strain UWE25), is referred to as PamTTT2, and has the following sequence SEQ ID NO:3

```
  1 MSQQESEFGK LRAFFWPIHG HEVKKVLPMM LMLFLICFNY
 41 SILRNVKDAI VVTAKASGAE VIPFIKVWVL LPTAVLFTLI
 81 FTKLSNRFSQ EKVFYIVIST FLLFFGSFTY IFYPLRDVLH
121 PHQLCDYLET ILPAGFKGLI AMFRNWSFTL FYVICELWGS
161 IVLTVLFWGF ANEITKMTEA RRFYSMLGVI ASFAATIAGI
201 IANLLSNDQS WEQTLNILMV AVIVSGTIAM VIFRWMNKNV
241 NGPEFQEFH EAKRIQKMKK RLSIRESFTY LANSKYLICI
281 AVLVISYNLV INLVEIVWKD QLRQLYSSAL DYNRYMNNMT
321 SAVGIIATIT SLFMSTMITR FGWTRTALVT PTIMLVTSVG
361 FFAFMLFRND LADPVYILTG TTPLTIAVFF GAAQVCMSKA
401 CKYSVFDSTK EMAFIPLDYE SKLKGKAAID GVGSRLGKSG
441 GSLIHQSLLM IFATVSSSAP YVAVILIGVI IVWMLCVRSL
481 GKQFAAIIGE KAREDIGEST PRTSEEQVLH PLKAAS
```

An example of a nucleotide sequence for the above PamTTT2 protein is provided below as SEQ ID NO:4

```
  1 ATGTCTCAAC AAGAATCAGA GTTTGGTAAA TTGAGGGCAT
 41 TTTTTTGGCC TATTCACGGC CATGAAGTCA AAAAAGTGCT
 81 GCCGATGATG TTGATGCTAT TTTTGATTTG TTTCAACTAT
121 AGTATTTTAC GCAATGTTAA AGATGCTATT GTTGTGACTG
161 CTAAGGCTTC AGGGGCTGAA GTTATTCCAT TTATTAAAGT
201 ATGGGTGCTG TTACCCACGG CAGTCTTATT TACTTTAATT
241 TTTACTAAGT TGTCTAACCG TTTTAGCCAA GAAAAAGTTT
281 TTTATATTGT CATTTCTACA TTTTTGCTAT TTTTTGGTTC
321 GTTTACTTAT ATTTTTTATC CTTTACGTGA CGTACTACAT
361 CCTCATCAAC TATGCGATTA CTTAGAAACG ATTTTACCAG
401 CGGGATTTAA AGGATTAATT GCCATGTTCC GTAATTGGTC
441 ATTTACTTTG TTTTATGTAA TTTGTGAACT TTGGGGCAGT
481 ATTGTTTTAA CTGTCCTTTT TTGGGGATTT GCGAATGAAA
521 TCACAAAAAT GACTGAAGCT CGTCGTTTTT ATAGTATGCT
561 TGGTGTCATT GCAAGTTTTG CCGCGACGAT AGCAGGAATC
601 ATAGCCAATC TTCTTTCTAA TGATCAAAGT TGGGAACAGA
641 CTTTAAATAT TCTCATGGTT GCTGTAATTG TAAGTGGAAC
681 GATAGCCATG GTTATTTTTC GTTGGATGAA TAAAAATGTA
721 CTCAATGGCC CAGAATTCCA AGAATTCCAT GAAGCAAAAC
761 GCATTCAAAA AATGAAAAAA AGATTATCGA TCCGAGAAAG
801 TTTTACCTAT CTCGCTAATT CTAAATATCT TATTTGTATT
841 GCAGTTTTAG TTATTTCTTA TAATCTTGTC ATTAACTTAG
881 TTGAAATTGT ATGGAAAGAC CAGCTTCGCC AACTTTATTC
921 GTCAGCCCTT GATTATAATC GCTATATGAA TAACATGACA
961 TCAGCAGTCG GAATTATTGC CACAATCACA TCCTTATTTA
```

-continued

```
1001 TGTCTACAAT GATTACTCGG TTTGGATGGA CACGGACAGC
1041 TCTAGTAACA CCGACTATTA TGCTTGTCAC AAGTGTGGGA
1081 TTTTTTGCTT TTATGCTATT TCGAAATGAT TTGGCTGATC
1121 CTGTTTATAT ATTAACAGGA ACGACACCTT TAACTATAGC
1161 CGTCTTTTTT GGTGCAGCTC AAGTCTGCAT GAGTAAAGCC
1201 TGTAAGTATT CTGTTTTTGA TTCTACAAAA GAAATGGCTT
1241 TTATCCCTCT GGATTATGAA AGTAAATTGA AAGGAAAAGC
1281 TGCGATTGAT GGTGTGGGTT CTCGTCTTGG TAAATCGGGC
1321 GGTTCCTTAA TTCATCAAAG TTTATTGATG ATTTTTGCAA
1361 CTGTTAGCTC CAGCGCTCCT TATGTAGCTG TGATCTTAAT
1401 TGGCGTTATC ATTGTTTGGA TGCTCTGCGT ACGTTCATTA
1441 GGTAAGCAAT TTGCTGCTAT TATTGGGGAA AAGGCTCGAG
1481 AAGATATTGG TGAATCTACT CCAAGAACGA GTGAAGAGCA
1521 AGTTTTACAT CCCTTAAAAG CTGCATCTTAA
```

An example of a nucleotide triphosphate transporter 3 from *Protochlamydia amoebophila* (strain UWE25), is referred to as PamTTT3, and has the following sequence SEQ ID NO:5

```
  1 MSQTPTGSRE FSPWRSNLWP VHRYELKKLI PMLLIFFFIS
 41 FDYNILRTLK DSLLITAKSS GAEVIPFVKV WAMFPGAILM
 81 TLLFTWLSNR LSREIVFYLI TSLFLSYFFI FTFILYPIRD
121 IIHPHATADY LETILPIGFK GLVAMFRYWT FTIFYVMSEL
161 WGSTVLFVLF WGFANQVTKI SEAKRFYGLF GVGANLSGIF
201 AGQASVYCCQ FNKQNDLGIL GSDPWYQSLV MMVSLILLSG
241 ALVLALFRWM NVEVLTDKRF YDPSSVKTEG EAKGKLSLKQ
281 SFSYLLRSNY LLCIALIVIS YNLVINLTEV LWKHQVRELY
321 PDPNDYTLYM NHIVSIIGVV ATLSSLFVSG NAIRKFGWTT
361 TALITPIILA VTSLGFFSFF FLKKASPEIF LSFSGVTPLV
401 LVVFFGTAQN ILSRGAKYSV FDATKEMSFV PLNPESKLVG
441 KAAIDGVCSR LGKSGGSVVH QSLLLLFSTI NASAPYVAIV
481 LFAVILVWAM AIRVLGKQFN ELTSQVENNE TSGTLMTPIR
521 AVNILSDTIL KEQKAV
```

An example of a nucleotide sequence for the above PamTTT3 protein is provided below as SEQ ID NO:6

```
  1 ATGTCACAGA CACCAACAGG GTCCCGTGAA TTTAGTCCAT
 41 GGCGGAGCAA TCTTTGGCCC GTTCATCGCT ATGAGCTTAA
 81 AAAACTCATC CCAATGTTGT TAATATTCTT TTTTATTTCT
121 TTTGATTACA ACATATTACG TACTTTAAAA GACTCACTAC
161 TTATAACTGC AAAATCTTCA GGTGCTGAGG TCATTCCTTT
201 TGTAAAGGTT TGGGCTATGT TCCCTGGAGC TATTTTAATG
241 ACCCTTTTGT TCACTTGGTT GTCTAATCGC CTGTCAAGAG
```

-continued

```
281 AAATCGTTTT TTACCTTATC ACTTCTCTTT TTTTATCTTA
321 TTTTTTTATT TTCACTTTTA TTCTCTATCC TATTCGAGAT
361 ATTATCCATC CTCACGCAAC TGCTGACTAT CTTGAAACAA
401 TTTTACCGAT TGGATTTAAA GGGCTAGTTG CGATGTTTCG
441 TTACTGGACT TTTACTATTT TCTATGTGAT GTCAGAACTT
481 TGGGGAAGTA CTGTTTTATT TGTCTTATTT TGGGGTTTTG
521 CTAATCAAGT GACTAAAATT AGTGAGGCAA AAAGATTTTA
561 CGGTCTGTTT GGGGTAGGTG CTAATCTTTC GGGTATTTTC
601 GCAGGACAAG CTTCTGTGTA CTGTTGTCAA TTTAATAAGC
641 AGAACGATTT GGGAATCCTT GGTAGTGATC CATGGTATCA
681 ATCATTAGTG ATGATGGTTT CTTTAATTTT ATTATCGGGT
721 GCTTTAGTTT TAGCTTTATT TCGTTGGATG AATGTAGAAG
761 TCTTAACCGA TAAACGTTTT TATGATCCTT CTTCGGTTAA
801 AACAGAAGGA GAAGCTAAAG GTAAGCTTTC TCTAAAGCAA
841 AGCTTTTCCT ATCTTCTTCG CTCTAATTAC TTACTTTGTA
881 TTGCTCTTAT TGTTATTTCT TATAACCTAG TTATTAACCT
921 CACAGAAGTT TTATGGAAAC ATCAAGTCCG AGAGCTATAT
961 CCTGATCCTA ATGATTATAC TTTATATATG AATCATATCG
1001 TATCCATTAT TGGGGTAGTA GCGACCTTAA GTTCCCTTTT
1041 CGTATCAGGA AATGCGATTC GCAAATTTGG GTGGACCACT
1081 ACTGCTTTAA TTACACCTAT CATTTTAGCT GTAACAAGTT
1121 TGGGCTTTTT CTCCTTTTTC TTCCTTAAAA AGGCATCTCC
1161 CGAAATTTTC TTATCTTTTT CCGGAGTAAC TCCTTTGGTT
1201 TTAGTGGTTT TCTTTGGAAC TGCTCAAAAC ATATTGAGTC
1241 GAGGAGCTAA ATACTCTGTA TTTGATGCCA CTAAAGAAAT
1281 GAGTTTTGTT CCTTTAAATC CTGAATCCAA ACTCGTTGGA
1321 AAAGCGGCGA TTGATGGAGT TTGTTCTCGC CTCGGAAAAT
1361 CGGGTGGATC TGTGGTTCAT CAGAGCCTTC TACTTTTGTT
1401 TTCTACAATT AATGCAAGTG CCCCTTATGT AGCTATCGTC
1441 TTGTTCGCCG TAATTCTAGT CTGGGCAATG GCAATTCGCG
1481 TTTTAGGTAA ACAATTTAAT GAATTGACAA GTCAGGTAGA
1521 AAACAATGAA ACTTCTGGGA CATTGATGAC TCCTATTCGA
1561 GCTGTTAATA TTCTTTCAGA CACAATTTTG AAAGAACAGA
1601 AAGCTGTATA A
```

An example of a nucleotide triphosphate transporter 5 from *Protochlamydia amoebophila* (strain UWE25), is referred to as PamTTT5, and has the following sequence SEQ ID NO:7

```
1 MKNQQNSVSS TLLILKKRSL ILFQFFLIII VYHTLKDLKD
41 TIVITASDAG AEIIPFIKIW GMLPLAICAS YFFAKFYNKF
81 GREKTFYIFS SFLLVNYLFF AFVLYPFRKF FYLENVADYL
```

-continued

```
121 HMILPVGAKG FVAMVSYWHY TLFYLTAELW SMLILSILFW
161 GYVSDTTSLV EAKKFYPLCM FVGNMAGIIS GQLSHFLCQH
201 LSDFMSWERT LQWMIGIVCV CGLLIMIINR RLALTTDFSA
241 IKQKVKKQIA PSSFKDNVMD VLRTGPLLCI AVLVVGFGLT
281 TNLIEVIWKE NIRQLHPTPQ AYNAYINQLT SLIGTGAVCI
321 ALLSSWIFRK FTWTQIALTT PLCLLITSSA FFSSLLMPKE
361 LLAEIASFFQ FSPTQLIVTL GSICYVFSMS AKYTIFDTSK
401 EIAFLSIETE KRTYAKSVID SIGSRLGKSG ASCFYQFLLI
441 AFGIASEHIL LIGVVSIIMI GISIFATKKL GGQLSGKNEN
481 HRFIEASHG
```

An example of a nucleotide sequence for the above PamTTT5 protein is provided below as SEQ ID NO:8

```
1 ATGAAAAATC AACAAAATTC TGTATCTTCT ACCTTACTAA
41 TCTTAAAAAA GCGTAGCTTG ATCCTATTTC AATTTTTTCT
81 AATTATCATT GTTTATCATA CATTAAAAGA CCTCAAAGAT
121 ACGATTGTTA TCACAGCAAG TGATGCAGGT GCAGAGATCA
161 TTCCTTTTAT TAAAATTTGG GGAATGCTTC CTCTTGCCAT
201 TTGTGCTAGT TATTTTTTTG CTAAATTTTA TAATAAATTT
241 GGAAGAGAAA AAACATTTTA TATTTTTAGC TCTTTCTTAC
281 TAGTTAACTA TCTTTTCTTT GCTTTTGTAT TATATCCATT
321 CCGCAAGTTT TTTTATTTAG AAAATGTTGC AGATTATTTA
361 CATATGATTT TACCTGTTGG AGCGAAAGGG TTTGTTGCCA
401 TGGTAAGCTA TTGGCATTAC ACTCTATTTT ATTTAACGGC
441 AGAATTATGG TCGATGCTCA TTCTATCTAT CCTTTTTTGG
481 GGTTATGTGA GTGATACGAC TTCTTTAGTA GAAGCCAAAA
521 AATTTTACCC CCTCTGTATG TTCGTTGGAA ATATGGCAGG
561 AATTATTTCT GGTCAGCTCT CTCATTTCTT ATGTCAACAT
601 TTGTCTGATT TCATGTCATG GGAAAGAACC CTGCAATGGA
641 TGATTGGTAT TGTCTGTGTT TGCGGCCTTT TAATTATGAT
681 TATTAATAGA CGGCTGGCTC TTACAACTGA TTTTTCGGCA
721 ATTAAACAAA AAGTAAAAAA ACAAATAGCT CCCTCTTCTT
761 TCAAAGATAA TGTTATGGAT GTTTTAAGAA CAGGTCCCTT
801 ACTTTGTATA GCTGTATTGG TAGTGGGGTT TGGACTGACA
841 ACGAATCTAA TTGAAGTTAT TTGGAAAGAA AATATTAGGC
881 AACTACACCC GACACCTCAA GCCTACAATG CTTATATTAA
921 TCAATTGACT TCTTTAATTG GGACTGGTGC TGTTTGTATA
961 GCCTTGTTAT CAAGCTGGAT TTTTAGAAAG TTTACTTGGA
1001 CGCAAATTGC CCTCACAACC CCTTTATGTT TATTAATCAC
1041 AAGCTCTGCT TTTTTTTCAT CGCTTCTTAT GCCTAAAGAG
1081 CTGTTAGCGG AAATTGCTTC TTTTTTTCAG TTTTCCCCAA
```

-continued

```
1121 CTCAATTGAT AGTGACACTA GGATCTATTT GCTATGTTTT
1161 TAGCATGTCT GCGAAGTACA CAATTTTTGA TACTAGTAAA
1201 GAAATAGCTT TTCTTTCTAT TGAAACAGAA AAAAGAACGT
1241 ATGCTAAATC TGTAATTGAT AGCATTGGCT CTCGTTTGGG
1281 AAAATCTGGC GCTTCTTGTT TTTATCAATT TCTTCTTATT
1321 GCCTTTGGAA TTGCTTCCGA ACATATTTTA TTAATTGGAG
1361 TTGTATCCAT TATAATGATT GGAATTTCGA TTTTTGCTAC
1401 GAAAAAATTG GGTGGGCAGC TGTCTGGTAA AAATGAAAAC
1441 CATCGCTTTA TAGAAGCTTC CCATGGATAA
```

An example of a nucleotide triphosphate transporter 2 from *Thalassiosira pseudonana*, is referred to as TpTTT2, and has the following sequence SEQ ID NO:9

```
  1 MKTSCTIQRR VKSISSKHSI IDTHHSTSRR LSVILLFFLL
 41 HSSAEMLFAS ATGNHNANTS PPPANIPMIS TNNKSCMMRR
 81 TRSQSRRDSS RSPDSVASAN VVGRGGDGGT IMGAKSVFQT
121 ASKALPPNTV SSTASGSVSK ASRLRTVLFP IQNDEMKKFL
161 LIGSIKFFVI LALTLTRDNK DTMVVTECGA EAIAFLKIYG
201 VLPSATLFIA LYSKMATIFD KKTLFYATCI PFFAFFFLFD
241 AIIYPNRNVI QPSLESVQRV MRITADSSGA MSIFAKLFAN
281 WTSALFYIVA EVYSSVSVGI LFWQYANDVV SVSQAKRFYP
321 LFAQMSGLAP IVAGQYVVRY ASRANDFEES LHRLTWMVSF
361 SGVMICLFYK WSNEYNDQTS GGLNGGIEDG VKETKVVKKK
401 KAKMSMRDSA KFLASSEYLR LIAALVVGYG LSINFTDIMW
441 KSIVKRQYPD PLDYQRFMGN FSSVVGLSTC IVIFLGVHAI
481 RILGWRMGAL ATPAVMAILA FPYFSSILVG LDSPGSLRIA
521 VIFGTIQCLL SKTAKYALFD PTTQMAYIPL DDESKIKGKA
561 AIEVLGSRIG KSGGSLIQQG LVLVFGNIIN AAPALVVLYY
601 SVLAWWVYSA NRLGSLFLAK TAMQEETKEH QK
```

An example of a nucleotide sequence for the above TpTTT2 protein is provided below as SEQ ID NO:10

```
   1 ATGAAAACAT CTTGTACAAT CCAACGTCGT GTCAAATCCA
  41 TCTCATCCAA ACACAGTATC ATCGACACAC ACCACTCTAC
  81 TTCTCGCCGT TTAAGTGTCA TCCTACTCTT CTTTCTACTA
 121 CACTCCTCGG CAGAGATGCT ATTTGCTTCC GCCACGGGCA
 161 ATCACAACGC CAATACATCA CCACCACCTG CGAATATTCC
 201 CATGATTAGC ACTAACAACA AATCATGTAT GATGCGACGA
 241 ACCAGGAGTC AATCACGACG AGATAGCAGC CGTTCGCCTG
 281 ATTCGGTGGC CTCGGCCAAT GTTGTTGGGA GGGGCGGCGA
 321 TGGGGGTACC ATTATGGGTG CCAAGAGTGT CTTCCAGACT
 361 GCTTCGAAAG CATTACCTCC CAACACTGTG TCGTCCACAG
```

-continued

```
 401 CAAGCGGCAG TGTATCCAAA GCATCGCGCC TACGAACGGT
 441 CCTCTTCCCC ATTCAAAATG ACGAGATGAA GAAGTTTCTC
 481 TTGATTGGAA GTATCAAGTT CTTTGTAATT CTAGCGTTGA
 521 CACTCACGAG AGATAATAAG GATACAATGG TGGTTACCGA
 561 GTGTGGAGCT GAGGCCATCG CTTTTCTAAA GATCTACGGA
 601 GTACTACCAT CCGCCACACT CTTCATAGCA CTCTACTCGA
 641 AAATGGCCAC TATCTTTGAC AAAAAGACCT TATTCTACGC
 681 CACGTGCATT CCATTCTTTG CATTCTTCTT CTTATTCGAT
 721 GCAATCATCT ATCCTAACCG GAATGTCATT CAGCCTTCCT
 761 TAGAGAGTGT TCAGCGTGTC ATGAGAATCA CAGCCGATTC
 801 ATCGGGTGCC ATGTCCATCT TTGCAAAGTT GTTCGCCAAT
 841 TGGACGTCGG CCTTGTTTTA TATTGTAGCA GAGGTATACT
 881 CGTCTGTTTC AGTGGGGATA TTGTTCTGGC AGTATGCCAA
 921 TGATGTGGTG TCTGTCTCGC AAGCAAAACG ATTTTACCCA
 961 CTCTTTGCAC AGATGAGTGG ACTTGCCCCC ATTGTGGCTG
1001 GACAGTATGT GGTACGATAT GCTAGTAGAG CCAATGACTT
1041 TGAAGAATCA TTGCATAGGT TGACGTGGAT GGTATCCTTT
1081 TCGGGAGTGA TGATTTGTCT GTTTTACAAG TGGAGCAATG
1121 AGTACAATGA TCAGACGTCT GGAGGGTTAA ATGGGGGAAT
1161 TGAGGATGGA GTAAAAGAGA CGAAGGTGGT GAAGAAAAAG
1201 AAAGCCAAAA TGTCAATGAG GGATTCAGCC AAGTTTTTGG
1241 CTTCATCCGA GTATTTGAGA CTGATTGCTG CTTTGGTTGT
1281 GGGATATGGT CTGTCGATCA ACTTTACAGA TATAATGTGG
1321 AAATCAATCG TCAAGAGACA ATATCCCGAT CCTCTCGACT
1361 ATCAACGTTT CATGGGGAAC TTTTCATCAG TAGTTGGATT
1401 GTCTACGTGC ATCGTTATCT TTCTCGGTGT ACATGCTATT
1441 CGTATACTAG GCTGGCGAAT GGGTGCCCTA GCGACTCCAG
1481 CCGTCATGGC AATCTTGGCA TTCCCTTACT TCTCGAGCAT
1521 TCTCGTTGGG TTGGACAGTC CAGGTAGTTT ACGAATTGCA
1561 GTGATCTTTG GTACTATTCA ATGCCTGCTT AGTAAGACAG
1601 CAAAGTATGC CCTGTTCGAT CCGACAACTC AAATGGCCTA
1641 CATTCCTTTG GATGACGAAT CAAAGATCAA GGGAAAGGCA
1681 GCAATAGAAG TACTTGGTTC TCGGATTGGA AAAAGTGGTG
1721 GTTCGTTGAT ACAACAAGGT CTTGTGTTGG TGTTTGGGAA
1761 CATTATCAAT GCTGCTCCCG CGTTGGTTGT TCTTTACTAC
1801 TCAGTGTTGG CGTGGTGGGT GTACTCAGCA AATCGGCTCG
1841 GATCATTGTT CTTGGCAAAG ACAGCTATGC AAGAGGAAAC
1881 AAAAGAGCAC CAGAAGTAG
```

An example of a nucleotide triphosphate transporter 3 from *Simkania negevensis*, is referred to as SnTTT3, and has the following sequence SEQ ID NO:11

```
  1 MSSTEYEKST WTQKIWPIRR FELKKVLPLL ILKFLVSMVY
 41 ATLTLIKDPL VVTAKHSGAE VIPVLKGWIV FPLSILCAIG
 81 YSKLSNHFKR STLFYGIITA FLAIVLIYGF VLYPNMGILT
121 PSDSANLLTA KFGEKYTHWI AVYRNWIHSL FFVTTELWGQ
161 VVIFLLYWGF ANHICQVKEA KRSYTLFIAA GDLATILAGP
201 LTYYYGKKFL GQSYALTLQS LLGYVLVCGL LIMAVYWWMN
241 RYVLTDKRYY DPSVTKQTVN QKTKLSLRDS IRHIFSSKYL
281 LAIAVLVVGC ALTINMVEVT WKAHLKMQYP TTADYQMFMG
321 RVTTIVGVVA LITVFFLGGN FLRRFGWHFS AQITPWAIGI
361 TGGVFFLLCL LKPYLGSFAH YVGLTPLMMI VIFGAFQNIT
401 SKVVKYSFFD STKEMAYIPL DPESKVKGKA AIDMVGSRLG
441 KSSSSWLQIG LIELVGTGSV ISITPYLLPI VLGAALYWSY
481 SVRYLNKELS VREETLLEEE EAKKRAGELQ PEPEPAT
```

An example of a nucleotide sequence for the above *Simkania negevensis* SnTTT3 protein is provided below as SEQ ID NO:12

1 ATGAGTAGTA CCGAATATGA GAAGTCCACA TGGACTCAAA
41 AAATCTGGCC AATAAGGCGC TTTGAACTTA AGAAAGTCCT
81 TCCTCTTTTA ATCCTTAAAT TTCTAGTCTC TATGGTTTAT
121 GCCACTCTCA CCTTAATCAA GGATCCCCTT GTGGTGACGG
161 CAAAACATTC TGGAGCAGAA GTCATTCCAG TTCTAAAAGG
201 TTGGATTGTT TTCCCCTTAT CGATTCTTTG TGCTATTGGT
241 TACTCAAAGT TAAGCAACCA CTTCAAACGT TCCACCCTCT
281 TTTACGGAAT CATTACAGCT TTCCTAGCTA TTGTTCTTAT
321 CTACGGCTTC GTTTTGTATC CCAATATGGG AATTCTCACA
361 CCAAGCGACT CTGCAAACTT GTTAACAGCT AAATTTGGGG
401 AAAAATACAC ACACTGGATT GCAGTTTATC GGAATTGGAT
441 CCATTCTCTC TTTTTCGTCA CCACAGAGCT TTGGGGGCAA
481 GTTGTCATTT TCCTCCTCTA CTGGGGATTT GCCAACCACA
521 TTTGCCAAGT GAAAGAAGCT AAAAGATCTT ACACTCTTTT
561 CATCGCTGCA GGCGATTTAG CAACGATCTT GGCTGGTCCA
601 CTTACCTATT ACTACGGAAA AAAGTTTCTA GGACAAAGCT
641 ATGCTCTCAC TCTTCAATCC CTACTAGGAT ATGTCTTAGT
681 CTGCGGGCTA CTCATCATGG CAGTCTATTG GTGGATGAAT
721 CGATATGTCC TAACAGACAA A*CGG*TACTAC GATCCATCAG
761 TGACGAAGCA AACAGTCAAC CAAAAGACCA AACTCTCTCT
801 GCGTGATAGT ATCCGGCATA TCTTTTCATC AAAGTATCTC
841 CTTGCTATTG CGGTCCTCGT TGTCGGTTGC GCTCTCACCA
881 TCAACATGGT AGAAGTCACC TGGAAAGCTC ACTTAAAGAT
921 GCAATACCCA ACAACTGCTG ATTACCAAAT GTTCATGGGG
961 CGAGTCACAA CTATTGTTGG AGTTGTTGCC CTCATCACTG

-continued

1001 TATTCTTCTT AGGAGGAAAC TTCCTGAGAC GGTTTGGATG
1041 GCACTTCAGT GCTCAAATCA CCCCATGGGC GATTGGAATC
1081 ACAGGTGGTG TTTTCTTTTT ACTCTGCCTT TTGAAGCCCT
1121 ATCTCGGGTC TTTCGCTCAT TATGTTGGAC TCACCCCTCT
1161 TATGATGATT GTCATCTTTG GAGCCTTCCA AAATATCACT
1201 AGTAAAGTCG TCAAATACTC GTTCTTTGAT TCGACGAAAG
1241 AAATGGCTTA TATTCCACTA GACCCTGAAT CTAAAGTGAA
1281 AGGAAAAGCA GCCATCGACA TGGTCGGTTC AAGATTGGGT
1321 AAGTCGAGCT CCTCCTGGCT ACAAATTGGC TTGATTGAAC
1361 TAGTTGGGAC TGGTTCGGTG ATCTCAATCA CTCCTTATCT
1401 ACTGCCTATC GTTCTAGGTG CCGCCCTCTA TTGGAGCTAC
1441 TCTGTACGCT ACCTCAATAA AGAGCTTTCT GTGCGTGAAG
1481 AAACACTCCT CGAGGAAGAA GAAGCTAAGA AAAGAGCGGG
1521 AGAGCTTCAG CCTGAACCTG AGCCTGCCAC TTGA

A single nucleotide mismatch resulted in an amino acid substitution at position 248 of the SEQ ID NO:11 sequence where arginine (R), which is a basic amino acid, is replaced with a tryptophan (W), which is a nonpolar/hydrophobic amino acid. This mutant nucleotide triphosphate transporter 3 from *Simkania negevensis* has the following sequence SEQ ID NO:13

1 MSSTEYEKST WTQKIWPIRR FELKKVLPLL ILKFLVSMVY
41 ATLTLIKDPL VVTAKHSGAE VIPVLKGWIV FPLSILCAIG
81 YSKLSNHFKR STLFYGIITA FLAIVLIYGF VLYPNMGILT
121 PSDSANLLTA KFGEKYTHWI AVYRNWIHSL FFVTTELWGQ
161 VVIFLLYWGF ANHICQVKEA KRSYTLFIAA GDLATILAGP
201 LTYYYGKKFL GQSYALTLQS LLGYVLVCGL LIMAVYWWMN
241 RYVLTDKWYY DPSVTKQTVN QKTKLSLRDS IRHIFSSKYL
281 LAIAVLVVGC ALTINMVEVT WKAHLKMQYP TTADYQMFMG
321 RVTTIVGVVA LITVFFLGGN FLRRFGWHFS AQITPWAIGI
361 TGGVFFLLCL LKPYLGSFAH YVGLTPLMMI VIFGAFQNIT
401 SKVVKYSFFD STKEMAYIPL DPESKVKGKA AIDMVGSRLG
441 KSSSSWLQIG LIELVGTGSV ISITPYLLPI VLGAALYWSY
481 SVRYLNKELS VREETLLEEE EAKKRAGELQ PEPEPAT

An example of a nucleotide triphosphate transporter 2 from *Simkania negevensis*, is referred to as SnTTT2, and has the following sequence SEQ ID NO:14

1 MSTQTDVSFS KWRSFLWPIQ GREIKKFLPL LLIYALICLN
41 YSVLKVAKDT LVITAPGSGA EAIPFIKVWV ILPMALLVTY
81 LFTRLFNRFS QEQVFYIMIG SFISFFALFA FVLYPLRDFL
121 HPHDTADKLQ AMLPQGFQGL IAIFRNWSYT LFYVMSELWG
161 TAIMSVLFWG FTNEIISVGE AKRYYGILSV GANIATIFSG

-continued

```
201 YITTFLSLQV IDMSFIFGPD RWGQSLGLVT CVVVAAGLLI

241 MALFRWYNKR VINRDAVLLK MKQDHTETKK TMKMGMRKNF

281 AYLAKSKYLI CIAVLVVAFN VGINMVEIIW KDQIKELYPN

321 PNDFIVYMGK VMSAIGWVAT FVGLFLSSNL IRRLGWTVSA

361 LITPVALLVT GVFFFGFILF KNNPTLVGWT AAIGFTPLAL

401 GVLFGTIQNV MSRACKYTLF DSTKEIAFIP LSPESKLKGK

441 AAIDGVGSRV GKSGGSIVHG GLLMLFGSVS LSAPYVGLIL

481 LAVVFGWIGA ARSLGRQFNL LTTHHEKLEI NEEAQPSEKK

521 PLLESV
```

An example of a nucleotide sequence for the above *Simkania negevensis* SnTTT2 protein with SEQ ID NO:13 is provided below as SEQ ID NO:15.

```
   1 ATGTCAACAC AGACTGATGT GAGTTTCAGT AAATGGCGCT

  41 CATTTTTGTG GCCAATTCAA GGAAGAGAAA TTAAAAAATT

  81 TCTTCCTCTT CTCCTGATTT ACGCTCTCAT TTGTCTTAAC

 121 TATAGCGTCT TAAAAGTCGC AAAAGACACA CTTGTCATTA

 161 CAGCCCCTGG ATCAGGCGCA GAAGCAATCC CGTTTATCAA

 201 GGTCTGGGTC ATTCTCCCCA TGGCACTCCT CGTAACTTAT

 241 CTCTTTACTC GCCTCTTCAA TCGATTTAGC CAAGAACAAG

 281 TGTTTTACAT CATGATCGGG AGCTTCATTT CGTTTTTCGC

 321 TCTATTTGCA TTTGTCCTCT ACCCCTTGCG AGATTTTCTT

 361 CATCCTCATG ACACAGCTGA TAAATTACAA GCCATGCTTC

 401 CACAGGGATT CCAAGGGCTC ATAGCCATTT TCCGTAACTG

 441 GTCCTATACC CTCTTTTATG TGATGTCTGA GCTATGGGGA

 481 ACCGCTATTA TGTCTGTCCT CTTTTGGGGA TTCACAAATG

 521 AAATTATTTC TGTAGGTGAG GCCAAAAGGT ATTATGGAAT

 561 TCTCAGTGTA GGGGCCAATA TTGCAACTAT TTTTTCAGGG

 601 TACATCACCA CCTTTCTCTC TTTGCAAGTG ATTGACATGT

 641 CATTCATTTT TGGACCTGAC CGCTGGGGAC AATCATTAGG

 681 TCTTGTGACA TGTGTTGTTG TTGCAGCAGG TCTCCTTATT

 721 ATGGCCCTTT TCAGATGGTA CAACAAGCGA GTCATTAATC

 761 GTGATGCAGT ACTATTAAAA ATGAAACAAG ACCACACAGA

 801 AACGAAGAAG ACCATGAAAA TGGGAATGCG TAAGAATTTT

 841 GCTTACCTTG CAAAATCAAA GTATTTAATT TGCATTGCAG

 881 TTCTGGTTGT TGCATTCAAT GTTGGAATCA ACATGGTCGA

 921 AATTATCTGG AAAGATCAAA TCAAAGAACT GTATCCCAAT

 961 CCCAACGATT TTATTGTTTA TATGGGGAAG GTCATGAGTG

1001 CAATTGGTTG GGTTGCAACA TTTGTCGGAC TATTTCTCAG

1041 TAGTAATTTA ATCAGGCGCT TAGGATGGAC TGTCAGCGCC

1081 TTAATCACTC CTGTTGCTCT CCTCGTAACA GGTGTTTTCT

1121 TTTTCGGATT CATTCTCTTT AAAAACAACC CTACATTAGT
```

-continued

```
1161 GGGTTGGACA GCCGCCATAG GATTTACACC TCTTGCACTA

1201 GGGGTTCTCT TTGGGACAAT CCAAAATGTG ATGTCTCGAG

1241 CATGTAAATA CACCTTATTT GACTCTACAA AAGAAATAGC

1281 GTTTATCCCC CTTAGCCCTG AGTCCAAGCT AAAAGGAAAA

1321 GCTGCAATTG ATGGAGTAGG CTCTCGCGTT GGAAAGTCCG

1361 GAGGGTCGAT TGTTCATGGT GGACTACTGA TGCTCTTCGG

1401 CTCCGTTTCT CTCAGCGCAC CTTACGTCGG CTTGATCTTA

1441 CTCGCCGTTG TTTTCGGTTG GATTGGTGCA GCTCGTTCAC

1481 TCGGGAGACA ATTTAATCTC CTTACGACGC ATCATGAAAA

1521 ACTCGAGATT AACGAGGAGG CACAGCCCTC CGAAAAAAAG

1561 CCCTTACTTG AATCCGTTTA A
```

An example of a nucleotide triphosphate transporter from *Rickettsia prowazekii*, is referred to as RPTlc1, and has the following sequence SEQ ID NO:16

```
  1 MSTSKSENYL SELRKIIWPI EQYENKKFLP LAFMMFCILL

 41 NYSTLRSIKD GFVVTDIGTE SISFLKTYIV LPSAVIAMII

 81 YVKLCDILKQ ENVFYVITSF FLGYFALFAF VLYPYPDLVH

121 PDHKTIESLS LAYPNFKWFI KIVGKWSFAS FYTIAELWGT

161 MMLSLLFWQF ANQITKIAEA KRFYSMFGLL ANLALPVTSV

201 VIGYFLHEKT QIVAEHLKFV PLFVIMITSS FLIILTYRWM

241 NKNVLTDPRL YDPALVKEKK TKAKLSFIES LKMIFTSKYV

281 GYIALLIIAY GVSVNLVEGV WKSKVKELYP TKEAYTIYMG

321 QFQFYQGWVA IAFMLIGSNI LRKVSWLTAA MITPLMMFIT

361 GAAFFSFIFF DSVIAMNLTG ILASSPLTLA VMIGMIQNVL

401 SKGVKYSLFD ATKNMAYIPL DKDLRVKGQA AVEVIGGRLG

441 KSGGAIIQST FFILFPVFGF IEATPYFASI FFIIVILWIF

481 AVKGLNKEYQ VLVNKNEK
```

An example of a nucleotide sequence for the above *Rickettsia prowazekii* RPTlc1 protein is provided below as SEQ ID NO:17

```
  1 ATGAGTACTT CCAAAAGTGA AAATTATCTT TCAGAACTAA

 41 GAAAGATAAT TTGGCCTATA GAACAATATG AAAATAAGAA

 81 GTTTTTGCCA CTTGCATTTA TGATGTTCTG TATTTTATTA

121 AACTACTCAA CTCTTCGTTC AATTAAAGAC GGTTTTGTAG

161 TAACAGATAT AGGTACAGAA TCGATAAGTT TTTTAAAAAC

201 ATATATAGTA CTACCTTCTG CTGTAATTGC TATGATAATT

241 TATGTTAAGC TATGTGATAT TTTAAAGCAA GAAAACGTAT

281 TTTATGTTAT TACTTCATTT TTTTTAGGGT ATTTTGCATT

321 ATTTGCCTTT GTTCTTTACC CATATCCTGA TTTAGTCCAC

361 CCTGATCATA AAACTATAGA ATCTTTAAGT TTAGCTTATC

401 CTAATTTCAA ATGGTTTATA AAAATAGTTG GTAAATGGAG
```

-continued

441 TTTTGCATCT TTTTATACTA TTGCCGAGCT TTGGGGAACA

481 ATGATGCTTA GTTTATTATT TTGGCAATTT GCTAATCAAA

521 TTACTAAAAT CGCTGAAGCT AAACGTTTCT ACTCAATGTT

561 TGGTTTACTT GCGAATTTAG CATTGCCTGT AACATCAGTG

601 GTTATTGGAT ATTTTCTACA CGAAAAAACT CAAATAGTTG

641 CAGAACATTT AAAATTTGTA CCTTTATTTG TTATAATGAT

681 AACAAGTAGT TTCTTAATAA TATTAACATA TAGATGGATG

721 AATAAAAATG TTCTAACTGA TCCTAGACTA TATGATCCAG

761 CATTAGTAAA AGAAAAAAAA ACTAAAGCTA AATTGTCGTT

801 CATAGAAAGT TTAAAAATGA TCTTTACTTC GAAATATGTA

841 GGTTATATTG CATTATTAAT TATTGCTTAT GGTGTTTCAG

881 TAAATTTAGT TGAAGGTGTT TGGAAATCCA AAGTAAAAGA

921 ATTATATCCG ACAAAGGAGG CTTATACCAT ATATATGGGT

961 CAGTTCCAAT TTTATCAGGG TTGGGTTGCA ATTGCTTTTA

1001 TGCTGATAGG TAGTAATATT TTAAGAAAAG TATCATGGCT

1041 AACTGCAGCT ATGATCACTC CATTAATGAT GTTCATAACA

1081 GGTGCGGCAT TTTTTTCATT TATATTTTTT GATAGCGTTA

1121 TTGCAATGAA TTTAACCGGC ATCCTTGCTT CAAGTCCTTT

1161 AACACTTGCT GTTATGATCG GTATGATTCA AAATGTTTTA

1201 AGTAAAGGTG TGAAATATTC TTTATTTGAT GCAACTAAAA

1241 ATATGGCGTA TATTCCACTT GATAAGGATT TACGAGTCAA

1281 AGGGCAAGCT GCCGTTGAAG TTATCGGAGG AAGGCTCGGT

1321 AAATCAGGCG GTGCTATTAT TCAATCTACA TTCTTTATTT

1361 TATTTCCTGT ATTTGGTTTT ATAGAGGCGA CTCCTTATTT

1401 TGCTTCTATA TTCTTTATAA TAGTAATATT ATGGATATTT

1441 GCAGTTAAAG GTTTAAATAA AGAGTATCAA GTTTTGGTAA

1481 ATAAAAATGA AAAATAG

Another example of a nucleotide triphosphate transporter from *Rickettsia prowazekii*, is referred to as RPTlc2, and has the following sequence SEQ ID NO:18

1 MNIVDSNCTI WHKARNSKFR HIVWPIRSYE LTKFIPMTLL

41 MFFILLNQNL VRSIKDSFVV TLISSEVLSF IKLWGEMPMG

81 VLFVILYSKL CNIMTTEQVF RIITSTFLFF FAIFGFILFP

121 YKEFFHPNPE LINQYIIVLP HLKWFLIIWG QWSLVLFYIM

161 GELWPVIVFT LLYWQLANKI TKVEEAPRFY SFFTLFGQTN

201 LLFSGTVIIY FAKSEHFLLP LFAHLNDTNE ILLKSFITVI

241 LISGLICLAL HKLIDKSVVE ADKNIKFKNQ RTDILKLSLL

281 ESAKIILTSR YLGFICLLVM SYSMSINLIE GLWMSKVKQL

321 YPATKDFISY HGEVLFWTGV LTLVSAFLGS SLIRIYGWFW

361 GAIITPIMMF VAGVMFFSFT IFEQHLGNIV NTLGYSSPLV

401 IIVFIGGLWH VFAKSVKYSL FDATKEMVYI PLDNEIKTKG

-continued

441 KAAVDVMGAK IGKSIGAIIQ FISFSIFPNA VHNDIAGLLM

481 VTFIIVCILW LYGVKVLSQN YNKMIKR

An example of a nucleotide sequence for the above *Rickettsia prowazekii* RPTlc2 protein is provided below as SEQ ID NO:19

1 ATGAATATAG TAGATTCTAA CTGTACAATT TGGCATAAAG

41 CAAGAAATAG TAAATTTAGG CATATAGTAT GGCCAATTAG

81 ATCGTATGAA TTAACAAAAT TCATCCCGAT GACTTTATTA

121 ATGTTTTTTA TTTTACTTAA TCAAAATTTA GTGCGTAGTA

161 TTAAAGATAG TTTTGTTGTT ACATTAATTA GTTCAGAAGT

201 ATTAAGTTTT ATAAAACTTT GGGGTGAAAT GCCGATGGGG

241 GTTTTATTTG TTATTCTTTA TTCTAAACTC TGTAATATTA

281 TGACCACAGA GCAAGTTTTT AGGATAATTA CCAGTACCTT

321 TTTATTTTTC TTTGCAATTT TTGGTTTTAT TTTATTCCCA

361 TACAAAGAGT TTTTTCATCC TAACCCTGAA TTAATTAATC

401 AATATATCAT TGTTCTGCCT CACTTAAAGT GGTTTTTAAT

441 AATTTGGGGA CAATGGAGTT TAGTATTATT TTATATAATG

481 GGTGAGTTAT GGCCTGTTAT AGTTTTTACT CTTTTATATT

521 GGCAGCTTGC AAATAAAATC ACCAAAGTCG AAGAAGCACC

561 AAGATTTTAC TCATTTTTTA CTTTATTTGG ACAAACTAAT

601 TTGCTCTTCT CAGGCACTGT AATTATTTAT TTTGCTAAGA

641 GCGAACATTT TTTATTACCT TTATTTGCTC ATTTAAATGA

681 CACAAATGAA ATTCTTTTAA AATCATTCAT CACAGTTATT

721 TTAATATCAG GATTAATTTG TTTAGCTCTC CATAAGCTAA

761 TTGATAAATC AGTTGTAGAA GCTGATAAAA ATATAAAATT

801 TAAAAACCAA AGAACAGATA TATTAAAATT AAGCTTGCTC

841 GAAAGTGCAA AAATAATCTT AACGTCTAGA TATCTTGGTT

881 TTATTTGTCT TCTCGTAATG TCTTATTCTA TGAGTATTAA

921 CCTAATAGAA GGATTGTGGA TGTCAAAAGT AAAACAACTC

961 TATCCTGCTA CAAAGGATTT TATATCATAT CACGGTGAAG

1001 TATTGTTTTG GACTGGAGTG TTAACTTTAG TTAGTGCATT

1041 TTTAGGCAGT AGTTTAATTA GAATTTATGG CTGGTTTTGG

1081 GGGGCTATTA TAACACCGAT TATGATGTTT GTAGCAGGGG

1121 TTATGTTTTT TTCATTCACA ATTTTTGAAC AACACTTAGG

1161 AAATATAGTA AATACTCTTG GCTATAGTTC TCCACTTGTC

1201 ATTATAGTTT TTATTGGTGG ACTTTGGCAT GTATTTGCTA

1241 AATCTGTAAA GTATTCCCTT TTCGATGCTA CTAAAGAAAT

1281 GGTGTATATT CCACTAGATA ATGAAATTAA GACTAAAGGT

1321 AAAGCAGCAG TTGATGTTAT GGGTGCTAAA ATTGGTAAGT

1361 CAATAGGTGC TATTATTCAA TTCATATCCT TTAGTATCTT

1401 TCCAAATGCT GTACATAACG ACATAGCAGG CTTATTGATG

-continued

```
1441 GTTACTTTTA TTATCGTATG TATATTATGG CTATATGGAG
1481 TGAAAGTTTT ATCACAAAAT TATAATAAAA TGATAAAACG
1501 TTAA
```

Another example of a nucleotide triphosphate transporter from *Rickettsia prowazekii*, is referred to as RPTlc3, and has the following sequence SEQ ID NO:20

```
  1 MLPPKIFFEK VKEIIWPIER KELKLFIPMA LMMLCILFNF
 41 GALRSIKDSL VVPSMGAEII SFLKLWLVLP SCVIFTILYV
 81 KLSNKLNFEY IFYSIVGTFL LFFLLFAYII YPNQDIYHPN
121 DAMINNLIAS YPNLKWFIKI GSKWSYALMY IFSELWSAVV
161 INLMFWQFAN HIFDTAKAKR FYPVLGMVGN IGLIIAGSVL
201 VFFSSGQYII DSELLTDSYN SSSNNSIMLQ PIISIIVTAG
241 IIAMFLFRII NKFILTNSIN VLDVKKVAAK TKTKLALIES
281 IKLIIHSKYI GRIALLIICY GLLINIVEGP WKAKIKELHP
321 NTVDYVNFMG MFNIWMGISC VTFMIIGSNI LRRLGWLISA
361 LLTPIMLSIT GFMFFIFIIF IEEIGTCFGD FNLLYVAIIV
401 GAIQNILSKS SKYSLFDSTK EMAYIPLSLE LRTKGKAAVE
441 VIGTKFGKSL GAFIQSLIFI IIPTATFDSI IIYLLVIFIV
481 MMNLWIWNII KLNKEYIKLC Q
```

An example of a nucleotide sequence for the above *Rickettsia prowazekii* RPTlc3 protein is provided below as SEQ ID NO:21

```
  1 ATGTTACCGC CTAAAATTTT CTTTGAAAAA GTTAAAGAAA
 41 TAATTTGGCC TATAGAAAGG AAAGAATTAA AGCTATTTAT
 81 ACCAATGGCT TTAATGATGT TATGTATCCT GTTTAATTTT
121 GGGGCTTTAA GATCTATTAA AGATAGTTTA GTAGTACCCT
161 CTATGGGGGC TGAAATTATT AGTTTCTTAA AATTATGGTT
201 AGTGCTACCC TCGTGCGTAA TTTTTACGAT ACTTTACGTT
241 AAACTTAGTA ATAAATTAAA TTTTGAATAT ATTTTCTATA
281 GTATAGTCGG TACTTTTTTA CTATTTTTCT TATTATTTGC
321 CTATATTATT TATCCAAATC AAGATATTTA TCATCCTAAT
361 GATGCAATGA TAAATAATTT AATTGCTTCA TACCCTAATT
401 TAAAGTGGTT TATTAAAATA GGTAGTAAAT GGAGTTATGC
441 GCTAATGTAT ATTTTCTCAG AATTATGGAG TGCAGTAGTT
481 ATAAACTTAA TGTTTTGGCA ATTTGCTAAT CACATTTTTG
521 ATACTGCTAA AGCTAAACGA TTTTATCCTG TTCTTGGGAT
561 GGTTGGTAAT ATCGGTCTTA TAATAGCAGG CAGCGTACTT
601 GTTTTTTTTT CAAGTGGGCA GTACATCATT GATTCAGAAT
641 TATTAACGGA TTCTTATAAT TCATCTTCTA ACAATTCTAT
681 CATGCTTCAG CCAATCATAT CAATTATTGT TACTGCAGGA
721 ATAATTGCTA TGTTTTTATT TAGAATAATA AATAAATTTA
```

-continued

```
 761 TTTTAACTAA TTCTATAAAT GTTTTAGATG TAAAAAAAGT
 801 TGCTGCTAAA ACAAAAACAA AACTTGCATT AATTGAAAGT
 841 ATAAAATTAA TAATTCATTC AAAATATATA GGTCGTATTG
 881 CATTATTAAT AATCTGTTAT GGATTACTAA TAAATATAGT
 921 TGAAGGACCT TGGAAAGCGA AAATAAAAGA ATTACATCCA
 961 AATACTGTAG ATTATGTTAA TTTTATGGGC ATGTTTAATA
1001 TTTGGATGGG GATCTCATGT GTTACTTTCA TGATAATAGG
1041 TAGTAATATT CTTAGAAGGC TTGGTTGGCT CATTTCTGCA
1081 TTATTAACTC CTATTATGTT ATCTATTACA GGCTTCATGT
1121 TTTTTATCTT TATAATTTTT ATTGAAGAAA TAGGTACATG
1161 TTTTGGTGAT TTTAATCTTC TATATGTAGC GATTATTGTC
1201 GGAGCAATTC AGAATATACT TAGTAAATCG TCTAAATATT
1241 CATTATTCGA TTCAACAAAA GAAATGGCAT ATATTCCTTT
1281 ATCTTTAGAA CTGAGAACTA AGGGAAAAGC CGCTGTAGAG
1321 GTAATAGGAA CGAAATTTGG TAAATCACTT GGAGCATTTA
1361 TCCAGTCTTT GATATTTATT ATTATTCCAA CGGCTACCTT
1401 TGATTCTATT ATAATATATT TACTAGTAAT TTTTATAGTG
1441 ATGATGAATT TATGGATTTG GAATATTATA AAATTAAATA
1481 AGGAATATAT AAAGCTGTGT CAATAA
```

Another example of a nucleotide triphosphate transporter from *Rickettsia prowazekii*, is referred to as RPTlc4, and has the following sequence SEQ ID NO:22

```
  1 MTINASNIEN SFSKINSHFS KLTDYIWPIK RHEISKFLFI
 41 TLLMFCILFI QNLIRALKDS IVTTMIGAET ISFLKFWGVM
 81 PSAFLITVIY VKLVNRMKAE NIFYLIISIF LTFFALFAYV
121 IFPNHEMLHL RPVTVHNLTA SLPNLKWFIL LLSKWSFSLF
161 YIIAELWPNV VFALLFWQFV NNITTVEESK RFYPLFGLLS
201 QTGIYLAGHF LENLSNINYY VTNKFALQSS FHTLSIQIIL
241 TIVLILGIVS IKTFWLLNHK VLDKKHMALL RFKTKNKSIT
281 IAKSFQMILS SRHIRLIATL LICYGIAINL VEGPWKAAAT
321 KIYKTPTEYA AFIGSYLSYT GVFTIFFVLL GSNIVRRMGW
361 FTSAVITPSI VFITGILFFA VNNFEGFAGL IIANFILTDP
401 ALVAITIGAI QNVLSKSSKY TLFDSTKEMA YVPLEPEIKI
441 SGKAAADVIG TKLGKSGSAF LQSLIFIILP SASYQSISIC
481 LMIIFILTCV TWIWATKELN KEYKNSIKFS QK
```

An example of a nucleotide sequence for the above *Rickettsia prowazekii* RPTlc4 protein is provided below as SEQ ID NO:23

```
  1 ATGACGATTA ACGCCAGTAA TATAGAAAAT TCTTTTTCTA
 41 AAATCAATAG CCATTTTTCT AAGCTTACAG ATTATATCTG
 81 GCCTATAAAA CGCCACGAAA TTTCTAAGTT TTTATTCATT
```

-continued

```
 121 ACATTATTAA TGTTCTGTAT TTTATTTATT CAAAATCTCA
 161 TCAGAGCTTT AAAAGATAGT ATTGTTACTA CTATGATAGG
 201 TGCTGAGACT ATATCATTTT TGAAATTTTG GGGCGTGATG
 241 CCGTCAGCAT TCTTAATAAC TGTTATATAT GTTAAACTTG
 281 TCAATAGGAT GAAAGCAGAA AATATATTTT ATCTTATTAT
 321 ATCAATTTTT TTAACATTCT TTGCTTTGTT TGCATACGTT
 361 ATTTTCCCAA ATCATGAAAT GCTGCATTTA AGGCCTGTAA
 401 CCGTGCATAA TTTAACGGCA AGTTTACCGA ATTTAAAATG
 441 GTTTATACTT CTTTTATCAA AATGGAGTTT TTCACTATTT
 481 TATATAATAG CCGAATTATG GCCAAATGTA GTTTTTGCAT
 521 TACTGTTTTG GCAGTTTGTG AATAATATTA CTACAGTAGA
 561 AGAATCGAAA AGATTTTATC CATTATTTGG TTTACTTAGT
 601 CAAACAGGTA TTTATTTAGC AGGACATTTT TTAGAAAATC
 641 TAAGTAATAT AAATTATTAT GTCACTAATA AATTTGCATT
 681 GCAATCGTCT TTTCATACAC TTTCTATACA AATTATACTA
 721 ACTATAGTAT TAATTTTAGG CATAGTATCG ATAAAAACTT
 761 TTTGGTTACT TAATCATAAA GTACTAGACA AAAAGCATAT
 801 GGCATTACTC AGGTTCAAAA CAAAAAATAA ATCTATTACT
 841 ATTGCTAAAA GTTTTCAGAT GATTCTATCG TCAAGACACA
 881 TTAGATTAAT TGCAACTTTG CTTATCTGCT ATGGCATTGC
 921 AATTAATTTA GTAGAAGGCC CTTGGAAAGC AGCAGCAACT
 961 AAAATTTATA AAACTCCAAC CGAATATGCA GCTTTTATAG
1001 GAAGTTATTT AAGCTACACT GGAGTATTTA CTATTTTCTT
1041 TGTTCTACTT GGTTCCAATA TAGTTAGAAG AATGGGCTGG
1081 TTTACTTCAG CTGTGATCAC ACCTTCAATA GTTTTTATTA
1121 CCGGTATATT ATTTTTTGCT GTTAATAATT TTGAAGGCTT
1201 TGCTGGCTTA ATAATAGCAA ATTTTATTTT GACCGATCCT
1241 GCTTTAGTTG CTATAACAAT AGGTGCTATT CAAAATGTAC
1281 TTAGTAAATC AAGCAAATAT ACTTTATTTG ATTCTACAAA
1321 AGAAATGGCT TATGTTCCTT TAGAACCAGA AATCAAAATA
1361 AGTGGTAAGG CTGCTGCCGA CGTTATAGGT ACAAAACTCG
1401 GTAAATCCGG TAGTGCATTT TTACAATCAT TAATATTTAT
1441 AATATTACCT TCTGCTAGTT ATCAATCTAT TTCAATCTGT
1481 TTAATGATTA TATTTATCCT CACTTGCGTA ACTTGGATTT
1521 GGGCTACTAA AGAACTAAAT AAAGAATATA AAAATTCTAT
1561 TAAATTTTCT CAAAAATAA
```

Another example of a nucleotide triphosphate transporter from *Rickettsia prowazekii*, is referred to as RPTlc5, and has the following sequence SEQ ID NO:24

```
  1 MLSTSPSRSF KNKFRAAFWP VHNYELGKFI PISALMFCIL
 41 FNQNILRILK DSILISEISA EIAGFAKVYC VTPVAALFVI
```

-continued

```
 81 IYAKMINHLT FEKIFYYLSA FFISCFILFA FVIYPNIHIF
121 HVHPDTLSDW MNKYPHFKWY ISLVGNWGYI VYYSLAELWP
161 NIFYVLLFWQ FTNELTTTEE AKRFYTLFSL FGNSSLILVG
201 FLMMNLSSED TIIKKFISIS DSKITLVQVS TTIIAIVAII
241 CCLLVRFISK YIFTNPLFYH KTKSSRSTAQ RMGLIKSFKY
281 IVKSKYLWLL LICSAAFGFA INLVEAVWKA KIKELYPTVN
321 TYAEFNSLYI LWTGVAIIVM TIIGNNVMRM HNWFVAAVIS
361 PVIIMVTGVL FFGLIVFDQQ ILSLFDGAIL MSPLALAVSI
401 GGIQNILAKG TKYSIWDTSR EMLYIPLDDE LKTKGKAAVD
441 VISAKVGKSS SGLVQSIIFT LVPNATFTSI SPILMVVFTF
481 VCFAWIYAVR KIYFEYQKIA
```

An example of a nucleotide sequence for the above *Rickettsia prowazekii* RPTlc5 protein is provided below as SEQ ID NO:25

```
   1 ATGCTAAGTA CCTCACCGTC ACGATCGTTT AAAAACAAAT
  41 TTAGAGCAGC ATTTTGGCCT GTGCATAATT ATGAACTTGG
  81 GAAATTTATT CCGATCAGCG CCTTAATGTT TTGTATTTTA
 121 TTTAATCAAA ATATTTTGCG AATCTTAAAG GATAGTATTT
 161 TAATCTCTGA GATTAGTGCA GAAATAGCAG GATTTGCTAA
 201 AGTTTACTGC GTTACACCTG TAGCTGCTTT GTTTGTTATT
 241 ATTTATGCTA AAATGATCAA TCATTTGACA TTTGAAAAAA
 281 TCTTTTATTA TTTAAGTGCA TTTTTTATAA GCTGTTTTAT
 321 TTTATTTGCC TTTGTGATTT ATCCTAATAT TCATATTTTT
 361 CATGTACATC CTGATACACT ATCAGACTGG ATGAACAAAT
 401 ATCCTCATTT TAAGTGGTAT ATCTCATTAG TAGGTAATTG
 441 GGGTTATATA GTATATTATA GTCTTGCCGA GCTTTGGCCT
 481 AATATTTTTT ACGTATTATT ATTTTGGCAG TTTACTAATG
 521 AACTTACTAC TACCGAAGAA GCAAAAAGAT TTTATACTCT
 561 CTTTTCGCTA TTCGGTAATT CTTCCTTAAT ATTAGTCGGC
 601 TTTTTAATGA TGAATTTATC ATCGGAAGAT ACTATTATTA
 641 AGAAATTTAT AAGTATTTCA GATAGTAAAA TCACTTTAGT
 681 TCAAGTATCA ACGACGATTA TAGCAATTGT TGCAATCATT
 721 TGTTGTTTGT TAGTTAGGTT TATTAGCAAG TACATTTTTA
 761 CTAATCCATT ATTTTATCAT AAAACAAAAA GCAGTAGATC
 801 AACTGCACAA CGGATGGGAC TAATTAAAAG CTTTAAATAT
 841 ATTGTGAAAT CAAAATATTT ATGGCTACTT TTAATTTGTT
 881 CTGCAGCTTT CGGATTTGCT ATAAACTTAG TCGAAGCAGT
 921 ATGGAAAGCA AAAATTAAGG AATTATATCC GACTGTAAAT
 961 ACCTACGCTG AATTCAATAG TCTGTATATA CTTTGGACAG
1001 GCGTTGCGAT AATTGTTATG ACAATTATCG GTAATAACGT
1041 CATGCGTATG CATAATTGGT TTGTAGCCGC AGTTATTTCC
```

-continued

```
1081 CCAGTGATAA TAATGGTGAC AGGTGTTTTG TTCTTTGGAC
1121 TAATTGTATT TGATCAACAA ATTTTATCAT TATTTGATGG
1161 CGCGATTTTA ATGTCACCTC TTGCACTTGC TGTTTCTATT
1201 GGCGGTATTC AGAATATTTT AGCCAAAGGC ACTAAATATT
1241 CTATATGGGA TACTTCAAGA GAAATGTTAT ATATACCACT
1281 TGATGATGAA CTTAAAACAA AGGGTAAAGC AGCAGTTGAT
1321 GTTATAAGTG CAAAAGTTGG AAAATCCTCT AGTGGTCTTG
1361 TACAATCCAT TATTTTTACT TTAGTGCCAA ATGCGACCTT
1401 TACCTCAATC TCGCCGATTT TAATGGTAGT ATTTACGTTC
1441 GTATGCTTTG CTTGGATTTA TGCAGTAAGA AAAATATATT
1481 TTGAATATCA AAAAATAGCC TGA
```

Examples of nucleotide triphosphate transporters that can be employed include those in Table 1:

TABLE 1

Exemplary nucleotide triphosphate transporters

| Host Organism | NTT | Amino Acid Seq ID | Nucleic Seq ID |
|---|---|---|---|
| *Phaeodactylum tricornutum* | nucleotide triphosphate transporter 2 PtNTT2 EEC49227.1 GI: 217409295 | SEQ ID NO: 1 | SEQ ID NO: 2 |
| *Protochlamydia amoebophila* (strain UWE25) | nucleotide triphosphate transporter 2 PamTTT2 | SEQ ID NO: 3 | SEQ ID NO: 4 |
| *Protochlamydia amoebophila* (strain UWE25) | nucleotide triphosphate transporter 3 PamTTT3 | SEQ ID NO: 5 | SEQ ID NO: 6 |
| *Protochlamydia amoebophila* (strain UWE25) | nucleotide triphosphate transporter 5 PamTTT5 | SEQ ID NO: 7 | SEQ ID NO: 8 |
| *Thalassiosira pseudonana* | nucleotide triphosphate transporter 2 TpTTT2 | SEQ ID NO: 9 | SEQ ID NO: 10 |
| *Simkania negevensis* | nucleotide triphosphate transporter 3 SnTTT3 | SEQ ID NO: 11 | SEQ ID NO: 12 |
| *Simkania negevensis* | nucleotide triphosphate transporter 3 SnTTT3(R248W) | SEQ ID NO: 13 | SEQ ID NO: 15 |
| *Simkania negevensis* | nucleotide triphosphate transporter 3 SnTTT3 | SEQ ID NO: 14 | |
| *Rickettsia prowazekii* | nucleotide triphosphate transporter 1 RPTlc1 | SEQ ID NO: 16 | SEQ ID NO: 17 |
| *Rickettsia prowazekii* | nucleotide triphosphate transporter 2 RPTlc2 | SEQ ID NO: 18 | SEQ ID NO: 19 |
| *Rickettsia prowazekii* | nucleotide triphosphate transporter 3 RPTlc3 | SEQ ID NO: 20 | SEQ ID NO: 21 |
| *Rickettsia prowazekii* | nucleotide triphosphate transporter 3 RPTlc4 | SEQ ID NO: 22 | SEQ ID NO: 23 |
| *Rickettsia prowazekii* | nucleotide triphosphate transporter 3 RPTlc5 | SEQ ID NO: 24 | SEQ ID NO: 25 |

A sequence of a pACS plasmid with a PtNTT2 gene sequence (pACS_PtNTT2) corresponds to SEQ ID NO:28.

Sequence of the pACS plasmid with the PtNTT2 gene sequence capitalized (SEQ ID NO:28)>pACS_PtNTT2:

```
ggggaattgtgagcggataacaattcccctgtagaaataattttgtttaa
ctttaataaggagatataccATGAGACCATTTCCGACGATTGCCTTGATT
TCGGTTTTTCTTTCGGCGGCGACTCGCATTTCGGCAACTTCCTCTCATCA
AGCAAGTGCACTTCCTCTCAAAAAGGGAACGCATGTCCCGGACTCTCCGA
```

-continued

```
AGTTGTCAAAGCTATATATCATGGCCAAAACCAAGAGTGTATCCTCGTCC
TTCGACCCCCCTCGGGGAGGCAGTACTGTTGCACCAACTACACCGTTGGC
AACCGGCGGTGCGCTCCGCAAAGTGCGACAAGCCGTCTTTCCCATCTACG
GAAACCAAGAAGTCACCAAATTTCTGCTCATCGGATCCATTAAATTCTTT
ATAATCTTGGCACTCACGCTCACGCGTGATACCAAGGACACGTTGATTGT
CACGCAATGTGGTGCCGAAGCGATTGCCTTTCTCAAAATATACGGGGTGC
TACCCGCAGCGACCGCATTTATCGCGCTCTATTCCAAAATGTCCAACGCC
ATGGGCAAAAAAATGCTATTTTATTCCACTTGCATTCCTTTCTTTACCTT
TTTCGGGCTGTTTGATGTTTTCATTTACCCGAACGCGGAGCGACTGCACC
CTAGTTTGGAAGCCGTGCAGGCAATTCTCCCGGGCGGTGCCGCATCTGGC
GGCATGGCGGTTCTGGCCAAGATTGCGACACACTGGACATCGGCCTTATT
TTACGTCATGGCGGAAATATATTCTTCCGTATCGGTGGGGCTATTGTTTT
```

-continued

```
GGCAGTTTGCGAACGACGTCGTCAACGTGGATCAGGCCAAGCGCTTTTAT
CCATTATTTGCTCAAATGAGTGGCCTCGCTCCAGTTTTAGCGGGCCAGTA
TGTGGTACGGTTTGCCAGCAAAGCGGTCAACTTTGAGGCATCCATGCATC
GACTCACGGCGGCCGTAACATTTGCTGGTATTATGATTTGCATCTTTTAC
CAACTCAGTTCGTCATATGTGGAGCGAACGGAATCAGCAAAGCCAGCGGC
AGATAACGAGCAGTCTATCAAACCGAAAAAGAAGAAACCCAAAATGTCCA
TGGTTGAATCGGGGAAATTTCTCGCGTCAAGTCAGTACCTGCGTCTAATT
```

-continued

GCCATGCTGGTGCTGGGATACGGCCTCAGTATTAACTTTACCGAAATCAT

GTGGAAAAGCTTGGTGAAGAAACAATATCCAGACCCGCTAGATTATCAAC

GATTTATGGGTAACTTCTCGTCAGCGGTTGGTTTGAGCACATGCATTGTT

ATTTTCTTCGGTGTGCACGTGATCCGTTTGTTGGGGTGGAAAGTCGGAGC

GTTGGCTACACCTGGGATCATGGCCATTCTAGCGTTACCCTTTTTTGCTT

GCATTTTGTTGGGTTTGGATAGTCCAGCACGATTGGAGATCGCCGTAATC

TTTGGAACAATTCAGAGTTTGCTGAGCAAAACCTCCAAGTATGCCCTTTT

CGACCCTACCACACAAATGGCTTATATTCCTCTGGACGACGAATCAAAGG

TCAAAGGAAAAGCGGCAATTGATGTTTTGGGATCGCGGATTGGCAAGAGT

GGAGGCTCACTGATCCAGCAGGGCTTGGTCTTTGTTTTTGGAAATATCAT

TAATGCCGCACCTGTAGTAGGGGTTGTCTACTACAGTGTCCTTGTTGCGT

GGATGAGCGCAGCTGGCCGACTAAGTGGGCTTTTTCAAGCACAAACAGAA

ATGGATAAGGCCGACAAAATGGAGGCAAAGACCAACAAAGAAAAGTAGtt aacctaggctgctgccaccgctgagcaataactagcataaccccttgggg cctctaaacgggtcttgaggggttttttgctgaaacctcaggcatttgag aagcacacggtcacactgcttccggtagtcaataaaccggtaaaccagca atagacataagcggctatttaacgaccctgccctgaaccgacgaccgggt catcgtggccggatcttgcggcccctcggcttgaacgaattgttagacat tatttgccgactaccttggtgatctcgcctttcacgtagtggacaaattc ttccaactgatctgcgcgcgaggccaagcgatcttcttcttgtccaagat aagcctgtctagcttcaagtatgacgggctgatactgggccggcaggcgc tccattgcccagtcggcagcgacatccttcggcgcgattttgccggttac tgcgctgtaccaaatgcgggacaacgtaagcactacatttcgctcatcgc cagcccagtcgggcggcgagttccatagcgttaaggtttcatttagcgcc tcaaatagatcctgttcaggaaccggatcaaagagttcctccgccgctgg acctaccaaggcaacgctatgttctcttgcttttgtcagcaagatagcca gatcaatgtcgatcgtggctggctcgaagatacctgcaagaatgtcattg cgctgccattctccaaattgcagttcgcgcttagctggataacgccacgg aatgatgtcgtcgtgcacaacaatggtgacttctacagcgcggagaatct cgctctctccaggggaagccgaagtttccaaaaggtcgttgatcaaagct cgccgcgttgtttcatcaagccttacggtcaccgtaaccagcaaatcaat atcactgtgtggcttcaggccgccatccactgcggagccgtacaaatgta cggccagcaacgtcggttcgagatggcgctcgatgacgccaactacctct gatagttgagtcgatacttcggcgatcaccgcttccctcatactcttcct ttttcaatattattgaagcatttatcagggttattgtctcatgagcggat acatatttgaatgtatttagaaaaataaacaaatagctagctcactcggt cgctacgctccgggcgtgagactgcggcgggcgctgcggacacatacaaa gttacccacagattccgtggataagcaggggactaacatgtgaggcaaaa cagcagggccgcgccggtggcgtttttccataggctccgccctcctgcca gagttcacataaacagacgcttttccggtgcatctgtgggagccgtgagg ctcaaccatgaatctgacagtacgggcgaaacccgacaggacttaaagat ccccaccgtttccggcgggtcgctccctcttgcgctctcctgttccgacc ctgccgtttaccggatacctgttccgcctttctcccttacgggaagtgtg gcgctttctcatagctcacacactggtatctcggctcggtgtaggtcgtt cgctccaagctgggctgtaagcaagaactccccgttcagcccgactgctg cgccttatccggtaactgttcacttgagtccaacccggaaaagcacggta aaacgccactggcagcagccattggtaactgggagttcgcagaggatttg tttagctaaacacgcggttgctcttgaagtgtgcgccaaagtccggctac actggaaggacagatttggttgctgtgctctgcgaaagccagttaccacg gttaagcagttccccaactgacttaaccttcgatcaaaccacctccccag gtggttttttcgtttacagggcaaaagattacgcgcagaaaaaaaggatc tcaagaagatcctttgatcttttctactgaaccgctctagatttcagtgc aatttatctcttcaaatgtagcacctgaagtcagccccatacgatataag ttgtaattctcatgttagtcatgccccgcgcccaccggaaggagctgact gggttgaaggctctcaagggcatcggtcgagatcccggtgcctaatgagt gagctaacttacattaattgcgttgcgctcactgcccgctttccagtcgg gaaacctgtcgtgccagctgcattaatgaatcggccaacgcgcggggaga ggcggtttgcgtattgggcgccagggtggtttttcttttcaccagtgaga cgggcaacagctgattgcccttcaccgcctggccctgagagagttgcagc aagcggtccacgctggtttgccccagcaggcgaaaatcctgtttgatggt ggttaacggcgggatataacatgagctgtcttcggtatcgtcgtatccca ctaccgagatgtccgcaccaacgcgcagcccggactcggtaatggcgcgc attgcgcccagcgccatctgatcgttggcaaccagcatcgcagtgggaac gatgccctcattcagcatttgcatggtttgttgaaaaccggacatggcac tccagtcgccttcccgttccgctatcggctgaatttgattgcgagtgaga tatttatgccagccagccagacgcagacgcgccgagacagaacttaatgg gcccgctaacagcgcgatttgctggtgacccaatgcgaccagatgctcca cgcccagtcgcgtaccgtcttcatgggagaaaataatactgttgatgggt gtctggtcagagacatcaagaaataacgccggaacattagtgcaggcagc ttccacagcaatggcatcctggtcatccagcggatagttaatgatcagcc cactgacgcgttgcgcgagaagattgtgcaccgccgctttacaggcttcg acgccgcttcgttctaccatcgacaccaccacgctggcacccagttgatc ggcgcgagatttaatcgccgcgacaatttgcgacggcgcgtgcagggcca gactggaggtggcaacgccaatcagcaacgactgtttgcccgccagttgt tgtgccacgcggttgggaatgtaattcagctccgccatcgccgcttccac tttttcccgcgttttcgcagaaacgtggctggcctggttcaccacgcggg aaacggtctgataagagacaccggcatactctgcgacatcgtataacgtt actggtttcacattcaccaccctgaattgactctcttccgggcgctatca tgccataccgcgaaaggttttgcgccattcgatggtgtccgggatctcga cgctctcccttatgcgactcctgcattaggaaattaatacgactcactat a In some embodiments, a nucleotide triphosphate transporter is from bacteria, plant, or algae. In some embodiments, a nucleotide triphosphate transporter is TpNTT1, TpNTT2, TpNTT3, TpNTT4, TpNTT5, TpNTT6, TpNTT7, TpNTT8 (*T. pseudonana*), PtNTT1, PtNTT2, PtNTT3, PtNTT4, PtNTT5, PtNTT6 (*P. tricornutum*), GsNTT (*Galdieria sulphuraria*), AtNTT1, AtNTT2 (*Arabidopsis thaliana*), CtNTT1, CtNTT2 (*Chlamydia trachomatis*), PamNTT1, PamNTT2 (*Protochlamydia amoebophila*), CcNTT (*Caedibacter caryophilus*), RpNTT1 (*Rickettsia prowazekii*).

As used herein, the term "transporter" refers to a large group of membrane transport proteins which transport nucleotides (and particularly unnatural or modified nucleotides) across the membranes of cells and/or vesicle. Nucleoside transporters can encompass, but are not limited to, equilibrate nucleoside transporters (ENT) and concentrate nucleoside transporters (CNT). According to the invention, the term also encompasses the organic anion transporters (OAT) and the organic cation transporters (OCT). According to the invention, the nucleoside transporter may for example be selected in the group comprising, but not limited to, CNT1, CNT2, CNT3, ENT1, ENT2, OAT1, OAT3 and OCT1.

A nucleotide triphosphate transporter can have at least 40%, 50%, 60%, 70%, 75%, 80%, 85%, 90%, 95%, 97%, 98%, 99%, 99.5%, 99.9% sequence identity to any one of amino acid sequences SEQ ID NOs:1, 3, 5, 7, 9, 11, 13, 14, 16, 18, 19, 20, 22, or 24, or fragments thereof. A nucleotide triphosphate transporter can also have one or more amino acid substitutions, so that they are not identical to those with any of amino acid sequence SEQ ID NOs:1, 3, 5, 7, 9, 11, 13, 14, 16, 18, 19, 20, 22, or 24.

One or more nucleic acids can encode for one or more nucleotide triphosphate transporters having at least about 40, 50%, 60%, 70%, 75%, 80%, 85%, 90%, 95%, 97%, 98%, 99%, 99.5%, 99.9% sequence identity to any of nucleic acid sequence SEQ ID NOs: 1, 3, 5, 7, 9, 11, 13, 14, 16, 18, 19, 20, 22, or 24. The One or more nucleic acids that encode for the one or more nucleotide triphosphate transporters can also have one or more nucleotide substitutions, so that they are not identical to those with any of nucleotide sequence SEQ ID NOs: 1, 3, 5, 7, 9, 11, 13, 14, 16, 18, 19, 20, 22, or 24. Despite such nucleotide substitutions, the nucleotide triphosphate transporters can encode any of the nucleotide triphosphate transporter proteins described herein.

One or more nucleic acids encoding one or more nucleotide triphosphate transporter can have at least 40%, 50%, 60%, 70%, 75%, 80%, 85%, 90%, 95%, 97%, 98%, 99%, 99.5%, 99.9% sequence identity to any of nucleic acid sequence SEQ ID NOs:2, 4, 6, 8, 10, 12, 15, 17, 19, 21, 23, 25, or 28. The nucleotide triphosphate transporters can also have one or more nucleotide substitutions, so that they are not identical to those with any of nucleotide sequence SEQ ID NOs: 2, 4, 6, 8, 10, 12, 15, 17, 19, 21, 23, 25, or 28. Despite such nucleotide substitutions, the nucleotide triphosphate transporters can encode any of the nucleotide triphosphate transporter proteins described herein.

The invention includes NTTs that import unnatural nucleic acids into cell. In some embodiments, NTTs can be modified such that the nucleotide biding site of the NTT is modified to reduce steric entry inhibition of the unnatural nucleic acid into the nucleotide biding site. In some embodiments, NTTs can be modified to provide increased interaction with one or more unnatural features of the unnatural nucleic acids. Such NTTs can be expressed or engineered in cells for stably importing a UBP into the cells. Accordingly, the invention includes compositions that include a heterologous or recombinant NTT and methods of use thereof.

NTTs can be modified using methods pertaining to protein engineering. For example, molecular modeling can be carried out based on crystal structures to identify the locations of the NTTs where mutations can be made to modify a target activity or binding site. A residue identified as a target for replacement can be replaced with a residue selected using energy minimization modeling, homology modeling, and/or conservative amino acid substitutions, such as described in Bordo et al., J. Mol. Biol. 217: 721-729 (1991) and Hayes et al., Proc Natl Acad Sci, USA 99: 15926-15931 (2002).

Any of a variety of NTTs can be used in a method or composition set forth herein including, for example, protein-based enzymes isolated from biological systems and functional variants thereof. Reference to a particular NTT, such as those exemplified below, will be understood to include functional variants thereof unless indicated otherwise. In some embodiments, a NTT is a wild type NTT. In some embodiments, a NTT is a modified, or mutant, NTT.

NTTs, with features for improving entry of unnatural nucleic acids into cells and for coordinating with unnatural nucleotides in the nucleotide biding region, can also be used. In some embodiments, a modified NTT has a modified nucleotide binding site. In some embodiments, a modified or wild type NTT has a relaxed specificity for an unnatural nucleic acid.

Polymerases, with features for improving entry of unnatural nucleic acids into active site regions and for coordinating with unnatural nucleotides in the active site region, can also be used. In some embodiments, a modified polymerase has a modified nucleotide binding site.

In some embodiments, a modified NTT has a specificity for an unnatural nucleic acid that is at least about 10%, 20%, 30%, 40%, 50%, 60%, 70%, 80%, 90%, 95%, 97%, 98%, 99%, 99.5%, 99.99% the specificity of the wild type NTT toward the unnatural nucleic acid. In some embodiments, a modified or wild type NTT has a specificity for an unnatural nucleic acid comprising a modified sugar that is at least about 10%, 20%, 30%, 40%, 50%, 60%, 70%, 80%, 90%, 95%, 97%, 98%, 99%, 99.5%, 99.99% the specificity of the wild type NTT toward a natural nucleic acid and/or the unnatural nucleic acid without the modified sugar. In some embodiments, a modified or wild type NTT has a specificity for an unnatural nucleic acid comprising a modified base that is at least about 10%, 20%, 30%, 40%, 50%, 60%, 70%, 80%, 90%, 95%, 97%, 98%, 99%, 99.5%, 99.99% the specificity of the wild type NTT toward a natural nucleic acid and/or the unnatural nucleic acid without the modified base. In some embodiments, a modified or wild type polymerase has a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type NTT toward a nucleic acid comprising a triphosphate and/or the unnatural nucleic acid without the triphosphate. For example, a modified or wild type NTT can have a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type NTT toward the unnatural nucleic acid with a diphosphate or monophosphate, or no phosphate, or a combination thereof.

In some embodiments, a modified or wild type NTT has a specificity for an unnatural nucleic acid and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type NTT toward the natural nucleic acid. In some embodiments, a modified or wild type NTT has a specificity for an unnatural nucleic acid comprising a modified sugar and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type NTT toward the natural nucleic acid. In some embodiments, a modified or wild type NTT has a specificity for an unnatural nucleic acid comprising a modified base and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type NTT toward the natural nucleic acid.

NTTs can be characterized according to their rate of dissociation from nucleic acids. In some embodiments a NTT has a relatively low dissociation rate for one or more natural and unnatural nucleic acids. In some embodiments a NTT has a relatively high dissociation rate for one or more natural and unnatural nucleic acids. The dissociation rate is an activity of a NTT that can be adjusted to tune reaction rates in methods set forth herein.

NTTs from native sources or variants thereof can be screened using an assay that detects importation of an unnatural nucleic acid having a particular structure. For example, NTTs can be screened for the ability to import an unnatural nucleic acid or UBP; e.g., (d)5SICSTP, (d)NaMTP, (d)TPT3TP, (d)TPT3TP-(d)NaMTP UBP, or (d)5SICSTP-(d)NaMTP UBP. A NTT, e.g., a heterologous NTT, can be used that displays a modified property for the unnatural nucleic acid as compared to the wild-type NTT. For example, the modified property can be, e.g., $K_m$, $k_{cat}$, $V_{max}$, NTT importation in the presence of an unnatural nucleic acid (or of a naturally occurring nucleotide), average template read-length by a cell with the NTT in the presence of an unnatural nucleic acid, specificity of the NTT for an unnatural nucleic acid, rate of binding of an unnatural nucleic acid, or rate of product release, or any combination thereof. In one embodiment, the modified property is a reduced $K_m$ for an unnatural nucleic acid and/or an increased $k_{cat}/K_m$ or $V_{max}/K_m$ for an unnatural nucleic acid. Similarly, the NTT optionally has an increased rate of binding of an unnatural nucleic acid, an increased rate of product release, and/or an increased cell importation rate, as compared to a wild-type NTT.

At the same time, a NTT can import natural nucleic acids, e.g., A, C, G, and T, into cell. For example, a NTT optionally displays a specific importation activity for a natural nucleic acid that is at least about 5% as high (e.g., 5%, 10%, 25%, 50%, 75%, 100% or higher), as a corresponding wild-type NTT. Optionally, the NTT displays a $k_{cat}/K_m$ or $V_{max}/K_m$ for a naturally occurring nucleotide that is at least about 5% as high (e.g., about 5%, 10%, 25%, 50%, 75% or 100% or higher) as the wild-type NTT.

NTTs used herein that can have the ability to import an unnatural nucleic acid of a particular structure can also be produced using a directed evolution approach. A nucleic acid synthesis assay can be used to screen for NTT variants having specificity for any of a variety of unnatural nucleic acids. For example, NTT variants can be screened for the ability to import an unnatural nucleic acid or UBP; e.g., (d)5SICSTP, (d)NaMTP, (d)TPT3TP, (d)TPT3TP-(d) NaMTP UBP, or (d)5SICSTP-(d)NaMTP UBP into nucleic acids. In some embodiments, such an assay is an in vitro assay, e.g., using a recombinant NTT variant. In some embodiments, such an assay is an in vivo assay, e.g., expressing a NTT variant in a cell. Such directed evolution techniques can be used to screen variants of any suitable NTT for activity toward any of the unnatural nucleic acids set forth herein.

Polymerase Activity

A particularly useful function of a polymerase is to catalyze the polymerization of a nucleic acid strand using an existing nucleic acid as a template. Other functions that are useful are described elsewhere herein. Examples of useful polymerases include DNA polymerases and RNA polymerases.

The ability to improve specificity, processivity, or other features of polymerases unnatural nucleic acids would be highly desirable in a variety of contexts where, e.g., unnatural nucleic acid incorporation is desired, including amplification, sequencing, labeling, detection, cloning, and many others. The present invention provides polymerases with modified properties for unnatural nucleic acids, methods of making such polymerases, methods of using such polymerases, and many other features that will become apparent upon a complete review of the following.

The invention includes polymerases that incorporate unnatural nucleic acids into a growing template copy, e.g., during DNA amplification. In some embodiments, polymerases can be modified such that the active site of the polymerase is modified to reduce steric entry inhibition of the unnatural nucleic acid into the active site. In some embodiments, polymerases can be modified to provide complementarity with one or more unnatural features of the unnatural nucleic acids. Such polymerases can be expressed or engineered in cells for stably incorporating a UBP into the cells. Accordingly, the invention includes compositions that include a heterologous or recombinant polymerase and methods of use thereof.

Polymerases can be modified using methods pertaining to protein engineering. For example, molecular modeling can be carried out based on crystal structures to identify the locations of the polymerases where mutations can be made to modify a target activity. A residue identified as a target for replacement can be replaced with a residue selected using energy minimization modeling, homology modeling, and/or conservative amino acid substitutions, such as described in Bordo et al., J. Mol. Biol. 217: 721-729 (1991) and Hayes et al., Proc Natl Acad Sci, USA 99: 15926-15931 (2002).

Any of a variety of polymerases can be used in a method or composition set forth herein including, for example, protein-based enzymes isolated from biological systems and functional variants thereof. Reference to a particular polymerase, such as those exemplified below, will be understood to include functional variants thereof unless indicated otherwise. In some embodiments, a polymerase is a wild type polymerase. In some embodiments, a polymerase is a modified, or mutant, polymerase.

Polymerases, with features for improving entry of unnatural nucleic acids into active site regions and for coordinating with unnatural nucleotides in the active site region, can also be used. In some embodiments, a modified polymerase has a modified nucleotide binding site.

In some embodiments, a modified polymerase has a specificity for an unnatural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the unnatural nucleic acid. In some embodiments, a modified or wild type polymerase has a specificity for an unnatural nucleic acid comprising a modified sugar that is at least about 10%, 20%, 30%, 40%, 50%, 60%, 70%, 80%, 90%, 95%, 97%, 98%, 99%, 99.5%, 99.99% the specificity of the wild type polymerase toward a natural nucleic acid and/or the unnatural nucleic acid without the modified sugar. In some embodiments, a modified or wild type polymerase has a specificity for an unnatural nucleic acid comprising a modified base that is at least about 10%, 20%, 30%, 40%, 50%, 60%, 70%, 80%, 90%, 95%, 97%, 98%, 99%, 99.5%, 99.99% the specificity of the wild type polymerase toward a natural nucleic acid and/or the unnatural nucleic acid without the modified base. In some embodiments, a modified or wild type polymerase has a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type polymerase toward a nucleic acid comprising a triphosphate and/or the unnatural nucleic acid without the triphosphate. For example, a modified or wild type polymerase can have a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type polymerase toward the unnatural nucleic acid with a diphosphate or monophosphate, or no phosphate, or a combination thereof.

In some embodiments, a modified or wild type polymerase has a relaxed specificity for an unnatural nucleic acid. In some embodiments, a modified or wild type polymerase has a specificity for an unnatural nucleic acid and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the natural nucleic acid. In some embodiments, a modified or wild type polymerase has a specificity for an unnatural nucleic acid comprising a modified sugar and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the natural nucleic acid. In some embodiments, a modified or wild type polymerase has a specificity for an unnatural nucleic acid comprising a modified base and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the natural nucleic acid.

Absence of exonuclease activity can be a wild type characteristic or a characteristic imparted by a variant or engineered polymerase. For example, an exo minus Klenow fragment is a mutated version of Klenow fragment that lacks 3' to 5' proofreading exonuclease activity.

The method of the invention may be used to expand the substrate range of any DNA polymerase which lacks an intrinsic 3' to 5'exonuclease proofreading activity or where a 3' to 5' exonuclease proofreading activity has been disabled, e.g. through mutation. Examples of DNA polymerases include polA, polB (see e.g. Parrel & Loeb, Nat. Struc. Biol. 2001) polC, polD, polY, polX and reverse transcriptases (RT) but preferably are processive, high-fidelity polymerases (PCT/GB2004/004643). In some embodiments a modified or wild type polymerase substantially lacks 3' to 5' proofreading exonuclease activity. In some embodiments a modified or wild type polymerase substantially lacks 3' to 5' proofreading exonuclease activity for an unnatural nucleic acid. In some embodiments, a modified or wild type polymerase has a 3' to 5' proofreading exonuclease activity. In some embodiments, a modified or wild type polymerase has a 3' to 5' proofreading exonuclease activity for a natural nucleic acid and substantially lacks 3' to 5' proofreading exonuclease activity for an unnatural nucleic acid.

In some embodiments, a modified polymerase has a 3' to 5' proofreading exonuclease activity that is at least about 60%, 70%, 80%, 90%, 95%, 97%, 98%, 99%, 99.5%, 99.99% the proofreading exonuclease activity of the wild type polymerase. In some embodiments, a modified polymerase has a 3' to 5' proofreading exonuclease activity for an unnatural nucleic acid that is at least about 60%, 70%, 80%, 90%, 95%, 97%, 98%, 99%, 99.5%, 99.99% the proofreading exonuclease activity of the wild type polymerase to a natural nucleic acid. In some embodiments, a modified polymerase has a 3' to 5' proofreading exonuclease activity for an unnatural nucleic acid and a 3' to 5' proofreading exonuclease activity for a natural nucleic acid that is at least about 60%, 70%, 80%, 90%, 95%, 97%, 98%, 99%, 99.5%, 99.99% the proofreading exonuclease activity of the wild type polymerase to a natural nucleic acid. In some embodiments, a modified polymerase has a 3' to 5' proofreading exonuclease activity for a natural nucleic acid that is at least about 60%, 70%, 80%, 90%, 95%, 97%, 98%, 99%, 99.5%, 99.99% the proofreading exonuclease activity of the wild type polymerase to the natural nucleic acid.

In a related aspect, the invention provides methods of making a modified polymerase that include structurally modeling a parental polymerase, e.g., a DNA polymerase, identifying one or more complex stability or nucleotide interaction feature affecting complex stability or nucleotide access or binding in the active site or a complementarity feature for a nucleotide analog at the active site, and mutating the parental polymerase to include or remove these features. For example, the polymerase can be mutated to improve steric access of the unnatural nucleotide to the active site or to improve charge-charge or hydrophobic interactions between the unnatural nucleotide and the polymerase. The methods also include determining whether the resulting modified polymerase displays an increased incorporation of a nucleotide or unnatural nucleotide into a growing nucleic acid copy as compared to the parental polymerase.

Polymerases can be characterized according to their rate of dissociation from nucleic acids. In some embodiments a polymerase has a relatively low dissociation rate for one or more natural and unnatural nucleic acids. In some embodiments a polymerase has a relatively high dissociation rate for one or more natural and unnatural nucleic acids. The dissociation rate is an activity of a polymerase that can be adjusted to tune reaction rates in methods set forth herein.

Polymerases can be characterized according to their fidelity when used with a particular natural and/or unnatural nucleic acid or collections of natural and/or unnatural nucleic acid. Fidelity generally refers to the accuracy with which a polymerase incorporates correct nucleic acids into a growing nucleic acid chain when making a copy of a nucleic acid template. DNA polymerase fidelity can be measured as the ratio of correct to incorrect natural and unnatural nucleic acid incorporations when the natural and unnatural nucleic acid are present, e.g., at equal concentrations, to compete for strand synthesis at the same site in the polymerase-strand-template nucleic acid binary complex. DNA polymerase fidelity can be calculated as the ratio of $(k_{cat}/K_m)$ for the natural and unnatural nucleic acid and $(k_{cat}/K_m)$ for the incorrect natural and unnatural nucleic acid; where $k_{cat}$ and $K_m$ are Michaelis-Menten parameters in steady state enzyme kinetics (Fersht, (1985) Enzyme Structure and Mechanism, 2nd ed., p 350, W. H. Freeman & Co., New York., incorporated herein by reference). In some embodiments, a polymerase has a fidelity value of at least about 100, 1000, 10,000, 100,000, or $1\times10^6$, with or without a proofreading activity.

Polymerases from native sources or variants thereof can be screened using an assay that detects incorporation of an unnatural nucleic acid having a particular structure. In one example, polymerases can be screened for the ability to incorporate an unnatural nucleic acid or UBP; e.g., (d)5SICSTP, (d)NaMTP, (d)TPT3TP, (d)TPT3TP-(d)NaMTP UBP, or (d)5SICSTP-(d)NaMTP UBP. A polymerase, e.g., a heterologous polymerase, can be used that displays a modified property for the unnatural nucleic acid as compared to the wild-type polymerase. For example, the modified property can be, e.g., $K_m$, $k_{cat}$, $V_{max}$, polymerase processivity in the presence of an unnatural nucleic acid (or of a naturally occurring nucleotide), average template read-length by the polymerase in the presence of an unnatural nucleic acid, specificity of the polymerase for an unnatural nucleic acid, rate of binding of an unnatural nucleic acid, rate of product (pyrophosphate, triphosphate, etc.) release, branching rate, or any combination thereof. In one embodiment, the modified property is a reduced $K_m$ for an unnatural nucleic acid and/or an increased $k_{cat}/K_m$ or $V_{max}/K_m$ for an unnatural nucleic acid. Similarly, the polymerase optionally has an increased rate of binding of an unnatural nucleic acid, an increased rate of product release, and/or a decreased branching rate, as compared to a wild-type polymerase.

At the same time, a polymerase can incorporate natural nucleic acids, e.g., A, C, G, and T, into a growing nucleic acid copy. For example, a polymerase optionally displays a specific activity for a natural nucleic acid that is at least about 5% as high (e.g., 5%, 10%, 25%, 50%, 75%, 100% or higher), as a corresponding wild-type polymerase and a processivity with natural nucleic acids in the presence of a template that is at least 5% as high (e.g., 5%, 10%, 25%, 50%, 75%, 100% or higher) as the wild-type polymerase in the presence of the natural nucleic acid. Optionally, the polymerase displays a $k_{cat}/K_m$ or $V_{max}/K_m$ for a naturally occurring nucleotide that is at least about 5% as high (e.g., about 5%, 10%, 25%, 50%, 75% or 100% or higher) as the wild-type polymerase.

Polymerases used herein that can have the ability to incorporate an unnatural nucleic acid of a particular structure can also be produced using a directed evolution approach. A nucleic acid synthesis assay can be used to screen for polymerase variants having specificity for any of a variety of unnatural nucleic acids. For example, polymerase variants can be screened for the ability to incorporate an unnatural nucleic acid or UBP; e.g., (d)5SICSTP, (d)NaMTP, (d)TPT3TP, (d)TPT3TP-(d)NaMTP UBP, or (d)5SICSTP-(d)NaMTP UBP into nucleic acids. In some embodiments, such an assay is an in vitro assay, e.g., using a recombinant polymerase variant. In some embodiments, such an assay is an in vivo assay, e.g., expressing a polymerase variant in a cell. Such directed evolution techniques can be used to screen variants of any suitable polymerase for activity toward any of the unnatural nucleic acids set forth herein.

Modified polymerases of the compositions described can optionally be a modified and/or recombinant Φ29-type DNA polymerase. Optionally, the polymerase can be a modified and/or recombinant Φ29, B103, GA-1, PZA, Φ15, BS32, M2Y, Nf, G1, Cp-1, PRD1, PZE, SF5, Cp-5, Cp-7, PR4, PR5, PR722, or L17 polymerase.

Nucleic acid polymerases generally useful in the invention include DNA polymerases, RNA polymerases, reverse transcriptases, and mutant or altered forms thereof. DNA polymerases and their properties are described in detail in, among other places, DNA Replication 2nd edition, Kornberg and Baker, W. H. Freeman, New York,N.Y. (1991). Known conventional DNA polymerases useful in the invention include, but are not limited to, *Pyrococcus furiosus* (Pfu) DNA polymerase (Lundberg et al., 1991, Gene, 108: 1, Stratagene), *Pyrococcus woesei* (Pwo) DNA polymerase (Hinnisdaels et al., 1996, Biotechniques, 20:186-8, Boehringer Mannheim), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent™ DNA polymerase, Cariello et al., 1991, Polynucleotides Res, 19: 4193, New England Biolabs), 9° Nm™ DNA polymerase (New England Biolabs), Stoffel fragment, Thermo Sequenase® (Amersham Pharmacia Biotech UK), Therminator™ (New England Biolabs), *Thermotoga maritima* (Tma) DNA polymerase (Diaz and Sabino, 1998 Braz J Med. Res, 31:1239), *Thermus aquaticus* (Taq) DNA polymerase (Chien et al., 1976, J. Bacteoriol, 127: 1550), DNA polymerase, *Pyrococcus kodakaraensis* KOD DNA polymerase (Takagi et al., 1997, Appl. Environ. Microbiol. 63:4504), JDF-3 DNA polymerase (from *thermococcus* sp. JDF-3, Patent application WO/0132887), *Pyrococcus* GB-D (PGB-D) DNA polymerase (also referred as Deep Vent™ DNA polymerase, Juncosa-Ginesta et al., 1994, Biotechniques, 16:820, New England Biolabs), UlTma DNA polymerase (from thermophile *Thermotoga maritima*; Diaz and Sabino, 1998 Braz J. Med. Res, 31:1239; PE Applied Biosystems), Tgo DNA polymerase (from *Thermococcus gorgonarius*, Roche Molecular Biochemicals), *E. coli* DNA polymerase I (Lecomte and Doubleday, 1983, Polynucleotides Res. 11:7505), T7 DNA polymerase (Nordstrom et al., 1981, J. Biol. Chem. 256:3112), and archaeal DP1I/DP2 DNA polymerase II (Cann et al., 1998, Proc. Natl. Acad. Sci. USA 95:14250). Both mesophilic polymerases and thermophilic polymerases are contemplated. Thermophilic DNA polymerases include, but are not limited to, ThermoSequenase®, 9° Nm™, Therminator™, Taq, Tne, Tma, Pfu, Tfl, Tth, Tli, Stoffel fragment, Vent™ and Deep Vent™ DNA polymerase, KOD DNA polymerase, Tgo, JDF-3, and mutants, variants and derivatives thereof. A polymerase that is a 3' exonuclease-deficient mutant is also contemplated. Reverse transcriptases useful in the invention include, but are not limited to, reverse transcriptases from HIV, HTLV-I, HTLV-II, FeLV, FIV, SIV, AMV, MMTV, MoMuLV and other retroviruses (see Levin, Cell 88:5-8 (1997); Verma, Biochim Biophys Acta. 473:1-38 (1977); Wu et al., CRC Crit Rev Biochem. 3:289-347 (1975)). Further examples of polymerases include, but are not limited to 9° N DNA Polymerase, Taq DNA polymerase, Phusion® DNA polymerase, Pfu DNA polymerase, RB69 DNA polymerase, KOD DNA polymerase, and VentR® DNA polymerase (Gardner et al. (2004) "Comparative Kinetics of Nucleotide Analog Incorporation by Vent DNA Polymerase, J. Biol. Chem., 279(12), 11834-11842; Gardner and Jack "Determinants of nucleotide sugar recognition in an archaeon DNA polymerase" Nucleic Acids Research, 27(12) 2545-2553). Polymerases isolated from non-thermophilic organisms can be heat inactivatable. Examples are DNA polymerases from phage. It will be understood that polymerases from any of a variety of sources can be modified to increase or decrease their tolerance to high temperature conditions. In some embodiments, a polymerase can be thermophilic. In some embodiments, a thermophilic polymerase can be heat inactivatable. Thermophilic polymerases are typically useful for high temperature conditions or in thermocycling conditions such as those employed for polymerase chain reaction (PCR) techniques.

Additionally, such polymerases can be used for DNA amplification and/or sequencing applications, including real-time applications, e.g., in the context of amplification or sequencing that include incorporation of unnatural nucleic acid residues into DNA by the polymerase. In other embodiments, the unnatural nucleic acid that is incorporated can be the same as a natural residue, e.g., where a label or other moiety of the unnatural nucleic acid is removed by action of the polymerase during incorporation, or the unnatural nucleic acid can have one or more feature that distinguishes it from a natural nucleic acid.

Ribonucleotide Reductase Activity

A particularly useful function of a ribonucleotide reductase (RNR), also known as (ribonucleoside diphosphate reductase) is to catalyze the formation of deoxyribonucleotides from ribonucleotides. Deoxyribonucleotides can then be, e.g., used in the synthesis of DNA polymerization of a nucleic acid strand using an existing nucleic acid as a template. Other functions that are useful are described elsewhere herein. Natural substrates for RNR can include ADP, GDP, CDP and UDP. The natural activity catalyzes the conversion of 2'-deoxyribonucleoside diphosphate to ribonucleoside diphosphate.

Examples of useful ribonucleotide reductases include CDP reductase; ribonucleoside diphosphate reductase; UDP reductase; ADP reductase; nucleoside diphosphate reductase; ribonucleoside 5'-diphosphate reductase; ribonucleotide diphosphate reductase; and 2'-deoxyribonucleoside-diphosphate:oxidized-thioredoxin 2'-oxidoreductase.

The ability to improve specificity, processivity, or other features of ribonucleotide reductases unnatural nucleic acids would be highly desirable in a variety of contexts where, e.g., unnatural nucleic acid incorporation is desired, including amplification, sequencing, labeling, detection, cloning, and many others. The present invention provides ribonucleotide reductases with modified properties for unnatural nucleic acids, methods of making such ribonucleotide reductases, methods of using such ribonucleotide reductases, and many other features that will become apparent upon a complete review of the following.

The invention includes ribonucleotide reductases that catalyze the formation of deoxyribonucleotides from ribonucleotides, e.g., for use during DNA synthesis or amplification. In some embodiments, ribonucleotide reductases can be modified such that the active site of the ribonucleotide reductases is modified to reduce steric entry inhibition of the unnatural nucleic acid into the active site. In some embodiments, ribonucleotide reductases can be modified to provide complementarity with one or more unnatural features of an unnatural nucleic acid. In some embodiments, ribonucleotide reductases can be modified to provide complementarity with one or more natural features of an unnatural nucleic acid. Such ribonucleotide reductases can be expressed or engineered in cells for stably incorporating a UBP into the cells. Accordingly, the invention includes compositions that include a heterologous or recombinant ribonucleotide reductases and methods of use thereof.

Ribonucleotide reductases can be modified using methods pertaining to protein engineering. For example, molecular modeling can be carried out based on crystal structures to identify the locations of the ribonucleotide reductases where mutations can be made to modify a target activity. A residue identified as a target for replacement can be replaced with a residue selected using energy minimization modeling, homology modeling, and/or conservative amino acid substitutions, such as described in Bordo et al., J Mol Biol 217: 721-729 (1991) and Hayes et al., Proc Natl Acad Sci, USA 99: 15926-15931 (2002).

Any of a variety of ribonucleotide reductases can be used in a method or composition set forth herein including, for example, protein-based enzymes isolated from biological systems and functional variants thereof. Reference to a particular ribonucleotide reductase, such as those exemplified below, will be understood to include functional variants thereof unless indicated otherwise. In some embodiments, a ribonucleotide reductase is a wild type polymerase. In some embodiments, a ribonucleotide reductase is a modified, or mutant, ribonucleotide reductase.

Ribonucleotide reductases, with features for improving conversion of natural and/or unnatural deoxyribonucleotide triphosphate nucleic acids to natural and/or unnatural ribonucleotide triphosphates. Ribonucleotide reductases, with features for coordinating with unnatural nucleotides in the active site region, can also be used. In some embodiments, a modified ribonucleotide reductase has a modified nucleotide binding site. In some embodiments, a modified or wild type ribonucleotide reductase has a relaxed specificity for an unnatural nucleic acid.

In some embodiments, a modified ribonucleotide reductase has a specificity for an unnatural nucleic acid that is at least about 10%, 20%, 30%, 40%, 50%, 60%, 70%, 80%, 90%, 95%, 97%, 98%, 99%, 99.5%, 99.99% the specificity of the wild type ribonucleotide reductase toward the unnatural nucleic acid. In some embodiments, a modified or wild type ribonucleotide reductase has a specificity for an unnatural nucleic acid comprising a modified sugar that is at least about 10%, 20%, 30%, 40%, 50%, 60%, 70%, 80%, 90%, 95%, 97%, 98%, 99%, 99.5%, 99.99% the specificity of the wild type ribonucleotide reductase toward a natural nucleic acid and/or the unnatural nucleic acid without the modified sugar. In some embodiments, a modified or wild type ribonucleotide reductase has a specificity for an unnatural nucleic acid comprising a modified base that is at least about 10%, 20%, 30%, 40%, 50%, 60%, 70%, 80%, 90%, 95%, 97%, 98%, 99%, 99.5%, 99.99% the specificity of the wild type ribonucleotide reductase toward a natural nucleic acid and/or the unnatural nucleic acid without the modified base. In some embodiments, a modified or wild type ribonucleotide reductase has a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type ribonucleotide reductase toward a nucleic acid comprising a triphosphate and/or the unnatural nucleic acid without the triphosphate. For example, a modified or wild type ribonucleotide reductase can have a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type ribonucleotide reductase toward the unnatural nucleic acid with a diphosphate or monophosphate, or no phosphate, or a combination thereof.

In some embodiments, a modified or wild type ribonucleotide reductase has a specificity for an unnatural nucleic acid and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type ribonucleotide reductase toward the natural nucleic acid. In some embodiments, a modified or wild type ribonucleotide reductase has a specificity for an unnatural nucleic acid comprising a modified sugar and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type ribonucleotide reductase toward the natural nucleic acid. In some embodiments, a modified or wild type ribonucleotide reductase has a specificity for an unnatural nucleic acid comprising a modified base and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type ribonucleotide reductase toward the natural nucleic acid. In some embodiments, a modified or wild type ribonucleotide reductase has a specificity for an unnatural nucleic acid comprising a triphosphate and a specificity to a natural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type ribonucleotide reductase toward the natural nucleic acid triphosphate.

In a related aspect, the invention provides methods of making a modified ribonucleotide reductase that include structurally modeling a parental ribonucleotide reductase, e.g., a DNA ribonucleotide reductase, identifying one or more complex stability or nucleotide interaction feature affecting complex stability or nucleotide access or binding in the active site or a complementarity feature for a nucleotide analog at the active site, and mutating the parental ribonucleotide reductase to include or remove these features. For example, the ribonucleotide reductase can be mutated to improve steric access of the unnatural nucleotide to the active site or to improve charge-charge or hydrophobic interactions between the unnatural nucleotide and the ribonucleotide reductase. The methods also include determining whether the resulting modified ribonucleotide reductase displays an increased incorporation of a nucleotide or unnatural nucleotide into a growing nucleic acid copy as compared to the parental ribonucleotide reductase.

Ribonucleotide reductases can be characterized according to their rate of dissociation from nucleic acids. In some embodiments a ribonucleotide reductase has a relatively low dissociation rate for one or more natural and unnatural nucleic acids. In some embodiments a ribonucleotide reductase has a relatively high dissociation rate for one or more natural and unnatural nucleic acids. The dissociation rate is an activity of a ribonucleotide reductase that can be adjusted to tune reaction rates in methods set forth herein.

Ribonucleotide reductases from native sources or variants thereof can be screened using an assay that detects incorporation of an unnatural nucleic acid having a particular structure. In one example, ribonucleotide reductases can be screened for the ability to incorporate an unnatural nucleic acid or UBP; e.g., (d)5SICSTP, (d)NaMTP, (d)TPT3TP, (d)TPT3TP-(d)NaMTP UBP, or (d)5SICSTP-(d)NaMTP UBP. A ribonucleotide reductase, e.g., a heterologous ribonucleotide reductase, can be used that displays a modified property for the unnatural nucleic acid as compared to the wild-type ribonucleotide reductase. For example, the modified property can be, e.g., $K_m$, $k_{cat}$, $V_{max}$, ribonucleotide reductase processivity in the presence of an unnatural nucleic acid (or of a naturally occurring nucleotide), turnover rate by the ribonucleotide reductase in the presence of an unnatural nucleic acid, specificity of the ribonucleotide reductase for an unnatural nucleic acid, rate of binding of an unnatural nucleic acid, rate of product (pyrophosphate, triphosphate, etc.), or any combination thereof. In one embodiment, the modified property is a reduced $K_m$ for an unnatural nucleic acid and/or an increased $k_{cat}/K_m$ or $V_{max}/K_m$ for an unnatural nucleic acid. Similarly, the ribonucleotide reductase optionally has an increased rate of binding of an unnatural nucleic acid and/or an increased rate of product release, as compared to a wild-type ribonucleotide reductase.

At the same time, a ribonucleotide reductase can process natural deoxyribonucleic acids, e.g., dA, dC, and dG, into natural deoxyribonucleic acids. For example, a ribonucleotide reductase optionally displays a specific activity for a natural nucleic acid that is at least about 5% as high (e.g., 5%, 10%, 25%, 50%, 75%, 100% or higher), as a corresponding wild-type ribonucleotide reductase and a $k_{cat}$ that is at least 5% as high (e.g., 5%, 10%, 25%, 50%, 75%, 100% or higher) as the wild-type ribonucleotide reductase in the presence of the natural nucleic acid. Optionally, the ribonucleotide reductase displays a $k_{cat}/K_m$ or $V_{max}/K_m$ for a naturally occurring nucleotide that is at least about 5% as high (e.g., about 5%, 10%, 25%, 50%, 75% or 100% or higher) as the wild-type ribonucleotide reductase.

Ribonucleotide reductases used herein that can have the ability to incorporate an unnatural nucleic acid of a particular structure can also be produced using a directed evolution approach. A nucleic acid synthesis assay can be used to screen for ribonucleotide reductase variants having specificity for any of a variety of unnatural nucleic acids. For example, ribonucleotide reductase variants can be screened for the ability to incorporate an unnatural nucleic acid or UBP; e.g., (d)5SICSTP, (d)NaMTP, (d)TPT3TP, (d)TPT3TP-(d)NaMTP UBP, or (d)5SICSTP-(d)NaMTP UBP into nucleic acids. In some embodiments, such an assay is an in vitro assay, e.g., using a recombinant ribonucleotide reductase variant. In some embodiments, such an assay is an in vivo assay, e.g., expressing a ribonucleotide reductase variant in a cell. Such directed evolution techniques can be used to screen variants of any suitable ribonucleotide reductase for activity toward any of the unnatural nucleic acids set forth herein.

Engineered Cells

Methods and compositions (e.g., nucleic acids and reagents) described herein can be used to generate engineered microorganisms, e.g., a living cell that incorporates and replicates at least one unnatural nucleotide or at least one UBP within its cellular environment. The cell employed can be genetically transformed with an expression cassette encoding a heterologous protein, e.g., a nucleotide triphosphate transporter capable of transporting unnatural nucleotide triphosphates into the cell and/or a polymerase with high fidelity for an unnatural nucleic acid, so that the unnatural nucleotides can be incorporated into cellular nucleic acids and can, e.g., form UBPs under in vivo conditions. Cells can comprise enhanced activity for unnatural nucleic acid uptake. Cells can comprise enhanced activity for unnatural nucleic acid import. Cells can comprise enhanced polymerase activity for unnatural nucleic acids.

Accordingly, by practice of a method of the invention, a living cell is generated that incorporates within its nucleic acids at least one unnatural nucleotide and/or at least one UBP. The UBP can include a pair of unnatural mutually base-pairing nucleotides capable of forming the UBP under in vivo conditions, when the unnatural mutually base-pairing nucleotides, as their respective triphosphates, are taken up into the cell by action of a nucleotide triphosphate transporter. The cell can be genetically transformed by an expression cassette encoding a nucleotide triphosphate transporter so that the nucleotide triphosphate transporter is expressed and is available to transport the unnatural nucleotides into the cell. The cell can be genetically transformed by an expression cassette encoding a polymerase so that the polymerase is expressed and is available to incorporate unnatural nucleotides into the cell's nucleic acids. The cell can be a prokaryotic or eukaryotic cell. The pair of unnatural mutually base-pairing nucleotides, as their respective triphosphates, can be a triphosphate of (d)5SICS ((d)5SICSTP) and a triphosphate of (d)NaM ((d)NaMTP). The pair of unnatural mutually base-pairing nucleotides, as their respective triphosphates, can be a triphosphate of (d)TPT3 ((d)TPT3TP) and a triphosphate of (d)NaM ((d)NaMTP).

The cell can comprise a template UBP. A template UBP can be a UBP present on a nucleic acid inside the cell that comprises a first and a second unnatural template nucleic acid. The unnatural template nucleic acids can base pair with the imported unnatural nucleic acids. For example, an imported nucleic acid can form a UBP by base pairing with an unnatural template nucleic acid present in the cell. In some embodiments, the template UBP is formed outside of the cell. In some embodiments, the template UBP is introduced into the cell, such as by transfection, electroporation, or the like.

Cells can be genetically transformed cells with a nucleic acid, e.g., an expression cassette encoding a nucleotide triphosphate transporter capable of transporting such unnatural nucleotides into the cell. A cell can comprise a heterologous nucleotide triphosphate transporter, where the heterologous nucleotide triphosphate transporter can transport natural and unnatural nucleotide triphosphates into the cell. A cell can comprise a heterologous polymerase, where the heterologous polymerase has activity for an unnatural nucleic acid.

A method can also include contacting a genetically transformed cell with the respective triphosphate forms unnatural nucleotides, in the presence of potassium phosphate and/or an inhibitor of phosphatases or nucleotidases. During or after such contact, the cell can be placed within a life-supporting medium suitable for growth and replication of the cell. The cell can be maintained in the life-supporting medium so that the respective triphosphate forms of unnatural nucleotides are incorporated into nucleic acids within the cells, and through at least one replication cycle of the cell. The pair of unnatural mutually base-pairing nucleotides as a respective triphosphate, can comprise a triphosphate of (d)5SICS ((d)5SICSTP) and a triphosphate of (d)NaM ((d)NaMTP). The pair of unnatural mutually base-pairing nucleotides as a respective triphosphate, can comprise a triphosphate of (d)TPT3 ((d)TPT3TP) and a triphosphate of (d)NaM ((d)NaMTP). The cell can be *E. coli*, and the (d)5SICSTP and (d)NaMTP or (d)TPT3TP and (d)NaMTP can be efficiently imported into *E. coli* by, for example, the transporter PtNTT2, wherein an *E. coli* polymerase, such as Pol I, can efficiently use the unnatural triphosphates to replicate DNA, thereby incorporating unnatural nucleotides and/or UBPs into cellular nucleic acids within the cellular environment.

By practice of a method of the invention, the person of ordinary skill can obtain a population of a living and propagating cells that has at least one unnatural nucleotide and/or at least one UBP within at least one nucleic acid maintained within at least some of the individual cells, wherein the at least one nucleic acid is stably propagated within the cell, and wherein the cell expresses a nucleotide triphosphate transporter suitable for providing cellular uptake of triphosphate forms of one or more unnatural nucleotides when contacted with (e.g., grown in the presence of) the unnatural nucleotide(s) in a life-supporting medium suitable for growth and replication of the organism.

After transport into the cell by the nucleotide triphosphate transporter, the unnatural base-pairing nucleotides are incorporated into nucleic acids within the cell by cellular machinery, e.g., the cell's own DNA and/or RNA polymerases, a heterologous polymerase, or a polymerase that has been evolved using directed evolution (Chen and Romesberg, FEBS Lett. (2014) 588(2):219-29). The unnatural nucleotides can be incorporated into cellular nucleic acids such as genomic DNA, genomic RNA, mRNA, structural RNA, microRNA, and autonomously replicating nucleic acids (e.g., plasmids, viruses, or vectors).

Genetically engineered cells can be generated by introduction of nucleic acids, e.g., heterologous nucleic acids, into cells. Any cell described herein can be a host cell and can comprise an expression vector. In one embodiment, the host cell is a prokaryotic cell. In another embodiment, the host cell is *E. coli*. In some embodiments, a cell comprises one or more heterologous polynucleotides. Nucleic acid reagents can be introduced into microorganisms using various techniques. Non-limiting examples of methods used to introduce heterologous nucleic acids into various organisms include; transformation, transfection, transduction, electroporation, ultrasound-mediated transformation, particle bombardment and the like. In some instances the addition of carrier molecules (e.g., bis-benzimdazolyl compounds, for example, see U.S. Pat. No. 5,595,899) can increase the uptake of DNA in cells typically though to be difficult to transform by conventional methods. Conventional methods of transformation are readily available to the artisan and can be found in Maniatis et al., (1982) Molecular Cloning: a Laboratory Manual; Cold Spring Harbor Laboratory, Cold Spring Harbor, N.Y.

Genetic transformation can be obtained using direct transfer of an expression cassette, in but not limited to, plasmids, viral vectors, viral nucleic acids, phage nucleic acids, phages, cosmids, and artificial chromosomes, or via transfer of genetic material in cells or carriers such as cationic liposomes. Such methods are available in the art and readily adaptable for use in the method described herein. Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)). Appropriate means for transfection, including viral vectors, chemical transfectants, or physico-mechanical methods such as electroporation and direct diffusion of DNA, are described by, for example, Wolff et al., Science, 247, 1465-1468, (1990); and Wolff, Nature, 352, 815-818, (1991).

For example, a nucleotide triphosphate transporter or polymerase nucleic acid molecule, expression cassette and/or vector can be introduced to a cell by any method including, but not limited to, calcium-mediated transformation, electroporation, microinjection, lipofection, particle bombardment and the like.

A cell can comprise unnatural nucleotide triphosphates incorporated into one or more nucleic acids within the cell. For example, the cell can be a living cell capable of incorporating at least one unnatural nucleotide within DNA or RNA maintained within the cell. The cell can also incorporate at least one UBP comprising a pair of unnatural mutually base-pairing nucleotides into nucleic acids within the cell under in vivo conditions, wherein the unnatural mutually base-pairing nucleotides, e.g., their respective triphosphates, are taken up into the cell by action of a nucleotide triphosphate transporter, the gene for which is present (e.g., was introduced) into the cell by genetic transformation. For example, upon incorporation into the nucleic acid maintained within a cell, (d)5SICS and (d)NaM can form a stable UBP that can be stably propagated by the DNA replication machinery of an organism, e.g., when grown in a life-supporting medium comprising (d)5SICS and (d)NaM. For example, upon incorporation into the nucleic acid maintained within a cell, (d)TPT3 and (d)NaM can form a stable UBP that can be stably propagated by the DNA replication machinery of an organism, e.g., when grown in a life-supporting medium comprising (d)TPT3 and (d)NaM.

Cells can be capable of replicating an unnatural nucleic acid. Provided herein, is a method of generating a living cell with nucleic acids that incorporate and/or replicate at least one unnatural nucleotide and/or at least one UBP comprising a pair of unnatural mutually base-pairing nucleotides, into the cell's nucleic acids under in vivo conditions. Such methods can include genetically transforming the cell with an expression cassette encoding a nucleotide triphosphate transporter capable of transporting into the cell, as a respective triphosphate, one or more unnatural nucleotides under in vivo conditions. Alternatively, a cell can be employed that has previously been genetically transformed with an expression cassette that can express an encoded nucleotide triphosphate transporter. The method can also include contacting or exposing the genetically transformed cell to potassium phosphate and the respective triphosphate forms of at least one unnatural nucleotide (e.g., two mutually base-pairing nucleotides capable of forming the UBP) in a life-supporting medium suitable for growth and replication of the cell, and maintaining the transformed cell in the life-supporting medium in the presence of the respective triphosphate forms of at least one unnatural nucleotide (e.g., two mutually base-pairing nucleotides capable of forming the UBP) under in vivo conditions, through at least one replication cycle of the cell.

Cells can comprise a stably propagated unnatural nucleic acid. Provided herein is a population of a living and propagating cells, comprising within the nucleic acids of at least some of the individual cells of the population at least one unnatural nucleotide (e.g., two mutually base-pairing nucleotides capable of forming the UBP) or at least one UBP, as a stably propagated component of the DNA of the cell, wherein the cell is genetically transformed with a nucleotide triphosphate transporter suitable for providing cellular uptake of triphosphate forms of the pair of unnatural nucleotides. The population of cells can be grown in the presence of the respective triphosphate forms of the pair of unnatural nucleotides, in a life-supporting medium suitable for growth and replication of the organism.

A cell can comprise a stably incorporated unnatural nucleic acid. Some embodiments comprise a cell (e.g., as *E. coli*) that stably incorporates nucleotides other than A, G, T, and C within nucleic acids maintained within the cell. For example, the nucleotides other than A, G, T, and C can be (d)5SICS, (d)TPT3 and (d)NaM, which upon incorporation into nucleic acids of the cell, can form a stable UBP within the nucleic acids. In one aspect, unnatural nucleotides and UBPs can be stably propagated by the replication apparatus of the organism, when an organism transformed with the gene for the triphosphate transporter, is grown in a life-supporting medium that includes potassium phosphate and the triphosphate forms of (d)5SICS, (d)TPT3 and (d)NaM.

A cell can comprise an expanded genetic alphabet. A cell can comprise a stably incorporated unnatural nucleic acid. In some embodiments, a cell with an expanded genetic alphabet comprises an unnatural nucleic acid that can form a base pair (bp) with another nucleic acid, e.g., a natural or unnatural nucleic acid. In some embodiments, a cell with an expanded genetic alphabet comprises an unnatural nucleic acid that is hydrogen bonded to another nucleic acid. In some embodiments, a cell with an expanded genetic alphabet comprises an unnatural nucleic acid that is not hydrogen bonded to another nucleic acid to which it is base paired. In some embodiments, a cell with an expanded genetic alphabet comprises an unnatural nucleic acid that base pairs to another nucleic acid via hydrophobic interactions. In some embodiments, a cell with an expanded genetic alphabet comprises an unnatural nucleic acid that base pairs to another nucleic acid via non-hydrogen bonding interactions. A cell with an expanded genetic alphabet can be a cell that can copy a homologous nucleic acid to form a nucleic acid comprising an unnatural nucleic acid. A cell with an expanded genetic alphabet can be a cell comprising an unnatural nucleic acid base paired with another unnatural nucleic acid (UBP).

Cells can form UBPs from the imported unnatural nucleotides under in vivo conditions. In some embodiments potassium phosphate and/or inhibitors of phosphatase and/or nucleotidase activities can facilitate transport of unnatural nucleic acids. The methods include use of a cell that expresses a heterologous nucleotide triphosphate transporter. When such a cell is contacted with one or more nucleotide triphosphates, the nucleotide triphosphates are transported into the cell. The cell can be in the presence of potassium phosphate and/or inhibitors of phosphatase and nucleotidase. Unnatural nucleotide triphosphates can be incorporated into nucleic acids within the cell by the cell's natural machinery and, for example, can mutually base-pair to form UBPs within the nucleic acids of the cell.

In some embodiments a UBP can be incorporated into a cell or population of cells when exposed to unnatural triphosphates. In some embodiments a UBP can be incorporated into a cell or population of cells when substantially consistently exposed to unnatural triphosphates. In some embodiments, replication of a UBP does not result in a substantially reduced growth rate. In some embodiments, replication expression of a heterologous protein, e.g., a nucleotide triphosphate transport does not result in a substantially reduced growth rate.

In some embodiments, induction of expression of a heterologous gene, e.g., an NTT, in a cell can result in slower cell growth and increased natural and/or unnatural nucleic acid uptake compared to the growth and uptake of a cell without induction of expression of the heterologous gene. In some embodiments, induction of expression of a heterologous gene, e.g., an NTT, in a cell can result in increased cell growth and increased natural and/or unnatural nucleic acid uptake compared to the growth and uptake of a cell without induction of expression of the heterologous gene.

In some embodiments, induction of expression of a heterologous gene, e.g., an NTT, in a cell treated with a first concentration of an induction reagent can result in slower cell growth and increased natural and/or unnatural nucleic acid uptake compared to the growth and uptake of a cell without induction of expression of the heterologous gene. In some embodiments, induction of expression of a heterologous gene, e.g., an NTT, can result in increased cell growth and increased natural and/or unnatural nucleic acid uptake compared to the growth and uptake of a cell treated with a first concentration of an induction reagent.

In some embodiments, a UBP is incorporated during a log growth phase. In some embodiments, a UBP is incorporated during a non-log growth phase. In some embodiments, a UBP is incorporated during a substantially linear growth phase. In some embodiments a UBP is stably incorporated into a cell or population of cells after growth for a time period. For example, a UBP can be stably incorporated into a cell or population of cells after growth for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 50 or more duplications. For example, a UBP can be stably incorporated into a cell or population of cells after growth for at least about 1, 2, 3, 4, 5, 6, 7, 8, 9, 10, 11, 12, 13, 14, 15, 16, 17, 18, 19, 20, 21, 22, 23, or 24 hours of growth. For example, a UBP can be stably incorporated into a cell or population of cells after growth for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days of growth. For example, a UBP can be stably incorporated into a cell or population of cells after growth for at least about 1, 2, 3, 4, 5, 6, 7, 8, 9, 10, 11, or 12 months of growth. For example, a UBP can be stably incorporated into a cell or population of cells after growth for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50 years of growth.

In some embodiments a UBP is not efficiently recognized by DNA repair pathways of a cell. In some embodiments a UBP is not efficiently removed by a cell. In some embodiments a UBP is not efficiently excised by a cell. In some embodiments a UBP is not efficiently removed from a cell or population of cells after a time period. For example, a UBP cannot be efficiently removed from a cell or population of cells after growth for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 50 or more duplications. For example, a UBP cannot be efficiently removed from a cell or population of cells after growth for at least about 1, 2, 3, 4, 5, 6, 7, 8, 9, 10, 11, 12, 13, 14, 15, 16, 17, 18, 19, 20, 21, 22, 23, or 24 hours of growth. For example, a UBP cannot be efficiently removed from a cell or population of cells after growth for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days of growth. For example, a UBP cannot be efficiently removed from a cell or population of cells after growth for at least about 1, 2, 3, 4, 5, 6, 7, 8, 9, 10, 11, or 12 months of growth. For example, a UBP cannot be efficiently removed from a cell or population of cells after growth for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50 years of growth.

Thus an organism can be generated that stably harbors an expanded genetic alphabet.

Cell Types

Many types of cells/microorganisms can be used, e.g., for transforming or genetically engineering. A cell can be a prokaryotic or eukaryotic cell. For example, the cell can be a microorganism such as a bacterial cell, fungal cell, yeast, or unicellular protozoan. Alternatively, the cell can be a eukaryotic cell, such as a cultured animal, plant, or human cell. The cell can be present in an organism such as a plant or animal.

In some embodiments an engineered microorganism is a single cell organism, often capable of dividing and proliferating. A microorganism can include one or more of the following features: aerobe, anaerobe, filamentous, non-filamentous, monoploid, dipoid, auxotrophic and/or non-auxotrophic. In certain embodiments, an engineered microorganism is a prokaryotic microorganism (e.g., bacterium), and in certain embodiments, an engineered microorganism is a non-prokaryotic microorganism. In some embodiments, an engineered microorganism is a eukaryotic microorganism (e.g., yeast, fungi, amoeba). In some embodiments, an engineered microorganism is a fungus. In some embodiments, an engineered organism is yeast.

Any suitable yeast may be selected as a host microorganism, engineered microorganism, genetically modified organism or source for a heterologous or modified polynucleotide. Yeast include, but are not limited to, *Yarrowia* yeast (e.g., *Y. lipolytica* (formerly classified as *Candida lipolytica*)), *Candida* yeast (e.g., *C. revkaufi, C. viswanathii, C. pulcherrima, C. tropicalis, C. utilis*), *Rhodotorula* yeast (e.g., *R. glutinus, R. graminis*), *Rhodosporidium* yeast (e.g., *R. toruloides*), *Saccharomyces* yeast (e.g., *S. cerevisiae, S. bayanus, S. pastorianus, S. carlsbergensis*), *Cryptococcus* yeast, *Trichosporon* yeast (e.g., *T. pullans, T. cutaneum*), *Pichia* yeast (e.g., *P. pastoris*) and *Lipomyces* yeast (e.g., *L. starkeyii, L. lipoferus*). In some embodiments, a suitable yeast is of the genus *Arachniotus, Aspergillus, Aureobasidium, Auxarthron, Blastomyces, Candida, Chrysosporuim, Chrysosporuim Debaryomyces, Coccidiodes, Cryptococcus, Gymnoascus, Hansenula, Histoplasma, Issatchenkia, Kluyveromyces, Lipomyces, Lssatchenkia, Microsporum, Myxotrichum, Myxozyma, Oidiodendron, Pachysolen, Penicillium, Pichia, Rhodosporidium, Rhodotorula, Rhodotorula, Saccharomyces, Schizosaccharomyces, Scopulariopsis, Sepedonium, Trichosporon*, or *Yarrowia*. In some embodiments, a suitable yeast is of the species *Arachniotus flavoluteus, Aspergillus flavus, Aspergillus fumigatus, Aspergillus niger, Aureobasidium pullulans, Auxarthron thaxteri, Blastomyces dermatitidis, Candida albicans, Candida dubliniensis, Candida famata, Candida glabrata, Candida guilliermondii, Candida kefyr, Candida krusei, Candida lambica, Candida lipolytica, Candida lustitaniae, Candida parapsilosis, Candida pulcherrima, Candida revkaufi, Candida rugosa, Candida tropicalis, Candida utilis, Candida viswanathii, Candida xestobii, Chrysosporuim keratinophilum, Coccidiodes immitis, Cryptococcus albidus* var. *diffluens, Cryptococcus laurentii, Cryptococcus neofomans, Debaryomyces hansenii, Gymnoascus dugwayensis, Hansenula anomala, Histoplasma capsulatum, Issatchenkia occidentalis, Isstachenkia orientalis, Kluyveromyces lactis, Kluyveromyces marxianus, Kluyveromyces thermotolerans, Kluyveromyces waltii, Lipomyces lipoferus, Lipomyces starkeyii, Microsporum gypseum, Myxotrichum deflexum, Oidiodendron echinulatum, Pachysolen tannophilis, Penicillium notatum, Pichia anomala, Pichia pastoris, Pichia stipitis, Rhodosporidium toruloides, Rhodotorula glutinus, Rhodotorula graminis, Saccharomyces cerevisiae, Saccharomyces kluyveri, Schizosaccharomyces pombe, Scopulariopsis acremonium, Sepedonium chrysospermum, Trichosporon cutaneum, Trichosporon pullans, Yarrowia lipolytica*, or *Yarrowia lipolytica* (formerly classified as *Candida lipolytica*). In some embodiments, a yeast is a *Y. lipolytica* strain that includes, but is not limited to, ATCC20362, ATCC8862, ATCC18944, ATCC20228, ATCC76982 and LGAM S(7)1 strains (Papanikolaou S., and Aggelis G., Bioresour. Technol. 82(1):43-9 (2002)). In certain embodiments, a yeast is a *Candida* species (i.e., *Candida* spp.) yeast. Any suitable *Candida* species can be used and/or genetically modified for production of a fatty dicarboxylic acid (e.g., octanedioic acid, decanedioic acid, dodecanedioic acid, tetradecanedioic acid, hexadecanedioic acid, octadecanedioic acid, eicosanedioic acid). In some embodiments, suitable *Candida* species include, but are not limited to *Candida albicans, Candida dubliniensis, Candida famata, Candida glabrata, Candida guilliermondii, Candida kefyr, Candida krusei, Candida lambica, Candida lipolytica, Candida lustitaniae, Candida parapsilosis, Candida pulcherrima, Candida revkaufi, Candida rugosa, Candida tropicalis, Candida utilis, Candida viswanathii, Candida xestobii* and any other *Candida* spp. yeast described herein. Non-limiting examples of *Candida* spp. strains include, but are not limited to, sAA001 (ATCC20336), sAA002 (ATCC20913), sAA003 (ATCC20962), sAA496 (US2012/0077252), sAA106 (US2012/0077252), SU-2 (ura3-/ura3-), H5343 (beta oxidation blocked; U.S. Pat. No. 5,648,247) strains. Any suitable strains from *Candida* spp. yeast may be utilized as parental strains for genetic modification.

Yeast genera, species and strains are often so closely related in genetic content that they can be difficult to distinguish, classify and/or name. In some cases strains of *C. lipolytica* and *Y. lipolytica* can be difficult to distinguish, classify and/or name and can be, in some cases, considered the same organism. In some cases, various strains of *C. tropicalis* and *C. viswanathii* can be difficult to distinguish, classify and/or name (for example see Arie et al., J. Gen. Appl. Microbiol., 46, 257-262 (2000). Some *C. tropicalis* and *C. viswanathii* strains obtained from ATCC as well as from other commercial or academic sources can be considered equivalent and equally suitable for the embodiments described herein. In some embodiments, some parental strains of *C. tropicalis* and *C. viswanathii* are considered to differ in name only.

Any suitable fungus may be selected as a host microorganism, engineered microorganism or source for a heterologous polynucleotide. Non-limiting examples of fungi include, but are not limited to, *Aspergillus* fungi (e.g., *A. parasiticus, A. nidulans*), *Thraustochytrium* fungi, *Schizochytrium* fungi and *Rhizopus* fungi (e.g., *R. arrhizus, R. oryzae, R. nigricans*). In some embodiments, a fungus is an *A. parasiticus* strain that includes, but is not limited to, strain ATCC24690, and in certain embodiments, a fungus is an *A. nidulans* strain that includes, but is not limited to, strain ATCC38163.

Any suitable prokaryote may be selected as a host microorganism, engineered microorganism or source for a heterologous polynucleotide. A Gram negative or Gram positive bacteria may be selected. Examples of bacteria include, but are not limited to, *Bacillus* bacteria (e.g., *B. subtilis, B. megaterium*), *Acinetobacter* bacteria, *Norcardia* baceteria, *Xanthobacter* bacteria, *Escherichia* bacteria (e.g., *E. coli* (e.g., strains DH10B, Stb12, DH5-alpha, DB3, DB3.1), DB4, DB5, JDP682 and ccdA-over (e.g., U.S. application Ser. No. 09/518,188))), *Streptomyces* bacteria, *Erwinia* bacteria, *Klebsiella* bacteria, *Serratia* bacteria (e.g., *S. marcessans*), *Pseudomonas* bacteria (e.g., *P. aeruginosa*), *Salmonella* bacteria (e.g., *S. typhimurium, S. typhi*), *Megasphaera* bacteria (e.g., *Megasphaera elsdenii*). Bacteria also include, but are not limited to, photosynthetic bacteria (e.g., green non-sulfur bacteria (e.g., *Choroflexus* bacteria (e.g., *C. aurantiacus*), *Chloronema* bacteria (e.g., *C. gigateum*)), green sulfur bacteria (e.g., *Chlorobium* bacteria (e.g., *C. limicola*), *Pelodictyon* bacteria (e.g., *P. luteolum*), purple sulfur bacteria (e.g., *Chromatium* bacteria (e.g., *C. okenii*)), and purple non-sulfur bacteria (e.g., *Rhodospirillum* bacteria (e.g., *R. rubrum*), *Rhodobacter* bacteria (e.g., *R. sphaeroides, R. capsulatus*), and *Rhodomicrobium* bacteria (e.g., *R. vanellii*).

Cells from non-microbial organisms can be utilized as a host microorganism, engineered microorganism or source for a heterologous polynucleotide. Examples of such cells, include, but are not limited to, insect cells (e.g., *Drosophila* (e.g., *D. melanogaster*), *Spodoptera* (e.g., *S. frugiperda* Sf9 or Sf21 cells) and *Trichoplusa* (e.g., High-Five cells); nematode cells (e.g., *C. elegans* cells); avian cells; amphibian cells (e.g., *Xenopus laevis* cells); reptilian cells; mammalian cells (e.g., NIH3T3, 293, CHO, COS, VERO, C127, BHK, Per-C6, Bowes melanoma and HeLa cells); and plant cells (e.g., *Arabidopsis thaliana, Nicotania tabacum, Cuphea acinifolia, Cuphea aequipetala, Cuphea angustifolia, Cuphea appendiculata, Cuphea avigera, Cuphea avigera* var. *pulcherrima, Cuphea axilliflora, Cuphea bahiensis, Cuphea baillonis, Cuphea brachypoda, Cuphea bustamanta, Cuphea calcarata, Cuphea calophylla, Cuphea calophylla* subsp. *mesostemon, Cuphea carthagenensis, Cuphea circaeoides, Cuphea confertiflora, Cuphea cordata, Cuphea crassiflora, Cuphea cyanea, Cuphea decandra, Cuphea denticulata, Cuphea disperma, Cuphea epilobiifolia, Cuphea ericoides, Cuphea flava, Cuphea flavisetula, Cuphea fuchsiifolia, Cuphea gaumeri, Cuphea glutinosa, Cuphea heterophylla, Cuphea hookeriana, Cuphea hyssopifolia* (Mexican-heather), *Cuphea hyssopoides, Cuphea ignea, Cuphea ingrata, Cuphea jorullensis, Cuphea lanceolata, Cuphea linarioides, Cuphea llavea, Cuphea lophostoma, Cuphea lutea, Cuphea lutescens, Cuphea melanium, Cuphea melvilla, Cuphea micrantha, Cuphea micropetala, Cuphea mimuloides, Cuphea nitidula, Cuphea palustris, Cuphea parsonsia, Cuphea pascuorum, Cuphea paucipetala, Cuphea procumbens, Cuphea pseudosilene, Cuphea pseudovaccinium, Cuphea pulchra, Cuphea racemosa, Cuphea repens, Cuphea salicifolia, Cuphea salvadorensis, Cuphea schumannii, Cuphea sessiliflora, Cuphea sessilifolia, Cuphea setosa, Cuphea spectabilis, Cuphea spermacoce, Cuphea splendida, Cuphea splendida* var. *viridiflava, Cuphea strigulosa, Cuphea subuligera, Cuphea teleandra, Cuphea thymoides, Cuphea tolucana, Cuphea urens, Cuphea utriculosa, Cuphea viscosissima, Cuphea watsoniana, Cuphea wrightii*, and *Cuphea lanceolata*).

Microorganisms or cells used as host organisms or source for a heterologous polynucleotide are commercially available. Microorganisms and cells described herein, and other suitable microorganisms and cells are available, for example, from Invitrogen Corporation, (Carlsbad, Calif.), American Type Culture Collection (Manassas, Va.), and Agricultural Research Culture Collection (NRRL; Peoria, Ill.). Host microorganisms and engineered microorganisms may be provided in any suitable form. For example, such microorganisms may be provided in liquid culture or solid culture (e.g., agar-based medium), which may be a primary culture or may have been passaged (e.g., diluted and cultured) one or more times. Microorganisms also may be provided in frozen form or dry form (e.g., lyophilized). Microorganisms may be provided at any suitable concentration.

Stabilization of Nucleic Acids for Cellular Import

Figure 6A:
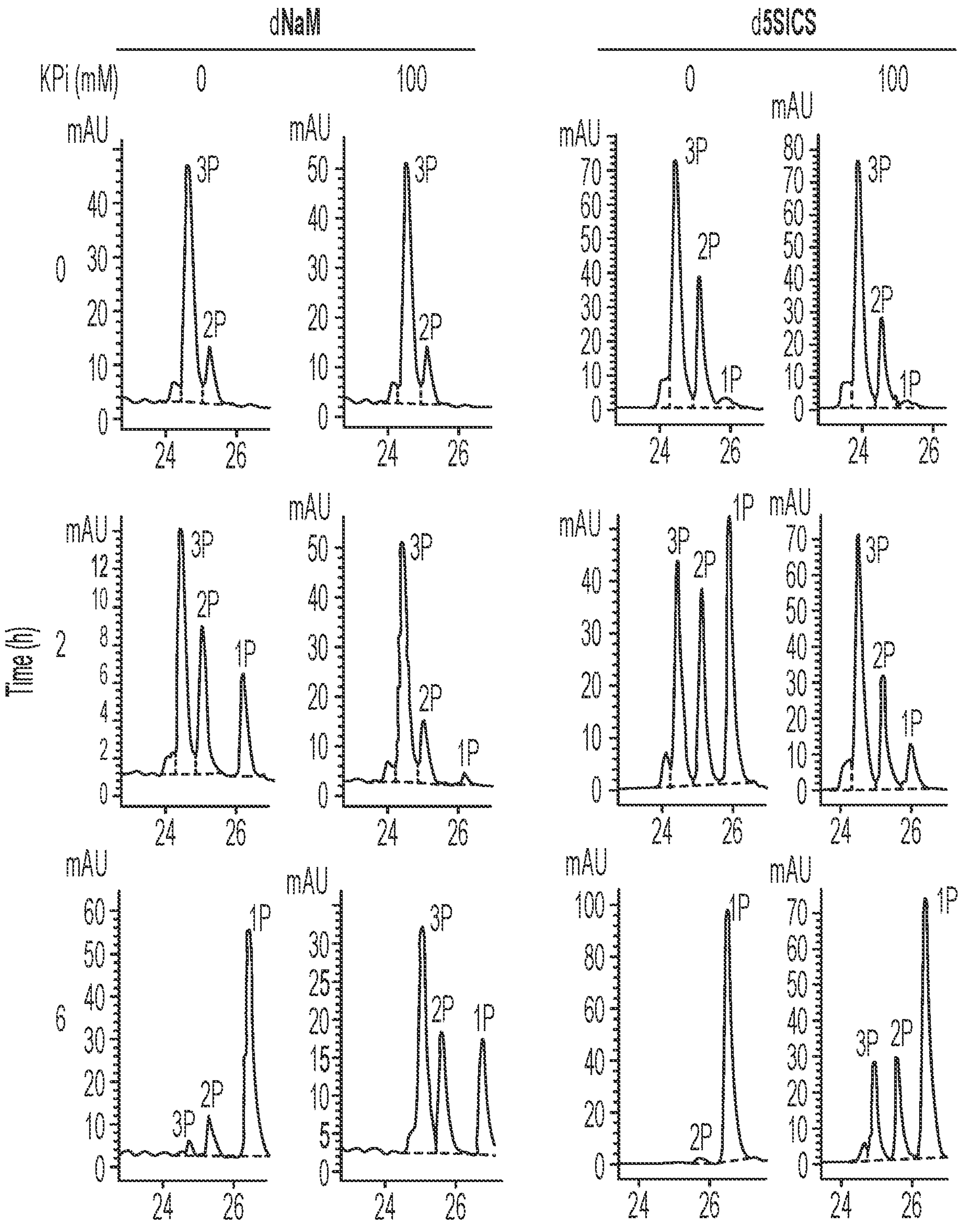
FIG. 6A depicts HPLC of unnatural triphosphates (3P) of dNaM and d5SICS from growing bacterial culture in the presence or absence of potassium phosphate (KPi).
Figure 6B:
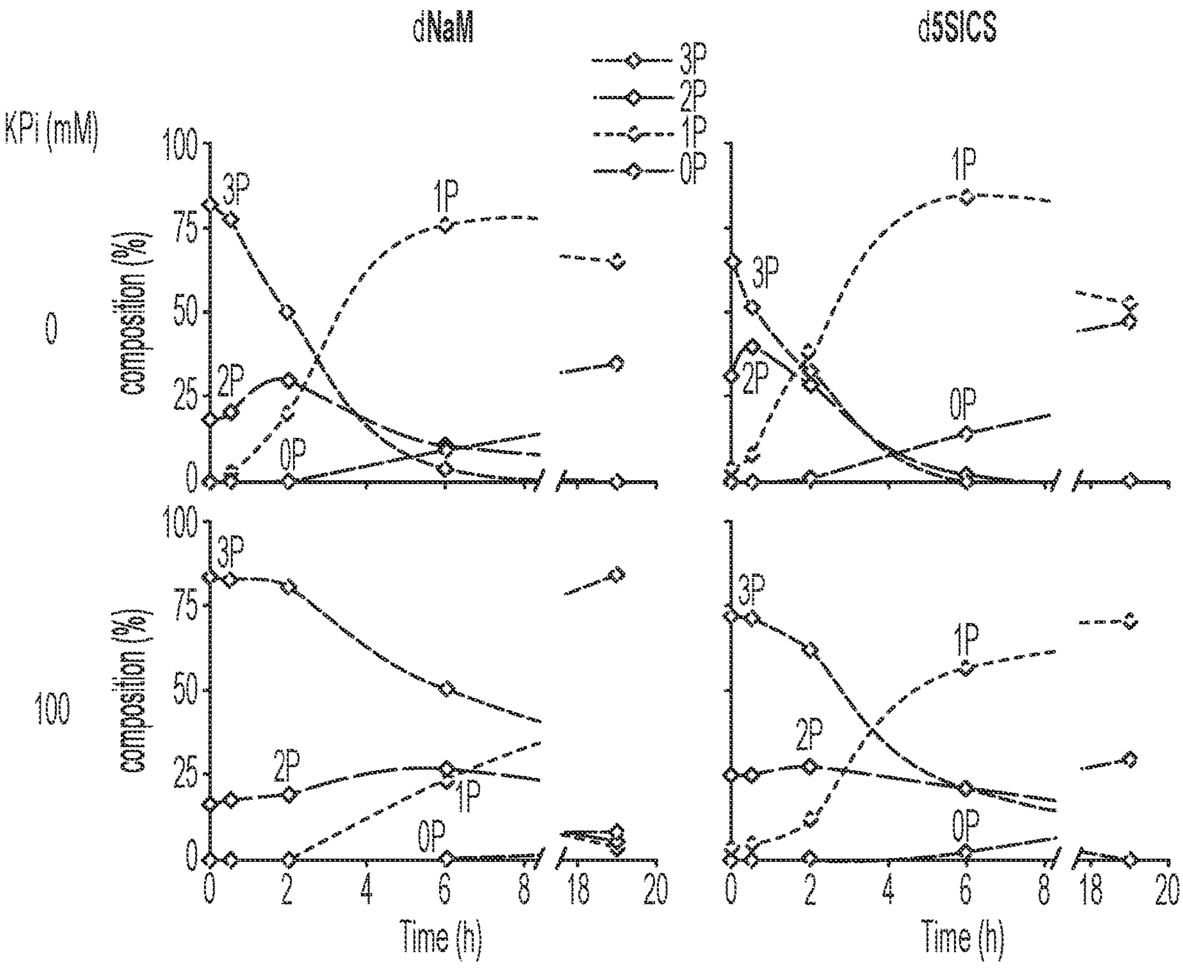
FIG. 6B depicts composition profiles of unnatural triphosphates of dNaM and d5SICS from growing bacterial culture in the presence or absence of KPi.

Active transport via a nucleotide triphosphate transporter has been discovered to be optimal when the transported unnatural nucleotide triphosphates are sufficiently stable, e.g., stable in culture media. Preliminary characterization of unnatural nucleic acids, e.g., d5SICSTP and dNaMTP, indicated that they are degraded in the presence of actively growing *E. coli* (FIG. 6B). Similar behavior was observed with [$\alpha$-$^{32}$P]-dATP, and the dephosphorylation products detected by thin layer chromatography for [$\alpha$-$^{32}$P]-dATP or by HPLC and MALDI for d5SICSTP and dNaMTP (FIG.

6A), suggested that decomposition was mediated by phosphatases. Minimal to negligent degradation was observed in spent media, suggesting that decomposition may occur within the periplasm. No improvement in stability was observed in cultures of single-gene deletion mutants of *E. coli* BW25113 lacking a specific periplasmic phosphatase (as identified by the presence of a Sec-type N-terminal leader sequence), including phoA, ushA, appA, aphA, yjjX, surE, yfbR, yjjG, yfaO, mutT, nagD, yggV, yrfG, or ymfB, suggesting that decomposition may occur as a result of the activity of multiple phosphatases.

The cells that express the nucleotide triphosphate transporter can be modified in a variety of other ways to facilitate nucleotide triphosphate importation and/or improve the stability of nucleotide triphosphates. For example, the cells can be modified by deletion or disruption, e.g., mutation, of one or more genes that encode a phosphatase or a nucleotidase. Such modifications can increase the stability of nucleotide triphosphates that can be imported by the nucleotide triphosphate transporter. Cells can be modified by deletion of one or more genes that encode phosphatases such as a 5' or 3' nucleotidase.

A nucleotidase is a hydrolytic enzyme that catalyzes the hydrolysis of a nucleotide into a nucleoside and a phosphate. For example, it converts adenosine monophosphate to adenosine, and guanosine monophosphate to guanosine. The nucleotidase that is modified or deleted from the cell can be a 5'-nucleotidase (such as EC 3.1.3.5) or a 3'-nucleotidase (such as EC 3.1.3.6). In some embodiments, it can be more useful to modify or eliminate a gene encoding a 5'-nucleotidase to improve the stability of nucleotide triphosphates that can be imported by the nucleotide triphosphate transporter.

Cells can also be modified by deletion of one or more genes that encode a 5'-nucleotidase (ENZYME entry: EC 3.1.3.5), such as one or more genes in Table 2.

TABLE 2

| 5'-Nucleotidases | | |
|---|---|---|
| Q7ZWS2, 5N3BA_XENLA; | Q7ZWS2, 5N3BA_XENLA; | Q7ZWS2, 5N3BA_XENLA; |
| Q2TAG6, 5N3BB_XENLA; | Q2TAG6, 5N3BB_XENLA; | Q2TAG6, 5N3BB_XENLA; |
| Q9BXI3, 5NT1A_HUMAN; | Q9BXI3, 5NT1A_HUMAN; | Q9BXI3, 5NT1A_HUMAN; |
| A3KFX0, 5NT1A_MOUSE; | A3KFX0, 5NT1A_MOUSE; | A3KFX0, 5NT1A_MOUSE; |
| Q96P26, 5NT1B_HUMAN; | Q96P26, 5NT1B_HUMAN; | Q96P26, 5NT1B_HUMAN; |
| Q91YE9, 5NT1B_MOUSE; | Q91YE9, 5NT1B_MOUSE; | Q91YE9, 5NT1B_MOUSE; |
| Q5ZID6, 5NT3A_CHICK; | Q5ZID6, 5NT3A_CHICK; | Q5ZID6, 5NT3A_CHICK; |
| Q9H0P0, 5NT3A_HUMAN; | Q9H0P0, 5NT3A_HUMAN; | Q9H0P0, 5NT3A_HUMAN; |
| Q9D020, 5NT3A_MOUSE; | Q9D020, 5NT3A_MOUSE; | Q9D020, 5NT3A_MOUSE; |
| Q5ZKF6, 5NT3B_CHICK; | Q5ZKF6, 5NT3B_CHICK; | Q5ZKF6, 5NT3B_CHICK; |
| Q9W197, 5NT3B_DROME; | Q9W197, 5NT3B_DROME; | Q9W197, 5NT3B_DROME; |
| Q969T7, 5NT3B_HUMAN; | Q969T7, 5NT3B_HUMAN; | Q969T7, 5NT3B_HUMAN; |
| Q3UFY7, 5NT3B_MOUSE; | Q3UFY7, 5NT3B_MOUSE; | Q3UFY7, 5NT3B_MOUSE; |
| Q6AYP7, 5NT3B_RAT; | Q6AYP7, 5NT3B_RAT; | Q6AYP7, 5NT3B_RAT; |
| Q09315, 5NT3_CAEEL; | Q09315, 5NT3_CAEEL; | Q09315, 5NT3_CAEEL; |
| Q7SYN4, 5NT3_DANRE; | Q7SYN4, 5NT3_DANRE; | Q7SYN4, 5NT3_DANRE; |
| O46411, 5NTC_BOVIN; | O46411, 5NTC_BOVIN; | O46411, 5NTC_BOVIN; |
| Q5ZIZ4, 5NTC_CHICK; | Q5ZIZ4, 5NTC_CHICK; | Q5ZIZ4, 5NTC_CHICK; |
| Q54XC1, 5NTC_DICDI; | Q54XC1, 5NTC_DICDI; | Q54XC1, 5NTC_DICDI; |
| P49902, 5NTC_HUMAN; | P49902, 5NTC_HUMAN; | P49902, 5NTC_HUMAN; |
| Q3V1L4, 5NTC_MOUSE; | Q3V1L4, 5NTC_MOUSE; | Q3V1L4, 5NTC_MOUSE; |
| Q5RA22, 5NTC_PONAB; | Q5RA22, 5NTC_PONAB; | Q5RA22, 5NTC_PONAB; |
| Q6DKB0, 5NTC_XENLA; | Q6DKB0, 5NTC_XENLA; | Q6DKB0, 5NTC_XENLA; |
| Q5EBF1, 5NTC_XENTR; | Q5EBF1, 5NTC_XENTR; | Q5EBF1, 5NTC_XENTR; |
| Q05927, 5NTD_BOVIN; | Q05927, 5NTD_BOVIN; | Q05927, 5NTD_BOVIN; |
| P29240, 5NTD_DIPOM; | P29240, 5NTD_DIPOM; | P29240, 5NTD_DIPOM; |
| P44569, 5NTD_HAEIN; | P44569, 5NTD_HAEIN; | P44569, 5NTD_HAEIN; |
| P21589, 5NTD_HUMAN; | P21589, 5NTD_HUMAN; | P21589, 5NTD_HUMAN; |
| Q9XZ43, 5NTD_LUTLO; | Q9XZ43, 5NTD_LUTLO; | Q9XZ43, 5NTD_LUTLO; |
| Q61503, 5NTD_MOUSE; | Q61503, 5NTD_MOUSE; | Q61503, 5NTD_MOUSE; |
| Q9I767, 5NTD_PSEAE; | Q9I767, 5NTD_PSEAE; | Q9I767, 5NTD_PSEAE; |
| P21588, 5NTD_RAT; | P21588, 5NTD_RAT; | P21588, 5NTD_RAT; |
| P52307, 5NTD_RHIMP; | P52307, 5NTD_RHIMP; | P52307, 5NTD_RHIMP; |
| O83142, 5NTD_TREPA; | O83142, 5NTD_TREPA; | O83142, 5NTD_TREPA; |
| Q9KQ30, 5NTD_VIBCH; | Q9KQ30, 5NTD_VIBCH; | Q9KQ30, 5NTD_VIBCH; |
| P22848, 5NTD_VIBPA; | P22848, 5NTD_VIBPA; | P22848, 5NTD_VIBPA; |
| Q8DFG4, 5NTD_VIBVU; | Q8DFG4, 5NTD_VIBVU; | Q8DFG4, 5NTD_VIBVU; |
| P0AF25, NAGD_ECO57; | P0AF25, NAGD_ECO57; | P0AF25, NAGD_ECO57; |
| P0AF24, NAGD_ECOLI; | P0AF24, NAGD_ECOLI; | P0AF24, NAGD_ECOLI; |
| O34313, NTPES_BACSU; | O34313, NTPES_BACSU; | O34313, NTPES_BACSU; |
| P15309, PPAP_HUMAN; | P15309, PPAP_HUMAN; | P15309, PPAP_HUMAN; |
| Q8CE08, PPAP_MOUSE; | Q8CE08, PPAP_MOUSE; | Q8CE08, PPAP_MOUSE; |
| P20646, PPAP_RAT; | P20646, PPAP_RAT; | P20646, PPAP_RAT; |
| Q390V3, SURE1_BURS3; | Q390V3, SURE1_BURS3; | Q390V3, SURE1_BURS3; |
| Q823A6, SURE1_CHLCV; | Q823A6, SURE1_CHLCV; | Q823A6, SURE1_CHLCV; |
| Q8ZU79, SURE1_PYRAE; | Q8ZU79, SURE1_PYRAE; | Q8ZU79, SURE1_PYRAE; |
| Q72H70, SURE1_THET2; | Q72H70, SURE1_THET2; | Q72H70, SURE1_THET2; |
| Q39FP8, SURE2_BURS3; | Q39FP8, SURE2_BURS3; | Q39FP8, SURE2_BURS3; |
| Q823A7, SURE2_CHLCV; | Q823A7, SURE2_CHLCV; | Q823A7, SURE2_CHLCV; |
| Q8ZSY4, SURE2_PYRAE; | Q8ZSY4, SURE2_PYRAE; | Q8ZSY4, SURE2_PYRAE; |
| Q746M5, SURE2_THET2; | Q746M5, SURE2_THET2; | Q746M5, SURE2_THET2; |
| B0C6V3, SURE_ACAM1; | B0C6V3, SURE_ACAM1; | B0C6V3, SURE_ACAM1; |
| Q6FCV6, SURE_ACIAD; | Q6FCV6, SURE_ACIAD; | Q6FCV6, SURE_ACIAD; |
| B7GZ27, SURE_ACIB3; | B7GZ27, SURE_ACIB3; | B7GZ27, SURE_ACIB3; |
| B7I4K2, SURE_ACIB5; | B7I4K2, SURE_ACIB5; | B7I4K2, SURE_ACIB5; |

TABLE 2-continued

| 5'-Nucleotidases | | |
|---|---|---|
| B2HVM9, SURE_ACIBC; | B2HVM9, SURE_ACIBC; | B2HVM9, SURE_ACIBC; |
| B0VUE2, SURE_ACIBS; | B0VUE2, SURE_ACIBS; | B0VUE2, SURE_ACIBS; |
| A3M7F7, SURE_ACIBT; | A3M7F7, SURE_ACIBT; | A3M7F7, SURE_ACIBT; |
| B0VBZ1, SURE_ACIBY; | B0VBZ1, SURE_ACIBY; | B0VBZ1, SURE_ACIBY; |
| B9MFW6, SURE_ACIET; | B9MFW6, SURE_ACIET; | B9MFW6, SURE_ACIET; |
| A3N3M1, SURE_ACTP2; | A3N3M1, SURE_ACTP2; | A3N3M1, SURE_ACTP2; |
| B3H2Z8, SURE_ACTP7; | B3H2Z8, SURE_ACTP7; | B3H2Z8, SURE_ACTP7; |
| B0BTK8, SURE_ACTPJ; | B0BTK8, SURE_ACTPJ; | B0BTK8, SURE_ACTPJ; |
| A6VLU0, SURE_ACTSZ; | A6VLU0, SURE_ACTSZ; | A6VLU0, SURE_ACTSZ; |
| A0KGH8, SURE_AERHH; | A0KGH8, SURE_AERHH; | A0KGH8, SURE_AERHH; |
| Q9YDW8, SURE_AERPE; | Q9YDW8, SURE_AERPE; | Q9YDW8, SURE_AERPE; |
| A4SRB6, SURE_AERS4; | A4SRB6, SURE_AERS4; | A4SRB6, SURE_AERS4; |
| B9JEH2, SURE_AGRRK; | B9JEH2, SURE_AGRRK; | B9JEH2, SURE_AGRRK; |
| Q8UEQ3, SURE_AGRT5; | Q8UEQ3, SURE_AGRT5; | Q8UEQ3, SURE_AGRT5; |
| B9JXD7, SURE_AGRVS; | B9JXD7, SURE_AGRVS; | B9JXD7, SURE_AGRVS; |
| Q0A7L4, SURE_ALKEH; | Q0A7L4, SURE_ALKEH; | Q0A7L4, SURE_ALKEH; |
| A6TRH0, SURE_ALKMQ; | A6TRH0, SURE_ALKMQ; | A6TRH0, SURE_ALKMQ; |
| B8JDR1, SURE_ANAD2; | B8JDR1, SURE_ANAD2; | B8JDR1, SURE_ANAD2; |
| Q2INZ4, SURE_ANADE; | Q2INZ4, SURE_ANADE; | Q2INZ4, SURE_ANADE; |
| A7H8F6, SURE_ANADF; | A7H8F6, SURE_ANADF; | A7H8F6, SURE_ANADF; |
| B9KI89, SURE_ANAMF; | B9KI89, SURE_ANAMF; | B9KI89, SURE_ANAMF; |
| Q5PB34, SURE_ANAMM; | Q5PB34, SURE_ANAMM; | Q5PB34, SURE_ANAMM; |
| B4UE89, SURE_ANASK; | B4UE89, SURE_ANASK; | B4UE89, SURE_ANASK; |
| Q3MB98, SURE_ANAVT; | Q3MB98, SURE_ANAVT; | Q3MB98, SURE_ANAVT; |
| O67004, SURE_AQUAE; | O67004, SURE_AQUAE; | O67004, SURE_AQUAE; |
| A8EX03, SURE_ARCB4; | A8EX03, SURE_ARCB4; | A8EX03, SURE_ARCB4; |
| O29320, SURE_ARCFU; | O29320, SURE_ARCFU; | O29320, SURE_ARCFU; |
| Q5P832, SURE_AROAE; | Q5P832, SURE_AROAE; | Q5P832, SURE_AROAE; |
| A8I066, SURE_AZOC5; | A8I066, SURE_AZOC5; | A8I066, SURE_AZOC5; |
| A1K4E9, SURE_AZOSB; | A1K4E9, SURE_AZOSB; | A1K4E9, SURE_AZOSB; |
| C1DSR8, SURE_AZOVD; | C1DSR8, SURE_AZOVD; | C1DSR8, SURE_AZOVD; |
| Q5LHD7, SURE_BACFN; | Q5LHD7, SURE_BACFN; | Q5LHD7, SURE_BACFN; |
| Q64YA5, SURE_BACFR; | Q64YA5, SURE_BACFR; | Q64YA5, SURE_BACFR; |
| Q8A0L8, SURE_BACTN; | Q8A0L8, SURE_BACTN; | Q8A0L8, SURE_BACTN; |
| A6L1M6, SURE_BACV8; | A6L1M6, SURE_BACV8; | A6L1M6, SURE_BACV8; |
| B2IJG0, SURE_BEII9; | B2IJG0, SURE_BEII9; | B2IJG0, SURE_BEII9; |
| Q2L006, SURE_BORA1; | Q2L006, SURE_BORA1; | Q2L006, SURE_BORA1; |
| Q7WI36, SURE_BORBR; | Q7WI36, SURE_BORBR; | Q7WI36, SURE_BORBR; |
| Q7W670, SURE_BORPA; | Q7W670, SURE_BORPA; | Q7W670, SURE_BORPA; |
| A9IP06, SURE_BORPD; | A9IP06, SURE_BORPD; | A9IP06, SURE_BORPD; |
| Q7VXN2, SURE_BORPE; | Q7VXN2, SURE_BORPE; | Q7VXN2, SURE_BORPE; |
| Q89L02, SURE_BRADU; | Q89L02, SURE_BRADU; | Q89L02, SURE_BRADU; |
| A5EJV7, SURE_BRASB; | A5EJV7, SURE_BRASB; | A5EJV7, SURE_BRASB; |
| A4YV68, SURE_BRASO; | A4YV68, SURE_BRASO; | A4YV68, SURE_BRASO; |
| C0ZGV3, SURE_BREBN; | C0ZGV3, SURE_BREBN; | C0ZGV3, SURE_BREBN; |
| B2S5B9, SURE_BRUA1; | B2S5B9, SURE_BRUA1; | B2S5B9, SURE_BRUA1; |
| Q2YNM5, SURE_BRUA2; | Q2YNM5, SURE_BRUA2; | Q2YNM5, SURE_BRUA2; |
| Q57DM1, SURE_BRUAB; | Q57DM1, SURE_BRUAB; | Q57DM1, SURE_BRUAB; |
| A9MAQ9, SURE_BRUC2; | A9MAQ9, SURE_BRUC2; | A9MAQ9, SURE_BRUC2; |
| C0RIL9, SURE_BRUMB; | C0RIL9, SURE_BRUMB; | C0RIL9, SURE_BRUMB; |
| P66879, SURE_BRUME; | P66879, SURE_BRUME; | P66879, SURE_BRUME; |
| A5VQ63, SURE_BRUO2; | A5VQ63, SURE_BRUO2; | A5VQ63, SURE_BRUO2; |
| B0CLL1, SURE_BRUSI; | B0CLL1, SURE_BRUSI; | B0CLL1, SURE_BRUSI; |
| P66880, SURE_BRUSU; | P66880, SURE_BRUSU; | P66880, SURE_BRUSU; |
| A3MK87, SURE_BURM7; | A3MK87, SURE_BURM7; | A3MK87, SURE_BURM7; |
| A2S290, SURE_BURM9; | A25290, SURE_BURM9; | A2S290, SURE_BURM9; |
| Q62JV2, SURE_BURMA; | Q62JV2, SURE_BURMA; | Q62JV2, SURE_BURMA; |
| A1V4L3, SURE_BURMS; | A1V4L3, SURE_BURMS; | A1V4L3, SURE_BURMS; |
| A3NVY2, SURE_BURP0; | A3NVY2, SURE_BURP0; | A3NVY2, SURE_BURP0; |
| Q3JRP0, SURE_BURP1; | Q3JRP0, SURE_BURP1; | Q3JRP0, SURE_BURP1; |
| A3NA65, SURE_BURP6; | A3NA65, SURE_BURP6; | A3NA65, SURE_BURP6; |
| Q63UU4, SURE_BURPS; | Q63UU4, SURE_BURPS; | Q63UU4, SURE_BURPS; |
| Q2SWF5, SURE_BURTA; | Q2SWF5, SURE_BURTA; | Q2SWF5, SURE_BURTA; |
| A4JEQ1, SURE_BURVG; | A4JEQ1, SURE_BURVG; | A4JEQ1, SURE_BURVG; |
| Q13Z72, SURE_BURXL; | Q13Z72, SURE_BURXL; | Q13Z72, SURE_BURXL; |
| A8MBQ3, SURE_CALMQ; | A8MBQ3, SURE_CALMQ; | A8MBQ3, SURE_CALMQ; |
| A7ZCD9, SURE_CAMC1; | A7ZCD9, SURE_CAMC1; | A7ZCD9, SURE_CAMC1; |
| A7H0A1, SURE_CAMC5; | A7H0A1, SURE_CAMC5; | A7H0A1, SURE_CAMC5; |
| A0RMU4, SURE_CAMFF; | A0RMU4, SURE_CAMFF; | A0RMU4, SURE_CAMFF; |
| A7I2X3, SURE_CAMHC; | A7I2X3, SURE_CAMHC; | A7I2X3, SURE_CAMHC; |
| A8FK82, SURE_CAMJ8; | A8FK82, SURE_CAMJ8; | A8FK82, SURE_CAMJ8; |
| A7H578, SURE_CAMJD; | A7H578, SURE_CAMJD; | A7H578, SURE_CAMJD; |
| Q9PIK6, SURE_CAMJE; | Q9PIK6, SURE_CAMJE; | Q9PIK6, SURE_CAMJE; |
| A1VY14, SURE_CAMJJ; | A1VY14, SURE_CAMJJ; | A1VY14, SURE_CAMJJ; |
| Q5HWH7, SURE_CAMJR; | Q5HWH7, SURE_CAMJR; | Q5HWH7, SURE_CAMJR; |
| B9KDQ8, SURE_CAMLR; | B9KDQ8, SURE_CAMLR; | B9KDQ8, SURE_CAMLR; |
| Q3ADI0, SURE_CARHZ; | Q3ADI0, SURE_CARHZ; | Q3ADI0, SURE_CARHZ; |
| B8GX52, SURE_CAUCN; | B8GX52, SURE_CAUCN; | B8GX52, SURE_CAUCN; |

TABLE 2-continued

| 5'-Nucleotidases | | |
|---|---|---|
| Q9A6T5, SURE_CAUCR; | Q9A6T5, SURE_CAUCR; | Q9A6T5, SURE_CAUCR; |
| B0T1Q2, SURE_CAUSK; | B0T1Q2, SURE_CAUSK; | B0T1Q2, SURE_CAUSK; |
| Q5L5X3, SURE_CHLAB; | Q5L5X3, SURE_CHLAB; | Q5L5X3, SURE_CHLAB; |
| B8G513, SURE_CHLAD; | B8G513, SURE_CHLAD; | B8G513, SURE_CHLAD; |
| Q3ATV8, SURE_CHLCH; | Q3ATV8, SURE_CHLCH; | Q3ATV8, SURE_CHLCH; |
| Q254M8, SURE_CHLFF; | Q254M8, SURE_CHLFF; | Q254M8, SURE_CHLFF; |
| B3EFW1, SURE_CHLL2; | B3EFW1, SURE_CHLL2; | B3EFW1, SURE_CHLL2; |
| Q9PKH4, SURE_CHLMU; | Q9PKH4, SURE_CHLMU; | Q9PKH4, SURE_CHLMU; |
| A1BI19, SURE_CHLPD; | A1BI19, SURE_CHLPD; | A1BI19, SURE_CHLPD; |
| Q9Z8S6, SURE_CHLPN; | Q9Z8S6, SURE_CHLPN; | Q9Z8S6, SURE_CHLPN; |
| B0B9W8, SURE_CHLT2; | B0B9W8, SURE_CHLT2; | B0B9W8, SURE_CHLT2; |
| Q3KME4, SURE_CHLTA; | Q3KME4, SURE_CHLTA; | Q3KME4, SURE_CHLTA; |
| B0BBJ8, SURE_CHLTB; | B0BBJ8, SURE_CHLTB; | B0BBJ8, SURE_CHLTB; |
| Q8KC69, SURE_CHLTE; | Q8KC69, SURE_CHLTE; | Q8KC69, SURE_CHLTE; |
| O84220, SURE_CHLTR; | O84220, SURE_CHLTR; | O84220, SURE_CHLTR; |
| Q1QU76, SURE_CHRSD; | Q1QU76, SURE_CHRSD; | Q1QU76, SURE_CHRSD; |
| Q7NRV1, SURE_CHRVO; | Q7NRV1, SURE_CHRVO; | Q7NRV1, SURE_CHRVO; |
| A8ANV8, SURE_CITK8; | A8ANV8, SURE_CITK8; | A8ANV8, SURE_CITK8; |
| A7FQP3, SURE_CLOB1; | A7FQP3, SURE_CLOB1; | A7FQP3, SURE_CLOB1; |
| C3KZ52, SURE_CLOB6; | C3KZ52, SURE_CLOB6; | C3KZ52, SURE_CLOB6; |
| A6LS61, SURE_CLOB8; | A6LS61, SURE_CLOB8; | A6LS61, SURE_CLOB8; |
| B2UXL6, SURE_CLOBA; | B2UXL6, SURE_CLOBA; | B2UXL6, SURE_CLOBA; |
| B2TPM3, SURE_CLOBB; | B2TPM3, SURE_CLOBB; | B2TPM3, SURE_CLOBB; |
| A5HYC6, SURE_CLOBH; | A5HYC6, SURE_CLOBH; | A5HYC6, SURE_CLOBH; |
| C1FQW9, SURE_CLOBJ; | C1FQW9, SURE_CLOBJ; | C1FQW9, SURE_CLOBJ; |
| B1IDC2, SURE_CLOBK; | B1IDC2, SURE_CLOBK; | B1IDC2, SURE_CLOBK; |
| A7G9Y6, SURE_CLOBL; | A7G9Y6, SURE_CLOBL; | A7G9Y6, SURE_CLOBL; |
| B1KTK1, SURE_CLOBM; | B1KTK1, SURE_CLOBM; | B1KTK1, SURE_CLOBM; |
| B9E0C7, SURE_CLOK1; | B9E0C7, SURE_CLOK1; | B9E0C7, SURE_CLOK1; |
| A5N6V8, SURE_CLOK5; | A5N6V8, SURE_CLOK5; | A5N6V8, SURE_CLOK5; |
| Q899M5, SURE_CLOTE; | Q899M5, SURE_CLOTE; | Q899M5, SURE_CLOTE; |
| Q487E6, SURE_COLP3; | Q487E6, SURE_COLP3; | Q487E6, SURE_COLP3; |
| B6J4X6, SURE_COXB1; | B6J4X6, SURE_COXB1; | B6J4X6, SURE_COXB1; |
| B6J3X6, SURE_COXB2; | B6J3X6, SURE_COXB2; | B6J3X6, SURE_COXB2; |
| A9KDH9, SURE_COXBN; | A9KDH9, SURE_COXBN; | A9KDH9, SURE_COXBN; |
| A9N9U7, SURE_COXBR; | A9N9U7, SURE_COXBR; | A9N9U7, SURE_COXBR; |
| Q9KI21, SURE_COXBU; | Q9KI21, SURE_COXBU; | Q9KI21, SURE_COXBU; |
| A7MJ60, SURE_CROS8; | A7MJ60, SURE_CROS8; | A7MJ60, SURE_CROS8; |
| Q0K950, SURE_CUPNH; | Q0K950, SURE_CUPNH; | Q0K950, SURE_CUPNH; |
| Q46ZH1, SURE_CUPPJ; | Q46ZH1, SURE_CUPPJ; | Q46ZH1, SURE_CUPPJ; |
| B3R1L4, SURE_CUPTR; | B3R1L4, SURE_CUPTR; | B3R1L4, SURE_CUPTR; |
| B1WXT3, SURE_CYAA5; | B1WXT3, SURE_CYAA5; | B1WXT3, SURE_CYAA5; |
| B8HSQ9, SURE_CYAP4; | B8HSQ9, SURE_CYAP4; | B8HSQ9, SURE_CYAP4; |
| B7KB74, SURE_CYAP7; | B7KB74, SURE_CYAP7; | B7KB74, SURE_CYAP7; |
| Q11WK5, SURE_CYTH3; | Q11WK5, SURE_CYTH3; | Q11WK5, SURE_CYTH3; |
| Q47D24, SURE_DECAR; | Q47D24, SURE_DECAR; | Q47D24, SURE_DECAR; |
| Q3Z8C0, SURE_DEHE1; | Q3Z8C0, SURE_DEHE1; | Q3Z8C0, SURE_DEHE1; |
| A5FR64, SURE_DEHSB; | A5FR64, SURE_DEHSB; | A5FR64, SURE_DEHSB; |
| Q3ZXG5, SURE_DEHSC; | Q3ZXG5, SURE_DEHSC; | Q3ZXG5, SURE_DEHSC; |
| Q1J2E1, SURE_DEIGD; | Q1J2E1, SURE_DEIGD; | Q1J2E1, SURE_DEIGD; |
| Q9RRT8, SURE_DEIRA; | Q9RRT8, SURE_DEIRA; | Q9RRT8, SURE_DEIRA; |
| B8FC91, SURE_DESAA; | B8FC91, SURE_DESAA; | B8FC91, SURE_DESAA; |
| C6BUG4, SURE_DESAD; | C6BUG4, SURE_DESAD; | C6BUG4, SURE_DESAD; |
| B1I3V7, SURE_DESAP; | B1I3V7, SURE_DESAP; | B1I3V7, SURE_DESAP; |

Cells can also be modified by deletion of one or more genes that encode a 3'-nucleotidase, such as one or more genes in Table 3.

TABLE 3

| 3'-Nucleotidases | | |
|---|---|---|
| P08331, CPDB_ECOLI; | P08331, CPDB_ECOLI; | P08331, CPDB_ECOLI; |
| P44764, CPDB_HAEIN; | P44764, CPDB_HAEIN; | P44764, CPDB_HAEIN; |
| P26265, CPDB_SALTY; | P26265, CPDB_SALTY; | P26265, CPDB_SALTY; |
| P53052, CPDB_YEREN; | P53052, CPDB_YEREN; | P53052, CPDB_YEREN; |
| O34313, NTPES_BACSU; | O34313, NTPES_BACSU; | O34313, NTPES_BACSU; |
| P24504, NUP3_PENSQ; | P24504, NUP3_PENSQ; | P24504, NUP3_PENSQ; |
| A8ANV8, SURE_CITK8; | A8ANV8, SURE_CITK8; | A8ANV8, SURE_CITK8; |
| A7MJ60, SURE_CROS8; | A7MJ60, SURE_CROS8; | A7MJ60, SURE_CROS8; |
| A7ZQI8, SURE_ECO24; | A7ZQI8, SURE_ECO24; | A7ZQI8, SURE_ECO24; |
| B7UHG3, SURE_ECO27; | B7UHG3, SURE_ECO27; | B7UHG3, SURE_ECO27; |
| B7MKL8, SURE_ECO45; | B7MKL8, SURE_ECO45; | B7MKL8, SURE_ECO45; |
| B7LEG2, SURE_ECO55; | B7LEG2, SURE_ECO55; | B7LEG2, SURE_ECO55; |

TABLE 3-continued

| 3'-Nucleotidases | | |
|---|---|---|
| P0A842, SURE_ECO57; | P0A842, SURE_ECO57; | P0A842, SURE_ECO57; |
| B5Z3A6, SURE_ECO5E; | B5Z3A6, SURE_ECO5E; | B5Z3A6, SURE_ECO5E; |
| B7NT88, SURE_ECO7I; | B7NT88, SURE_ECO7I; | B7NT88, SURE_ECO7I; |
| B7MZ45, SURE_ECO81; | B7MZ45, SURE_ECO81; | B7MZ45, SURE_ECO81; |
| B7LXF6, SURE_ECO8A; | B7LXF6, SURE_ECO8A; | B7LXF6, SURE_ECO8A; |
| C4ZZP8, SURE_ECOBW; | C4ZZP8, SURE_ECOBW; | C4ZZP8, SURE_ECOBW; |
| B1XCS0, SURE_ECODH; | B1XCS0, SURE_ECODH; | B1XCS0, SURE_ECODH; |
| A8A3M3, SURE_ECOHS; | A8A3M3, SURE_ECOHS; | A8A3M3, SURE_ECOHS; |
| A1AET8, SURE_ECOK1; | A1AET8, SURE_ECOK1; | A1AET8, SURE_ECOK1; |
| Q0TEB4, SURE_ECOL5; | Q0TEB4, SURE_ECOL5; | Q0TEB4, SURE_ECOL5; |

A cell expressing a nucleotide triphosphate transporter can be modified to reduce or eliminate the activity of one or more phosphatases. Cells can also be modified by deletion of one or more genes that encode phosphatases such as alkaline phosphatase. Other examples of genes that can be modified to have loss of function include phoA, ushA, appA, aphA, yjjX, surE, yfbR, yjjG, yfaO, mutT, nagD, yggV, yrfG, ymfB, or combinations thereof. In some embodiments, the cells have loss of function mutations in more than one phosphatase gene.

Cells can also be modified by deletion of one or more genes that encode a polynucleotide phosphatase activity. Cells can also be modified by deletion of one or more genes that encode a Nucleotide phosphatase activity, acting on free nucleotides. Cells can also be modified by deletion of one or more genes that encode a nucleotide triphosphatase (NT-Pases), apyrase; ATP-diphosphatase; adenosine diphosphatase; ADPase; ATP diphosphohydrolase, or any combination thereof, such as one more genes in Table 4.

TABLE 4

| Polynucleotide phosphatases | | | |
|---|---|---|---|
| ZMA: | 100273224(TIDP3667) 100273583 100281594(pco140907) 100381419 | HSA: | 377841(ENTPD8) 953(ENTPD1) 956(ENTPD3) |
| SITA: | 101757382 101764324 101769705 101772875 101775667 101786001 | PTR: | 100614135(ENTPD1) 460286(ENTPD3) 736974(ENTPD8) |
| SMO: | SELMODRAFT_233281(APY-1) SELMODRAFT_94922 | PPS: | 100971059(ENTPD1) 100983594(ENTPD3) 100995976(ENTPD8) |
| PPP: | PHYPADRAFT_175090 PHYPADRAFT_201168 PHYPADRAFT_31384 | GGO: | 101132716(ENTPD1) 101132747(ENTPD3) |
| CRE: | CHLREDRAFT_167044 CHLREDRAFT_170567 | PON: | 100442938(ENTPD8) 100447406(ENTPD3) 100453241(ENTPD1) |
| VCN: | VOLCADRAFT_120373 VOLCADRAFT_78871 VOLCADRAFT_91259 | MCC: | 703591(ENTPD1) 704424(ENTPD8) 718311(ENTPD3) |
| OLU: | OSTLU_36812 | MCF: | 102134382(ENTPD8) 102138702(ENTPD3) |
| OTA: | Ot04g01290 | MMU: | 12495(Entpd1) 215446(Entpd3) 72090(Entpd8) |
| MIS: | MICPUN_84198 MICPUN_87507 | RNO: | 316077(Entpd3) 613267(Entpd8) 64519(Entpd1) |
| MPP: | MICPUCDRAFT_32900 | CGE: | 100751964(Entpd8) 100762593 100772668 |
| CSL: | COCSUDRAFT_28740 | HGL: | 101696417(Entpd3) 101708535(Entpd8) 101715301(Entpd1) |
| SCE: | YER005W(YND1) | CFA: | 100688937(ENTPD8) 485604(ENTPD3) 486810(ENTPD1) |
| AGO: | AGOS_ADR006W | AML: | 100468369 100473727(ENTPD3) 100474255 |
| ERC: | Ecym_4478 | FCA: | 101085582(ENTPD8) 101096356(ENTPD1) 101098083(ENTPD3) |
| KLA: | KLLA0D13662g | BTA: | 282223(ENTPD1) 506087(ENTPD3) 515532(ENTPD8) |
| LTH: | KLTH0F13178g | BOM: | 102269229(ENTPD8) 102270483(ENTPD1) 102273587(ENTPD3) |
| PPA: | PAS_chr1-1_0063 | PHD: | 102321352(ENTPD1) 102338946(ENTPD3) |
| VPO: | Kpol_312p10 | CHX: | 102189182(ENTPD1) 102190080(ENTPD3) |
| ZRO: | ZYRO0D09570g | SSC: | 100516719(ENTPD8) 100623360(ENTPD3) 397298(ENTPD1) |
| CGR: | CAGL0H09746g | ECB: | 100058558(ENTPD8) 100068004(ENTPD3) 100070956(ENTPD1) |
| NCS: | NCAS_0I00760(NCAS0I00760) | MYB: | 102255350(ENTPD3) 102256383(ENTPD1) |
| NDI: | NDAI_0A08280(NDAI0A08280) | MDO: | 100022843(ENTPD8) 100022899(ENTPD1) 100023686 100025436(ENTPD3) |
| TPF: | TPHA_0L00770(TPHA0L00770) | SHR: | 100914154(ENTPD1) 100919726 100926510(ENTPD3) 100932670(ENTPD8) |
| TBL: | TBLA_0A01060(TBLA0A01060) | OAA: | 100078824(ENTPD3) |
| TDL: | TDEL_0H03120(TDEL0H03120) | GGA: | 374095(ENTPD8) 417281(ENTPD8L) 423826(ENTPD1) 427778(ENTPD1) 428447(ENTPD3) |
| KAF: | KAFR_0L00600(KAFR0L00600) | MGP: | 100543984(ENTPD1) 100546469 100547592 100550087 |
| DHA: | DEHA2D16764g | TGU: | 100218994(ENTPD1) 100221575(ENTPD3) 100229162 |
| PIC: | PICST_75213(YND1) | FAB: | 101806865(ENTPD3) 101809481 101809685 101817605(ENTPD1) |

TABLE 4-continued

| Polynucleotide phosphatases | | | |
|---|---|---|---|
| PGU: | PGUG_00627 | PHI: | 102099317(ENTPD3) 102105445 102107727(ENTPD8) 102110072(ENTPD1) |
| LEL: | LELG_04414 | APLA: | 101795263 101795762(ENTPD8) 101796222 101801191(ENTPD1) 101804288(ENTPD3) |
| CAL: | CaO19.10432(YND1) CaO19.2915(YND1) | FPG: | 101912881(ENTPD3) 101915751(ENTPD1) 101918437 |
| CTP: | CTRG_04045 | FCH: | 102048208 102054936(ENTPD3) |
| CDU: | CD36_45750 | CLV: | 102083509 102083693 102095399(ENTPD1) 102096210 102097422(ENTPD3) |
| COT: | CORT_0E01960 | ACS: | 100553564 100561052(entpd3) |
| YLI: | YALI0C19712g | ASN: | 102373368(ENTPD1) 102373540(ENTPD3) 102380815 102381055 102381801 |
| CLU: | CLUG_01050 | XLA: | 444164(entpd1) |
| MBR: | MONBRDRAFT_28117 | XTR: | 100125010(entpd3) 448501(entpd1) 733458(entpd8) |
| PFA: | PF14_0297 | DRE: | 100005551(entpd3) 436652(entpd8) 445151(entpd1) |
| TET: | TTHERM_00684480 TTHERM_01256510 | TRU: | 101068571 101070429 |
| PTM: | GSPATT00035597001 GSPATT00037111001 | MZE: | 101473382 101487105 |
| EHX: | EMIHUDRAFT_52732 EMIHUDRAFT_52751 | OLA: | 101165837 101166588 |
| GTT: | GUITHDRAFT_95407 | XMA: | 102217482 102226175 |
| TVA: | TVAG_167570 | LCM: | 102348651(ENTPD3) 102360392(ENTPD8) |
| LPN: | lpg0971 | BFO: | BRAFLDRAFT_124940 |
| LPU: | LPE509_02235 | TSP: | Tsp_07798 |
| LPH: | LPV_1110 | SMM: | Smp_042020.1 |
| LPO: | LPO_1060 | HMG: | 100199550 |
| LPM: | LP6_0959 | AQU: | 100640703 |
| LPF: | lpl1000 | ATH: | AT1G14230 AT1G14240 AT1G14250 AT2G02970 AT3G04080(APY1) AT5G18280(APY2) |
| LPP: | lpp1033 | ALY: | ARALYDRAFT_471586 ARALYDRAFT_477668 ARALYDRAFT_679147 ARALYDRAFT_904563 ARALYDRAFT_909838 |
| LPC: | LPC_2316 | GMX: | 100780748 100781628 100786073 100807287 |
| LPA: | lpa_01464 | MTR: | MTR_5g040710 MTR_7g085090 |
| LPE: | lp12_0993 | CAM: | 101497346 101498578 |
| SLY: | 101250072 101252471 101258050 101262543 101268182 | FVE: | 101293262 101304566 |
| OSA: | 4332967 4344315 4345665 4351367 | CSV: | 101203551 101224969 |
| DOSA | Os03t0378000-01(Os03g0378000) Os07t0682800-01(Os07g0682800) Os08t0436100-01(Os08g0436100) Os12t0123500-01(Os12g0123500) | RCU: | RCOM_0836420 RCOM_1122480 |
| BDI | 100825383 100833921 100834806 100834835 100838315 | POP: | POPTR_573883 POPTR_729947 POPTR_765739 POPTR_833712 |
| SBI: | SORBI_01g034030(SORBIDRAFT_01g034030) SORBI_01g036510(SORBIDRAFT_01g036510) SORBI_07g021350(SORBIDRAFT_07g021350) | VVI: | 100244785 100267968 |

Cells can also be modified by deletion of one or more genes that encode a nucleoside diphosphate phosphatase; nucleoside-diphosphatase; thiaminpyrophosphatase; UDPase; inosine diphosphatase; adenosine diphosphatase; IDPase; ADPase; adenosinepyrophosphatase; guanosine diphosphatase; guanosine 5'-diphosphatase; inosine 5'-diphosphatase; uridine diphosphatase; uridine 5'-diphosphatase; type B nucleoside diphosphatase; GDPase; CDPase; nucleoside 5'-diphosphatase; type L nucleoside diphosphatase; NDPase; nucleoside diphosphate phosphohydrolase, or any combination thereof, such as one or more of the genes listed in Table 5.

TABLE 5

| Nucleoside diphosphate phosphatases | | | |
|---|---|---|---|
| HSA: | 124583(CANT1) 955(ENTPD6) 957(ENTPD5) 9583(ENTPD4) | XTR: | 394537(cant1) 677731(entpd4) 677734(entpd5) 677735(entpd6) |
| PTR | 453027(ENTPD5) 458146(ENTPD6) 464056(ENTPD4) 468345(CANT1) | DRE: | 406558(cant1a) 436692(entpd4) 445201(cant1b) 550560(entpd6) 556849 |
| PPS: | 100969324(ENTPD4) 100971740 100974659(CANT1) 100975707(ENTPD5) 100985458(ENTPD6) | TRU: | 101065382 101070342 101075790 101076188 |
| GGO: | 101126430(ENTPD6) 101142724(ENTPD5) 101148282(CANT1) 101148704(ENTPD4) | MZE: | 101466916 101470512 101474178 101481315 101483235 |
| PON: | 100433776(ENTPD4) 100449249(ENTPD6) 100453014(ENTPD5) 100454763(CANT1) | OLA: | 101158069 101165115 101171168 101172088 101173329 |

TABLE 5-continued

| Nucleoside diphosphate phosphatases | | | |
|---|---|---|---|
| MCC: | 698503(ENTPD5) 705663(ENTPD6) 710935(CANT1) 717197(ENTPD4) | XMA: | 102222595 102222865 102222913 102236347 |
| MCF: | 102118635(ENTPD5) 102127579(CANT1) 102133506(ENTPD6) 102139183(ENTPD4) | LCM: | 102345277(CANT1) 102354256(ENTPD6) 102364599(ENTPD4) 102364924(ENTPD5) |
| MMU: | 100862375(Gm21685) 12497(Entpd6) 12499(Entpd5) 67464(Entpd4) 76025(Cant1) | BFO: | BRAFLDRAFT_57510 BRAFLDRAFT_79389 |
| RNO: | 246272(Cant1) 314312(Entpd5) 361063(Entpd4) 85260(Entpd6) | CIN: | 100181442 100181727 |
| CGE: | 100751454(Entpd5) 100765414 100767250(Cant1) 100771637(Entpd4) | SPU: | 576801 580175(entpd4) 587808 |
| HGL: | 101700645(Entpd4) 101703881(Entpd5) 101708374(Cant1) 101717001(Entpd6) | DME: | Dmel_CG5276 |
| CFA: | 480384(ENTPD5) 485564(ENTPD6) 486117(ENTPD4) | DPO: | Dpse_GA18779 |
| AML: | 100470325(ENTPD5) 100474095 100475785(ENTPD4) 100476810 100477887 | DAN: | Dana_GF14909 Dana_GF16866 |
| FCA: | 101083380(CANT1) 101085117(ENTPD4) 101090270(ENTPD5) 101090852(ENTPD6) | DER: | Dere_GG18156 Dere_GG24477 |
| BTA: | 508097(ENTPD6) 518086(CANT1) 531411(ENTPD4) 533096(ENTPD5) | DPE: | Dper_GL12374 Dper_GL26295 |
| BOM: | 102264690(ENTPD6) 102272160(CANT1) 102278224(ENTPD5) 102283172(ENTPD4) | DSE: | Dsec_GM18184 Dsec_GM23945 |
| PHD: | 102316077(ENTPD6) 102317546(CANT1) 102321161(ENTPD4) 102323649(ENTPD5) | DSI: | Dsim_GD18755 Dsim_GD22791 |
| CHX: | 102174488(ENTPD6) 102177094(CANT1) 102177626(ENTPD4) 102187956(ENTPD5) | DWI: | Dwil_GK11295 Dwil_GK18683 |
| SSC: | 100154506(ENTPD5) 100155254(ENTPD4) 100620107(CANT1) 100626131(ENTPD6) | DYA: | Dyak_GE14979 Dyak_GE26097 |
| ECB: | 100053982(ENTPD4) 100056466(ENTPD5) 100057043(ENTPD6) 100057405(CANT1) | DGR: | Dgri_GH11050 Dgri_GH17322 |
| MYB: | 102243929(ENTPD6) 102251396(CANT1) 102251399(ENTPD4) 102262670(ENTPD5) | DMO: | Dmoj_GI10286 Dmoj_GI17567 |
| MDO: | 100021277(ENTPD4) 100024118 100026552(CANT1) 100033226(ENTPD6) | DVI: | Dvir_GJ11094 Dvir_GJ17910 |
| SHR: | 100914260(ENTPD4) 100934101(CANT1) 100934821(ENTPD5) 100935093(ENTPD6) | AGA: | AgaP_AGAP001217 AgaP_AGAP009265 |
| OAA: | 100075558(ENTPD4) 100088014 100088379 | AAG: | AaeL_AAEL005662 AaeL_AAEL006659 |
| GGA: | 416708(ENTPD6) 419531(ENTPD4) 423343(ENTPD5) 430103(CANT1) | CQU: | CpipJ_CPIJ005468 CpipJ_CPIJ006723 |
| MGP: | 100539042 100541241 100550411(ENTPD4) | AME: | 550987(GB18870) 551373 |
| TGU: | 100219260(CANT1) 100220000(ENTPD5) 100224923(ENTPD6) | NVI: | 100120729 |
| FAB: | 101811604(CANT1) 101814014(ENTPD6) 101820141(ENTPD5) | TCA: | 658576 662718 |
| PHI: | 102101855(ENTPD4) 102106545(ENTPD5) 102108288(CANT1) 102109632(ENTPD6) | BMOR: | 101739670 101746124 |
| APLA: | 101790396(CANT1) 101794207(ENTPD5) 101795352(ENTPD4) 101798772(ENTPD6) | API: | 100162387 100166504 |
| FPG: | 101910519(ENTPD4) 101911075(ENTPD5) 101912651(CANT1) 101920667(ENTPD6) | PHU: | Phum_PHUM421050 Phum_PHUM604210 |
| FCH: | 102047237(ENTPD6) 102056974(ENTPD5) 102057968(CANT1) 102058083(ENTPD4) | ISC: | IscW_ISCW018254 |
| CLV: | 102084705(ENTPD5) 102084729(CANT1) 102092438(ENTPD4) 102095170(ENTPD6) | CEL: | CELE_F08C6.6(apy-1) CELE_K08H10.4(uda-1) CELE_R07E4.4(mig-23) |
| ACS: | 100555642 100561218 100562980(entpd4) 100563392 | CBR: | CBG11542(Cbr-uda-1) CBG14198 CBG14784(Cbr-mig-23) CBG16731 |
| ASN: | 102377226(ENTPD5) 102382407(ENTPD4) 102384786(ENTPD6) 102387737(CANT1) | BMY: | Bm1_34420 |

TABLE 5-continued

| Nucleoside diphosphate phosphatases | | | |
|---|---|---|---|
| XLA: | 379060(cant1) 495422(entpd4) 734187(entpd6) | LOA: | LOAG_01305 |
| PTI: | PHATRDRAFT_14301 | TSP: | Tsp_09215 Tsp_09582 |
| TPS: | THAPSDRAFT_31247 | SMM: | Smp_081450 Smp_166520 |
| PIF: | PITG_20792 | NVE: | NEMVE_v1g175561 |
| EHX: | EMIHUDRAFT_43184 | HMG: | 100202807 100204155 |
| TBR: | Tb927.7.1930(Tb07.43M14.370) | TAD: | TRIADDRAFT_21256 TRIADDRAFT_32564 TRIADDRAFT_61888 |
| LMA: | LMJF_15_0030 | AQU: | 100640578 |
| LIF: | LINJ_15_0030 | CME: | CYME_CMQ456C |
| LDO: | LDBPK_150030 | GSL: | Gasu_48820 |
| LMI: | LMXM_15_0030 | CCP: | CHC_T00001236001 CHC_T00003677001 |
| LBZ: | LBRM_15_0030 | MBR: | MONBRDRAFT_2652 MONBRDRAFT_28836 |
| NGR: | NAEGRDRAFT_79292 | EHI: | EHI_053610(59.t00033) EHI_104590(415.t00008) EHI_112890(17.t00006) |
| CPV: | cgd6_1570 | EDI: | EDI_058390 EDI_125320 EDI_305410 |
| CHO: | Chro.60194 | ACAN: | ACA1_330420 |
| TGO: | TGME49_110810 | PFA: | PF14_0297 |

Figure 7A:
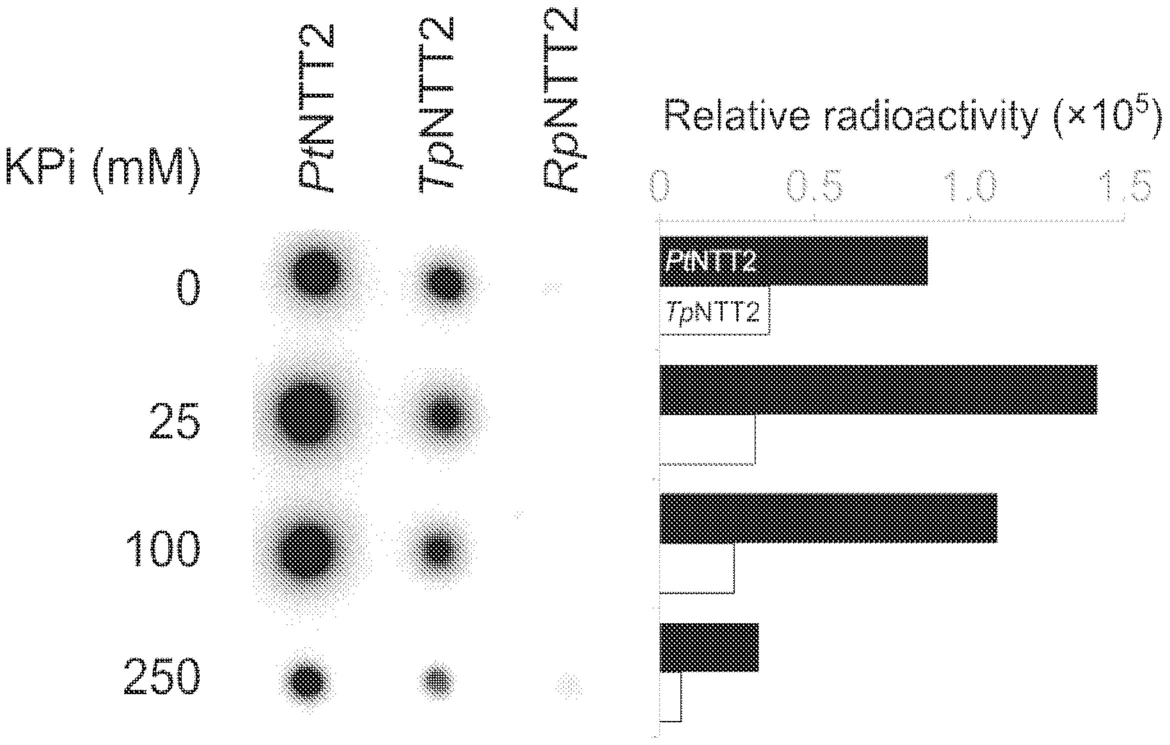
FIG. 7A depicts raw (left) and processed (right) data inhibits the uptake of [α-$^{32}$P]-dATP uptake into cells in the presence of the indicated KPi concentrations. The NTT from *Rickettsia prowazekii* (RpNTT2) was used as a negative control: its background signal was subtracted from those of PtNTT2 (black bars) and TpNTT2 (white bars). Relative radioactivity corresponds to the total number of counts produced by each sample.
Figure 7B:
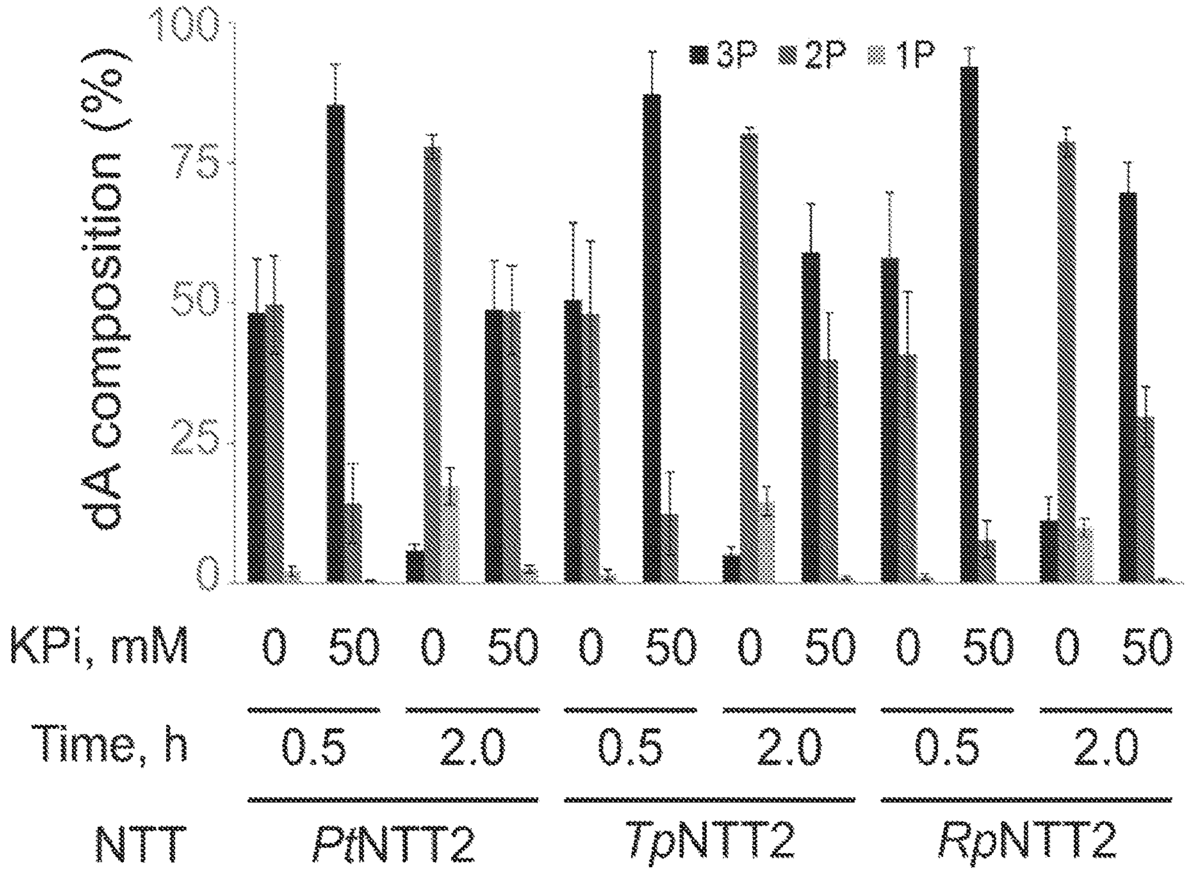
FIG. 7B depicts a graph showing the % composition of [α-$^{32}$P]-dATP in the presence or absence of 50 mM KPi in media from cells expressing the indicated NTTs.
Figure 8A:
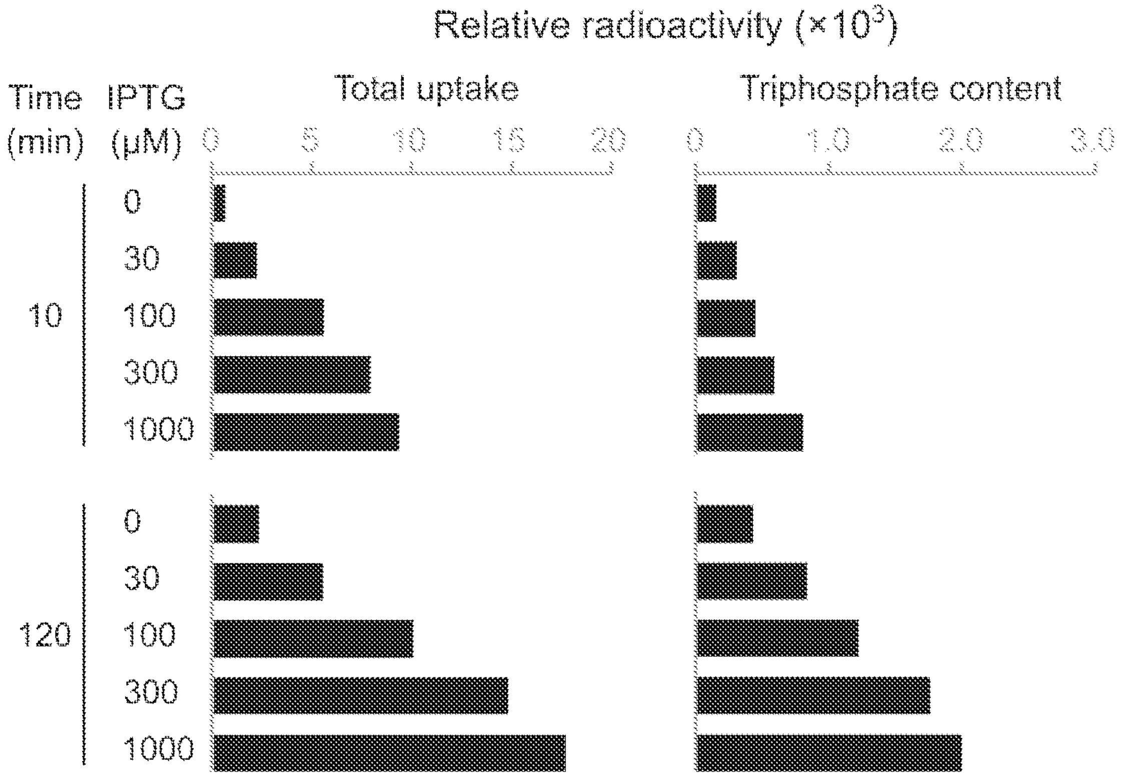
FIG. 8A depicts a graph of the total uptake of radioactive substrate (left) and total intracellular triphosphate content (right) at the indicated time points as a function of IPTG concentration. Relative radioactivity corresponds to the total number of counts produced by each sample.

The extracellular stability of natural nucleic acids, e.g., dATP, was discovered to be significantly increased in the presence of potassium phosphate (KPi) in the growth medium. KPi significantly inhibited the dephosphorylation of unnatural triphosphates (FIG. 6). Such addition of potassium phosphate may suppress phosphatase expression or inhibit phosphatase activity (FIG. 7). As with the natural triphosphate, the addition of potassium phosphate significantly increased the extracellular stability of d5SICSTP and dNaMTP (FIG. 6) by more than 2-fold. The uptake of [$\alpha$-$^{32}$P]-dATP from media containing 50 mM KPi as a function of transporter induction, e.g., with IPTG, can also be determined (FIG. 8). 1 mM IPTG induction resulted in maximal [$\alpha$-$^{32}$P]-dATP uptake (FIG. 8A).

Figure 8B:
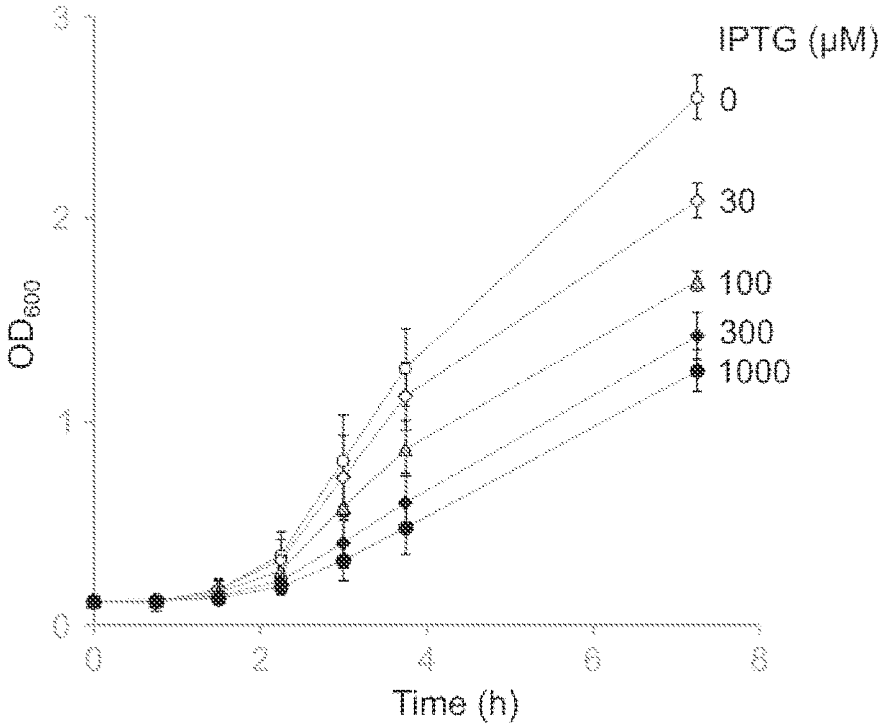
FIG. 8B depicts growth curves and [α-$^{32}$P]-dATP uptake by bacterial cells transformed with pCDF-1b-PtNTT2 (pACS) plasmid as a function of IPTG concentration.
Figure 9A:
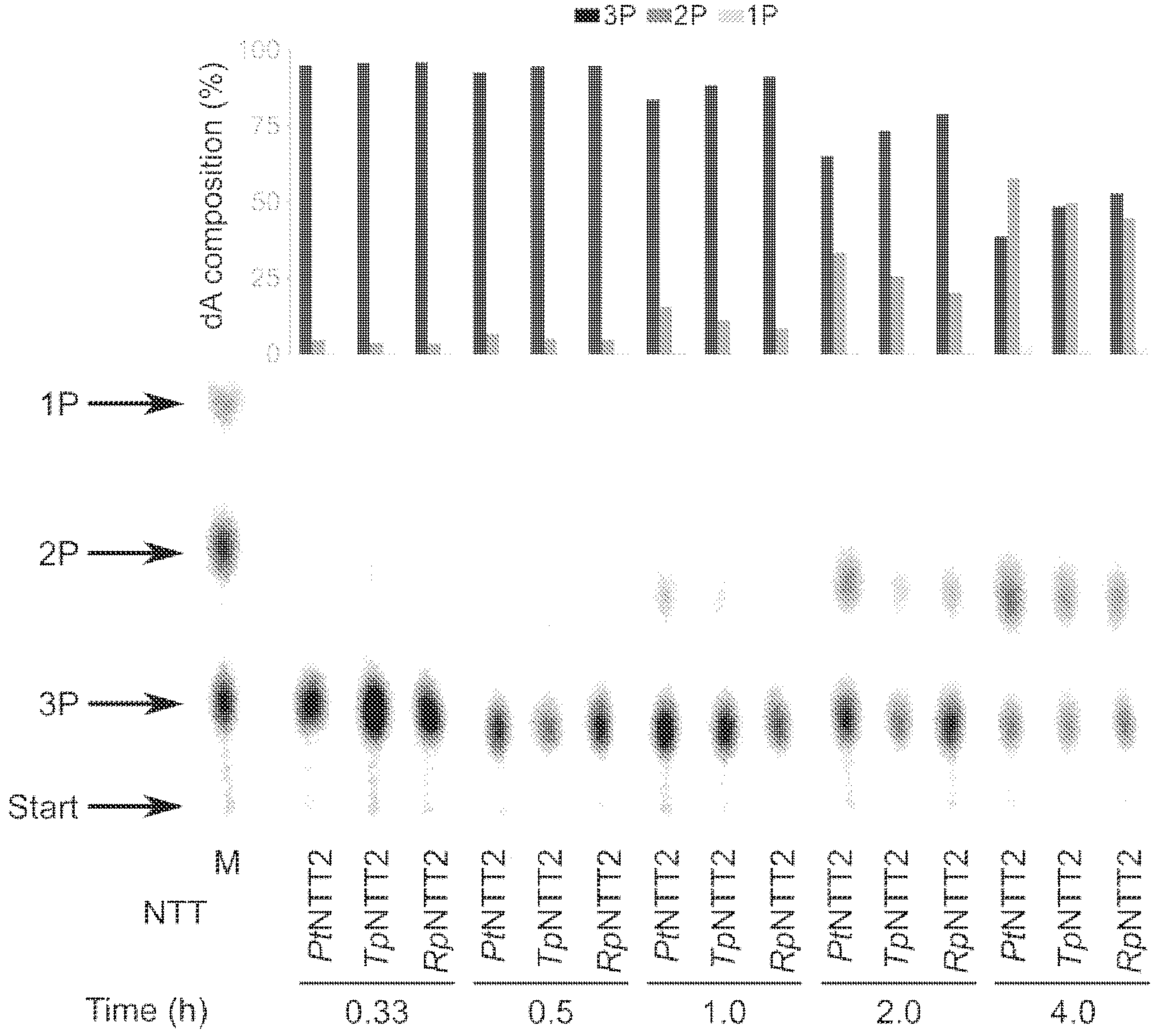
FIG. 9A depicts TLC images (bottom) [α-$^{32}$P]-dATP in the media as a function of time and their quantifications (top). M refers to a mixture of all three compounds [3P, 2P and 1P] that was used as a TLC standard. The position labeled “Start” corresponds to the position of sample spotting on the TLC plate.
Figure 9B:
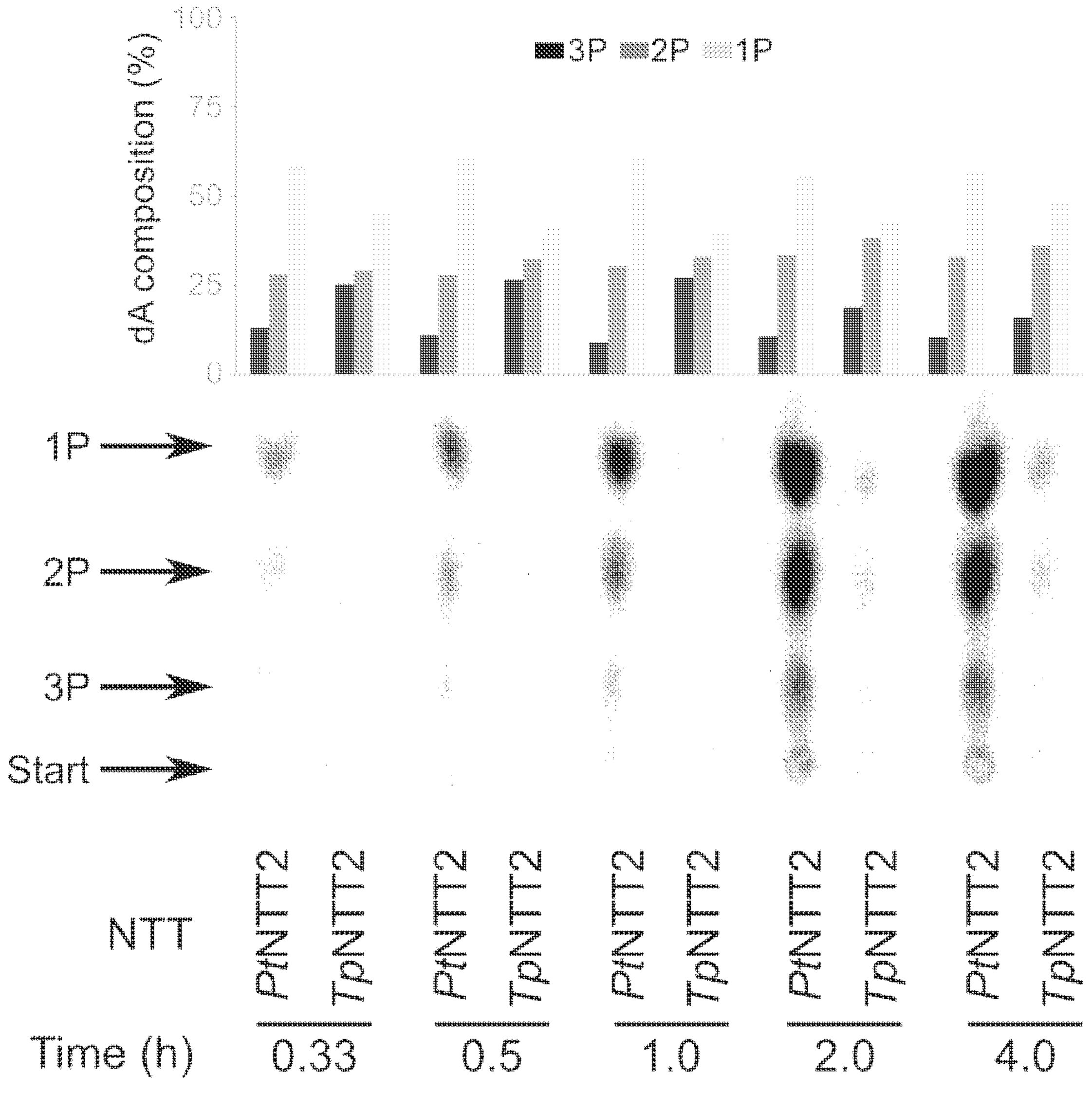
FIG. 9B depicts TLC images (bottom) [α-P]-dATP in cell lysates as a function of time and their quantifications (top). M refers to a mixture of all three compounds [3P, 2P and 1P] that was used as a TLC standard. The position labeled “Start” corresponds to the position of sample spotting on the TLC plate.

Inhibitors of phosphatases can be employed to increase the stability of one or more unnatural and/or natural nucleic acids. In this manner, inhibitors of phosphatases can be employed to facilitate intracellular import and transport of nucleic acids. The uptake of [$\alpha$-$^{32}$P]-dATP from media containing 50 mM KPi as a function of transporter induction, e.g., with IPTG, can be determined (FIG. 8).

Potassium phosphate can facilitate such transport. In some embodiments, a phosphatase inhibitor, e.g., KPi, facilitates intracellular import and transport of nucleic acids at a pH. In some embodiments, a phosphatase inhibitor, e.g., KPi, facilitates intracellular import and transport of nucleic acids at approximately neutral pH. Such a neutral pH can be between about pH 4.5 to pH 8.5, or between about pH 6.8 to about pH 7.6, or about pH 7.0 to about pH 7.4.

In some embodiments, a phosphatase inhibitor, e.g., KPi, facilitates intracellular import and transport of nucleic acids at a concentration. A variety of phosphatase inhibitor, e.g., KPi, concentrations can be employed. For example, the phosphatase inhibitor, e.g., KPi, can be present at a concentration of 0.1 mM to 500 mM, or 0.2 mM to 250 mM, or 0.25 mM to 200 mM, or 1.0 mM to 150 mM, or 2.5 mM to 125 mM, or 5 mM to 100 mM, or 25 mM to 75 mM, or 40 mM to 60 mM potassium phosphate. As illustrated, 50 mM phosphatase inhibitor, e.g., KPi, appears to be sufficient for initial contact of the cells and unnatural nucleotide triphosphates (FIG. 7B). Inhibitors of phosphatases can be employed, either with addition of potassium phosphate or without addition of potassium phosphate.

In some embodiments, disruption of a nucleotidase or phosphatase, or addition of a phosphatase inhibitor, e.g., KPi, can be used to increase the half-life of a natural and unnatural nucleotide triphosphates. For example, disruption of a nucleotidase or phosphatase, or addition of a phosphatase inhibitor can be used to increase the half-life of a natural nucleic acid and/or an unnatural nucleic acid by at least about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 10.5, 11.0, 11.5, 12.0, 12.5, 3.0, 13.5, 14.0, 14.5, 15.0, 15.5, 16.0, 16.5, 17.0, 17.5, 18.0, 18.5, 19.0, 19.5, 20, 25, 30, 35, 40, 45, 50, 55, 60, 65, 70, 75, 80, 85, 90, 95, 100 or more hours.

In some embodiments, disruption of a nucleotidase or phosphatase, or addition of a phosphatase inhibitor, e.g., KPi, can be used to increase the stability of a natural nucleic acid and/or an unnatural nucleic acid such that the natural or unnatural nucleic acid intracellular concentration is at least the $K_M$ value of the natural or unnatural nucleic acid for a polymerase. For example, disruption of a nucleotidase or phosphatase, or addition of a phosphatase inhibitor can be used increase the stability of natural and unnatural nucleotide triphosphates such that their intracellular concentration is at least about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 10.5, 11.0, 11.5, 12.0, 12.5, 3.0, 13.5, 14.0, 14.5, 15.0, 15.5, 16.0, 16.5, 17.0, 17.5, 18.0, 18.5, 19.0, 19.5, 20, 25, 30, 35, 40, 45, 50, 55, 60, 65, 70, 75, 80, 85, 90, 95, 100 or more times the $K_M$ value of the natural or unnatural nucleic acid for a polymerase.

Kits

Various combinations of the components set forth above in regard to exemplary reaction mixtures and reaction methods can be provided in a kit form. Such a kit can include individual components that are separated from each other, for example, being carried in separate vessels or packages. A kit can include one or more sub-combinations of the components set forth herein, the one or more sub-combinations being separated from other components of the kit. The sub-combinations can be combinable to create a reaction mixture set forth herein (or combined to perform a reaction set forth herein). In particular embodiments, a sub-combination of components that is present in an individual vessel or package is insufficient to perform a reaction set forth herein.

However, the kit as a whole can include a collection of vessels or packages the contents of which can be combined to perform a reaction set forth herein.

A kit can include a suitable packaging material to house the contents of the kit. The packaging material can be constructed by well-known methods, preferably to provide a sterile, contaminant-free environment. The packaging materials employed herein can include, for example, those customarily utilized in commercial kits sold for use with nucleic acid sequencing systems. Exemplary packaging materials include, without limitation, glass, plastic, paper, foil, and the like, capable of holding within fixed limits a component set forth herein.

The packaging material can include a label which indicates a particular use for the components. The use for the kit that is indicated by the label can be one or more of the methods set forth herein as appropriate for the particular combination of components present in the kit. For example, a label can indicate that the kit is useful for a method of synthesizing a polynucleotide or for a method of determining the sequence of a nucleic acid.

Instructions for use of the packaged reagents or components can also be included in a kit. The instructions will typically include a tangible expression describing reaction parameters, such as the relative amounts of kit components and sample to be admixed, maintenance time periods for reagent/sample admixtures, temperature, buffer conditions, and the like.

It will be understood that not all components necessary for a particular reaction need be present in a particular kit. Rather one or more additional components can be provided from other sources. The instructions provided with a kit can identify the additional component(s) that are to be provided and where they can be obtained.

According to an aspect of the present invention, a kit is provided that is useful for stably incorporating an unnatural nucleic acid into a cellular nucleic acid, e.g., using the methods provided by the present invention for preparing genetically engineered cells. In one embodiment, a kit of the invention includes a genetically engineered cell and one or more unnatural nucleic acids.

In another embodiment, a kit of the invention includes a primer that binds to a portion of a nucleic acid molecule containing an unnatural nucleic acid. In another embodiment, the kit includes a microarray that contains primers that binds to a portion of a nucleic acid molecule containing an unnatural nucleic acid and at least a fragment of a target gene of interest. In some embodiments, many reagents may be provided in a kit of the invention, only some of which should be used together in a particular reaction or procedure. For example, multiple primers may be provided, only two of which are needed for a particular application.

In another embodiment, the kit of the invention provides a cell and a nucleic acid molecule containing a heterologous gene for introduction into the cell to thereby provide a genetically engineered cell. For example, the invention provides expression vectors comprising the nucleic acid of any of the embodiments hereinabove described in this paragraph. In one embodiment, the expression vector of the foregoing further comprises a recombinant regulatory sequence operably linked to the polynucleotide sequence.

Nucleic Acid Reagents & Tools

A nucleic acid reagent sometimes comprises one or more ORFs. An ORF may be from any suitable source, sometimes from genomic DNA, mRNA, reverse transcribed RNA or complementary DNA (cDNA) or a nucleic acid library comprising one or more of the foregoing, and is from any organism species that contains a nucleic acid sequence of interest, protein of interest, or activity of interest. Non-limiting examples of organisms from which an ORF can be obtained include bacteria, yeast, fungi, human, insect, nematode, bovine, equine, canine, feline, rat or mouse, for example. In some embodiments, a nucleic acid reagent, protein reagent, protein fragment reagent or other reagent described herein is isolated or purified.

A nucleic acid reagent sometimes comprises a nucleotide sequence adjacent to an ORF that is translated in conjunction with the ORF and encodes an amino acid tag. The tag-encoding nucleotide sequence is located 3' and/or 5' of an ORF in the nucleic acid reagent, thereby encoding a tag at the C-terminus or N-terminus of the protein or peptide encoded by the ORF. Any tag that does not abrogate in vitro transcription and/or translation may be utilized and may be appropriately selected by the artisan. Tags may facilitate isolation and/or purification of the desired ORF product from culture or fermentation media.

A tag sometimes specifically binds a molecule or moiety of a solid phase or a detectable label, for example, thereby having utility for isolating, purifying and/or detecting a protein or peptide encoded by the ORF. In some embodiments, a tag comprises one or more of the following elements: FLAG (e.g., DYKDDDDKG) (SEQ ID NO:42), V5 (e.g., GKPIPNPLLGLDST) (SEQ ID NO:43), c-MYC (e.g., EQKLISEEDL) (SEQ ID NO: 44), HSV (e.g., QPELAPEDPED) (SEQ ID NO: 45), influenza hemaglutinin, HA (e.g., YPYDVPDYA) (SEQ ID NO: 46), VSV-G (e.g., YTDIEMNRLGK) (SEQ ID NO: 47), bacterial glutathione-S-transferase, maltose binding protein, a streptavidin- or avidin-binding tag (e.g., pcDNA™6 BioEase™ Gateway® Biotinylation System (Invitrogen)), thioredoxin, β-galactosidase, VSV-glycoprotein, a fluorescent protein (e.g., green fluorescent protein or one of its many color variants (e.g., yellow, red, blue)), a polylysine or polyarginine sequence, a polyhistidine sequence (e.g., His6) or other sequence that chelates a metal (e.g., cobalt, zinc, copper), and/or a cysteine-rich sequence that binds to an arsenic-containing molecule. In certain embodiments, a cysteine-rich tag comprises the amino acid sequence CC-Xn-CC, wherein X is any amino acid and n is 1 to 3, and the cysteine-rich sequence sometimes is CCPGCC. In certain embodiments, the tag comprises a cysteine-rich element and a polyhistidine element (e.g., CCPGCC (SEQ ID NO: 48), and His6).

A tag often conveniently binds to a binding partner. For example, some tags bind to an antibody (e.g., FLAG) and sometimes specifically bind to a small molecule. For example, a polyhistidine tag specifically chelates a bivalent metal, such as nickel, copper, zinc and cobalt; a polylysine or polyarginine tag specifically binds to a zinc finger; a glutathione S-transferase tag binds to glutathione; and a cysteine-rich tag specifically binds to an arsenic-containing molecule. Arsenic-containing molecules include LUMIO™ agents (Invitrogen, California), such as FlAsH™ (EDT2[4',5'-bis(1,3,2-dithioarsolan-2-yl)fluorescein-(1,2-ethanedithiol)2]) and ReAsH reagents (e.g., U.S. Pat. Nos. 5,932,474; 6,054,271; 6,451,569; and 6,008,378; U.S. Patent Publication No. US2003/0083373; and International Publication No. WO99/21013). Such antibodies and small molecules sometimes are linked to a solid phase for convenient isolation of the target protein or target peptide.

A tag sometimes comprises a signal sequence or localization signal sequence. A signal sequence can be incorporated at the N-terminus of a target protein or target peptide, and sometimes is incorporated at the C-terminus. Examples of signal sequences are known to the artisan, are readily incorporated into a nucleic acid reagent, and often are selected according to the organism in which expression of the nucleic acid reagent is performed. A signal sequence in some embodiments localizes a translated protein or peptide to a cell membrane. Examples of signal sequences include, but are not limited to, a nucleus targeting signal (e.g., steroid receptor sequence and N-terminal sequence of SV40 virus large T antigen); mitochondrial targeting signal (e.g., amino acid sequence that forms an amphipathic helix); peroxisome targeting signal (e.g., C-terminal sequence in YFG from *S. cerevisiae*); and a secretion signal (e.g., N-terminal sequences from invertase, mating factor alpha, PHO5 and SUC2 in *S. cerevisiae*; multiple N-terminal sequences of *B. subtilis* proteins (e.g., Tjalsma et al., Microbiol. Molec. Biol. Rev. 64: 515-547 (2000)); alpha amylase signal sequence (e.g., U.S. Pat. No. 6,288,302); pectate lyase signal sequence (e.g., U.S. Pat. No. 5,846,818); precollagen signal sequence (e.g., U.S. Pat. No. 5,712,114); OmpA signal sequence (e.g., U.S. Pat. No. 5,470,719); lam beta signal sequence (e.g., U.S. Pat. No. 5,389,529); *B. brevis* signal sequence (e.g., U.S. Pat. No. 5,232,841); and *P. pastoris* signal sequence (e.g., U.S. Pat. No. 5,268,273).

A tag sometimes is directly adjacent to the amino acid sequence encoded by an ORF (i.e., there is no intervening sequence) and sometimes a tag is substantially adjacent to an ORF encoded amino acid sequence (e.g., an intervening sequence is present). An intervening sequence sometimes includes a recognition site for a protease, which is useful for cleaving a tag from a target protein or peptide. In some embodiments, the intervening sequence is cleaved by Factor Xa (e.g., recognition site I (E/D)GR), thrombin (e.g., recognition site LVPRGS), enterokinase (e.g., recognition site DDDDK), TEV protease (e.g., recognition site ENLYFQG) or PreScission™ protease (e.g., recognition site LEVLFQGP), for example.

An intervening sequence sometimes is referred to herein as a "linker sequence," and may be of any suitable length selected by the artisan. A linker sequence sometimes is about 1 to about 20 amino acids in length, and sometimes about 5 to about 10 amino acids in length. The artisan may select the linker length to substantially preserve target protein or peptide function (e.g., a tag may reduce target protein or peptide function unless separated by a linker), to enhance disassociation of a tag from a target protein or peptide when a protease cleavage site is present (e.g., cleavage may be enhanced when a linker is present), and to enhance interaction of a tag/target protein product with a solid phase. A linker can be of any suitable amino acid content, and often comprises a higher proportion of amino acids having relatively short side chains (e.g., glycine, alanine, serine and threonine).

A nucleic acid reagent sometimes includes a stop codon between a tag element and an insertion element or ORF, which can be useful for translating an ORF with or without the tag. Mutant tRNA molecules that recognize stop codons (described above) suppress translation termination and thereby are designated "suppressor tRNAs." Suppressor tRNAs can result in the insertion of amino acids and continuation of translation past stop codons (e.g., U.S. Patent Application No. 60/587,583; Eggertsson, et al., (1988) Microbiological Review 52(3):354-374, and Engleerg-Kukla, et al. (1996) in *Escherichia coli* and *Salmonella* Cellular and Molecular Biology, Chapter 60, pps 909-921, Neidhardt, et al. eds., ASM Press, Washington, D.C.). A number of suppressor tRNAs are known, including but not limited to, supE, supP, supD, supF and supZ suppressors, which suppress the termination of translation of the amber stop codon; supB, glT, supL, supN, supC and supM suppressors, which suppress the function of the ochre stop codon and glyT, trpT and Su-9 suppressors, which suppress the function of the opal stop codon. In general, suppressor tRNAs contain one or more mutations in the anti-codon loop of the tRNA that allows the tRNA to base pair with a codon that ordinarily functions as a stop codon. The mutant tRNA is charged with its cognate amino acid residue and the cognate amino acid residue is inserted into the translating polypeptide when the stop codon is encountered. Mutations that enhance the efficiency of termination suppressors (i.e., increase stop codon read-through) have been identified. These include, but are not limited to, mutations in the uar gene (also known as the prfA gene), mutations in the ups gene, mutations in the sueA, sueB and sueC genes, mutations in the rpsD (ramA) and rpsE (spcA) genes and mutations in the rplL gene.

Thus, a nucleic acid reagent comprising a stop codon located between an ORF and a tag can yield a translated ORF alone when no suppressor tRNA is present in the translation system, and can yield a translated ORF-tag fusion when a suppressor tRNA is present in the system. Suppressor tRNA can be generated in cells transfected with a nucleic acid encoding the tRNA (e.g., a replication incompetent adenovirus containing the human tRNA-Ser suppressor gene can be transfected into cells, or a YAC containing a yeast or bacterial tRNA suppressor gene can be transfected into yeast cells, for example). Vectors for synthesizing suppressor tRNA and for translating ORFs with or without a tag are available to the artisan (e.g., Tag-On-Demand™ kit (Invitrogen Corporation, California); Tag-On-Demand™ Suppressor Supernatant Instruction Manual, Version B, 6 Jun. 2003; Tag-On-Demand™ Gateway® Vector Instruction Manual, Version B, 20 June, 2003; and Capone et al., EMBO J., 4:213, 1985).

A nucleic acid or nucleic acid reagent can comprise certain elements, e.g., regulatory elements, often selected according to the intended use of the nucleic acid. Any of the following elements can be included in or excluded from a nucleic acid reagent. A nucleic acid reagent, for example, may include one or more or all of the following nucleotide elements: one or more promoter elements, one or more 5' untranslated regions (5'UTRs), one or more regions into which a target nucleotide sequence may be inserted (an "insertion element"), one or more target nucleotide sequences, one or more 3' untranslated regions (3'UTRs), and one or more selection elements. A nucleic acid reagent can be provided with one or more of such elements and other elements may be inserted into the nucleic acid before the nucleic acid is introduced into the desired organism. In some embodiments, a provided nucleic acid reagent comprises a promoter, 5'UTR, optional 3'UTR and insertion element(s) by which a target nucleotide sequence is inserted (i.e., cloned) into the nucleotide acid reagent. In certain embodiments, a provided nucleic acid reagent comprises a promoter, insertion element(s) and optional 3'UTR, and a 5' UTR/target nucleotide sequence is inserted with an optional 3'UTR. The elements can be arranged in any order suitable for expression in the chosen expression system (e.g., expression in a chosen organism, or expression in a cell free system, for example), and in some embodiments a nucleic acid reagent comprises the following elements in the 5' to 3' direction: (1) promoter element, 5'UTR, and insertion element(s); (2) promoter element, 5'UTR, and target nucleotide sequence; (3) promoter element, 5'UTR, insertion element(s) and 3'UTR; and (4) promoter element, 5'UTR, target nucleotide sequence and 3'UTR.

Nucleic acid reagents, e.g., expression cassettes and/or expression vectors, can include a variety of regulatory elements, including promoters, enhancers, translational initiation sequences, transcription termination sequences and other elements. A "promoter" is generally a sequence or sequences of DNA that function when in a relatively fixed location in regard to the transcription start site. For example, the promoter can be upstream of the nucleotide triphosphate transporter nucleic acid segment. A "promoter" contains core elements required for basic interaction of RNA polymerase and transcription factors and can contain upstream elements and response elements. "Enhancer" generally refers to a sequence of DNA that functions at no fixed distance from the transcription start site and can be either 5' or 3" to the transcription unit. Furthermore, enhancers can be within an intron as well as within the coding sequence itself. They are usually between 10 and 300 by in length, and they function in cis. Enhancers function to increase transcription from nearby promoters. Enhancers, like promoters, also often contain response elements that mediate the regulation of transcription. Enhancers often determine the regulation of expression.

As noted above, nucleic acid reagents may also comprise one or more 5' UTR's, and one or more 3'UTR's. For example, expression vectors used in eukaryotic host cells (e.g., yeast, fungi, insect, plant, animal, human or nucleated cells) and prokaryotic host cells (e.g., virus, bacterium) can contain sequences that signal for the termination of transcription which can affect mRNA expression. These regions can be transcribed as polyadenylated segments in the untranslated portion of the mRNA encoding tissue factor protein. The 3" untranslated regions also include transcription termination sites. In some preferred embodiments, a transcription unit comprises a polyadenylation region. One benefit of this region is that it increases the likelihood that the transcribed unit will be processed and transported like mRNA. The identification and use of polyadenylation signals in expression constructs is well established. In some preferred embodiments, homologous polyadenylation signals can be used in the transgene constructs.

A 5' UTR may comprise one or more elements endogenous to the nucleotide sequence from which it originates, and sometimes includes one or more exogenous elements. A 5' UTR can originate from any suitable nucleic acid, such as genomic DNA, plasmid DNA, RNA or mRNA, for example, from any suitable organism (e.g., virus, bacterium, yeast, fungi, plant, insect or mammal). The artisan may select appropriate elements for the 5' UTR based upon the chosen expression system (e.g., expression in a chosen organism, or expression in a cell free system, for example). A 5' UTR sometimes comprises one or more of the following elements known to the artisan: enhancer sequences (e.g., transcriptional or translational), transcription initiation site, transcription factor binding site, translation regulation site, translation initiation site, translation factor binding site, accessory protein binding site, feedback regulation agent binding sites, Pribnow box, TATA box, −35 element, E-box (helix-loop-helix binding element), ribosome binding site, replicon, internal ribosome entry site (IRES), silencer element and the like. In some embodiments, a promoter element may be isolated such that all 5' UTR elements necessary for proper conditional regulation are contained in the promoter element fragment, or within a functional subsequence of a promoter element fragment.

A 5'UTR in the nucleic acid reagent can comprise a translational enhancer nucleotide sequence. A translational enhancer nucleotide sequence often is located between the promoter and the target nucleotide sequence in a nucleic acid reagent. A translational enhancer sequence often binds to a ribosome, sometimes is an 18S rRNA-binding ribonucleotide sequence (i.e., a 40S ribosome binding sequence) and sometimes is an internal ribosome entry sequence (IRES). An IRES generally forms an RNA scaffold with precisely placed RNA tertiary structures that contact a 40S ribosomal subunit via a number of specific intermolecular interactions. Examples of ribosomal enhancer sequences are known and can be identified by the artisan (e.g., Mignone et al., Nucleic Acids Research 33: D141-D146 (2005); Paulous et al., Nucleic Acids Research 31: 722-733 (2003); Akbergenov et al., Nucleic Acids Research 32: 239-247 (2004); Mignone et al., Genome Biology 3(3): reviews0004.1-0001.10 (2002); Gallie, Nucleic Acids Research 30: 3401-3411 (2002); Shaloiko et al., DOI: 10.1002/bit.20267; and Gallie et al., Nucleic Acids Research 15: 3257-3273 (1987)).

A translational enhancer sequence sometimes is a eukaryotic sequence, such as a Kozak consensus sequence or other sequence (e.g., hydroid polyp sequence, GenBank accession no. U07128). A translational enhancer sequence sometimes is a prokaryotic sequence, such as a Shine-Dalgarno consensus sequence. In certain embodiments, the translational enhancer sequence is a viral nucleotide sequence. A translational enhancer sequence sometimes is from a 5'UTR of a plant virus, such as Tobacco Mosaic Virus (TMV), Alfalfa Mosaic Virus (AMV); Tobacco Etch Virus (ETV); Potato Virus Y (PVY); Turnip Mosaic (poty) Virus and Pea Seed Borne Mosaic Virus, for example. In certain embodiments, an omega sequence about 67 bases in length from TMV is included in the nucleic acid reagent as a translational enhancer sequence (e.g., devoid of guanosine nucleotides and includes a 25 nucleotide long poly (CAA) central region).

A 3' UTR may comprise one or more elements endogenous to the nucleotide sequence from which it originates and sometimes includes one or more exogenous elements. A 3' UTR may originate from any suitable nucleic acid, such as genomic DNA, plasmid DNA, RNA or mRNA, for example, from any suitable organism (e.g., a virus, bacterium, yeast, fungi, plant, insect or mammal). The artisan can select appropriate elements for the 3' UTR based upon the chosen expression system (e.g., expression in a chosen organism, for example). A 3' UTR sometimes comprises one or more of the following elements known to the artisan: transcription regulation site, transcription initiation site, transcription termination site, transcription factor binding site, translation regulation site, translation termination site, translation initiation site, translation factor binding site, ribosome binding site, replicon, enhancer element, silencer element and polyadenosine tail. A 3' UTR often includes a polyadenosine tail and sometimes does not, and if a polyadenosine tail is present, one or more adenosine moieties may be added or deleted from it (e.g., about 5, about 10, about 15, about 20, about 25, about 30, about 35, about 40, about 45 or about 50 adenosine moieties may be added or subtracted).

In some embodiments, modification of a 5' UTR and/or a 3' UTR can be used to alter (e.g., increase, add, decrease or substantially eliminate) the activity of a promoter. Alteration of the promoter activity can in turn alter the activity of a peptide, polypeptide or protein (e.g., enzyme activity for example), by a change in transcription of the nucleotide sequence(s) of interest from an operably linked promoter element comprising the modified 5' or 3' UTR. For example, a microorganism can be engineered by genetic modification to express a nucleic acid reagent comprising a modified 5' or 3' UTR that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent comprising a modified 5' or 3' UTR that can decrease the expression of an activity by decreasing or substantially eliminating transcription from a homologous or heterologous promoter operably linked to a nucleotide sequence of interest, in certain embodiments.

Expression of a nucleotide triphosphate transporter from an expression cassette or expression vector can be controlled by any promoter capable of expression in prokaryotic cells or eukaryotic cells. A promoter element typically is required for DNA synthesis and/or RNA synthesis. A promoter element often comprises a region of DNA that can facilitate the transcription of a particular gene, by providing a start site for the synthesis of RNA corresponding to a gene. Promoters generally are located near the genes they regulate, are located upstream of the gene (e.g., 5' of the gene), and are on the same strand of DNA as the sense strand of the gene, in some embodiments. In some embodiments, a promoter element can be isolated from a gene or organism and inserted in functional connection with a polynucleotide sequence to allow altered and/or regulated expression. A non-native promoter (e.g., promoter not normally associated with a given nucleic acid sequence) used for expression of a nucleic acid often is referred to as a heterologous promoter. In certain embodiments, a heterologous promoter and/or a 5'UTR can be inserted in functional connection with a polynucleotide that encodes a polypeptide having a desired activity as described herein. The terms "operably linked" and "in functional connection with" as used herein with respect to promoters, refer to a relationship between a coding sequence and a promoter element. The promoter is operably linked or in functional connection with the coding sequence when expression from the coding sequence via transcription is regulated, or controlled by, the promoter element. The terms "operably linked" and "in functional connection with" are utilized interchangeably herein with respect to promoter elements.

A promoter often interacts with a RNA polymerase. A polymerase is an enzyme that catalyzes synthesis of nucleic acids using a preexisting nucleic acid reagent. When the template is a DNA template, an RNA molecule is transcribed before protein is synthesized. Enzymes having polymerase activity suitable for use in the present methods include any polymerase that is active in the chosen system with the chosen template to synthesize protein. In some embodiments, a promoter (e.g., a heterologous promoter) also referred to herein as a promoter element, can be operably linked to a nucleotide sequence or an open reading frame (ORF). Transcription from the promoter element can catalyze the synthesis of an RNA corresponding to the nucleotide sequence or ORF sequence operably linked to the promoter, which in turn leads to synthesis of a desired peptide, polypeptide or protein.

Promoter elements sometimes exhibit responsiveness to regulatory control. Promoter elements also sometimes can be regulated by a selective agent. That is, transcription from promoter elements sometimes can be turned on, turned off, up-regulated or down-regulated, in response to a change in environmental, nutritional or internal conditions or signals (e.g., heat inducible promoters, light regulated promoters, feedback regulated promoters, hormone influenced promoters, tissue specific promoters, oxygen and pH influenced promoters, promoters that are responsive to selective agents (e.g., kanamycin) and the like, for example). Promoters influenced by environmental, nutritional or internal signals frequently are influenced by a signal (direct or indirect) that binds at or near the promoter and increases or decreases expression of the target sequence under certain conditions.

Non-limiting examples of selective or regulatory agents that can influence transcription from a promoter element used in embodiments described herein include, without limitation, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like). In some embodiments, the regulatory or selective agent can be added to change the existing growth conditions to which the organism is subjected (e.g., growth in liquid culture, growth in a fermenter, growth on solid nutrient plates and the like for example).

In some embodiments, regulation of a promoter element can be used to alter (e.g., increase, add, decrease or substantially eliminate) the activity of a peptide, polypeptide or protein (e.g., enzyme activity for example). For example, a microorganism can be engineered by genetic modification to express a nucleic acid reagent that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent that can decrease expression of an activity by decreasing or substantially eliminating transcription from a homologous or heterologous promoter operably linked to a nucleotide sequence of interest, in certain embodiments.

Nucleic acids encoding heterologous proteins, e.g., nucleotide triphosphate transporters, can be inserted into or employed with any suitable expression system. In some embodiments, a nucleic acid reagent sometimes is stably integrated into the chromosome of the host organism, or a nucleic acid reagent can be a deletion of a portion of the host chromosome, in certain embodiments (e.g., genetically modified organisms, where alteration of the host genome confers the ability to selectively or preferentially maintain the desired organism carrying the genetic modification). Such nucleic acid reagents (e.g., nucleic acids or genetically modified organisms whose altered genome confers a selectable trait to the organism) can be selected for their ability to guide production of a desired protein or nucleic acid molecule. When desired, the nucleic acid reagent can be altered such that codons encode for (i) the same amino acid, using a different tRNA than that specified in the native sequence, or (ii) a different amino acid than is normal, including unconventional or unnatural amino acids (including detectably labeled amino acids).

Recombinant expression is usefully accomplished using an expression cassette that can be part of a vector, such as a plasmid. A vector can include a promoter operably linked to nucleic acid encoding a nucleotide triphosphate transporter. A vector can also include other elements required for transcription and translation as described herein. An expression cassette, expression vector, and sequences in a cassette or vector can be heterologous to the cell to which the unnatural nucleotides are contacted. For example, a nucleotide triphosphate transporter sequence can be heterologous to the cell.

A variety of prokaryotic and eukaryotic expression vectors suitable for carrying, encoding and/or expressing nucleotide triphosphate transporters can be produced. Such expression vectors include, for example, pET, pET3d, pCR2.1, pBAD, pUC, and yeast vectors. The vectors can be used, for example, in a variety of in vivo and in vitro situations. Non-limiting examples of prokaryotic promoters that can be used include SP6, T7, T5, tac, bla, trp, gal, lac, or maltose promoters. Non-limiting examples of eukaryotic promoters that can be used include constitutive promoters, e.g., viral promoters such as CMV, SV40 and RSV promoters, as well as regulatable promoters, e.g., an inducible or repressible promoter such as a tet promoter, a hsp70 promoter, and a synthetic promoter regulated by CRE. Vectors for bacterial expression include pGEX-5X-3, and for eukaryotic expression include pClneo-CMV. Viral vectors that can be employed include those relating to lentivirus, adenovirus, adeno-associated virus, herpes virus, vaccinia virus, polio virus, AIDS virus, neuronal trophic virus, Sindbis and other viruses. Also useful are any viral families which share the properties of these viruses which make them suitable for use as vectors. Retroviral vectors that can be employed include those described in Verma, American Society for Microbiology, pp. 229-232, Washington, (1985). For example, such retroviral vectors can include Murine Maloney Leukemia virus, MMLV, and other retroviruses that express desirable properties. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral nucleic acid Cloning Any convenient cloning strategy known in the art may be utilized to incorporate an element, such as an ORF, into a nucleic acid reagent. Known methods can be utilized to insert an element into the template independent of an insertion element, such as (1) cleaving the template at one or more existing restriction enzyme sites and ligating an element of interest and (2) adding restriction enzyme sites to the template by hybridizing oligonucleotide primers that include one or more suitable restriction enzyme sites and amplifying by polymerase chain reaction (described in greater detail herein). Other cloning strategies take advantage of one or more insertion sites present or inserted into the nucleic acid reagent, such as an oligonucleotide primer hybridization site for PCR, for example, and others described herein. In some embodiments, a cloning strategy can be combined with genetic manipulation such as recombination (e.g., recombination of a nucleic acid reagent with a nucleic acid sequence of interest into the genome of the organism to be modified, as described further herein). In some embodiments, the cloned ORF(s) can produce (directly or indirectly) modified or wild type nucleotide triphosphate transporters and/or polymerases), by engineering a microorganism with one or more ORFs of interest, which microorganism comprises altered activities of nucleotide triphosphate transporter activity or polymerase activity.

A nucleic acid may be specifically cleaved by contacting the nucleic acid with one or more specific cleavage agents. Specific cleavage agents often will cleave specifically according to a particular nucleotide sequence at a particular site. Examples of enzyme specific cleavage agents include without limitation endonucleases (e.g., DNase (e.g., DNase I, II); RNase (e.g., RNase E, F, H, P); Cleavase™ enzyme; Taq DNA polymerase; E. coli DNA polymerase I and eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I. Bgl II, Bln I, Bsm I, BssH II, BstE II, Cfo I, Cla I, Dde I, Dpn I, Dra I, EcIX I, EcoR I, EcoR I, EcoR II, EcoR V, Hae II, Hae II, Hind II, Hind III, Hpa I, Hpa II, Kpn I, Ksp I, Mlu I, MIuN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I); glycosylases (e.g., uracil-DNA glycolsylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes, and DNAzymes. Sample nucleic acid may be treated with a chemical agent, or synthesized using modified nucleotides, and the modified nucleic acid may be cleaved. In non-limiting examples, sample nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfite, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

In some embodiments, the nucleic acid reagent includes one or more recombinase insertion sites. A recombinase insertion site is a recognition sequence on a nucleic acid molecule that participates in an integration/recombination reaction by recombination proteins. For example, the recombination site for Cre recombinase is loxP, which is a 34 base pair sequence comprised of two 13 base pair inverted repeats (serving as the recombinase binding sites) flanking an 8 base pair core sequence (e.g., Sauer, Curr. Opin. Biotech. 5:521-527 (1994)). Other examples of recombination sites include attB, attP, attL, and attR sequences, and mutants, fragments, variants and derivatives thereof, which are recognized by the recombination protein λ, Int and by the auxiliary proteins integration host factor (IHF), FIS and excisionase (Xis) (e.g., U.S. Pat. Nos. 5,888,732; 6,143,557; 6,171,861; 6,270,969; 6,277,608; and 6,720,140; U.S. patent application Ser. Nos. 09/517,466, and 09/732,914; U.S. Patent Publication No. US2002/0007051; and Landy, Curr. Opin. Biotech. 3:699-707 (1993)).

Examples of recombinase cloning nucleic acids are in Gateway® systems (Invitrogen, California), which include at least one recombination site for cloning desired nucleic acid molecules in vivo or in vitro. In some embodiments, the system utilizes vectors that contain at least two different site-specific recombination sites, often based on the bacteriophage lambda system (e.g., att1 and att2), and are mutated from the wild-type (att0) sites. Each mutated site has a unique specificity for its cognate partner att site (i.e., its binding partner recombination site) of the same type (for example attB1 with attP1, or attL1 with attR1) and will not cross-react with recombination sites of the other mutant type or with the wild-type att0 site. Different site specificities allow directional cloning or linkage of desired molecules thus providing desired orientation of the cloned molecules. Nucleic acid fragments flanked by recombination sites are cloned and subcloned using the Gateway® system by replacing a selectable marker (for example, ccdB) flanked by att sites on the recipient plasmid molecule, sometimes termed the Destination Vector. Desired clones are then selected by transformation of a ccdB sensitive host strain and positive selection for a marker on the recipient molecule. Similar strategies for negative selection (e.g., use of toxic genes) can be used in other organisms such as thymidine kinase (TK) in mammals and insects.

A nucleic acid reagent sometimes contains one or more origin of replication (ORI) elements. In some embodiments, a template comprises two or more ORIs, where one functions efficiently in one organism (e.g., a bacterium) and another functions efficiently in another organism (e.g., a eukaryote, like yeast for example). In some embodiments, an ORI may function efficiently in one species (e.g., *S. cerevisiae*, for example) and another ORI may function efficiently in a different species (e.g., *S. pombe*, for example). A nucleic acid reagent also sometimes includes one or more transcription regulation sites.

A nucleic acid reagent, e.g., an expression cassette or vector, can include nucleic acid sequence encoding a marker product. A marker product is used to determine if a gene has been delivered to the cell and once delivered is being expressed. Example marker genes include the *E. coli* lacZ gene which encodes β-galactosidase and green fluorescent protein. In some embodiments the marker can be a selectable marker. When such selectable markers are successfully transferred into a host cell, the transformed host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin (Southern et al., J. Molec. Appl. Genet. 1: 327 (1982)), mycophenolic acid, (Mulligan et al., Science 209: 1422 (1980)) or hygromycin, (Sugden, et al., Mol. Cell. Biol. 5: 410-413 (1985)).

A nucleic acid reagent can include one or more selection elements (e.g., elements for selection of the presence of the nucleic acid reagent, and not for activation of a promoter element which can be selectively regulated). Selection elements often are utilized using known processes to determine whether a nucleic acid reagent is included in a cell. In some embodiments, a nucleic acid reagent includes two or more selection elements, where one functions efficiently in one organism, and another functions efficiently in another organism. Examples of selection elements include, but are not limited to, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like).

A nucleic acid reagent can be of any form useful for in vivo transcription and/or translation. A nucleic acid sometimes is a plasmid, such as a supercoiled plasmid, sometimes is a yeast artificial chromosome (e.g., YAC), sometimes is a linear nucleic acid (e.g., a linear nucleic acid produced by PCR or by restriction digest), sometimes is single-stranded and sometimes is double-stranded. A nucleic acid reagent sometimes is prepared by an amplification process, such as a polymerase chain reaction (PCR) process or transcription-mediated amplification process (TMA). In TMA, two enzymes are used in an isothermal reaction to produce amplification products detected by light emission (e.g., Biochemistry 1996 Jun. 25; 35(25):8429-38). Standard PCR processes are known (e.g., U.S. Pat. Nos. 4,683,202; 4,683,195; 4,965,188; and 5,656,493), and generally are performed in cycles. Each cycle includes heat denaturation, in which hybrid nucleic acids dissociate; cooling, in which primer oligonucleotides hybridize; and extension of the oligonucleotides by a polymerase (i.e., Taq polymerase). An example of a PCR cyclical process is treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Multiple cycles frequently are performed using a commercially available thermal cycler. PCR amplification products sometimes are stored for a time at a lower temperature (e.g., at 4° C.) and sometimes are frozen (e.g., at −20° C.) before analysis.

Nucleic Acid Fragmentation

In certain embodiments a nucleic acid can be from a library or can be obtained from enzymatically digested, sheared or sonicated genomic DNA (e.g., fragmented) from an organism of interest. In some embodiments, nucleic acid subjected to fragmentation or cleavage may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 base pairs. Fragments can be generated by any suitable method in the art, and the average, mean or nominal length of nucleic acid fragments can be controlled by selecting an appropriate fragment-generating procedure by the person of ordinary skill. In some embodiments, the fragmented DNA can be size selected to obtain nucleic acid fragments of a particular size range.

Nucleic acid can be fragmented by various methods known to the person of ordinary skill, which include without limitation, physical, chemical and enzymatic processes. Examples of such processes are described in US2005/0112590. Certain processes can be selected by the person of ordinary skill to generate non-specifically cleaved fragments or specifically cleaved fragments. Examples of processes that can generate non-specifically cleaved fragment sample nucleic acid include, without limitation, contacting sample nucleic acid with apparatus that expose nucleic acid to shearing force (e.g., passing nucleic acid through a syringe needle; use of a French press); exposing sample nucleic acid to irradiation (e.g., gamma, x-ray, UV irradiation; fragment sizes can be controlled by irradiation intensity); boiling nucleic acid in water (e.g., yields about 500 base pair fragments) and exposing nucleic acid to an acid and base hydrolysis process.

Amplification

A nucleic acid suitable for use in the embodiments described herein sometimes is amplified by any amplification process known in the art (e.g., PCR, RT-PCR and the like). Nucleic acid amplification may be particularly beneficial when using organisms that are typically difficult to culture (e.g., slow growing, require specialize culture conditions and the like).

Exemplary methods for amplifying nucleic acids include the polymerase chain reaction (PCR) (Mullis et al., (1986) Cold Spring Harb. Symp. Quant. Biol. 51 pt. 1:263; Cleary et al., (2004) Nature Methods 1:241; and U.S. Pat. Nos. 4,683,195 and 4,683,202), anchor PCR, RACE PCR, ligation chain reaction (LCR) (Landegran et al., (1988) Science 241:1077-1080; and Nakazawa et al., (1994) Proc. Natl. Acad. Sci. U.S.A. 91:360-364), self-sustained sequence replication (Guatelli et al., (1990) Proc. Natl. Acad. Sci. U.S.A. 87:1874), transcriptional amplification system (Kwoh et al., (1989) Proc. Natl. Acad. Sci. U.S.A. 86:1173), Q-Beta Replicase (Lizardi et al., (1988) BioTechnology 6:1197), recursive PCR (Jaffe et al., (2000) J. Biol. Chem. 275:2619; and Williams et al., (2002) I Biol. Chem. 277:7790), the amplification methods described in U.S. Pat. Nos. 6,391,544; 6,365,375; 6,294,323; 6,261,797; 6,124,090; and 5,612,199, isothermal amplification (e.g., rolling circle amplification (RCA), hyperbranched rolling circle amplification (HRCA), strand displacement amplification (SDA), helicase-dependent amplification (HDA), PWGA, polymerase and/or ligase chain reactions, thermal cycling (PCR) or isothermally (e.g. RCA, hRCA, SDA, HDA, PWGA), or any other nucleic acid amplification method using techniques well known to those of skill in the art.

In some embodiments, a limited amplification reaction, also known as pre-amplification, can be performed. Pre-amplification is a method in which a limited amount of amplification occurs due to a small number of cycles, for example 10 cycles, being performed. Pre-amplification can allow some amplification, but stops amplification prior to the exponential phase, and typically produces about 500 copies of the desired nucleotide sequence(s). Use of pre-amplification may also limit inaccuracies associated with depleted reactants in standard PCR reactions.

Sequencing

Sequencing can be accomplished through classic Sanger sequencing methods, which are known in the art. In some embodiments sequencing can be performed using high-throughput sequencing methods some of which allow detection of a sequenced nucleotide immediately after or upon its incorporation into a growing strand, for example, detection of sequence in substantially real time or real time. In some cases, high throughput sequencing generates at least 1,000, at least 5,000, at least 10,000, at least 20,000, at least 30,000, at least 40,000, at least 50,000, at least 100,000 or at least 500,000 sequence reads per hour; with each read being at least 50, at least 60, at least 70, at least 80, at least 90, at least 100, at least 120 or at least 150 bases per read (or 500-1,000 bases per read).

High-throughput sequencing methods can include but are not limited to, Massively Parallel Signature Sequencing (MPSS, Lynx Therapeutics), Polony sequencing, 454 pyrosequencing, Illumina (Solexa) sequencing, SOLiD sequencing, on semiconductor sequencing, DNA nanoball sequencing, Helioscope™ single molecule sequencing, Single Molecule SMRT™ sequencing, Single Molecule real time (RNAP) sequencing, Nanopore DNA sequencing, and/or sequencing by hybridization, for example, a non-enzymatic method that uses a DNA microarray, or microfluidic Sanger sequencing.

Homology and Identity

In addition to the regulated promoter sequences, regulatory sequences, and coding polynucleotides provided herein, a nucleic acid reagent may include a polynucleotide sequence 80% or more identical to the foregoing (or to the complementary sequences). That is, a nucleotide sequence that is at least 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to a nucleotide sequence described herein can be utilized. The term "identical" as used herein refers to two or more nucleotide sequences having substantially the same nucleotide sequence when compared to each other. One test for determining whether two nucleotide sequences or amino acids sequences are substantially identical is to determine the percent of identical nucleotide sequences or amino acid sequences shared.

Calculations of sequence identity can be performed as follows. Sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is sometimes 30% or more, 40% or more, 50% or more, often 60% or more, and more often 70% or more, 80% or more, 90% or more, or 100% of the length of the reference sequence. The nucleotides or amino acids at corresponding nucleotide or polypeptide positions, respectively, are then compared among the two sequences. When a position in the first sequence is occupied by the same nucleotide or amino acid as the corresponding position in the second sequence, the nucleotides or amino acids are deemed to be identical at that position. The percent identity between the two sequences is a function of the number of identical positions shared by the sequences, taking into account the number of gaps, and the length of each gap, introduced for optimal alignment of the two sequences.

Comparison of sequences and determination of percent identity between two sequences can be accomplished using a mathematical algorithm. Percent identity between two amino acid or nucleotide sequences can be determined using the algorithm of Meyers & Miller, CABIOS 4: 11-17 (1989), which has been incorporated into the ALIGN program (version 2.0), using a PAM120 weight residue table, a gap length penalty of 12 and a gap penalty of 4. Also, percent identity between two amino acid sequences can be determined using the Needleman & Wunsch, J. Mol. Biol. 48: 444-453 (1970) algorithm which has been incorporated into the GAP program in the GCG software package (available at the http address www.gcg.com), using either a Blossum 62 matrix or a PAM250 matrix, and a gap weight of 16, 14, 12, 10, 8, 6, or 4 and a length weight of 1, 2, 3, 4, 5, or 6. Percent identity between two nucleotide sequences can be determined using the GAP program in the GCG software package (available at http address www.gcg.com), using a NWSgapdna.CMP matrix and a gap weight of 40, 50, 60, 70, or 80 and a length weight of 1, 2, 3, 4, 5, or 6. A set of parameters often used is a Blossum 62 scoring matrix with a gap open penalty of 12, a gap extend penalty of 4, and a frameshift gap penalty of 5.

Sequence identity can also be determined by hybridization assays conducted under stringent conditions. An example of stringent hybridization conditions is hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C.

Definitions

As used herein, unless otherwise indicated, the article "a" means one or more unless explicitly otherwise provided for. As used herein, unless otherwise indicated, terms such as "contain," "containing," "include," "including," and the like mean "comprising." As used herein, unless otherwise indicated, the term "or" can be conjunctive or disjunctive. As used herein, unless otherwise indicated, any embodiment can be combined with any other embodiment. As used herein, unless otherwise indicated, some inventive embodiments herein contemplate numerical ranges. When ranges are present, the ranges include the range endpoints. Additionally, every sub-range and value within the range is present as if explicitly written out.

The terms "amplify", "amplification", "amplification reaction", or "amplifying" as used herein refer to any in vitro processes for multiplying the copies of a target sequence of nucleic acid. Amplification sometimes refers to an "exponential" increase in target nucleic acid. However, "amplifying" as used herein can also refer to linear increases in the numbers of a select target sequence of nucleic acid, but is different than a one-time, single primer extension step.

As used herein, "bicyclic nucleoside" refers to a nucleoside having a sugar moiety comprising a sugar-ring (including, but not limited to, furanose) comprising a bridge connecting two carbon atoms of the sugar ring to form a second ring. In certain embodiments, the bridge connects the 4' carbon to the 2' carbon of a 5-membered sugar ring group at the position of the sugar ring.

As used herein, the term "complementary cleavage reactions" refers to cleavage reactions that are carried out on the same nucleic acid using different cleavage reagents or by altering the cleavage specificity of the same cleavage reagent such that alternate cleavage patterns of the same target or reference nucleic acid or protein are generated. In certain embodiments, nucleic acids of interest may be treated with one or more specific cleavage agents (e.g., 1, 2, 3, 4, 5, 6, 7, 8, 9, 10 or more specific cleavage agents) in one or more reaction vessels (e.g., nucleic acid of interest is treated with each specific cleavage agent in a separate vessel).

The term "DNA polymerase" as used herein includes DNA polymerases that have been modified by e.g. natural process such as posttranslational processing, or non-natural process such as chemical modification. Such modifications can occur on the peptide backbone, amino acid side chains, or the N- or C-terminus. Modifications include e.g. acetylations, acylations, ADP-ribosylations, amidations, covalent attachment of flavines, haem-groups, nucleotides or nucleotide derivatives, lipids or lipid derivatives, cyclizations, disulfide bridges, methylations and demethylations, cystine linkages, formylations, γ-carboxylations, glycosylations, hydroxylations, phosphorylations and the tRNA-mediated addition of amino acids.

The term "engineered" as used herein, when referring to a microorganism or cell, refers to a modified organism or cell that includes one or more activities distinct from an activity present in a microorganism or cell utilized as a starting point for modification (e.g., host microorganism/cell or unmodified organism/cell). Engineered microorganisms typically arise as a result of a genetic modification, usually introduced or selected for, by one of skill in the art using readily available techniques. Non-limiting examples of methods useful for generating an altered activity include, introducing a heterologous polynucleotide (e.g., nucleic acid or gene integration, also referred to as "knock in"), removing an endogenous polynucleotide, altering the sequence of an existing endogenous nucleic acid sequence (e.g., site-directed mutagenesis), disruption of an existing endogenous nucleic acid sequence (e.g., knock outs and transposon or insertion element mediated mutagenesis), selection for an altered activity where the selection causes a change in a naturally occurring activity that can be stably inherited (e.g., causes a change in a nucleic acid sequence in the genome of the organism or in an epigenetic nucleic acid that is replicated and passed on to daughter cells), PCR-based mutagenesis, and the like.

The term "genetic modification" as used herein refers to any suitable nucleic acid addition, removal or alteration that facilitates transport, e.g., import, of a target nucleic acid in an engineered microorganism. Genetic modifications include, without limitation, insertion of one or more nucleotides in a native nucleic acid of a host organism in one or more locations, deletion of one or more nucleotides in a native nucleic acid of a host organism in one or more locations, modification or substitution of one or more nucleotides in a native nucleic acid of a host organism in one or more locations, insertion of a non-native nucleic acid into a host organism (e.g., insertion of an autonomously replicating vector), and removal of a non-native nucleic acid in a host organism (e.g., removal of a vector).

The term "heterologous" nucleic acid, as used herein, refers to a nucleic acid sequence not present in a host microorganism in some embodiments. In certain embodiments, a heterologous polynucleotide is present in a different amount (e.g., different copy number) than in a host microorganism, which can be accomplished, for example, by introducing more copies of a particular nucleotide sequence to a host microorganism (e.g., the particular nucleotide sequence may be in a nucleic acid autonomous of the host chromosome or may be inserted into a chromosome). A heterologous nucleic acid is from a different organism in some embodiments, and in certain embodiments, is from the same type of organism but from an outside source (e.g., a recombinant source). As used herein, the term "heterologous" when used in reference to a protein, promoter, or nucleic acid refers to a protein, promoter, or nucleic acid that has been manipulated in some way. For example, a heterologous nucleic acid, heterologous coding region, or a heterologous promoter includes a nucleic acid, coding region, or promoter that is not normally in the species to which it has been introduced or that is not normally linked to the nucleic acids to which it is linked. A heterologous nucleic acid or protein therefore includes a nucleic acid or protein that is native to one type of organism but that has been altered in some way (e.g., placed in a different chromosomal location, mutated, added in multiple copies, linked to a non-native promoter, or enhancer element, etc.). Heterologous genes include gene sequences that comprise cDNA forms of a gene. Heterologous coding regions can be distinguished from endogenous coding regions, for example, when the heterologous coding regions are joined to nucleotide sequences comprising regulatory elements such as promoters that are not found naturally associated with the coding region, or when the heterologous coding regions are associated with portions of a chromosome not found in nature (e.g., genes expressed in loci where the protein encoded by the coding region is not normally expressed). Similarly, heterologous promoters can be promoters that are linked to a coding region to which they are not linked in nature.

The term "isolated" as used herein refers to material removed from its original environment (e.g., the natural environment if it is naturally occurring, or a host cell if expressed exogenously), and thus is altered "by the hand of man" from its original environment.

As used herein, "modified nucleoside" refers to a nucleoside comprising at least one modification compared to naturally occurring RNA or DNA nucleosides. Such modification may be at the sugar moiety and/or at the nucleobases.

The term "mutagenesis" as used herein refers to any modification to a nucleic acid (e.g., nucleic acid reagent, or host chromosome, for example) that is subsequently used to generate a product in a host or modified organism. Non-limiting examples of mutagenesis include deletion, insertion, substitution, rearrangement, point mutations, suppressor mutations and the like. Mutagenesis methods are known in the art and are readily available to the artisan. Non-limiting examples of mutagenesis methods are described herein and can also be found in Maniatis et al., (1982) Molecular Cloning: a Laboratory Manual; Cold Spring Harbor Laboratory, Cold Spring Harbor, N.Y. Another non-limiting example of mutagenesis can be conducted using a Stratagene (San Diego, Calif.) "QuickChange" kit according to the manufacturer's instructions.

The term "native sequence" as used herein refers to an unmodified nucleotide sequence as found in its natural setting (e.g., a nucleotide sequence as found in an organism).

A "nucleic acid modification" as used herein refers to an alteration, typically a chemical alteration, which is present in the modified nucleic acid molecule compared to the commonly or naturally occurring nucleic acid molecule. A modification may have been made to any component of the nucleic acid, for example, to the backbone, sugar component, or base. By way of example, a modified nucleic acid may have a phosphorothioate backbone, instead of the naturally occurring phosphodiester backbone. Modifications of this kind are often made to nucleic acids which are to be used in therapy. Modifications and modified nucleic acids are described further herein.

As used herein, "nucleobase" refers to the heterocyclic base portion of a nucleoside. Nucleobases may be naturally occurring, may be modified, may bear no similarity to natural bases, and may be synthetized, e.g., by organic synthesis. In certain embodiments, a nucleobase may comprise any atom or group of atoms capable of hydrogen bonding to a base of another nucleic acid or lacking hydrogen bonds altogether. In certain embodiments, an unnatural nucleobase may not be derived from a natural nucleobase. In certain embodiments, an unnatural nucleobase may be a synthetic nucleobase. It should be noted that unnatural nucleobases do not necesseraly possess basic properties, however, are referred to as nucleobases for simplicity. When referring to a nucleobase, a "(d)" indicates that the nucleobase can be attached to a deoxyribose or a ribose.

As used herein, "nucleoside" refers to a compound comprising a nucleobase moiety and a sugar moiety. Nucleosides include, but are not limited to, naturally occurring nucleosides (as found in DNA and RNA), abasic nucleosides, modified nucleosides, and nucleosides having mimetic bases and/or sugar groups. Nucleosides may be modified with any of a variety of substituents. A nucleoside can be a glycoside compound formed through glycosidic linking between a nucleic acid base and a reducing group of a sugar. It should be noted that the term "nucleic acid base" is intended to encompass adenine, guanine, cytosine, thymine, uracil, and also derivatives thereof. The type of the above derivative is not limited in any way.

The term "nucleotide" refers to a compound in which the sugar moiety of the above nucleoside forms an ester with phosphoric acid, more preferably a mono-, di- or tri-phosphate ester. The sugar moiety of such a nucleoside or nucleotide may be ribofuranosyl, 2'-deoxyribofuranosyl, or 2'-substituted ribofuranosyl having a substituent at the 2'-position. Likewise, the phosphoric acid moiety may be thiophosphoric acid. Namely, the sugar and phosphoric acid moieties may be in the same form as found in known nucleosides, nucleotides, or derivatives thereof. A ribonucleotide whose sugar moiety is ribofuranosyl can be used as a member constituting RNA. A deoxyribonucleotide whose sugar moiety is deoxyribofuranosyl can be used as a member constituting DNA. A nucleotide can be a nucleoside further comprising a phosphate linking group. Nucleotides may include nucleosides containing a phosphate moiety. As used herein, "linked nucleosides" may or may not be linked by phosphate linkages and thus includes "linked nucleotides."

The term "probes" or "primers" as used herein refer to oligonucleotides that hybridize in a base-specific manner to a complementary strand of a nucleic acid molecule. Probes can include primers, which can be a single-stranded oligonucleotide probe that can act as a point of initiation of template-directed DNA synthesis or amplification using methods including but not limited to, polymerase chain reaction (PCR) and ligase chain reaction (LCR) for amplification of a target sequence. Oligonucleotides, as described herein, can include segments or fragments of nucleic acid sequences, or their complements. In some embodiments, DNA segments can be between 5 and 10,000 contiguous bases, and can range from 5, 10, 12, 15, 20, or 25 nucleotides to 10, 15, 20, 25, 30, 40, 50, 100, 200, 500, 1000 or 10,000 nucleotides. In addition to DNA and RNA, probes and primers can include polypeptide nucleic acids (PNA), as described in Nielsen et al., Science 254: 1497-1500 (1991). A probe or primer can comprise a region of nucleotide sequence that hybridizes to at least about 15, typically about 20-25, and in certain embodiments about 40, 50, 60 or 75, consecutive nucleotides of a nucleic acid molecule.

The term "protein" as used herein refers to a molecule having a sequence of amino acids linked by peptide bonds. This term includes fusion proteins, oligopeptides, peptides, cyclic peptides, polypeptides and polypeptide derivatives, whether native or recombinant, and also includes fragments, derivatives, homologs, and variants thereof.

The term "purified" as used herein with reference to molecules does not refer to absolute purity. Rather, "purified" refers to a substance in a composition that contains fewer substance species in the same class (e.g., nucleic acid or protein species) other than the substance of interest in comparison to the sample from which it originated. "Purified," if a nucleic acid or protein for example, refers to a substance in a composition that contains fewer nucleic acid species or protein species other than the nucleic acid or protein of interest in comparison to the sample from which it originated. Sometimes, a protein or nucleic acid is "substantially pure," indicating that the protein or nucleic acid represents at least 50% of protein or nucleic acid on a mass basis of the composition. Often, a substantially pure protein or nucleic acid is at least 75% on a mass basis of the composition, and sometimes at least 95% on a mass basis of the composition.

As used herein, a "signal sequence" or "localization signal sequence" refers to as sequence that localizes a translated protein or peptide to a component in a system.

The term "specific cleavage agent" as used herein refers to an agent, sometimes a chemical or an enzyme that can cleave a nucleic acid at one or more specific sites.

As used herein, the term "stringent conditions" refers to conditions for hybridization and washing. Stringent conditions are known to those skilled in the art and can be found in Current Protocols in Molecular Biology, John Wiley & Sons, N.Y., 6.3.1-6.3.6 (1989). Aqueous and non-aqueous methods are described in that reference and either can be used.

As used herein, "sugar moiety" means a natural or modified sugar ring. As used herein, "vector" refers to any carrier containing exogenous DNA. Thus, vectors are agents that transport the exogenous nucleic acid into a cell without degradation and include a promoter yielding expression of the nucleic acid in the cells into which it is delivered. Vectors include but are not limited to plasmids, viral nucleic acids, viruses, phage nucleic acids, phages, cosmids, and artificial chromosomes.

EXAMPLES

It should be understood that the following examples should not be construed as being limiting to the particular methodology, protocols, and compositions, etc., described herein and, as such, can vary. The following terms used herein are for the purpose of describing particular embodiments only, and are not intended to limit the scope of the embodiments disclosed herein.

Example 1

Preparation of Electrocompetent C41(DE3)-pACS

A single clone of freshly transformed *E. coli* C41(DE3)-pACS was grown overnight in 2×YT medium (3 ml) supplemented with streptomycin (50 μg/ml) and KPi (50 mM). After 100-fold dilution into the same medium (300 ml) and outgrowth at 37° C. to an $OD_{600}$ of 0.20, IPTG was added to a final concentration of 1 mM to induce the expression of PtNTT2. After 40 min, the cultures were rapidly cooled to 0° C., washed with sterile water (3×150 ml), and resuspended in 10% glycerol (1.5 ml).

Electroporation and Recovery

An aliquot of electrocompetent C41(DE3)-pACS cells (50 μL) was mixed with pINF (2 μL, 400 ng), and electroporated in a 0.2 cm gap cuvette. Pre-warmed 2×YT medium (0.95 ml, 50 μg/ml streptomycin, 1 mM IPTG, 50 mM KPi) was added, and after mixing, 45 μL was removed and combined with 105 μl of the same media (3.3× dilution) supplemented with 0.25 mM of dNaMTP and d5SICSTP. The resulting mixture was allowed to recover for 1 h at 37° C. with shaking (210 rpm).

Growth and Analysis

Figure 12A:
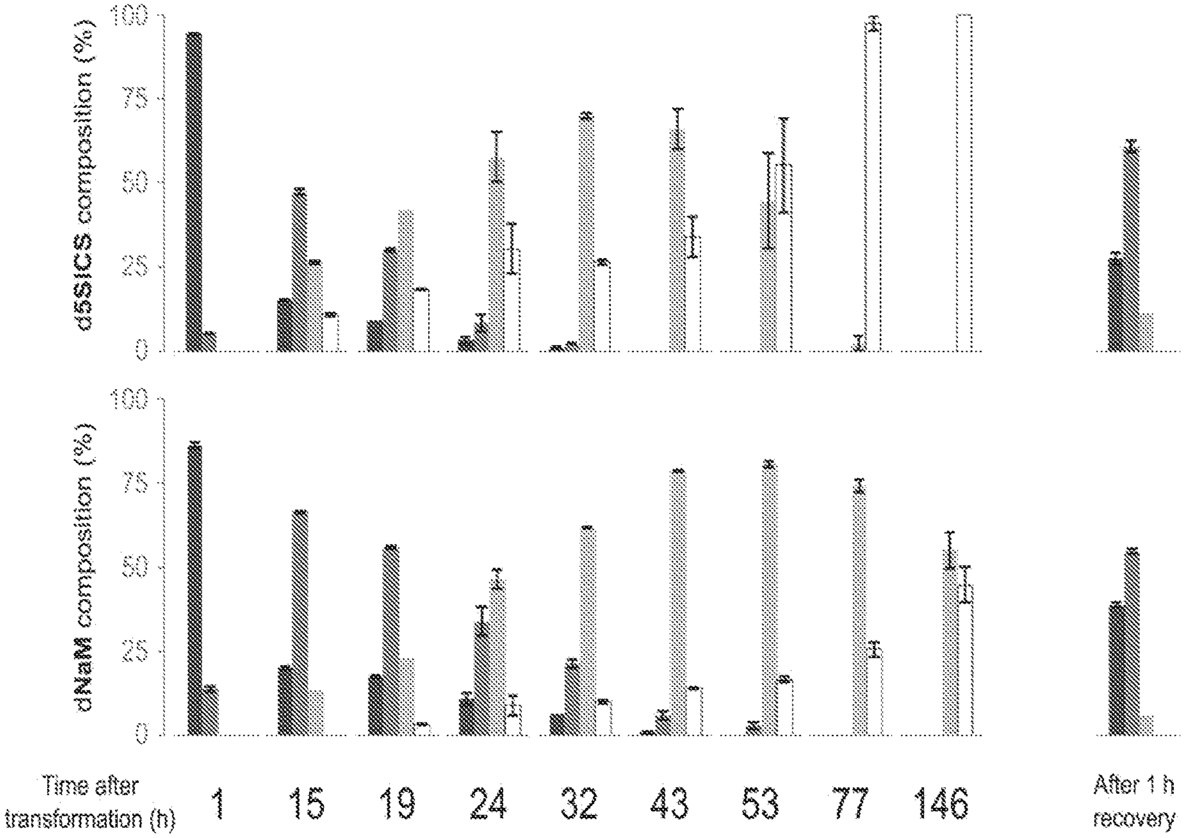
FIG. 12A depicts graphs of the % of the 3P (black), 2P (dark grey), 1P (light grey), and 0P (white) phosphorylation states of the indicated unnatural nucleoside triphosphates in the composition. The composition at the end of the 1 h recovery is shown at the right of each graph.
Figure 12B:
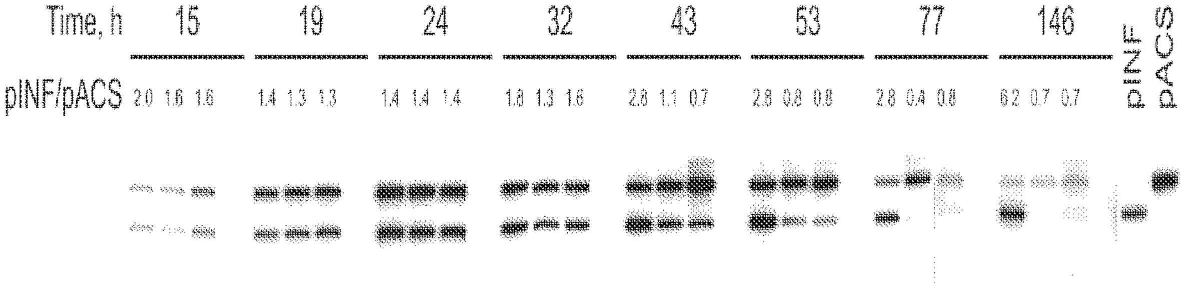
FIG. 12B depicts a restriction analysis of pINF and pACS plasmids purified from *E. coli*, linearized with NdeI restriction endonuclease, and separated on a 1% agarose gel. For each time point, triplicate data are shown in three lanes with untransformed control shown in the fourth, rightmost lane. Molar ratios of pINF/pACS plasmids are shown at the top of each lane.
Figure 12C:
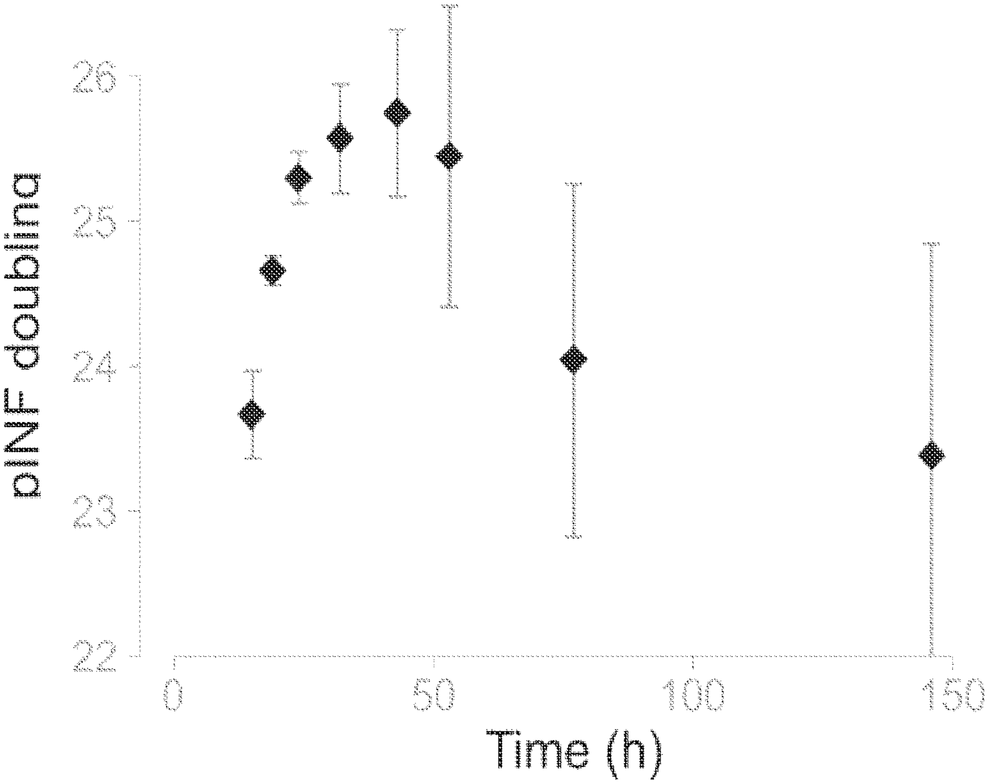
FIG. 12C depicts a graph showing the number of pINF doublings as a function of time. The decrease starting at ~50 h is due to the loss of the pINF plasmid that also results in increased error.
Figure 13A:
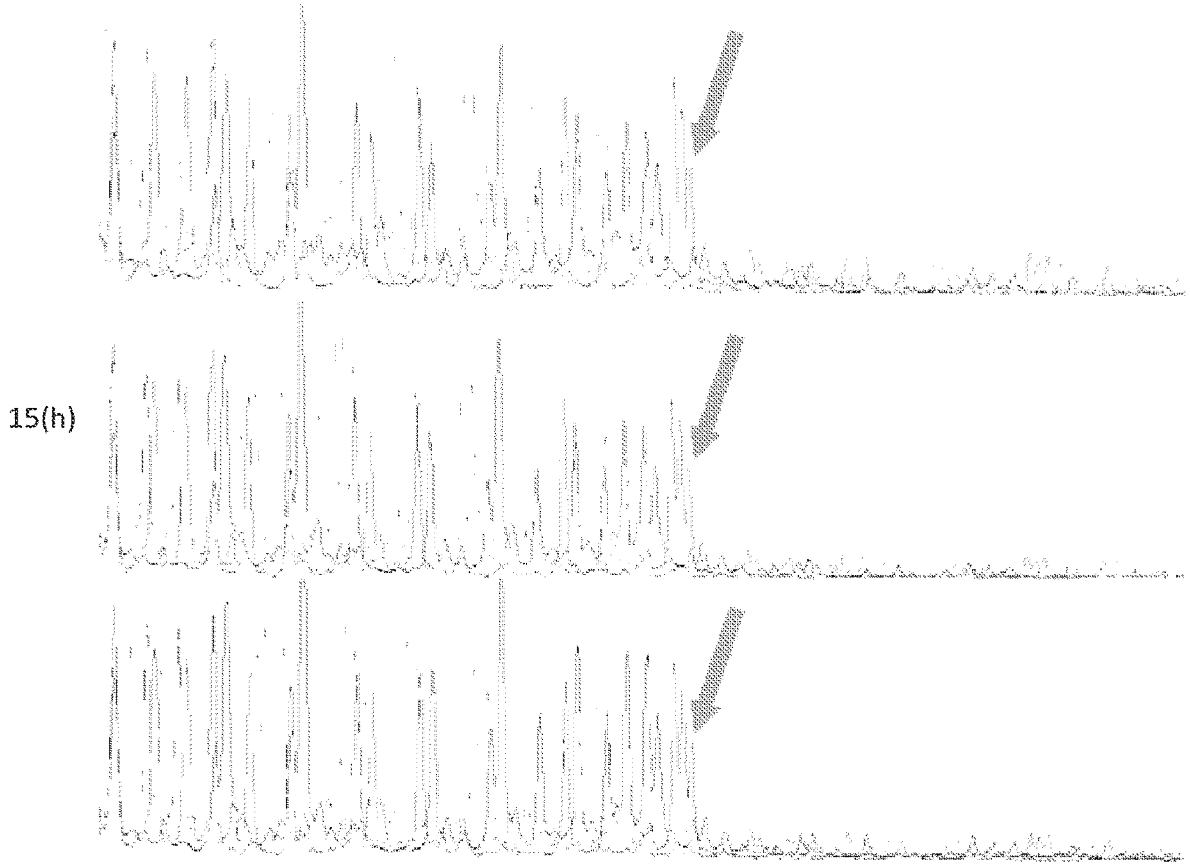
FIGS. 13A-H depict raw sequencing traces for PCR fragments generated from pINF plasmid propagated in *E. coli* at different time points. Triplicate data are shown. The position of the unnatural nucleotide is indicated with an arrow.
Figure 13B:
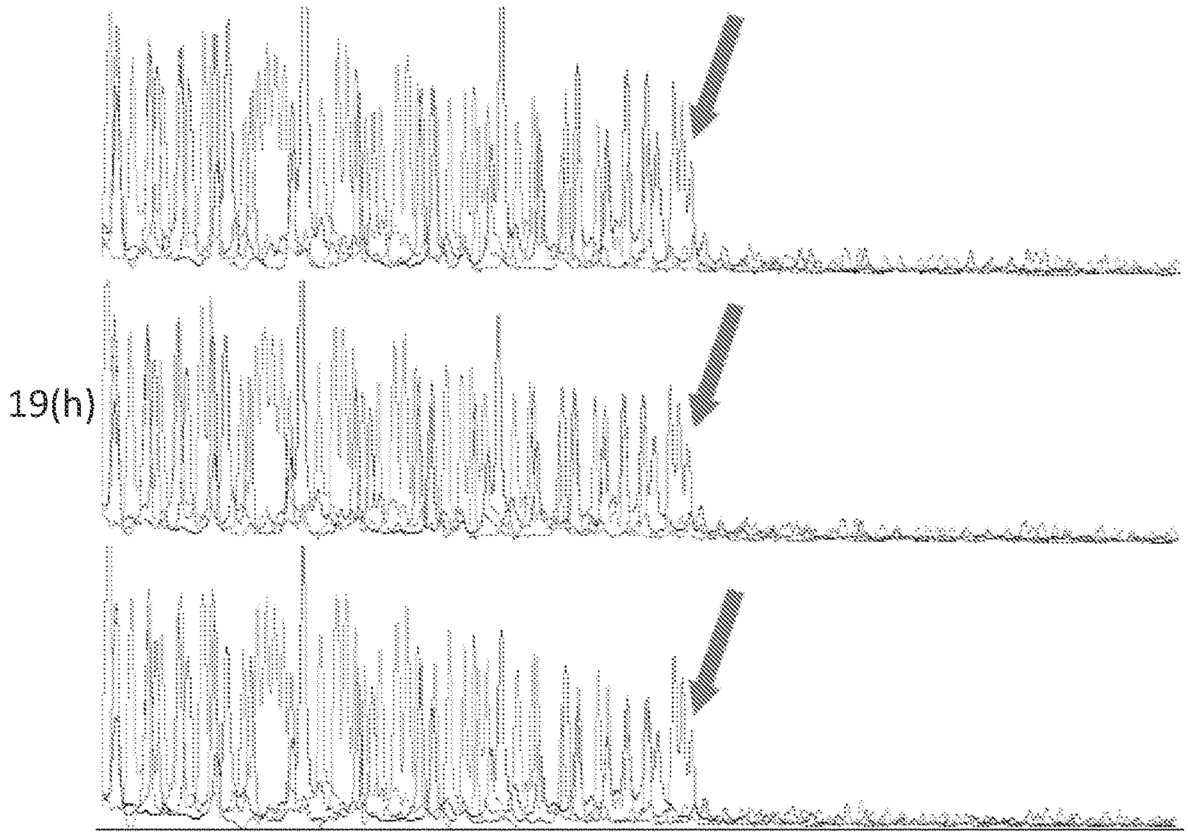
Figure 13C:
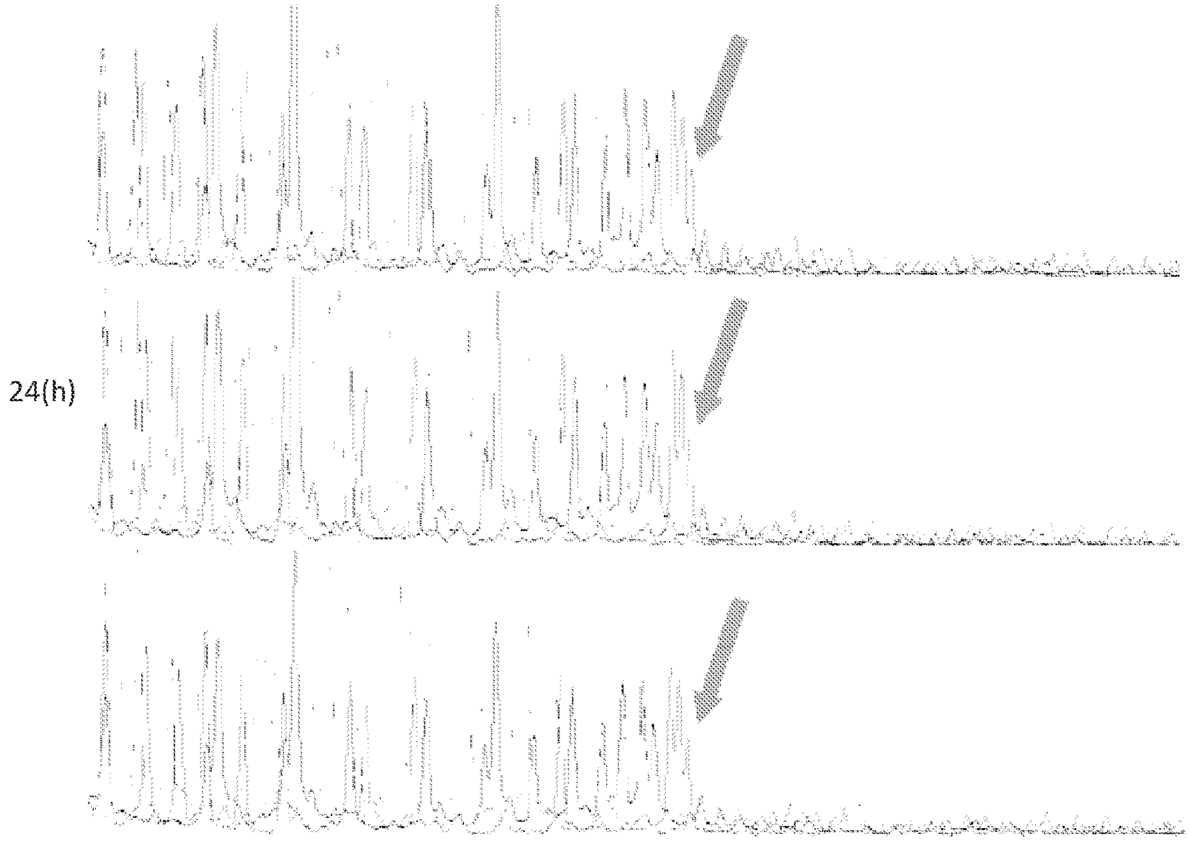
Figure 13D:
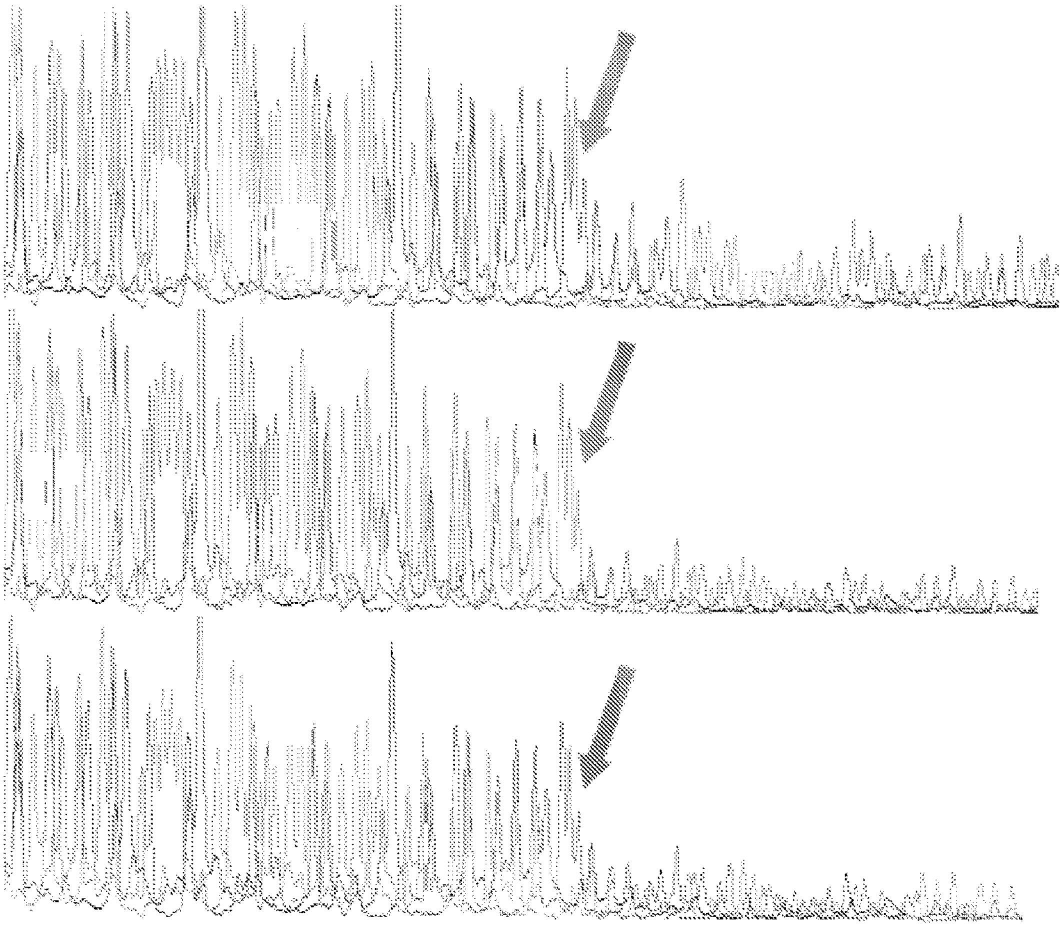
Figure 13E:
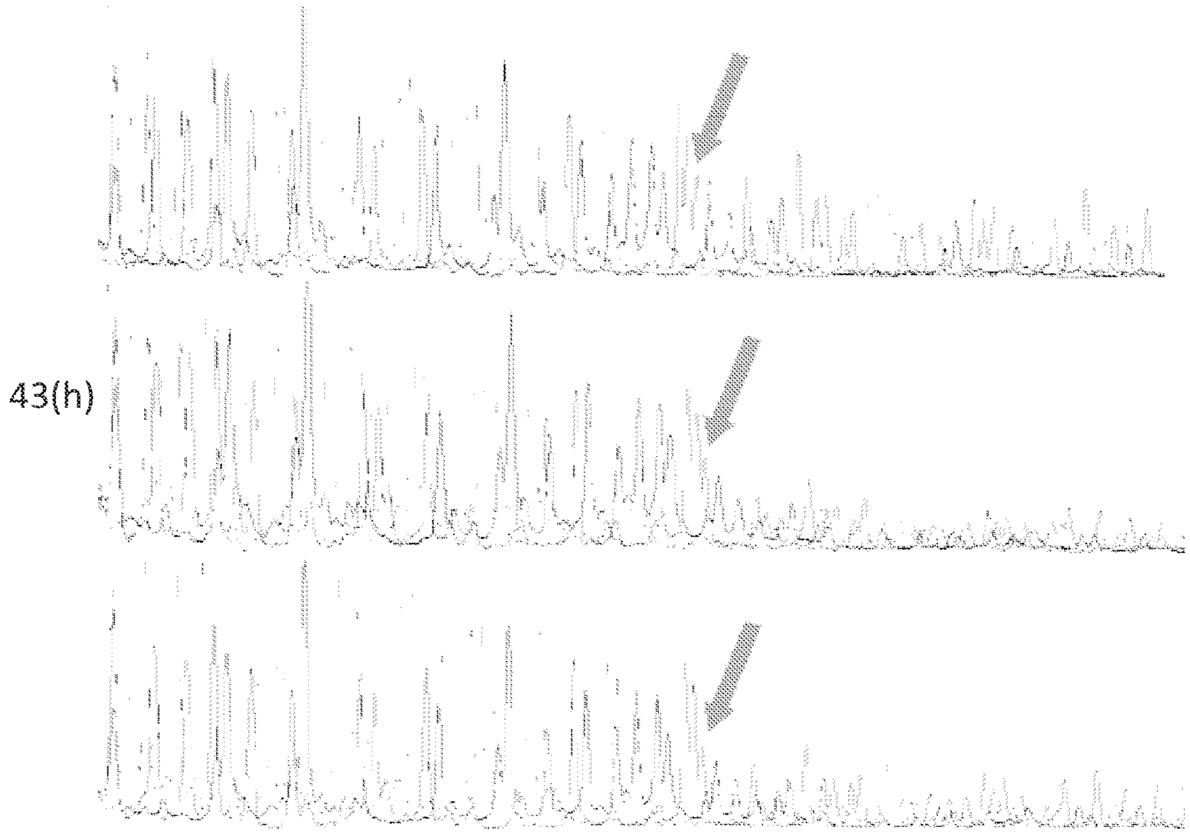
Figure 13F:
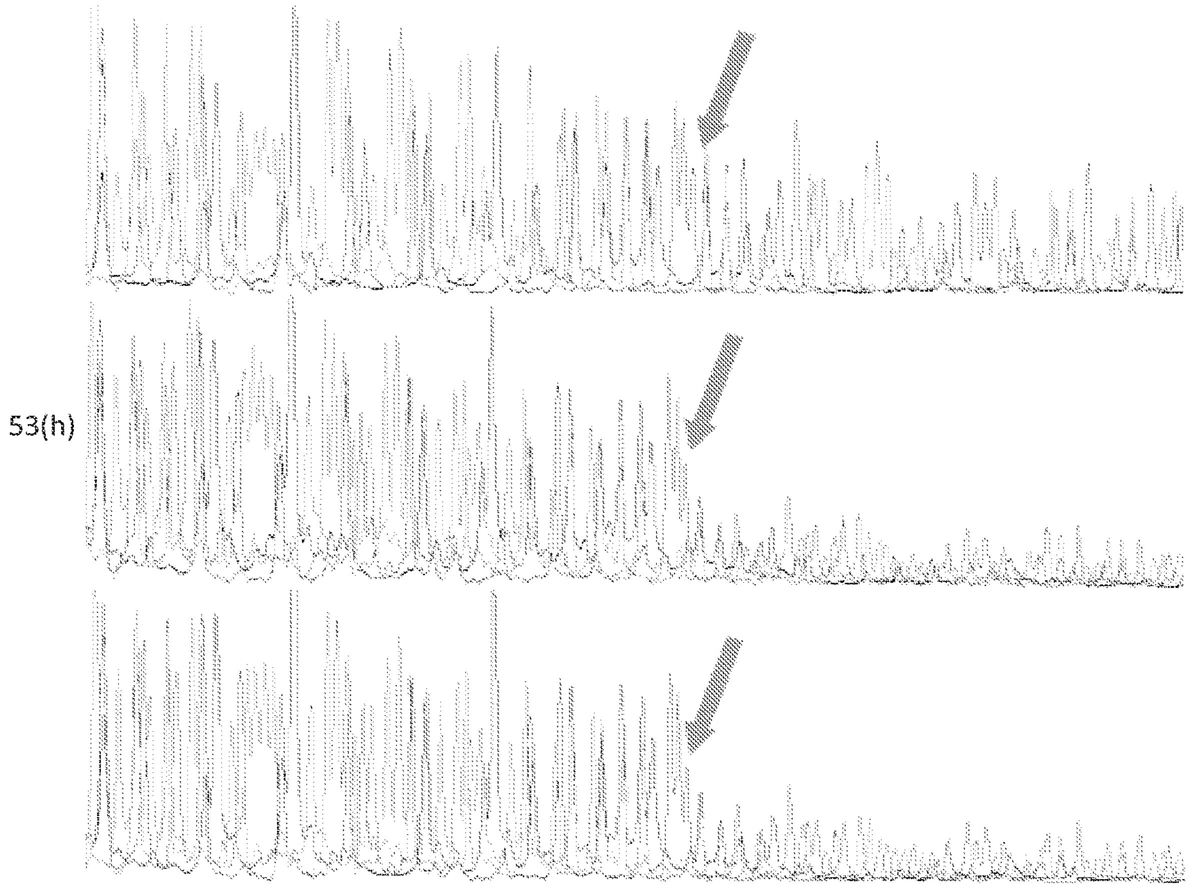
Figure 13G:
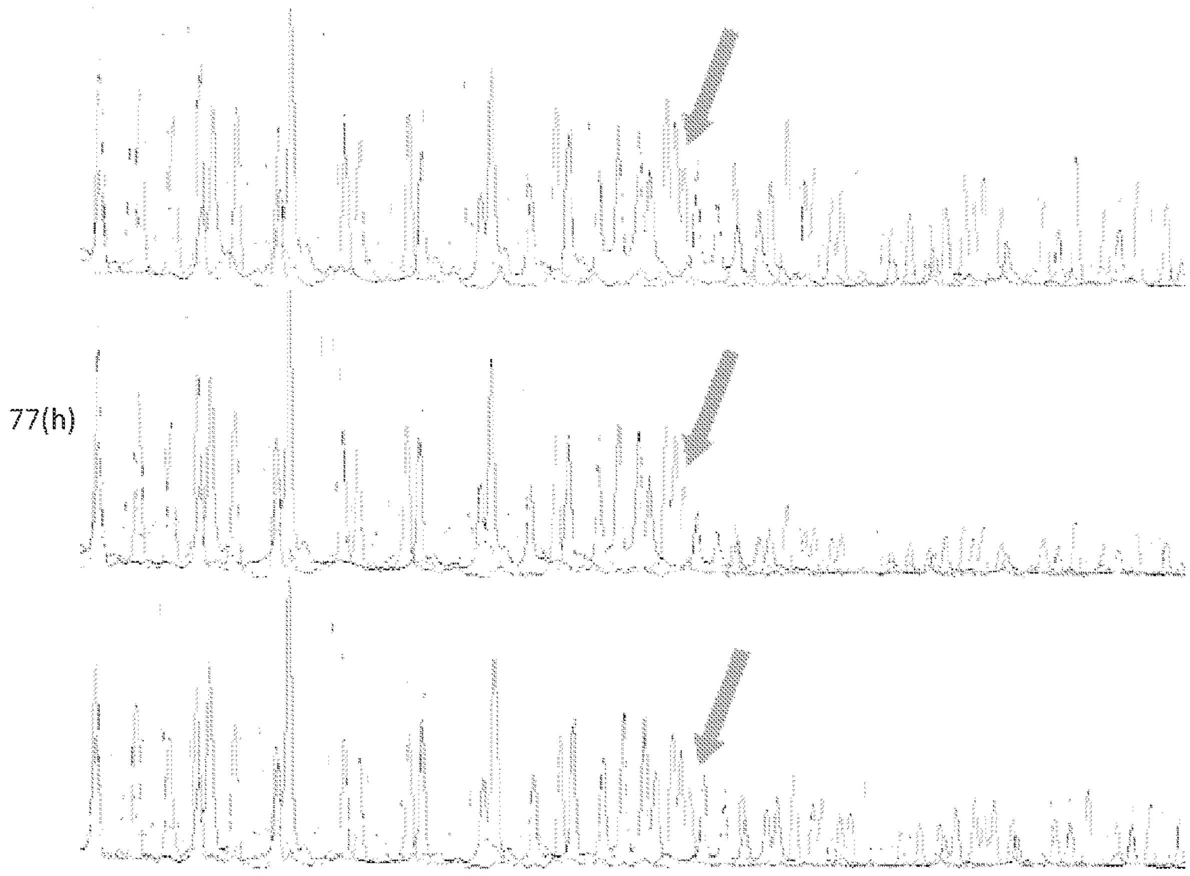
Figure 13H:
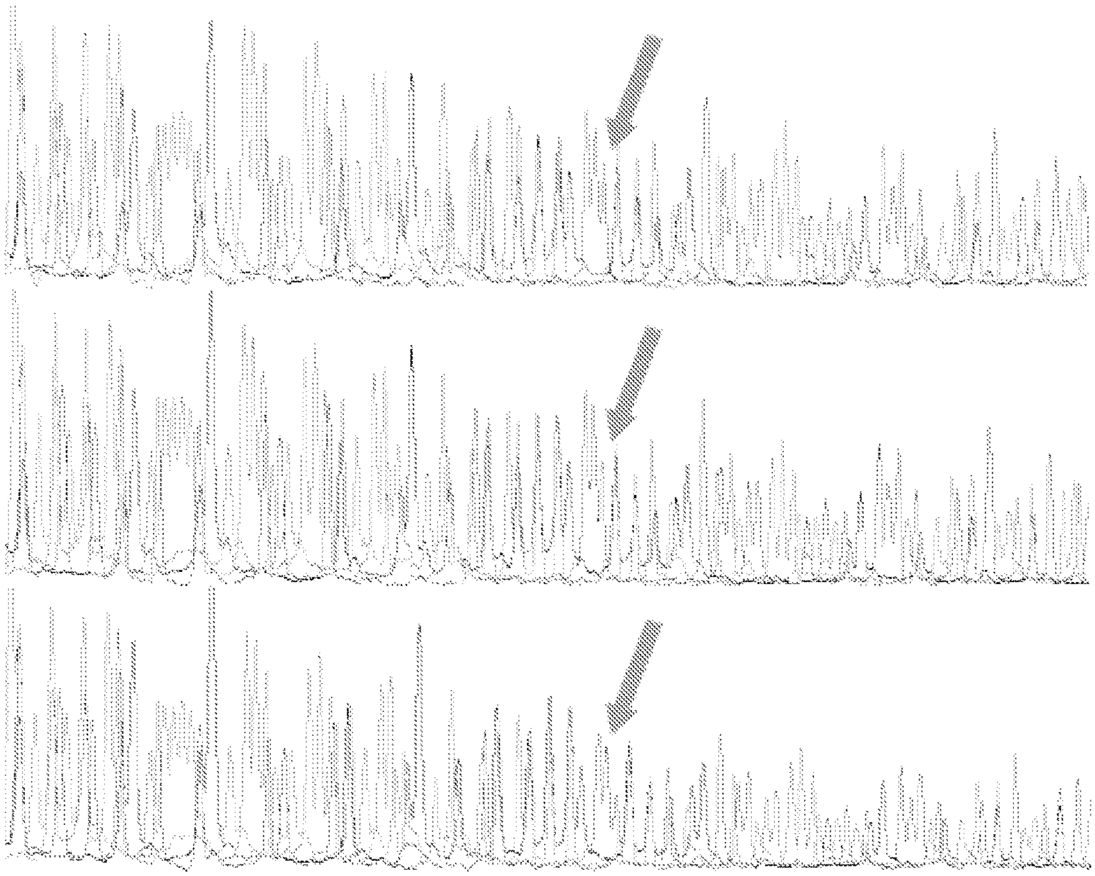

After recovery, cells were centrifuged and spent media (0.15 ml) was removed and analyzed for nucleotide composition by HPLC (FIG. 12A). The cells were resuspended in fresh 2×YT medium (1.5 ml, 50 μg/ml streptomycin, 100 μg/ml ampicillin, 1 mM IPTG, 50 mM KPi, 0.25 mM dNaMTP, 0.25 mM d5SICSTP) and grown at 37° C. with shaking (250 rpm). At defined time points, $OD_{600}$ was determined and aliquots (100 μl) were removed and centrifuged (8000 rfu for 5 min, 4° C.). Spent media was analyzed for nucleotide composition by HPLC and pINF was recovered by spin column purification (Zymo Research Corp.). Retention of the UBP was characterized by PCR amplification and gel electrophoresis or sequencing as described below. The data represents the average of three independent experiments. No PCR product was observed when pINF was added without electroporation, eliminating unamplified plasmid as a source of the PCR product (FIG. 12B).

Materials

2×YT, 2×YT-agar, IPTG, ampicillin and streptomycin were obtained from Fisher Scientific. Ampicillin and streptomycin were used at 100 μg/ml and 50 μg/ml, respectively. pET-16b constructs containing the nucleotide transporters, pET16b-RpNTT2, C41(DE3) *E. coli* strain. Plasmids pUC19 Thermo Scientific and pCDF-1b EMD Millipore. Plasmids were purified using the PureLink Quick Plasmid DNA Miniprep Kit (Life Technologies). OneTaq, DeepVent, Q5 Hot Start High-Fidelity DNA Polymerases, and all restriction endonucleases were obtained from New England Biolabs. In general, PCR reactions were divided into multiple aliquots with one followed in real time using 0.5×Sybr Green I (Life Technologies); following PCR, the aliquots were recombined, purified by spin column (DNA Clean and Concentrator-5; Zymo Research, Irvine, Calif.) with elution in 20 μl of water, then separated on an agarose gel, followed by band excision and recovery (Zymoclean Gel DNA Recovery Kit), eluting with 20 μl of water unless stated otherwise. PAGE gels were stained with 1×Sybr Gold (Life Technologies) for 30 min, agarose gels were cast with 1×Sybr Gold. Gels were visualized using a Molecular Imager Gel Doc XR+ equipped with 520DF30 filter (Bio-Rad) and quantified with Quantity One software (Bio-Rad). The sequences of exemplary DNA oligonucleotides used are shown in Table 8. Natural oligonucleotides were purchased from a commercial source. The concentration of dsDNA was measured by fluorescent dye binding (Quant-iT dsDNA HS Assay kit, Life Technologies) unless stated otherwise. The concentration of ssDNA was determined by UV absorption at 260 nm using a NanoDrop 1000 (Thermo Scientific). [α-$^{32}$P]-dATP (25 μCi). Polyethyleneiminecellulose precoated Bakerflex® TLC plates (0.5 mm). dNaM phosphoramidite, dNaM and d5SICS nucleosides. Free nucleosides of dNaM and d5SICS were converted to the corresponding triphosphates under Ludwig conditions. After purification by anion exchange chromatography (DEAE Sephadex A-25) followed by reverse phase (C18) HPLC and elution through a Dowex 50WX2-sodium column, both triphosphates were lyophilized and kept at −20° C. until use. The d5SICSTP analog dTPT3TP and the biotinylated dNaMTP analog dMMO2$^{SSBIO}$ TP[4] were made as reported previously. MALDI-TOF mass spectrometry was performed.

Construction of NTT Expression Plasmids

The PtNTT2 gene was amplified from plasmid pET-16b-PtNTT2 using primers PtNTT2-fwd and PtNTT2-rev; the TpNTT2 gene was amplified from plasmid pET-16b-TpNTT2 using primers TpNTT2-fwd and TpNTT2-rev. A linear fragment of pCDF-1b was generated using primers pCDF-1b-fwd and pCDF-1b-rev. Fragments were purified. The pCDF-1b fragment (100 ng, $4.4\times10^{-14}$ mol) and either the PtNTT2 (78 ng, $4.4\times10^{14}$ mol) or TpNTT2 (85 ng, $4.4\times10^{-14}$ mol) fragment were then assembled together using restriction-free circular polymerase extension cloning in 1×OneTaq reaction buffer, $MgSO_4$ adjusted to 3.0 mM, 0.2 mM of dNTP, and 0.02 U/μl of OneTaq DNA under the following thermal cycling conditions: Initial denaturation (96° C., 1 min); 10 cycles of denaturation (96° C., 30 s), touchdown annealing (54° C. to 49.5° C. for 30 s (−0.5° C. per cycles)), extension of 68° C. for 5 min, and final extension (68° C., 5 min). Upon completion, the samples were purified and used for heat-shock transformation of *E. coli* XL10. Individual colonies were selected on LB-agar containing streptomycin, and assayed by colony PCR with primers PtNTT2-fwd/rev or TpNTT2-fwd/rev. The presence of the NTT genes was confirmed by sequencing and double digestion with ApaI/EcoO109I restriction endonucleases with the following expected pattern: pCDF-1b-PtNTT2 (2546/2605 bp), pCDF-1b-TpNTT2 (2717/2605 bp), pCDF-1b (1016/2605 bp). The complete nucleotide sequence of the pCDF-1b/PtNTT2 plasmid (i.e. pACS) is provided as SEQ ID NO: 1.

Example 2: General Protocol to Quantify Nucleoside Triphosphate Uptake

Growth Conditions

*E. coli* C41(DE3) freshly transformed with pCDF-1b-PtNTT2 was grown in 2×YT with streptomycin overnight, then diluted (1:100) into fresh 2×YT medium (1 ml of culture per uptake with [α-$^{32}$P]-dATP; 2 ml of culture per uptake with d5SICSTP or dNaMTP) supplemented with 50 mM potassium phosphate (KPi) and streptomycin. A negative control with the inactive transporter pET-16b-RpNTT2, was treated identically except ampicillin was used instead of streptomycin. Cells were grown to an $OD_{600}$ of ~0.6 and expression was induced by the addition of IPTG (1 mM). The culture was allowed to grow for another hour (final $OD_{600}$~1.2) and then assayed directly for uptake as described below using a method adapted from Hafterkamp, et al.

Preparation of Media Fraction dNaMTP or d5SICSTP (10 mM each) were added to media to a final concentration of 0.25 mM. Cells were incubated with the substrate with shaking at 37° C. for 30 min and then pelleted (8,000 rfu for 5 min, 4° C.). An aliquot of the media fraction (40 μl) was mixed with acetonitrile (80 μl) to precipitate proteins, and then incubated at RT for 30 min. Samples were either analyzed immediately by HPLC or stored at −80° C. until analysis. Analysis began with centrifugation (12,000 rfu for 10 min, RT), then the pellet was discarded, and the supernatant was reduced to ~20 μl, resuspended in 95% 0.1 M TEAB, pH 7.5; 5% acetonitrile, to a final volume of 50 μl, and analyzed by HPLC.

Preparation of Cytoplasmic Fraction

To analyze the intracellular dephosphorylation of unnatural nucleoside triphosphates, cell pellets were subjected to 3×100 μl washes of ice cold KPi (50 mM). Pellets were then resuspended in 250 μl of ice cold KPi (50 mM) and lysed with 250 μl of Lysis buffer L7 of the PureLink Quick Plasmid DNA Miniprep Kit (200 mM NaOH, 1% w/v SDS), after which the resulting solution was incubated at RT for 5 min. Precipitation buffer N4 (350 μl, 3.1 M potassium acetate, pH 5.5) was added, and the sample was mixed to homogeneity. Following centrifugation (>12,000 rfu for 10 min, RT) the supernatant containing the unnatural nucleotides was applied to a C18 solid phase extraction column prewashed with acetonitrile (1 ml) and 95% 0.1 M TEAB, pH 7.5; 5% acetonitrile (1 ml). The column was then washed with 95% 0.1 M TEAB, pH 7.5; 5% acetonitrile and nucleotides were eluted with 1 ml of 50% acetonitrile:50% triethylammonium bicarbonate (TEAB) 0.1 M (pH 7.5). The eluent was reduced to ~50 μl and its volume was adjusted to 100 μl with 95% 0.1 M TEAB, pH 7.5; 5% acetonitrile before HPLC analysis.

HPLC

Samples were applied to a LC column (3 μm C18 300 Å, 250×4.6 mm) and subjected to a linear gradient of 0-40% with 20% 0.1 M TEAB, pH 7.5; 80% acetonitrile over 40 min at a flow rate of 1 ml/min.

Quantification

Injection series included two extra control samples containing 5 nmol of dNaMTP or d5SICSTP. The areas under the peaks that corresponded to triphosphate, diphosphate, monophosphate and free nucleoside (confirmed by MALDI-TOF) were integrated for both the control and the unknown samples. After peak integration, the ratio of the unknown peak to the control peak adjusted for the loss from the extraction step (62% and 70% loss for dNaM and d5SICS, respectively), provided a measure of the amount of each of the moieties in a sample. To determine the relative concentrations of unnatural nucleotide inside a cell, the amount of imported unnatural nucleotide was then divided by the volume of cells, which was calculated from the volume of a single *E. coli* cell of (1 $\mu m^3$) multiplied by the number of cells in each culture ($OD_{600}$ of 1.0 equal to $1\times10^9$ cells per ml). An RpNTT2 sample was used as a negative control and its signal was subtracted to account for any incomplete washing of nucleotide species from the media.

$$[dXTP] = \frac{dXTP(\mu\text{mol})}{\text{cell volume } (1\times10^{-9}\ \mu\text{l } cell^{-1})\times\text{number of cells}(2.4\times10^{9})}$$

dATP Uptake

To analyze the intracellular dephosphorylation of dATP, after induction of an NTT, an uptake reaction was initiated by the addition of dATP (spiked with [$\alpha$-$^{32}$P]-dATP) to a final concentration of 0.25 mM, followed by incubation at 37° C. with shaking for 30 min. A culture was then centrifuged (8,000 rfu for 5 min, RT). Supernatant was analyzed by thin layer chromatography (TLC), while cell pellets were washed 3 times with ice cold KPi (50 mM, 100 μl) to remove excess radioactive substrate, lysed with NaOH (0.2 M, 100 μl) and centrifuged (10,000 rfu for 5 min, RT) to pellet the cell debris, before the supernatant (1.5 μl) was analyzed by TLC.

TLC Analysis

Samples (1 μl) were applied on a 0.5 mm polyethyleneimine cellulose TLC plate and eluted first by sodium formate (0.5 M, pH 3.0) for 30 sec, then by sodium formate (2.5 M, pH 3.0) for 2.5 min, and finally by sodium formate (4.0 M, pH 3.0) for 40 min. Plates were dried using a heat gun and quantified by phosphorimaging and imaging software.

Example 3: Methods Developed for Nucleotide Extraction from Cells for HPLC Analysis To minimize the effect of the lysis and triphosphate extraction protocols on the decomposition of nucleoside triphosphate within the cell, the following extraction procedure was discovered that led to an unexpectedly highest recovery with and low extent of decomposition (Table 9). Cells were grown, washed, and then 5 nmol of either dNaMTP or d5SICSTP was added to the pellets, which were then subjected to various types of extractions including boiling water, hot ethanol, cold methanol, freeze and thaw, lysozyme, glass beads, NaOH, trichloroacetic acid (TCA) with Freon, and perchloric acid (PCA) with KOH. The recovery and composition of the control was quantified by HPLC. Method 3, i.e. cell lysis with NaOH (Table 6), was found to be unexpectedly effective and reproducible. Pellets were resuspended in ice cold KPi (50 mM, 250 μl) before addition of NaOH to decrease dephosphorylation after cell lysis (Method 4).

TABLE 6

Extraction methods

| | Method | Protocol summary | Total recovery, %[a] | | Triphosphate stability, %[b] | |
|---|---|---|---|---|---|---|
| | | | dNaM | d5SICS | dNaM | d5SICS |
| 1 | TCA with Freon | Lyse with cold TCA Extract aqueous phase using Freon with trioctylaminesolution. | 38 | 23 | 92 | 99 |
| 2 | PCA w/KOH | Lyse with cold PCA Precipitate proteins with KOH and KPi | 36 | 21 | 98 | 77 |
| 3 | NaOH w/KOAc | Lyse with NaOH and SDS Precipitate proteins with potassium acetate. | 21 | 26 | 86 | 100 |
| 4 | NaOH w/KOAc supplemented w/ KPi (50 mM) | Suspend cells in KPi Lyse with NaOH and SDS Precipitate proteins with potassium acetate. | 38 | 30 | 99 | 100 |

[a]Recovery of all nucleotides (3P, 2P, 1P and nucleoside).
[b]Calculated as a ratio of 3P composition (%) before and after the extraction.

Example 4: Construction of pINF

Preparation of the Unnatural Insert

The TK-1-dNaM oligonucleotide containing dNaM was prepared using solid phase DNA synthesis with ultra-mild DNA synthesis phosphoramidites on CPG ultramild supports (1 μmol) and a nucleic acid synthesizer. After the synthesis, the DMT-ON oligonucleotide was deprotected by treatment with concentrated ammonia hydroxide at 50° C. overnight, purified, and then subjected to 8 M urea 8% PAGE. The gel was visualized by UV shadowing, the band corresponding to a 75mer was excised, and DNA was recovered by crush and soak extraction, filtration (0.45 μm), and final desalting over Sephadex G-25. The concentration of single stranded oligonucleotide was determined by UV absorption at 260 nm (where extinction coefficient of dNaM at 260 nm assumed equal to that of dA.). TK-1-dNaM (4 ng) was next amplified by PCR under the following conditions: 1×OneTaq reaction buffer, $MgSO_4$ adjusted to 3.0 mM, 0.2 mM of dNTP, 0.1 mM of dNaMTP, 0.1 mM of the d5SICSTP analog dTPT3TP, 1 μM of each of the primers pUC19-fusion-fwd and pUC19-fusion-rev, and 0.02 U/μl of OneTaq DNA Polymerase (in a total of 4×50 μl reactions) under the following thermal cycling conditions: Initial denaturation (96° C., 1 min) followed by 12 cycles of denaturation (96° C., 10 s), annealing (60° C., 15 s), and extension (68° C., 2 min). A similar PCR without unnatural triphosphates was run to obtain fully natural insert under similar conditions for construction of natural control plasmid. Reactions were subjected to spin column purification and then the target PCR product (122 bp) was purified by a 4% agarose gel.

pUC19 Linearization pUC19 (20 ng) was amplified by PCR under the following conditions: 1×Q5 reaction buffer, $MgSO_4$ adjusted to 3.0 mM, 0.2 mM of dNTP, 1 μM of each primers pUC19-lin-fwd and pUC19-lin-rev, and 0.02 U/μl of Q5 Hot Start High-Fidelity DNA Polymerase (in a total of 4×50 μl reactions with one reaction containing 0.5×Sybr Green I) under the following thermal cycling conditions: Initial denaturation (98° C., 30 s); 20 cycles of denaturation (98° C., 10 s), annealing (60° C., 15 s), and extension (72° C., 2 min); and final extension (72° C., 5 min). The desired PCR product (2611 bp) was purified by a 4% agarose gel.

PCR Assembly of pINF and the Natural Control Plasmid

A linear fragment was amplified from pUC19 using primers pUC19-lin-fwd and pUC19-lin-rev. The resulting product (800 ng, $4.6\times10^{-13}$ mol) was combined with either the natural or unnatural insert (see above) (56 ng, $7.0\times10^{-13}$ mol) and assembled by circular overlap extension PCR under the following conditions: 1×OneTaq reaction buffer, $MgSO_4$ adjusted to 3.0 mM, 0.2 mM of dNTP, 0.1 mM of dNaMTP, 0.1 mM of the d5SICSTP analog dTPT3TP, and 0.02 U/μl of OneTaq DNA Polymerase (in a total of 4×50 μl reactions with one reaction containing 0.5×Sybr Green I) using the following thermal cycling conditions: Initial denaturation (96° C., 1 min); 12 cycles of denaturation (96° C., 30 s), annealing 62° C., 1 min), and extension (68° C., 5 min); final extension (68° C., 5 min); and slow cooling (68° C. to 10° C. at a rate of −0.1° C./s). The PCR product was analyzed by restriction digestion on 1% agarose and used directly for *E. coli* transformation. The d5SICS analog dTPT3 pairs with dNaM and dTPT3TP was used in place of d5SICSTP as DNA containing dTPT3-dNaM is better PCR amplified than DNA containing d5SICS-dNaM, and this facilitated the construction of high-quality pINF (UBP content >99%).

Example 5: pINF Replication in *E. coli*

Preparation of Electrocompetent Cells

C41(DE3) cells were transformed by heat shock with 200 ng of pACS plasmid, and the transformants were selected overnight on 2×YT-agar supplemented with streptomycin. A single clone of freshly transformed C41(DE3)-pACS was grown overnight in 2×YT medium (3 ml) supplemented with streptomycin and KPi (50 mM). After 100-fold dilution into the same fresh 2×YT media (300 ml), the cells were grown at 37° C. until they reached an $OD_{600}$ of 0.20 at which time IPTG was added to a final concentration of 1 mM to induce the expression of PtNTT2. Cells were grown for another 40 min and then growth was stopped by rapid cooling in ice water with intensive shaking. After centrifugation in a prechilled centrifuge (2400 rfu for 10 min, 4° C.), the spent media was removed, and the cells were prepared for electroporation by washing with ice-cold sterile water (3×150 ml). After washing, the cells were resuspended in ice cold 10% glycerol (1.5 ml) and split into 50 μl aliquots. Cells were frozen if to store for later use. Freshly prepared cells were used and frozen cells can be used.

Electroporation and Recovery

The aliquot of cells was mixed with 2 μl of plasmid (400 ng), transferred to 0.2 cm gap electroporation cuvette and electroporated using a Bio-Rad Gene Pulser according to the manufacturer's recommendations (voltage 25 kV, capacitor 2.5 μF, resistor 200Ω, time constant 4.8 ms). Pre-warmed 2×YT media (0.95 ml, streptomycin, 1 mM IPTG, 50 mM KPi) was added, and after mixing, 45 μl was taken and combined with 105 μl of the same media (3.33× dilution) supplemented with 0.25 mM of dNaMTP and d5SICSTP.

Growth and Analysis

After recovery, the cells were centrifuged (4000 rfu for 5 min, 4° C.), spent media (0.15 ml) was removed and analyzed for nucleotide composition by HPLC. The cells were resuspended in fresh 2×YT media (1.5 ml, streptomycin, ampicillin, 1 mM IPTG, 50 mM KPi, 0.25 mM dNaMTP, 0.25 mM d5SICSTP) and grown overnight at 37° C. while shaking (250 rpm), resulting in 10× dilution compared to recovery media or 33.3× dilution compared to the originally transformed cells. Aliquots (100 μl) were taken after 15, 19, 24, 32, 43, 53, 77, 146 h, $OD_{600}$ was determined, and the cells were centrifuged (8000 rfu for 5 min, 4° C.). Spent media was analyzed for nucleotide composition by HPLC and the pINF and pACS plasmid mixtures were purified by recovered by spin column, eluted in 30 μl of water and analyzed by restriction digestion. The retention of the UBP on the pINF plasmid was quantified by biotin gel shift mobility assay and sequencing.

Figure 11A:
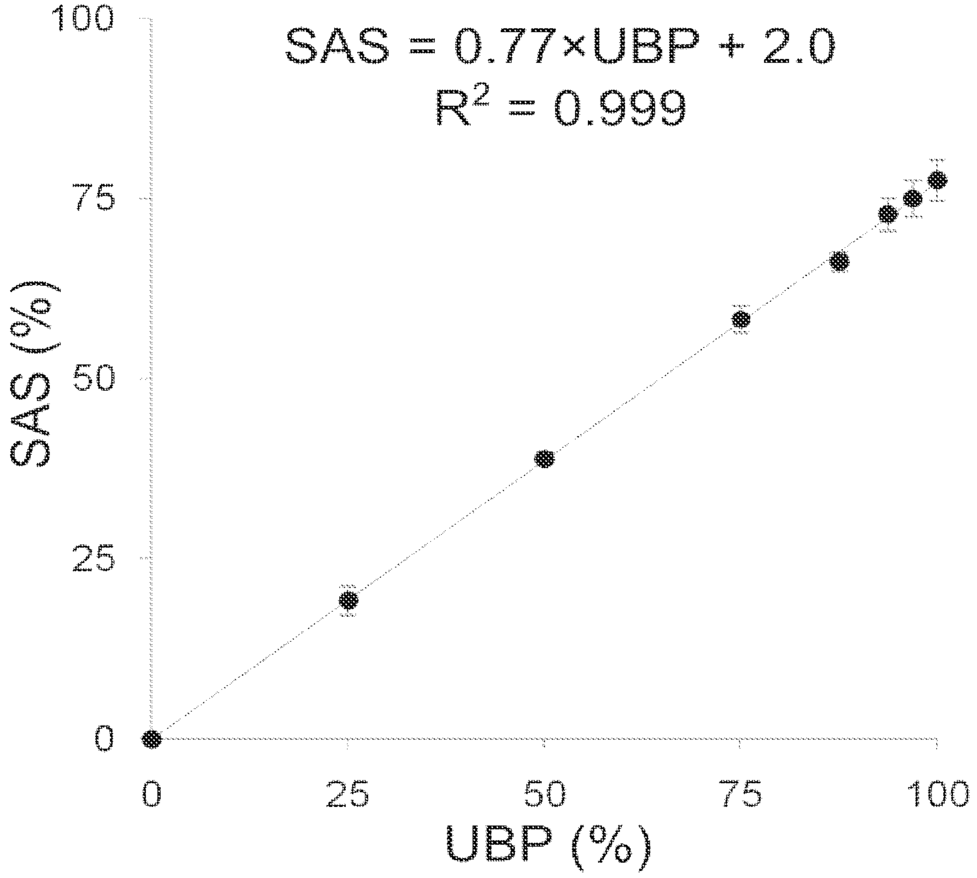
FIG. 11A illustrates a calibration graph of the streptavidin shift (SAS) as a function of the fraction of template containing the UBP.
Figure 11B:
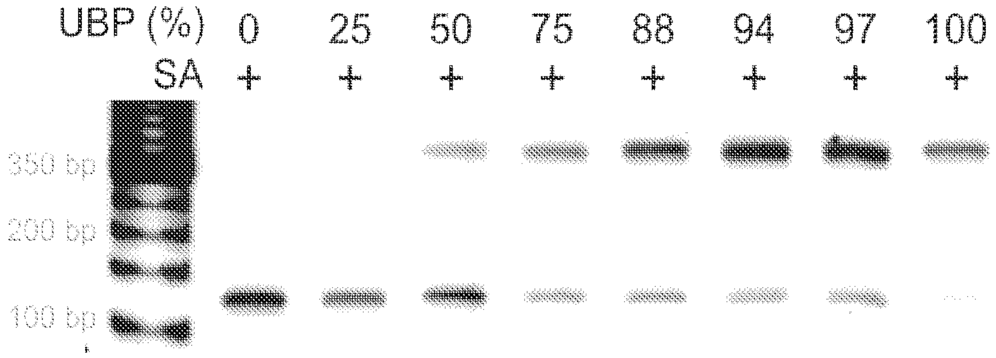
FIG. 11B illustrates and representative raw data from SAS samples run in triplicate. SA=streptavidin.

Transformation media (10 μl) was spread onto 2×YT-agar containing streptomycin with 10× and 50× dilutions to determine viable colony forming units after overnight growth at 37° C. to calculate the number of the transformed pINF molecules. Transformation, recovery, and growth were carried out similarly for the natural control plasmid. Additionally, a negative control was run and treated similarly to pINF transformation except that it was not subjected to electroporation (FIG. 11). No growth in the negative control samples was observed after at least 6 days. No PCR amplification of the negative control was detected. Thus, unamplified pINF plasmid was carried through cell growth and later detected erroneously as the propagated plasmid.

Example 6: Fidelity Measurement

DNA Biotinylation by PCR

Purified mixtures of pINF and pACS plasmids (1 ng) from growth experiments (FIGS. 3 and 4) were amplified by PCR under the following conditions: 1×OneTaq reaction buffer, $MgSO_4$ adjusted to 3.0 mM, 0.3 mM of dNTP, 0.1 mM of the biotinylated dNaMTP analog dMMO2$^{SSBIO}$TP, 0.1 mM of d5SICSTP, 1 μM of each of the primers pUC19-seq-fwd and pUC19-seq-rev, 0.02 U/μl of OneTaq DNA Polymerase, and 0.0025 U/μl of DeepVent DNA Polymerase in a total volume of 25 μl in an CFX Connect Real-Time PCR Detection System (Bio-Rad) under the following thermal cycling conditions: Initial denaturation (96° C., 1 min); 10 cycles of denaturation (96° C., 30 s), annealing (64° C., 30 s), and extension (68° C., 4 min). PCR products were purified as described in Materials, and the resulting biotinylated DNA duplexes (5 μl, 25-50 ng) were mixed with streptavidin (1 μl, 1 μg/μl, Promega) in phosphate buffer (50 mM sodium phosphate, pH 7.5, 150 mM NaCl, 1 mM EDTA), incubated for 30 min at 37° C., mixed with 5× non-denaturing loading buffer, and loaded onto 6% non-denaturing PAGE. After running at 110 V for 30 min, the gel was visualized and quantified. The resulting fragment (194 bp) with primer regions underlined and the unnatural nucleotide in bold (X=dNaM or its biotinylated analog dMMO2$^{SSBIO}$) is shown below (SEQ ID NO:26).

5'-GCAGGCATGCAAGCTTGGCGTAATCATGGTCATAGCTGTTTCCTGTG

TGAAATTGTTATCCGCTCACAXTTCCACACAACATACGAGCCGGAAGCAT

AAAGTGTAAAGCCTGGGGTGCCTAATGAGTGAGCTAACTCACATTAATTG

CGTTGCGCTCACTGCCCGCTTTCCAGTCGGGAAACCTGTCGTGCCAG

Streptavidin Shift Calibration

To build a calibration curve between streptavidin (SA) shift and the fraction of sequences with UBP in the population (UBP), a PCR method was developed where the reaction was spiked with DeepVent. The method improved the fidelity with which DNA containing d5SICS-dMMO2$^{SSBIO}$ was amplified. Calibration was conducted under similar conditions. To quantify the net retention of the UBP, nine mixtures of the TK-1-dNaM template and its natural counterpart with a known ratio of unnatural and natural were prepared, subjected to biotinylation by PCR, and analyzed by a mobility-shift assay on 6% non-denaturing PAGE. For calibration, the mixtures TK-1-dNaM template and its natural counterpart with a known ratio of unnatural and natural templates (0.04 ng) were amplified under similar conditions over nine cycles of PCR with pUC19-fusion primers and analyzed similar to samples from growth experiments described herein. Experiments were run in triplicate and the streptavidin shift (SAS, %) was plotted as function of the UBP content (UBP, %) and the data fit to a linear equation:

$$SAS=0.77\times UBP+2.0 R^2=0.999. \quad \text{Equation 1:}$$

where UBP corresponds to the retention of the UBP (%) in the analyzed samples after cellular replication and was calculated from the SAS shift using Equation 1.

Calculation of Plasmid Amplification

Cells were plated on 2×YT-agar containing ampicillin and streptavidin after transformation with pINF, and colonies were counted after overnight growth at 37° C. Transformed cells were assumed to contain one molecule of plasmid. Colony counts corresponded to the original amount of plasmid that was taken up by the cells. After overnight growth (FIG. 4), the plasmids were purified from a volume of the cell culture and quantified. Since purified plasmid DNA represent a mixture of pINF and pACS plasmid, digestion restriction analysis with NdeI exonuclease was performed that linearized both plasmids followed by 1% agarose gel. An example of calculations for the 19 h time point with one out of three triplicates is provided below.

Example of Calculation of Plasmid Amplification after 19 h: Known (or Measured) Parameters:

| | |
|---|---|
| Number of colonies after transformation (10 μl of culture plated) | 1750 ± 200 |
| Dilution for growth experiment, fold | 33.3 |
| Volume of culture purified for plasmid extraction, μl | 100 |
| Elution volume, μl | 30 |
| pINF fraction in total plasmid mixture, % | 43 |
| Total plasmid concentration, ng μl−1 | 2.97 |
| Biotin shift, % | 74.2 |

Calculation of Plasmid Concentration Before Growth:

$$\frac{175 \text{ molecules } \mu l^{-1}}{33.3} = 5.3 \text{ molecules } \mu l^{-1}$$

Calculation of Plasmid Amount in 100 μl of Media after Growth (19 h):

pINF Amount:

$$2.97 \text{ ng } \mu l^{-1}\times 43\%\times 30 \ \mu l=38 \text{ ng}$$

Number of pINF Molecules:

$$\frac{38\times 10^{-9} \text{ g}}{2686 \text{ bp}\times 660 \text{ g mol}^{-1} \ bp^{-1}}\times 6.02\times 10^{23} \text{ molecules mol}^{-1} = 1.3\times 10^{10} \text{ molecules}$$

Plasmid Concentration:

$1.3\times10^{10}$ molecules/100 μl=$1.3\times10^{8}$ molecules $\mu l^{-1}$

Calculation of Amplification (A), the Number of Doubling (n), Retention (F), and Fidelity (f)

$$A = \frac{1.3\times 10^{8} \text{ molecules } \mu l^{-1}}{5.3 \text{ molecules } \mu l^{-1}} = 2.4\times 10^{7}$$

$$n = \log_2(2.4\times 10^{7}) = 24.5$$

$$F = \frac{0.742 - 0.020}{0.772} = 93.5\%$$

$$f = 0.935^{\frac{1}{24.5}} = 99.7\%$$

Since plasmid recovery during purification is below 100%, our calculations underestimate the amplification level (A) and thus the number of doubling (n).

The fidelity (retention per doubling) is related to retention of the UBP (F) as $$f^{n}=F$$

and, since n=log 2(A), fidelity was calculated as $$f=F^{1/n}.$$

Figure 3A:
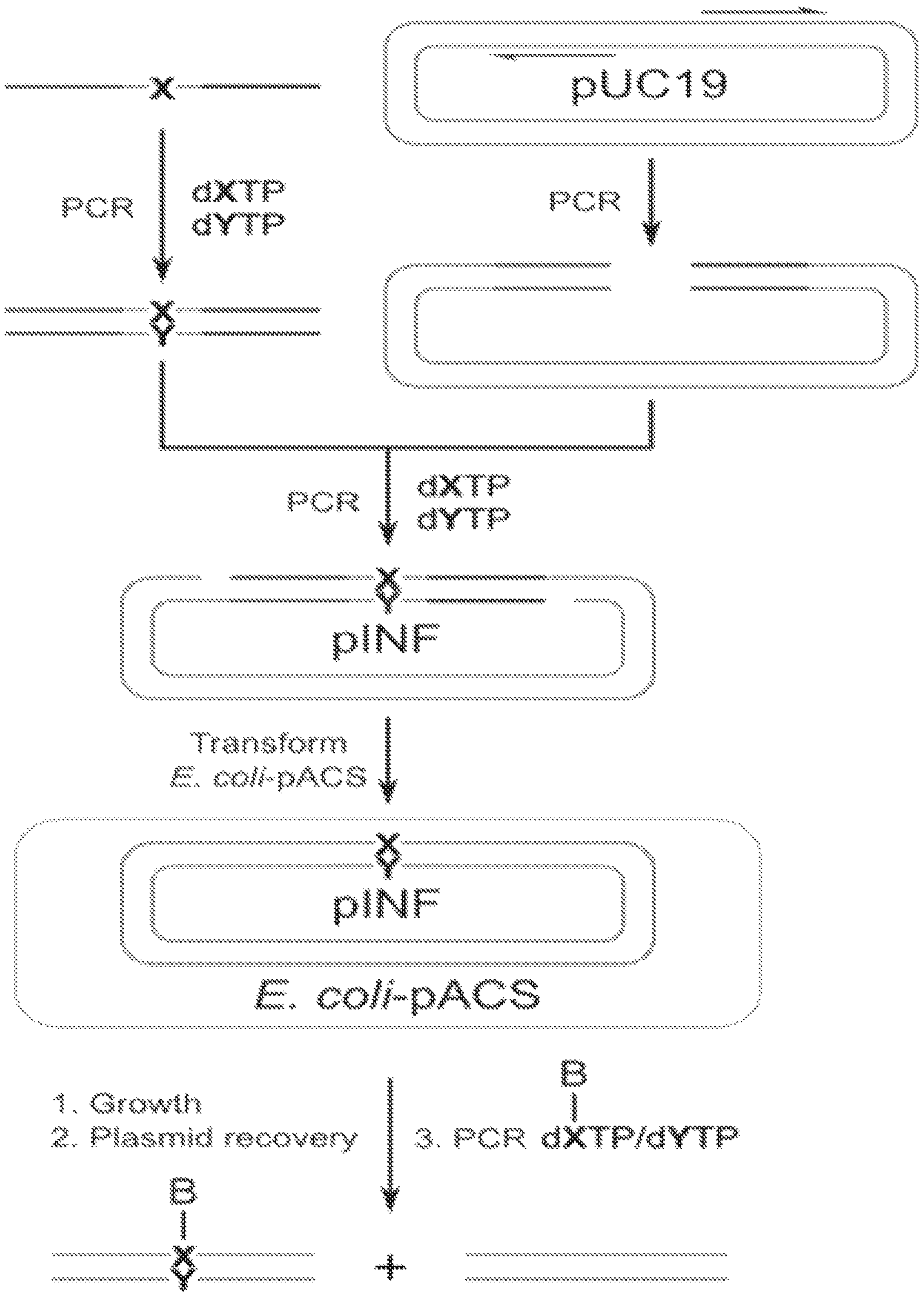
FIG. 3A depicts an exemplary pINF construction and scheme of an in vivo replication experiment. Regions of homology are depicted by shading. (Y=5SICS and X=NaM). B=biotin.
Figure 3B:
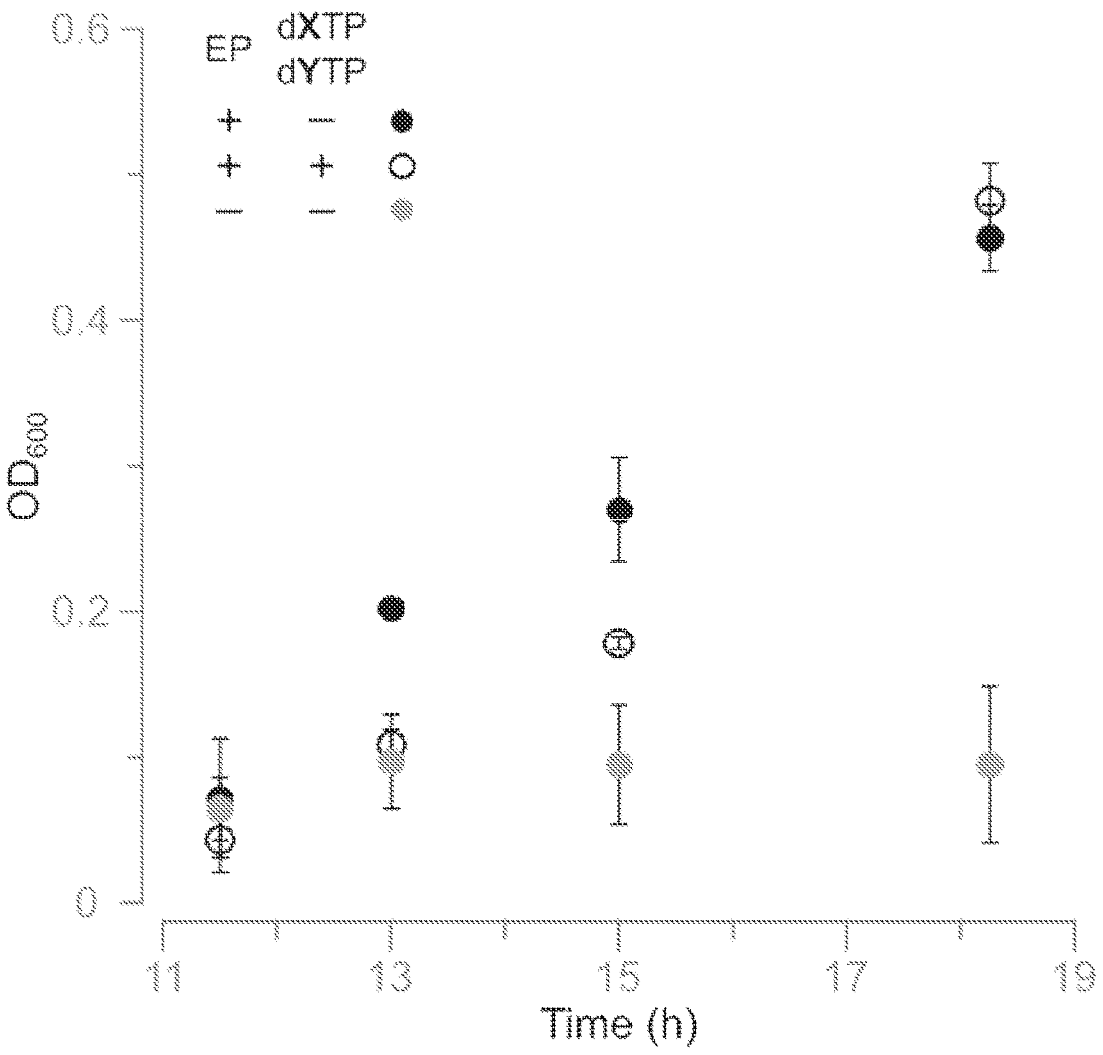
FIG. 3B depicts a growth curve of cells harboring pINF to which d5SICSTP and dNaMTP have been added. EP=electroporation.
Figure 3C:
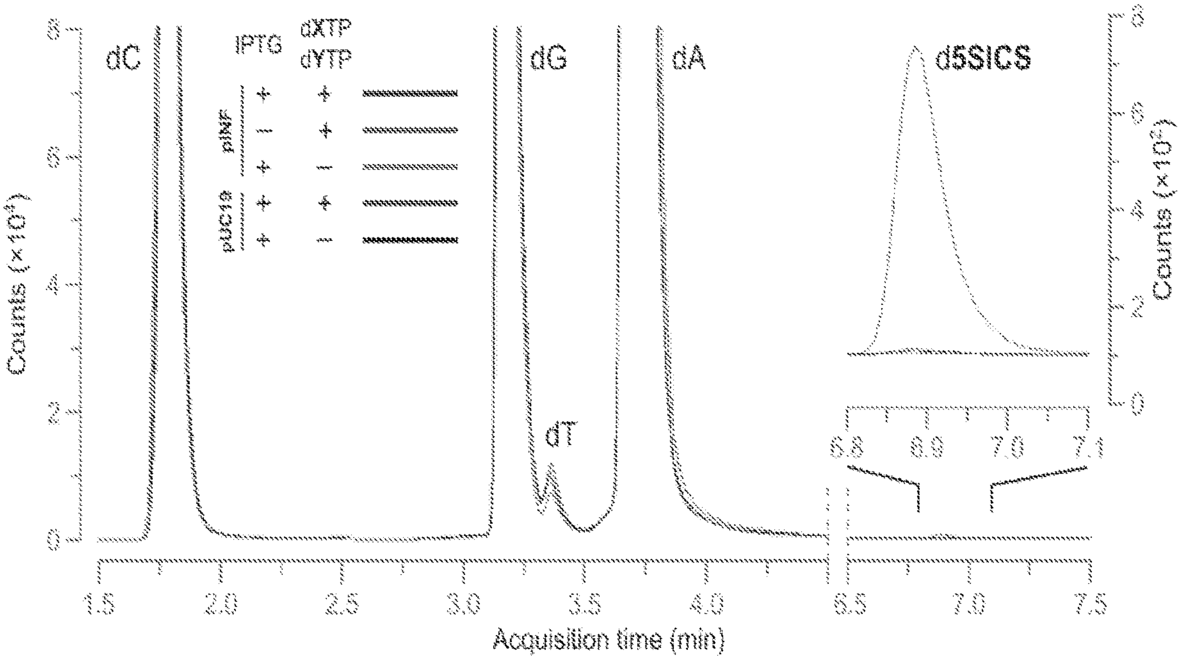
FIG. 3C depicts an LC-MS/MS total ion chromatogram of global nucleoside content in pINF and pUC19 recorded in Dynamic Multiple Reaction Monitoring (DMRM) mode. pINF and pUC19 (control) were propagated in *E. coli* in the presence or absence of unnatural triphosphates, and with or without PtNTT2 induction. The inset shows a 100× expansion of the mass count axis in the d5SICS region.
Figure 3D:
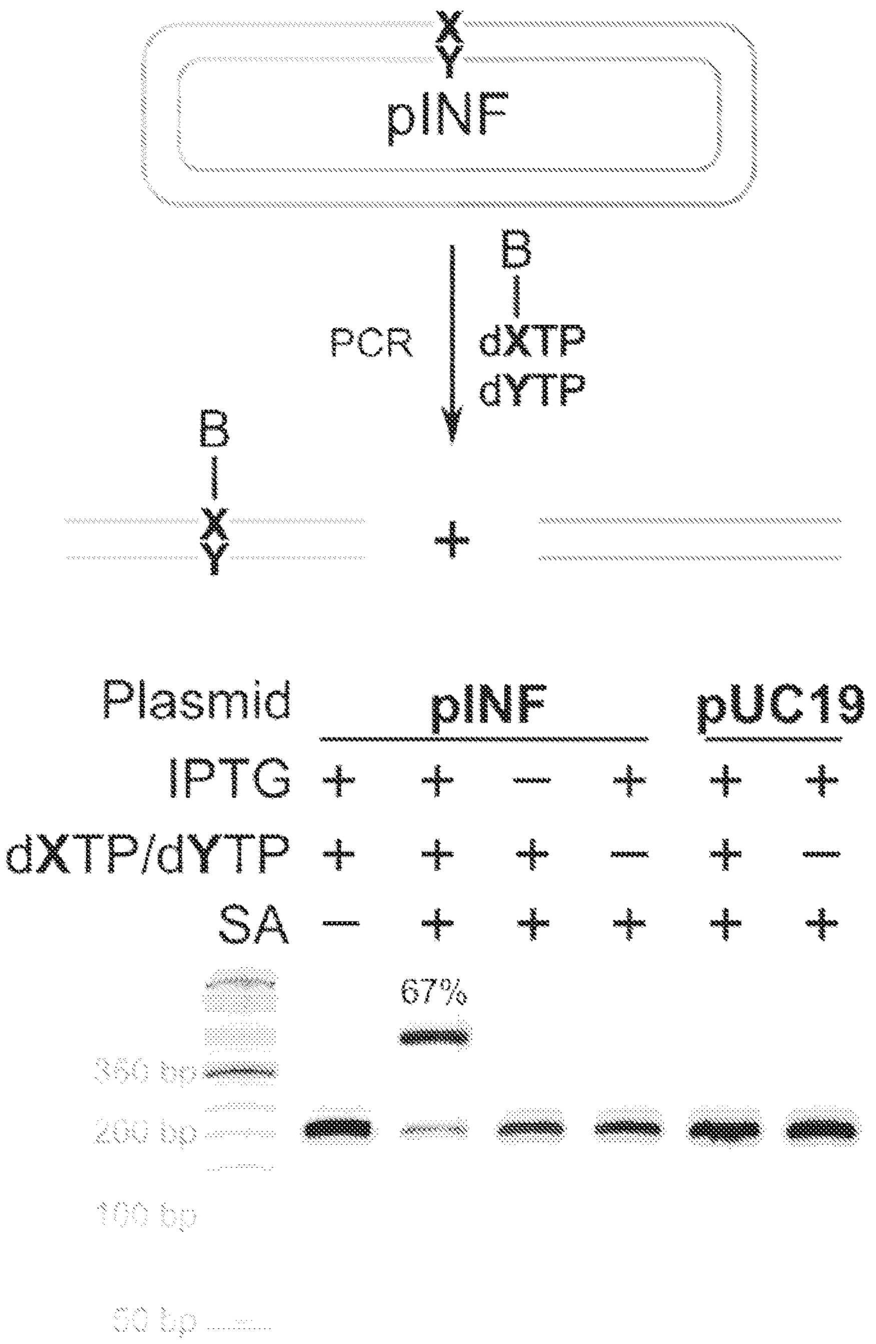
FIG. 3D depicts a gel shift analysis of PCR fragments demonstrating biotinylation in the presence of the UBP, unnatural triphosphates, and transporter induction. B=biotin. SA=streptavidin. A 50 bp DNA ladder is shown to the left.
Figure 3E:
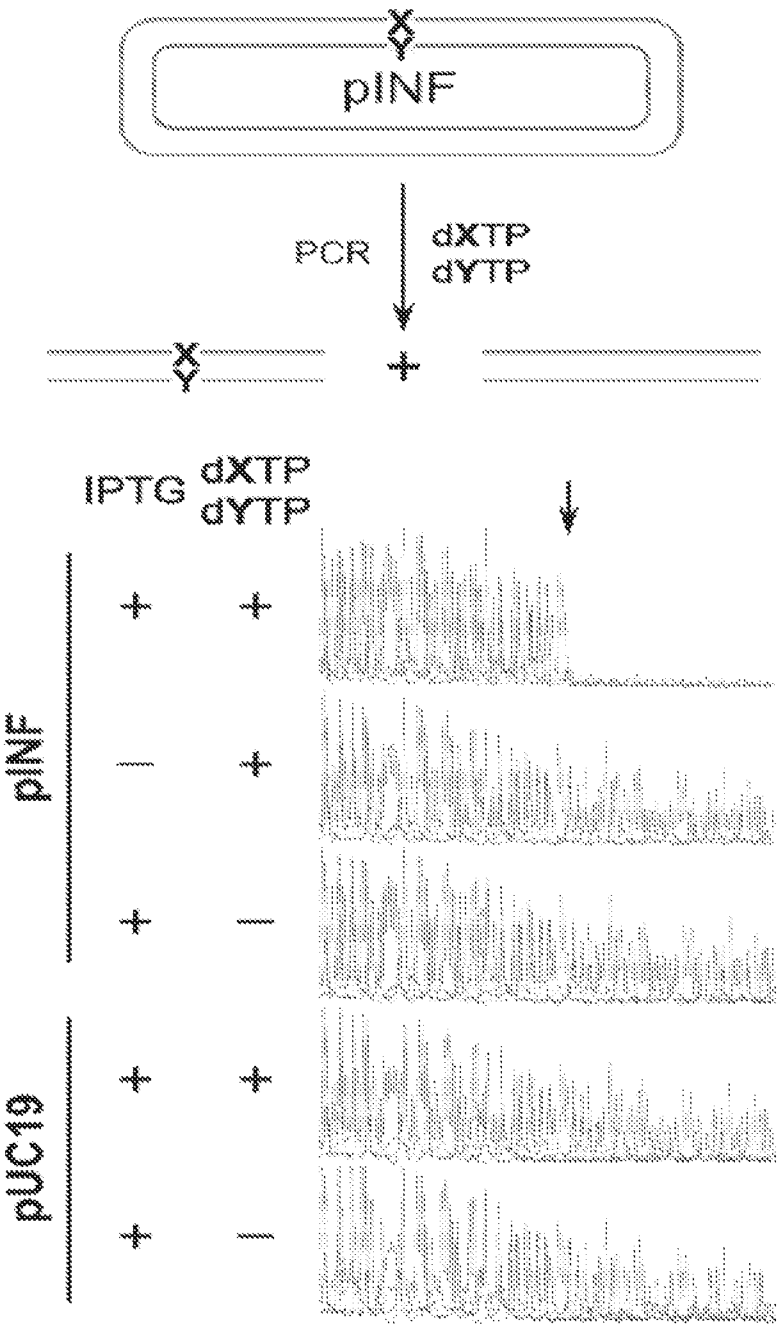
FIG. 3E depicts a Sanger sequencing analysis demonstrating retention of the UBP, as evidenced by an abrupt termination in the sequencing reaction at the position of UBP incorporation (indicated with arrow).

Example 7: Fidelity Measurement by Sequencing (FIG. 3E)

Fragment Generation for Sequencing

Purified mixtures of pINF and pACS plasmids (1 ng) after the overnight growth were amplified by PCR under the following conditions: 1×OneTaq reaction buffer, $MgSO_4$ adjusted to 3.0 mM, 0.2 mM of dNTP, 0.1 mM of dNaMTP, 0.1 mM of the d5SICSTP analog dTPT3TP, 1 μM of each of the primers pUC19-seq2-fwd and pUC19-seq-rev (see below), and 0.02 U/μl of OneTaq DNA Polymerase in a total volume of 25 μl under the following thermal cycling conditions: denaturation (96° C., 1 min); and 10 cycles of denaturation (96° C., 30 s), annealing 64° C., 30 s), and extension 68° C., 2 min. Products were purified by spin column, quantified to measure DNA concentration and then sequenced as described below. Sequencing fragment (304 bp) with primer regions are underlined and the unnatural nucleotide in bold (X=dNaM) is shown below.

(SEQ ID NO: 27)

5'-GCTGCAAGGCGATTAAGTTGGGTAACGCCAGGGTTTTCCCAGTCACG

ACGTTGTAAAACGACGGCCAGTGAATTCGAGCTCGGTACCCGGGGATCCT

CTAGAGTCGACCTGCAGGCATGCAAGCTTGGCGTAATCATGGTCATAGCT

GTTTCCTGTGTGAAATTGTTATCCGCTCACAXTTCCACACAACATACGAG

CCGGAAGCATAAAGTGTAAAGCCTGGGGTGCCTAATGAGTGAGCTAACTC

ACATTAATTGCGTTGCGCTCACTGCCCGCTTTCCAGTCGGGAAACCTGTC

GTGCCAG.

Sanger Sequencing

The cycle sequencing reactions (10 μl) were performed on a 9800 Fast Thermal Cycler (Applied Biosystems) with the Cycle Sequencing Mix (0.5 μl) of the BigDye Terminator v3.1 Cycle Sequencing Kit (Applied Biosystems) containing 1 ng template and 6 pmol of sequencing primer pUC19-seq-rev under the following thermal cycling conditions: initial denaturation (98° C., 1 min); and 25 cycles of denaturation (96° C., 10 s), annealing (60° C., 15 s), and extension (68° C., 2.5 min). Upon completion, residual dye terminators were removed from the reaction. Products were eluted off the beads with deionized water and sequenced directly. Sequencing traces were collected and analyzed with imaging software.

Analysis of Sanger Sequencing Traces

Sanger Sequencing traces were analyzed to determine the retention of the UBP. Briefly, the presence of an unnatural nucleotide leads to a sharp termination of the sequencing profile, while mutation to a natural nucleotide results in "read-through". The extent of this read-through after normalization is inversely correlated with the retention of an UBP. Raw sequencing traces were analyzed by first adjusting the start and stop points for the sequencing analysis software and then determining the average signal intensity individually for each channel (A, C, G and T) for peaks within the defined points. This was done separately for the parts of the sequencing trace before (section L) and after (section R) the unnatural nucleotide. The R/L ratio after normalization $(R/L)_{norm}$ for sequencing decay and read-through in the control unamplified sample ($R/L=0.55(R/L)_{norm}+7.2$, corresponds to the percentage of the natural sequences in the pool (Malyshev et al.). Therefore, an overall retention (F) of the incorporation of the UBP during PCR was calculated as:

$$1-\left(\frac{R}{L}\right)_{norm}.$$

Over 20% read-through occurred in the direction of pUC19-seq2-fwd primer using a control plasmid pINF. Sequencing of the opposite direction (pUC19-seq-rev) was performed and used to gauge fidelity and UDP retention as a function of growth (Table 7). Raw sequencing traces are shown in FIG. 3F.

TABLE 7

UBP retention (%) as a function of growth

| Time (h) | Sequencing Analysis | Gel Shift Analysis |
|---|---|---|
| 15 | >95 | 97 ± 5 |
| 19 | >95 | 91 ± 3 |
| 24 | >95 | 83 ± 1 |
| 32 | 85 ± 5 | 64 ± 10 |
| 43 | 71 ± 10 | 55 ± 13 |
| 53 | 68 ± 21 | 51 ± 18 |
| 77 | 60 ± 16 | 42 ± 18 |
| 146 | 30 ± 12 | 12 ± 8 |

TABLE 8

Exemplary oligonucleotide sequences

| Name | Sequence (5' to 3') | Purpose |
|---|---|---|
| pCDF-1b-fwd | GGTATATCTCCTTATTAAAGTTAAACAAAATTATT TCTACAGGGG (SEQ ID NO: 29) | Primers for pCDF-1b linearization |
| pCDF-1b-rev | TTAACCTAGGCTGCTGCCACCG (SEQ ID NO: 49) | |
| PtNTT2-fwd | GTTTAACTTTAATAAGGAGATATACCATGAGACCA TTTCCGAC (SEQ ID NO: 30) | Primers for PtNTT2 cloning |
| PtNTT2-rev | GCAGCAGCCTAGGTTAACTACTTTTCTTTGTTGGTC TTTG (SEQ ID NO: 31) | |
| TpNTT2-fwd | GTTTAACTTTAATAAGGAGATATACCATGAAAAAA TCTTGTACAATCC (SEQ ID NO: 32) | Primers for TpNTT2 cloning |
| TpNTT2-rev | GCAGCAGCCTAGGTTAACTACTTCTGGTGCTCTTT TG (SEQ ID NO: 33) | |
| pUC19-lin-fwd | TGGGGTGCCTAATGAGTGAGC (SEQ ID NO: 50) | Primers for pUC19 linearization |
| pUC19-lin-rev | CTATGACCATGATTACGCCAAGCTTG (SEQ ID NO: 34) | |
| TK-1-dNaM | CTGTTTCCTGTGTGAAATTGTTATCCGCTCACANa MTTCCACACAACATACGAGCCGGAAGCATAAAGT GTAAAGCC (SEQ ID NO: 35) | Unnatural fragment with dNaM |

TABLE 8-continued

| Exemplary oligonucleotide sequences | | |
|---|---|---|
| Name | Sequence (5' to 3') | Purpose |
| TK-1-dT | CTGTTTCCTGTGTGAAATTGTTATCCGCTCACAT TTCCACACAACATACGAGCCGGAAGCATAAAGTG TAAAGCC (SEQ ID NO: 36) | Natural fragment with dT |
| pUC19-fusion-fwd | CAAGCTTGGCGTAATCATGGTCATAGCTGTTTCCT GTGTGAAATTGTTATCCGC (SEQ ID NO: 37) | Primers for unnatural fragment cloning |
| pUC19-fusion-rev | GCTCACTCATTAGGCACCCCAGGCTTTACACTTTA TGCTTCCGGC (SEQ ID NO: 38) | |
| pUC19-seq-fwd | GCAGGCATGCAAGCTTGGCGTAATCATGG (SEQ ID NO: 39) | Primers for pINF analysis by gel shift and Sanger sequencing |
| pUC19-seq2-fwd | GCTGCAAGGCGATTAAGTTGGGTAACGCC (SEQ ID NO: 40) | |
| pUC19-seq-rev | CTGGCACGACAGGTTTCCCGACTGG (SEQ ID NO: 41) | |

Example 8: Polymerase Incorporation of Unnatural Nucleic Acids

Test reaction mixtures are added to the wells of a multiwell plate, where each well contains primed DNA templates attached to the bottoms of the wells. The test reaction mixtures contain a polymerase variant and an unnatural nucleic acid, an unnatural nucleic acid having (1) a base moiety that complements the appropriate position of the template for accurate extension to occur and (2) a biotinylated moiety attached to the sugar moiety. Following sufficient incubation time for extension to occur (e.g. for a control reaction having a polymerase of known reactivity with the unnatural nucleic acid), the reaction mixture is removed, the wells of the plate are washed to remove residual unnatural nucleic acids, and a development reagent is added to the wells. The development reagent includes a labeled streptavidin molecule that is capable of binding to nucleic acid molecules attached to well bottoms that have incorporated the unnatural nucleic acid. The label on the streptavidin molecule is any of a variety known in the art. The plate is washed again to remove unbound labeled streptavidin molecules. The label is then detected using a multiwell plate reader. The presence of signal from the labeled streptavidin indicates a polymerase having the ability to incorporate an unnatural nucleic acid. The same assay is used to determine kinetics or other quantitative parameters by varying the reaction time and or concentration of liquid-phase reagents. Similar screens are carried out for other unnatural nucleic acid by minor modification of the reagents exemplified above.

Example 9: Polymerase Incorporation of TPT3, (d)FTPT3, (d)NaM, (d)5SICS, (d)FEMO, (d)FIMO, and/or (d)MMO2 into DNA Polymerase (15 m/ml) is incubated at 30° C. in buffer (50 mM TRIS pH 7.5, 0.05% Tween 20, 6 mM $MgSO_4$, 1 mM EDTA, 50 mM NaCl) with 20 nM DNA. A time zero aliquot is taken for each concentration and then TPT3, (d)FTPT3, (d)NaM, (d)5SICS, (d)FEMO, (d)FIMO, and/or (d)MMO2 is added at 10, 5, 2 or 1 μM final concentration to start the reaction. Tubes are incubated at 30° C. and aliquots are taken at 0.33, 0.66, 1, 2, 5, and 15 mins from the 4 reaction tubes for quenching and 15% urea acrylamide gel analysis. 1 mM dNTPs are added to the remaining reaction tubes and after a further 10 mins an aliquot is taken for gel analysis (chase).

A photograph of the gel resulting from the above polymerase extension reaction is then taken. The results show the primer changing into larger band over the time course, with an increase in the amount of the larger band over time. The larger band demonstrates the addition of the (d)TPT3, (d)FTPT3, (d)NaM, (d)5SICS, (d)FEMO, (d)FIMO, and/or (d)MMO2 to the DNA (i.e. extension by one base). Following the addition of natural dNTPs the polymerase is able to extend the primer to the end of the template demonstrating that addition of the (d)TPT3, (d)FTPT3, (d)NaM, (d)5SICS, (d)FEMO, (d)FIMO, and/or (d)MMO2 does not create a 3' blocked primer and that the polymerase is able to extend the primer with natural and unnatural nucleic acids. The incorporation is more rapid at higher concentrations (10 μM) than at lower ones (1 μM) and shows time dependence indicative of genuine enzyme incorporation.

The results demonstrate the surprising finding that the polymerase can have selective primer extension reactivity for (d)TPT3, (d)FTPT3, (d)NaM, (d)5SICS, (d)FEMO, (d)FIMO, and/or (d)MMO2 and natural nucleic acids.

Example 10: Creation of a Cell with an Expanded Genetic Alphabet

Figure 5:
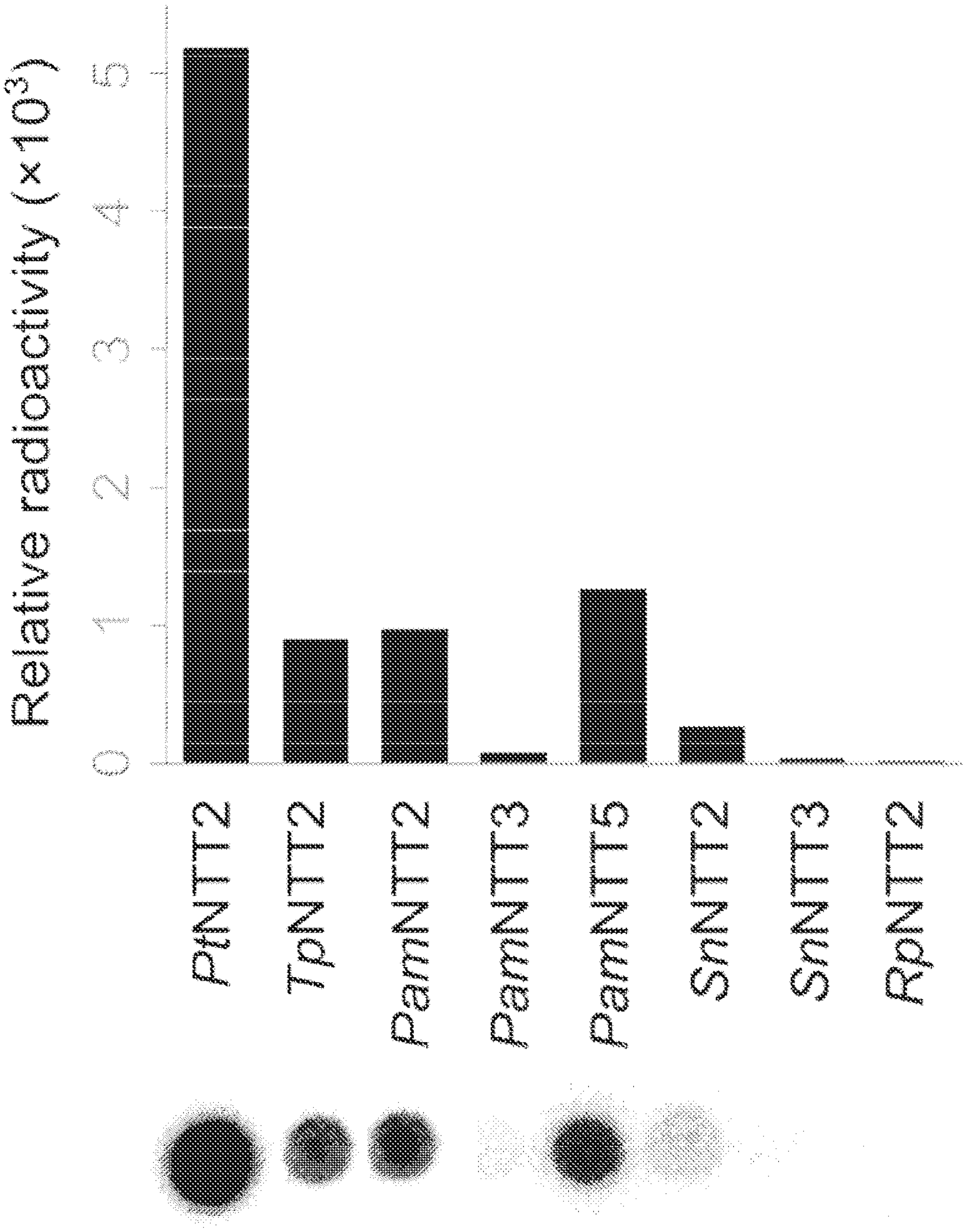
FIG. 5 depicts that PtNTT2 is significantly more active in the uptake of [α-$^{32}$P]-dATP compared to other nucleotide transporters. Raw (left) and processed (right) data are shown. Relative radioactivity corresponds to the total number of counts produced by each sample.

The experiments described herein illustrate the plasmid-based expression of eight different NTTs in *E. coli* C41 (DE3) (Table 9A). The uptake of [α-$^{32}$P]-dATP was examined as a surrogate for the unnatural triphosphates (FIG. 5). The dATP was efficiently transported into cells by the NTTs from *Phaeodactylum tricornutum* (PtNTT2) and *Thalassiosira pseudonana* (TpNTT2). Unexpectedly, the NTTs from *Protochlamydia amoebophila* (PamNTT2 and PamNTT5) were found to also import dATP. Both PamNTT2 and PamNTT5 exhibited a measurable uptake of dATP (FIG. 5). PtNTT2 showed the most activity, and both it and TpNTT2 are demonstrated broad specificity, making them putative NTTs for importing nucleotide triphosphates.

Figure 10:
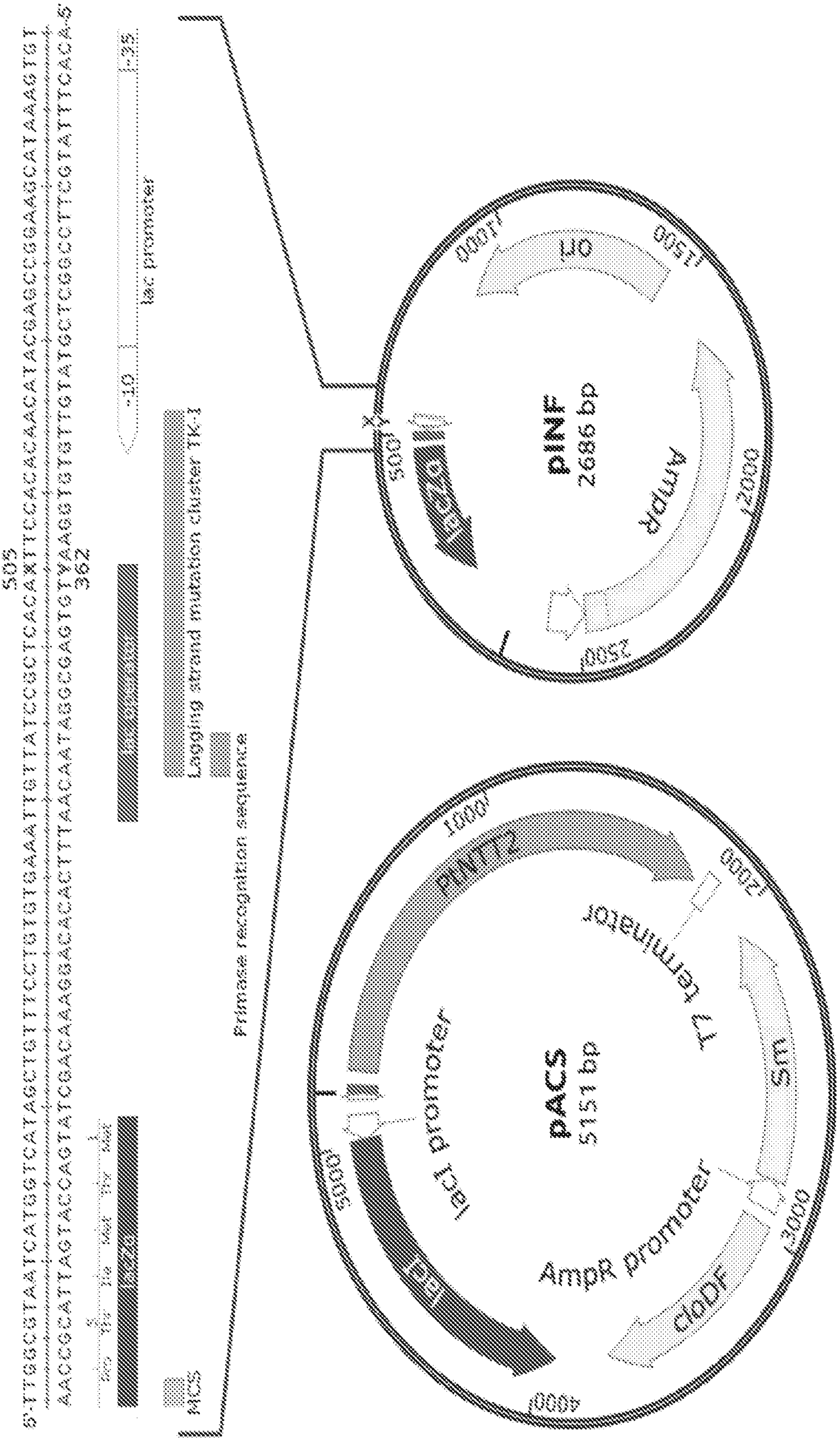
FIG. 10 shows schematic representations of the plasmid pINF, constructed from pUC19 by replacing $dT_{505}$ with dNaM, and of the pCDF-1b plasmid encoding PtNTT2 (pACS). dX and dY correspond to dNaM and a d5SICS analog. cloDF=origin of replication of pCDF-1b plasmid; Sm=streptomycin resistance gene; AmpR=ampicillin resistance gene; ori=ColE1 origin of replication; MCS=multiple cloning site; lacZα=β-galactosidase fragment gene.

The replication of DNA containing d5SICS-dNaM has been validated in vitro with different polymerases, but most so with the family A polymerases, such as the Klenow fragment of *E. coli* DNA Polymerase I (Pol I). While the majority of the *E. coli* genome is replicated by Pol III, an plasmid was engineered that focused on replication of the UBP by Pol I. The accessory plasmid (pACS) was derived from pCDF-1b by inserting the PtNTT2 gene (FIG. 10). The information plasmid (pINF) was derived from pUC19 by replacing $dT_{505}$ (standard numbering of the pUC19 map available for download at http://www.thermoscientificbio-.com/uploadedFiles/Resources/pUC18-pUC19-map.pdf) with dNaM. This places the UBP 362 nts downstream of the ColE1 origin (FIG. 10). Plasmid pINF (i.e. the information plasmid) was constructed from pUC19 by replacing $dT_{505}$ with dNaM using solid phase synthesis and circular extension PCR (FIG. 3A and FIG. 10). The dA-dT pair at position 505 was replaced with dNaM paired opposite an analog of d5SICS (dTPT3). This positions the UBP downstream of the ColE1 origin of replication where leading strand replication is mediated by Pol I, and within the TK-1 Okazaki processing site, where lagging strand synthesis is also expected to be mediated by Pol I. Synthetic pINF was constructed using the d5SICS analog because it should be efficiently replaced by d5SICS if replication occurs in vivo and thus makes it possible to differentiate in vivo replicated pINF from synthetic pINF.

To determine whether *E. coli* can use the imported unnatural triphosphates to stably propagate pINF, C41(DE3) cells were first transformed with a pCDF-1b plasmid encoding PtNTT2 (hereafter referred to as pACS, for accessory plasmid, FIG. 10, and see Seq ID No. 1, below) and grown in media containing 0.25 mM of both unnatural triphosphates, 50 mM KPi, and 1 mM IPTG to induce transporter production. Cells were then transformed with pINF, and after a 1 h recovery period, cultures were diluted 10-fold with the same media supplemented with ampicillin and growth was monitored via culture turbidity (FIG. 3A and Table 9A and B).

TABLE 9A

| | Deoxyribotriphosphates | | | | Ribotriphosphates | | | |
|---|---|---|---|---|---|---|---|---|
| Transporter | dG | dA | dC | T | G | A | C | U |
| PtNTT2 | 82 | 271 | 31 | 428 | 78 | 197 | 49 | 86 |
| TpNTT2 | 74 | 665 | 60 | 251 | 59 | 49 | 33 | 90 |
| PamNTT2 | | | | | 156 | 437 | 570 | 676 |
| PamNTT3 | | | | | | | | 1320 |
| PamNTT5 | 121 | | | | 22 | 360 | | |
| SnNTT2 | | | | | 179 | 654 | | |
| SnNTT3 | | | 42 | | 407 | 375 | 9 | 34 |
| RpNTT2 | | | Substrate is unknown | | | | | |

Substrate specificity ($K_M$, μM) of depicted NTT

TABLE 9B

| Plasmid | IPTG | dXTP/dYTP | Relative Copy Number | OD600 (15 h) | OD600 (19 h) |
|---|---|---|---|---|---|
| pINF | + | + | 1.8 | 0.34 | 0.75 |
| | + | − | 4.6 | 0.15 | 0.75 |
| | − | + | 8.9 | 3.13 | 3.98 |
| pUC19 | + | + | 2.8 | 0.54 | 1.25 |
| | − | − | 2.6 | 0.73 | 1.30 |

$OD_{600}$ and relative plasmid copy number of pINF as determined by its molar ratio to pACS after 15 and 19 h of growth. X = NaM and Y = 5SICS.

As controls, cells were also transformed with pUC19, or grown without either IPTG or the unnatural triphosphates. Growth was slower in the presence of IPTG, likely due to the effects of transporter induction. However, the addition of d5SICSTP and dNaMTP resulted in only a slight decrease in growth in the absence of pINF, and it eliminated a growth lag in the presence of pINF (FIG. 3B). This indicates that the unnatural triphosphates are not toxic and are required for the efficient replication of pINF.

To determine whether pINF is propagated with retention of the UBP, we recovered the plasmid from cells after 15 h of growth. The introduction of the UBP resulted in only a small reduction in plasmid copy number (<2-fold, Table 9B), and based on the amount of recovered plasmid and the transformation efficiency, pINF was amplified $2\times10^7$-fold during growth (~24 doublings).

To determine the level of UBP retention, the recovered plasmid was digested, dephosphorylated to single nucleosides, and analyzed by LC-MS/MS. While the detection and quantification of dNaM were precluded by its poor fragmentation efficiency and low product ion counts over background, signal for d5SICS was clearly observable (FIG. 3C). External calibration curves were constructed using the unnatural nucleoside and validated by determining its ratio to dA in synthetic oligonucleotides (Table 7). Using the resulting calibration curve, we determined the ratio of dA to d5SICS in recovered pINF was 1106 to 1, which when compared to the expected ratio of 1325 to 1, suggests the presence of approximately one UBP per plasmid. No d5SICS was detected in control experiments in which the transporter was not induced, nor when the unnatural triphosphates were not added to the media, nor when pUC19 was used instead of pINF (FIG. 3C), demonstrating that its presence results from the replication of the UBP and not from misinsertion of the unnatural triphosphates opposite a natural nucleotide. Importantly, as the synthetic pINF contained an analog of d5SICS, and d5SICS was only provided as a triphosphate added to the media, its presence in pINF confirms in vivo replication.

The region of pINF surrounding nucleotide 505 was then PCR amplified in the presence of d5SICSTP and a biotinylated dNaMTP analog. Analysis by streptavidin gel shift showed that 67% of the amplified DNA contained biotin (FIG. 3D). No shift was observed in control experiments in which the transporter was not induced, nor when the unnatural triphosphates were not added to the media, demonstrating that the shift required the import of the unnatural triphosphates. Similarly, no gel shift was observed with DNA isolated from identically treated control cells transformed with pUC19, demonstrating that the shift results from the retention of the UBP and not from misinsertion of the unnatural triphosphates opposite a natural nucleotide. Based on a calibration curve constructed from the shifts observed with the amplification products of controlled mixtures of DNA containing dNaM or its fully natural counterpart (Methods), the observed gel shift corresponds to a UBP retention of 86%, which in turn corresponds to a fidelity (retention per doubling) of 99.4% (0.994=0.86).

To confirm the high retention of the UBP, the same region of pINF was PCR amplified in the presence of d5SICSTP and dNaMTP, and the products were analyzed by Sanger sequencing (FIG. 3E). The presence of the UBP caused an abrupt termination in the sequencing reaction, and thus the level of UBP retention may be quantified from the ratio of the amplitudes of the peaks in the chromatogram before and after the site of UPB incorporation. Sequencing chromatograms of pINF isolated from cultures grown either without PtNTT2 induction or without addition of the unnatural triphosphates showed no termination. In contrast, chromatograms from the amplification products of pINF isolated from cells grown with PtNTT2 induction and with added unnatural triphosphates showed an abrupt termination at the expected position. With a lower limit of read-through detection estimated to be 5% (corresponding to 95% retention), this places a lower limit of 99.7% on the fidelity of UBP replication. The estimates of fidelity from both sets of experiments correspond to an error rate of $\sim 10^{-3}$, which is comparable to the intrinsic error-rate of some polymerases with natural DNA.

Figure 4:
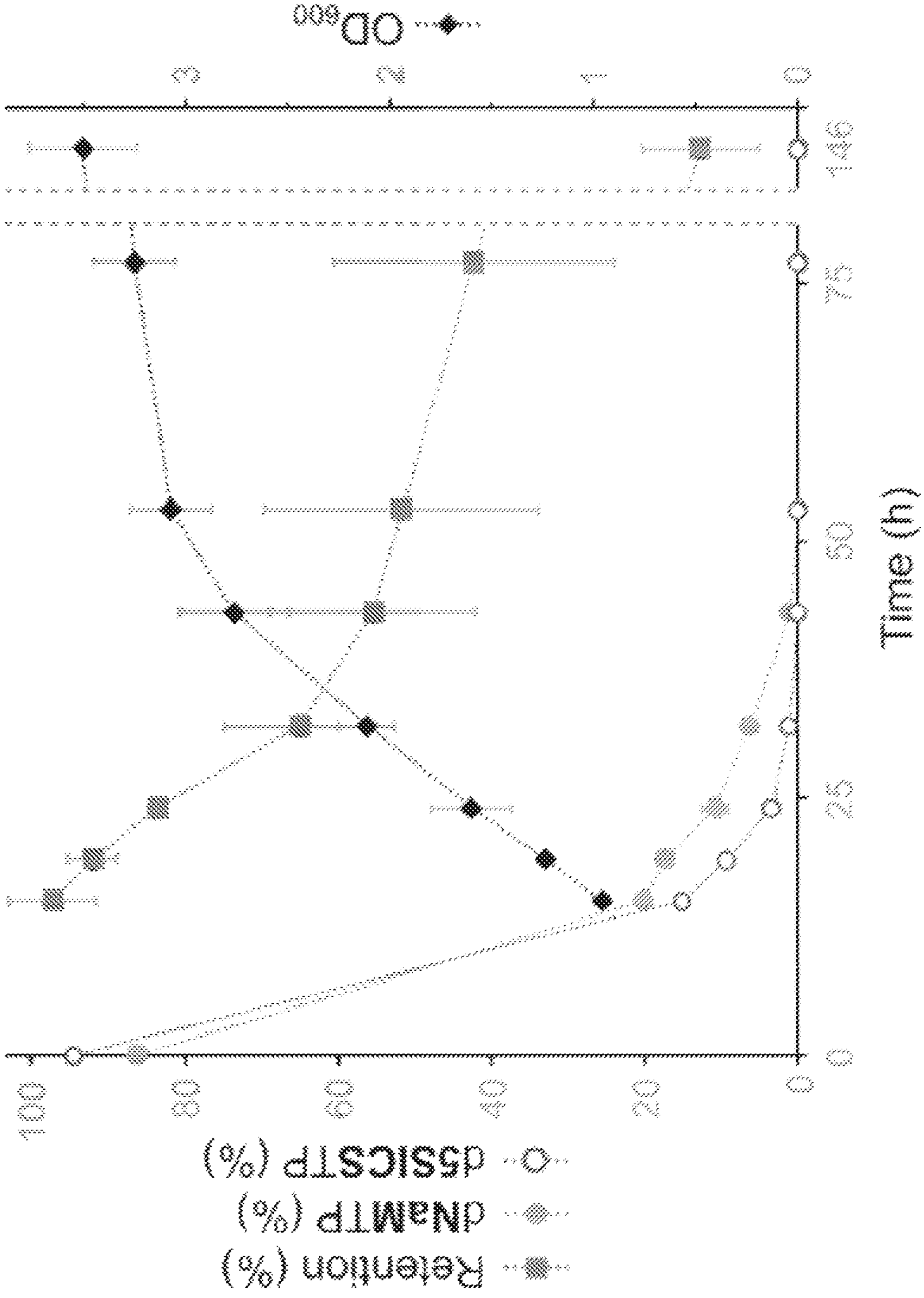
FIG. 4 depicts data relating to the intracellular stability of the UBP. *E. coli* C41(DE3)-pACS was transformed with pINF and grown after a single dose of d5SICSTP and dNaMTP was provided in the media. UBP retention (squares), $OD_{600}$ (diamonds), and relative amount of d5SICSTP and dNaMTP in the media (open and closed circles, respectively; 100%=0.25 mM), were determined as a function of time.

The high retention of the UBP over a 15 h period of growth indicates that it is not efficiently excised by DNA repair pathways. To further support this conclusion, we repeated the experiments, but monitored UBP retention, cell growth, and unnatural triphosphate decomposition for up to 6 days (FIG. 4).

At 15 and 19 h of growth, the cultures reached an $OD_{600}$ of ~0.9 and ~1.2, respectively, and both d5SICSTP and dNaMTP decomposed to only 17-20% and 10-16% of their initial 0.25 mM concentrations (FIG. 12A). In agreement with the above described experiments, retention of the UBP after 15 h was 97±5% and >95%, as determined by gel shift and sequencing, respectively, and after 19 h it was 91±3% and >95%. As the cultures entered stationary phase and the triphosphates decomposed completely, plasmid loss began to compete with replication (FIGS. 12B and C), but even then, retention of the UBP remained at ~45% and ~15%, at 3 and 6 days respectively. Moreover, when d5SICS-dNaM was lost, it was replaced by dA-dT, which is consistent with the mutational spectrum of Kf. Finally, the shape of the retention vs. time curve mirrors that of the growth vs. time curve. Taken together, these data strongly support the conclusion that loss of the UBP results from replication-mediated mispairing (which is unavoidable after unnatural triphosphate decomposition), and not from the activity of DNA repair pathways.

Example 11: Directed Evolution of Cells with Increased NTT Activity

Cells harboring endogenous NTTs are incubated in the presence of natural dNTPs and one or more unnatural nucleic acids. The concentration of one or more of the natural dNTPs in contact with the cells is decreased slowly over time and with growth. The concentration of one or more of the unnatural nucleic acids in contact with the cells is increased slowly over time and with growth. Surviving cells are subjected to further rounds of exposure to increasing concentrations of the unnatural nucleic acids and decreasing concentrations of the natural dNTPs. Surviving cells, lysates, or purified NTTs are assayed for binding kinetics, import, replication, and/or incorporation of the unnatural nucleic acids. Cell pools demonstrating increased import, replication, and/or incorporation of the unnatural nucleic acids compared to the initial cells harboring endogenous NTTs are further assayed for the NTT variants using PCR and sequencing methods. The cells and/or information of the NTT variant sequences are used to generate recombinant proteins and nucleic acid reagents for expression in host cells as described above. Further, genetically engineered cells are engineered that contain increased import activity, replication activity, and/or incorporation of the unnatural nucleic acids compared to the initial cells harboring endogenous NTTs.

Example 12: Directed Evolution of Cells with Polymerase Activity for Unnatural Nucleic Acids Cells harboring endogenous polymerases are incubated in the presence of natural dNTPs and one or more unnatural nucleic acids. The concentration of one or more of the natural dNTPs in contact with the cells is decreased slowly over time and with growth. The concentration of one or more of the unnatural nucleic acids in contact with the cells is increased slowly over time and with growth. Surviving cells are subjected to further rounds of exposure to increasing concentrations of the unnatural nucleic acids and decreasing concentrations of the natural dNTPs. Surviving cells, lysates, or purified polymerases are assayed for replication and/or incorporation of the unnatural nucleic acids. Cell pools demonstrating increased import, replication, and/or incorporation of the unnatural nucleic acids compared to the initial cells harboring endogenous polymerases are further assayed for the polymerase variants using PCR and sequencing methods. The cells and/or information of the polymerase variant sequences are used to generate recombinant proteins and nucleic acid reagents for expression in host cells as described above. Further, genetically engineered cells are engineered that contain increased polymerase activity, replication activity, and/or incorporation of the unnatural nucleic acids compared to the initial cells harboring endogenous polymerases.

Other Embodiments

Unless otherwise explained, all technical and scientific terms used herein have the same meaning as commonly understood by one of ordinary skill in the art to which this disclosure belongs. The following references contain embodiments of the methods and compositions that can be used herein: The Merck Manual of Diagnosis and Therapy, 18th Edition, published by Merck Research Laboratories, 2006 (ISBN 0-911910-18-2); Benjamin Lewin, Genes IX, published by Jones & Bartlett Publishing, 2007 (ISBN-13: 9780763740634); Kendrew et al. (eds.), The Encyclopedia of Mol. Biology, published by Blackwell Science Ltd., 1994 (ISBN 0-632-02182-9); and Robert A. Meyers (ed.), Mol. Biology and Biotechnology: a Comprehensive Desk Reference, published by VCH Publishers, Inc., 1995 (ISBN 1-56081-569-8).

Standard procedures of the present disclosure are described, e.g., in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl (eds.), Academic Press Inc., San Diego, USA (1987)). Current Protocols in Molecular Biology (CPMB) (Fred M. Ausubel, et al. ed., John Wiley and Sons, Inc.), Current Protocols in Protein Science (CPPS) (John E. coligan, et. al., ed., John Wiley and Sons, Inc.), Current Protocols in Immunology (CPI) (John E. coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), and Animal Cell Culture Methods (Methods in Cell Biology, Vol. 57, Jennie P. Mather and David Barnes editors, Academic Press, 1st edition, 1998), which are all incorporated by reference herein in their entireties.

Disclosed herein are molecules, materials, compositions, and components that can be used for, can be used in conjunction with, can be used in preparation for, or are products of methods and compositions disclosed herein. It is understood that when combinations, subsets, interactions, groups, etc. of these materials are disclosed and while specific reference of each various individual and collective combinations and permutation of these molecules and compounds cannot be explicitly disclosed, each is specifically contemplated and described herein. For example, if a nucleotide or nucleic acid is disclosed and discussed and a number of modifications that can be made to a number of molecules including the nucleotide or nucleic acid are discussed, each and every combination and permutation of nucleotide or nucleic acid and the modifications that are possible are specifically contemplated unless specifically indicated to the contrary. This concept applies to all aspects of this application including, but not limited to, steps in methods of making and using the disclosed molecules and compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

All publications, patents, and patent applications mentioned in the above specification are hereby incorporated by reference. Various modifications and variations of the described methods, compositions, and kits of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention. Other embodiments are in the claims.

What is claimed is:

1. A method of incorporating an unnatural nucleoside triphosphate into a prokaryotic cell, comprising: contacting the cell comprising a heterologous nucleoside triphosphate transporter with the unnatural nucleoside triphosphate; wherein the nucleoside triphosphate transporter transports the unnatural nucleoside triphosphate into the cell; and wherein the heterologous nucleoside triphosphate transporter comprises an amino acid sequence that is at least about 85% identical to SEQ ID NO: 1.

2. The method of claim 1, wherein the cell is an *Escherichia coli* cell.

3. The method of claim 1, wherein the nucleoside triphosphate transporter comprises an amino acid sequence with at least about 90% sequence identity to SEQ ID NO: 1.

4. The method of claim 3, wherein the cell is an *Escherichia coli* cell.

5. The method of claim 1, wherein the unnatural nucleoside triphosphate comprises a base selected from the group consisting of

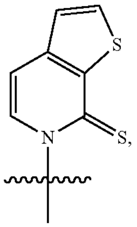 [SMILES: *n1ccc2ccsc2c1=S]
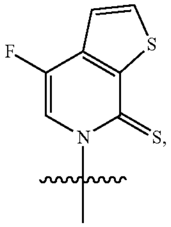
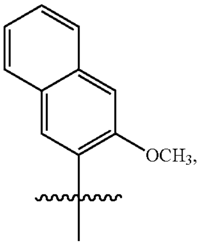 [SMILES: *c1cc2ccccc2cc1OC]
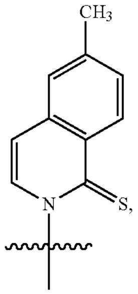
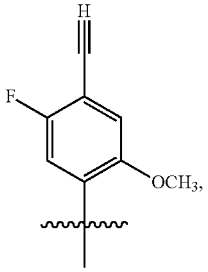
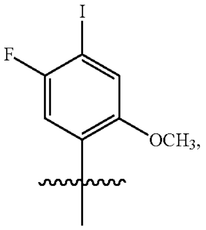
and
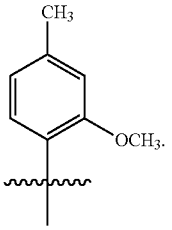

6. The method of claim 1, wherein the unnatural nucleoside triphosphate comprises a base selected from the group consisting of

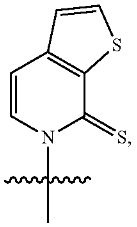 [SMILES: *n1ccc2ccsc2c1=S]
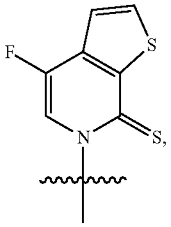
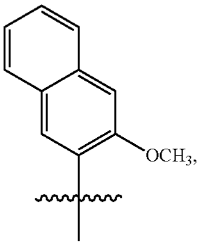
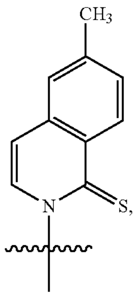
and
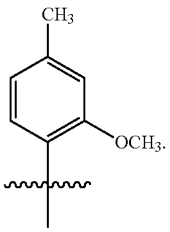

7. The method of claim 1, wherein the unnatural nucleoside triphosphate comprises a base selected from the group consisting of

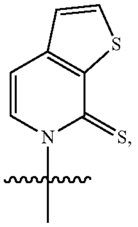
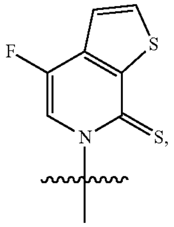
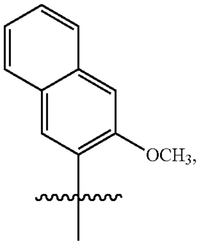
and
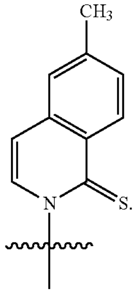

8. The method of claim 1, wherein the unnatural nucleoside triphosphate comprises a base having the formula

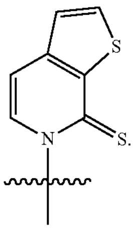

9. The method of claim 1, wherein the unnatural nucleoside triphosphate comprises a base having the formula

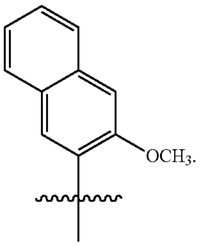

10. The method of claim 1, wherein:

(a) the unnatural nucleoside comprises a base having the formula

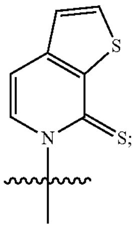

and (b) a second unnatural nucleoside triphosphate is transported into the cell, and the second unnatural nucleoside comprises a base selected from

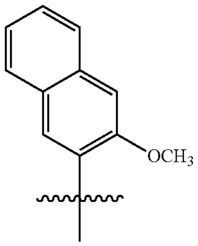 and 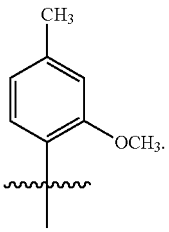

11. The method of claim 10, wherein the second unnatural nucleoside triphosphate comprises a base which is

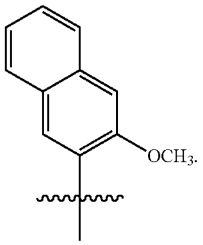 [SMILES: *c1cc2ccccc2cc1OC]

12. The method of claim 10, wherein the cell is an *Escherichia coli* cell.

13. The method of claim 1, wherein a second unnatural nucleoside triphosphate is transported into the cell, and the second unnatural nucleotide triphosphate comprises a base selected from the group consisting of

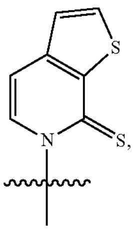
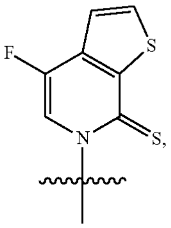
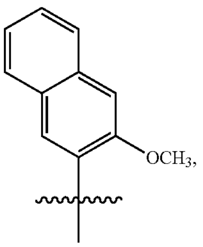
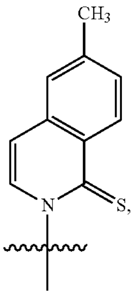
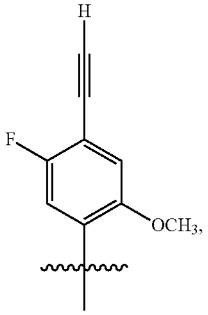
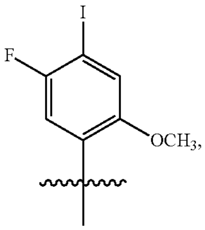 and 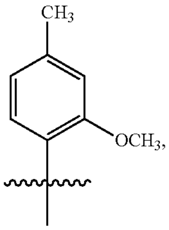

wherein the bases of the unnatural nucleoside triphosphate and the second unnatural nucleoside triphosphate are different.

14. The method of claim 13, wherein the second unnatural nucleoside triphosphate comprises a base selected from the group consisting of

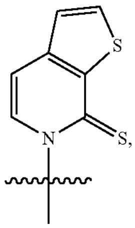
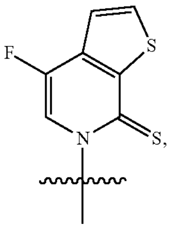
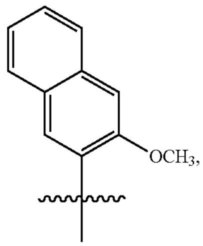
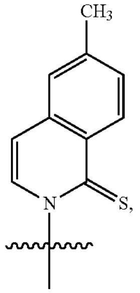 and

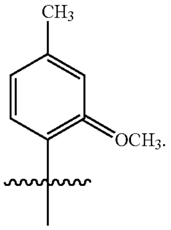

15. The method of claim 13, wherein (a) the unnatural nucleoside triphosphate comprises a base selected from

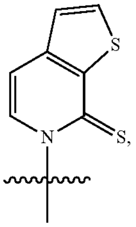
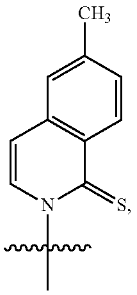 and

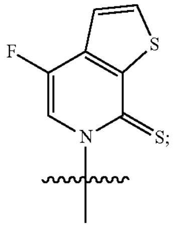

and (b) the second unnatural nucleoside triphosphate comprises a base selected from

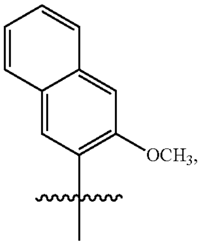,
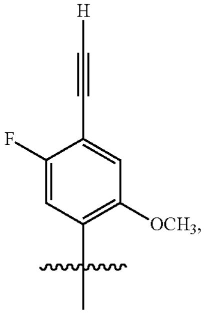,
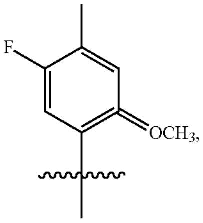,
and
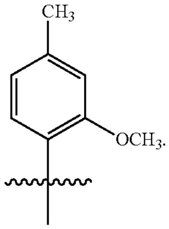.
16. The method of claim 2, wherein the unnatural nucleoside triphosphate comprises a base having the formula
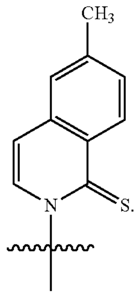 [SMILES: *n1ccc2cc(C)ccc2c1=S].
17. The method of claim 8, wherein the cell is an *Escherichia coli* cell.
18. The method of claim 9, wherein the cell is an *Escherichia coli* cell.
* * * * *

SEQUENCE LISTING

```
<160> NUMBER OF SEQ ID NOS: 50

<210> SEQ ID NO 1
<211> LENGTH: 575
<212> TYPE: PRT
<213> ORGANISM: Phaeodactylum tricornutum

<400> SEQUENCE: 1

Met Arg Pro Tyr Pro Thr Ile Ala Leu Ile Ser Val Phe Leu Ser Ala
1               5                   10                  15

Ala Thr Arg Ile Ser Ala Thr Ser Ser His Gln Ala Ser Ala Leu Pro
            20                  25                  30

Val Lys Lys Gly Thr His Val Pro Asp Ser Pro Lys Leu Ser Lys Leu
        35                  40                  45

Tyr Ile Met Ala Lys Thr Lys Ser Val Ser Ser Ser Phe Asp Pro Pro
    50                  55                  60

Arg Gly Gly Ser Thr Val Ala Pro Thr Thr Pro Leu Ala Thr Gly Gly
65                  70                  75                  80

Ala Leu Arg Lys Val Arg Gln Ala Val Phe Pro Ile Tyr Gly Asn Gln
                85                  90                  95

Glu Val Thr Lys Phe Leu Leu Ile Gly Ser Ile Lys Phe Phe Ile Ile
            100                 105                 110

Leu Ala Leu Thr Leu Thr Arg Asp Thr Lys Asp Thr Leu Ile Val Thr
        115                 120                 125

Gln Cys Gly Ala Glu Ala Ile Ala Phe Leu Lys Ile Tyr Gly Val Leu
    130                 135                 140

Pro Ala Ala Thr Ala Phe Ile Ala Leu Tyr Ser Lys Met Ser Asn Ala
145                 150                 155                 160

Met Gly Lys Lys Met Leu Phe Tyr Ser Thr Cys Ile Pro Phe Phe Thr
                165                 170                 175

Phe Phe Gly Leu Phe Asp Val Phe Ile Tyr Pro Asn Ala Glu Arg Leu
            180                 185                 190

His Pro Ser Leu Glu Ala Val Gln Ala Ile Leu Pro Gly Gly Ala Ala
        195                 200                 205

Ser Gly Gly Met Ala Val Leu Ala Lys Ile Ala Thr His Trp Thr Ser
    210                 215                 220

Ala Leu Phe Tyr Val Met Ala Glu Ile Tyr Ser Ser Val Ser Val Gly
225                 230                 235                 240

Leu Leu Phe Trp Gln Phe Ala Asn Asp Val Val Asn Val Asp Gln Ala
                245                 250                 255
```

-continued

```
Lys Arg Phe Tyr Pro Leu Phe Ala Gln Met Ser Gly Leu Ala Pro Val
            260                 265                 270

Leu Ala Gly Gln Tyr Val Val Arg Phe Ala Ser Lys Ala Val Asn Phe
        275                 280                 285

Glu Ala Ser Met His Arg Leu Thr Ala Ala Val Thr Phe Ala Gly Ile
    290                 295                 300

Met Ile Cys Ile Phe Tyr Gln Leu Ser Ser Ser Tyr Val Glu Arg Thr
305                 310                 315                 320

Glu Ser Ala Lys Pro Ala Ala Asp Asn Glu Gln Ser Ile Lys Pro Lys
                325                 330                 335

Lys Lys Lys Pro Lys Met Ser Met Val Glu Ser Gly Lys Phe Leu Ala
            340                 345                 350

Ser Ser Gln Tyr Leu Arg Leu Ile Ala Met Leu Val Leu Gly Tyr Gly
        355                 360                 365

Leu Ser Ile Asn Phe Thr Glu Ile Met Trp Lys Ser Leu Val Lys Lys
    370                 375                 380

Gln Tyr Pro Asp Pro Leu Asp Tyr Gln Arg Phe Met Gly Asn Phe Ser
385                 390                 395                 400

Ser Ala Val Gly Leu Ser Thr Cys Ile Val Ile Phe Phe Gly Val His
                405                 410                 415

Val Ile Arg Leu Leu Gly Trp Lys Val Gly Ala Leu Ala Thr Pro Gly
            420                 425                 430

Ile Met Ala Ile Leu Ala Leu Pro Phe Phe Ala Cys Ile Leu Leu Gly
        435                 440                 445

Leu Asp Ser Pro Ala Arg Leu Glu Ile Ala Val Ile Phe Gly Thr Ile
    450                 455                 460

Gln Ser Leu Leu Ser Lys Thr Ser Lys Tyr Ala Leu Phe Asp Pro Thr
465                 470                 475                 480

Thr Gln Met Ala Tyr Ile Pro Leu Asp Asp Glu Ser Lys Val Lys Gly
                485                 490                 495

Lys Ala Ala Ile Asp Val Leu Gly Ser Arg Ile Gly Lys Ser Gly Gly
            500                 505                 510

Ser Leu Ile Gln Gln Gly Leu Val Phe Val Phe Gly Asn Ile Ile Asn
        515                 520                 525

Ala Ala Pro Val Val Gly Val Val Tyr Tyr Ser Val Leu Val Ala Trp
    530                 535                 540

Met Ser Ala Ala Gly Arg Leu Ser Gly Leu Phe Gln Ala Gln Thr Glu
545                 550                 555                 560

Met Asp Lys Ala Asp Lys Met Glu Ala Lys Thr Asn Lys Glu Lys
                565                 570                 575


<210> SEQ ID NO 2
<211> LENGTH: 1728
<212> TYPE: DNA
<213> ORGANISM: Phaeodactylum tricornutum

<400> SEQUENCE: 2

atgagaccat atccgacgat tgccttgatt tcggtttttc tttcggcggc gactcgtatt      60

tcggccactt cctctcatca agcaagtgca cttcctgtca aaaagggaac gcatgtcccg     120

gactctccga agttgtcaaa gctatatatc atggccaaaa ccaagagtgt atcctcgtcc     180

ttcgaccccc ctcggggagg cagtactgtt gcgccaacta caccgttggc aaccggcggt     240

gcgctccgca aagtgcgaca agccgtcttt cccatctacg gaaaccaaga agtcaccaaa     300

tttctgctca tcggatccat taaattcttt ataatcttgg cactcacgct cacgcgtgat     360
```

```
accaaggaca cgttgattgt cacgcaatgt ggtgccgaag cgattgcctt tctcaaaata    420
tacggggtgc tacccgcagc gaccgcattt atcgcgctct attccaaaat gtccaacgcc    480
atgggcaaaa aaatgctatt ttattccact tgcattcctt tctttacctt tttcgggctg    540
tttgatgttt tcatttaccc gaacgcggag cgactgcacc ctagtttgga agccgtgcag    600
gcaattctcc cgggcggtgc cgcatctggc ggcatggcgg ttctggccaa gattgcgaca    660
cactggacat ccgccttatt ttacgtcatg gcggaaatat attcttccgt atcggtgggg    720
ctattgtttt ggcagtttgc gaacgacgtc gtcaacgtgg atcaggccaa gcgcttttat    780
ccattatttg ctcaaatgag tggcctcgct ccagttttag cgggccagta tgtggtacgg    840
tttgccagca aagcggtcaa ctttgaggca tccatgcatc gactcacggc ggccgtaaca    900
tttgctggta ttatgatttg catcttttac caactcagtt cgtcatatgt ggagcgaacg    960
gaatcagcaa agccagcggc agataacgag cagtctatca aaccgaaaaa gaagaaaccc   1020
aaaatgtcca tggttgaatc ggggaaattt ctcgcgtcaa gtcagtacct gcgtctaatt   1080
gccatgctgg tgctgggata cggcctcagt attaacttta ccgaaatcat gtggaaaagc   1140
ttggtgaaga aacaatatcc agacccgcta gattatcaac gatttatggg taacttctcg   1200
tcagcggttg gtttgagcac atgcattgtt attttcttcg gtgtgcacgt gatccgtttg   1260
ttggggtgga aagtcggagc gttggctaca cctgggatca tggccattct agcgttaccc   1320
ttttttgctt gcattttgtt gggtttggat agtccagcac gattggagat cgccgtaatc   1380
tttggaacaa ttcagagttt gctgagcaaa acctccaagt atgccctttt cgaccctacc   1440
acacaaatgg cttatattcc tctggacgac gaatcaaagg tcaaaggaaa agcggcaatt   1500
gatgttttgg gatcgcggat tggaaagagt ggaggctcac tgatccagca gggcttggtc   1560
tttgtttttg gaaatatcat taatgccgca cctgtagtag ggttgtctaa ctacagtgtc   1620
cttgttgcgt ggatgagcgc agctggccga ctaagtgggc tttttcaagc acaaacagaa   1680
atggataagg ccgacaaaat ggaggcaaag accaacaaag aaaagtag                1728
```

<210> SEQ ID NO 3
<211> LENGTH: 515
<212> TYPE: PRT
<213> ORGANISM: Protochlamydia amoebophila

<400> SEQUENCE: 3

```
Met Ser Gln Gln Glu Ser Glu Phe Gly Lys Leu Arg Ala Phe Phe Trp
1               5                   10                  15

Pro Ile His Gly His Glu Val Lys Lys Val Leu Pro Met Met Leu Met
            20                  25                  30

Leu Phe Leu Ile Cys Phe Asn Tyr Ser Ile Leu Arg Asn Val Lys Asp
        35                  40                  45

Ala Ile Val Val Thr Ala Lys Ala Ser Gly Ala Glu Val Ile Pro Phe
    50                  55                  60

Ile Lys Val Trp Val Leu Leu Pro Thr Ala Val Leu Phe Thr Leu Ile
65                  70                  75                  80

Phe Thr Lys Leu Ser Asn Arg Phe Ser Gln Glu Lys Val Phe Tyr Ile
                85                  90                  95

Val Ile Ser Thr Phe Leu Leu Phe Phe Gly Ser Phe Thr Tyr Ile Phe
            100                 105                 110

Tyr Pro Leu Arg Asp Val Leu His Pro His Gln Leu Cys Asp Tyr Leu
        115                 120                 125
```

-continued

```
Glu Thr Ile Leu Pro Ala Gly Phe Lys Gly Leu Ile Ala Met Phe Arg
    130                 135                 140

Asn Trp Ser Phe Thr Leu Phe Tyr Val Ile Cys Glu Leu Trp Gly Ser
145                 150                 155                 160

Ile Val Leu Thr Val Leu Phe Trp Gly Phe Ala Asn Glu Ile Thr Lys
                165                 170                 175

Met Thr Glu Ala Arg Arg Phe Tyr Ser Met Leu Gly Val Ile Ala Ser
            180                 185                 190

Phe Ala Ala Thr Ile Ala Gly Ile Ile Ala Asn Leu Leu Ser Asn Asp
        195                 200                 205

Gln Ser Trp Glu Gln Thr Leu Asn Ile Leu Met Val Ala Val Ile Val
    210                 215                 220

Ser Gly Thr Ile Ala Met Val Ile Phe Arg Trp Met Asn Lys Asn Val
225                 230                 235                 240

Asn Gly Pro Glu Phe Gln Glu Phe His Glu Ala Lys Arg Ile Gln Lys
                245                 250                 255

Met Lys Lys Arg Leu Ser Ile Arg Glu Ser Phe Thr Tyr Leu Ala Asn
            260                 265                 270

Ser Lys Tyr Leu Ile Cys Ile Ala Val Leu Val Ile Ser Tyr Asn Leu
        275                 280                 285

Val Ile Asn Leu Val Glu Ile Val Trp Lys Asp Gln Leu Arg Gln Leu
    290                 295                 300

Tyr Ser Ser Ala Leu Asp Tyr Asn Arg Tyr Met Asn Asn Met Thr Ser
305                 310                 315                 320

Ala Val Gly Ile Ile Ala Thr Ile Thr Ser Leu Phe Met Ser Thr Met
                325                 330                 335

Ile Thr Arg Phe Gly Trp Thr Arg Thr Ala Leu Val Thr Pro Thr Ile
            340                 345                 350

Met Leu Val Thr Ser Val Gly Phe Phe Ala Phe Met Leu Phe Arg Asn
        355                 360                 365

Asp Leu Ala Asp Pro Val Tyr Ile Leu Thr Gly Thr Thr Pro Leu Thr
    370                 375                 380

Ile Ala Val Phe Phe Gly Ala Ala Gln Val Cys Met Ser Lys Ala Cys
385                 390                 395                 400

Lys Tyr Ser Val Phe Asp Ser Thr Lys Glu Met Ala Phe Ile Pro Leu
                405                 410                 415

Asp Tyr Glu Ser Lys Leu Lys Gly Lys Ala Ala Ile Asp Gly Val Gly
            420                 425                 430

Ser Arg Leu Gly Lys Ser Gly Gly Ser Leu Ile His Gln Ser Leu Leu
        435                 440                 445

Met Ile Phe Ala Thr Val Ser Ser Ser Ala Pro Tyr Val Ala Val Ile
    450                 455                 460

Leu Ile Gly Val Ile Ile Val Trp Met Leu Cys Val Arg Ser Leu Gly
465                 470                 475                 480

Lys Gln Phe Ala Ala Ile Ile Gly Glu Lys Ala Arg Glu Asp Ile Gly
                485                 490                 495

Glu Ser Thr Pro Arg Thr Ser Glu Glu Gln Val Leu His Pro Leu Lys
            500                 505                 510

Ala Ala Ser
        515
```

-continued

<210> SEQ ID NO 4
<211> LENGTH: 1551
<212> TYPE: DNA
<213> ORGANISM: Protochlamydia amoebophila

<400> SEQUENCE: 4
atgtctcaac aagaatcaga gtttggtaaa ttgagggcat ttttttggcc tattcacggc 60
catgaagtca aaaaagtgct gccgatgatg ttgatgctat ttttgatttg tttcaactat 120
agtattttac gcaatgttaa agatgctatt gttgtgactg ctaaggcttc aggggctgaa 180
gttattccat ttattaaagt atgggtgctg ttacccacgg cagtcttatt tactttaatt 240
tttactaagt tgtctaaccg ttttagccaa gaaaaagttt tttatattgt catttctaca 300
tttttgctat tttttggttc gtttacttat attttttatc ctttacgtga cgtactacat 360
cctcatcaac tatgcgatta cttagaaacg attttaccag cgggatttaa aggattaatt 420
gccatgttcc gtaattggtc atttactttg ttttatgtaa tttgtgaact ttggggcagt 480
attgttttaa ctgtcctttt ttggggattt gcgaatgaaa tcacaaaaat gactgaagct 540
cgtcgttttt atagtatgct tggtgtcatt gcaagttttg ccgcgacgat agcaggaatc 600
atagccaatc ttctttctaa tgatcaaagt tgggaacaga ctttaaatat tctcatggtt 660
gctgtaattg taagtggaac gatagccatg gttatttttc gttggatgaa taaaaatgta 720
ctcaatggcc cagaattcca agaattccat gaagcaaaac gcattcaaaa aatgaaaaaa 780
agattatcga tccgagaaag ttttacctat ctcgctaatt ctaaatatct tatttgtatt 840
gcagttttag ttatttctta taatcttgtc attaacttag ttgaaattgt atggaaagac 900
cagcttcgcc aactttattc gtcagccctt gattataatc gctatatgaa taacatgaca 960
tcagcagtcg gaattattgc cacaatcaca tccttattta tgtctacaat gattactcgg 1020
tttggatgga cacggacagc tctagtaaca ccgactatta tgcttgtcac aagtgtggga 1080
ttttttgctt ttatgctatt tcgaaatgat ttggctgatc ctgtttatat attaacagga 1140
acgacacctt taactatagc cgtctttttt ggtgcagctc aagtctgcat gagtaaagcc 1200
tgtaagtatt ctgtttttga ttctacaaaa gaaatggctt ttatccctct ggattatgaa 1260
agtaaattga aaggaaaagc tgcgattgat ggtgtgggtt ctcgtcttgg taaatcgggc 1320
ggttccttaa ttcatcaaag tttattgatg atttttgcaa ctgttagctc cagcgctcct 1380
tatgtagctg tgatcttaat tggcgttatc attgtttgga tgctctgcgt acgttcatta 1440
ggtaagcaat ttgctgctat tattggggaa aaggctcgag aagatattgg tgaatctact 1500
ccaagaacga gtgaagagca agttttacat cccttaaaag ctgcatctta a 1551

<210> SEQ ID NO 5
<211> LENGTH: 536
<212> TYPE: PRT
<213> ORGANISM: Protochlamydia amoebophila

<400> SEQUENCE: 5

Met Ser Gln Thr Pro Thr Gly Ser Arg Glu Phe Ser Pro Trp Arg Ser
1 5 10 15

Asn Leu Trp Pro Val His Arg Tyr Glu Leu Lys Lys Leu Ile Pro Met
20 25 30

Leu Leu Ile Phe Phe Phe Ile Ser Phe Asp Tyr Asn Ile Leu Arg Thr
35 40 45

Leu Lys Asp Ser Leu Leu Ile Thr Ala Lys Ser Ser Gly Ala Glu Val
50 55 60

-continued

```
Ile Pro Phe Val Lys Val Trp Ala Met Phe Pro Gly Ala Ile Leu Met
65                  70                  75                  80

Thr Leu Leu Phe Thr Trp Leu Ser Asn Arg Leu Ser Arg Glu Ile Val
                85                  90                  95

Phe Tyr Leu Ile Thr Ser Leu Phe Leu Ser Tyr Phe Phe Ile Phe Thr
            100                 105                 110

Phe Ile Leu Tyr Pro Ile Arg Asp Ile Ile His Pro His Ala Thr Ala
        115                 120                 125

Asp Tyr Leu Glu Thr Ile Leu Pro Ile Gly Phe Lys Gly Leu Val Ala
    130                 135                 140

Met Phe Arg Tyr Trp Thr Phe Thr Ile Phe Tyr Val Met Ser Glu Leu
145                 150                 155                 160

Trp Gly Ser Thr Val Leu Phe Val Leu Phe Trp Gly Phe Ala Asn Gln
                165                 170                 175

Val Thr Lys Ile Ser Glu Ala Lys Arg Phe Tyr Gly Leu Phe Gly Val
            180                 185                 190

Gly Ala Asn Leu Ser Gly Ile Phe Ala Gly Gln Ala Ser Val Tyr Cys
        195                 200                 205

Cys Gln Phe Asn Lys Gln Asn Asp Leu Gly Ile Leu Gly Ser Asp Pro
    210                 215                 220

Trp Tyr Gln Ser Leu Val Met Met Val Ser Leu Ile Leu Leu Ser Gly
225                 230                 235                 240

Ala Leu Val Leu Ala Leu Phe Arg Trp Met Asn Val Glu Val Leu Thr
                245                 250                 255

Asp Lys Arg Phe Tyr Asp Pro Ser Ser Val Lys Thr Glu Gly Glu Ala
            260                 265                 270

Lys Gly Lys Leu Ser Leu Lys Gln Ser Phe Ser Tyr Leu Leu Arg Ser
        275                 280                 285

Asn Tyr Leu Leu Cys Ile Ala Leu Ile Val Ile Ser Tyr Asn Leu Val
    290                 295                 300

Ile Asn Leu Thr Glu Val Leu Trp Lys His Gln Val Arg Glu Leu Tyr
305                 310                 315                 320

Pro Asp Pro Asn Asp Tyr Thr Leu Tyr Met Asn His Ile Val Ser Ile
                325                 330                 335

Ile Gly Val Val Ala Thr Leu Ser Ser Leu Phe Val Ser Gly Asn Ala
            340                 345                 350

Ile Arg Lys Phe Gly Trp Thr Thr Thr Ala Leu Ile Thr Pro Ile Ile
        355                 360                 365

Leu Ala Val Thr Ser Leu Gly Phe Phe Ser Phe Phe Phe Leu Lys Lys
    370                 375                 380

Ala Ser Pro Glu Ile Phe Leu Ser Phe Ser Gly Val Thr Pro Leu Val
385                 390                 395                 400

Leu Val Val Phe Phe Gly Thr Ala Gln Asn Ile Leu Ser Arg Gly Ala
                405                 410                 415

Lys Tyr Ser Val Phe Asp Ala Thr Lys Glu Met Ser Phe Val Pro Leu
            420                 425                 430

Asn Pro Glu Ser Lys Leu Val Gly Lys Ala Ala Ile Asp Gly Val Cys
        435                 440                 445

Ser Arg Leu Gly Lys Ser Gly Gly Ser Val Val His Gln Ser Leu Leu
    450                 455                 460

Leu Leu Phe Ser Thr Ile Asn Ala Ser Ala Pro Tyr Val Ala Ile Val
465                 470                 475                 480
```

```
Leu Phe Ala Val Ile Leu Val Trp Ala Met Ala Ile Arg Val Leu Gly
                485                 490                 495

Lys Gln Phe Asn Glu Leu Thr Ser Gln Val Glu Asn Asn Glu Thr Ser
            500                 505                 510

Gly Thr Leu Met Thr Pro Ile Arg Ala Val Asn Ile Leu Ser Asp Thr
        515                 520                 525

Ile Leu Lys Glu Gln Lys Ala Val
    530                 535
```

<210> SEQ ID NO 6
<211> LENGTH: 1611
<212> TYPE: DNA
<213> ORGANISM: Protochlamydia amoebophila

<400> SEQUENCE: 6

```
atgtcacaga caccaacagg gtcccgtgaa tttagtccat ggcggagcaa tctttggccc     60

gttcatcgct atgagcttaa aaaactcatc ccaatgttgt taatattctt ttttatttct    120

tttgattaca acatattacg tactttaaaa gactcactac ttataactgc aaaatcttca    180

ggtgctgagg tcattccttt tgtaaaggtt tgggctatgt tccctggagc tattttaatg    240

accctttgt tcacttggtt gtctaatcgc ctgtcaagag aaatcgtttt ttaccttatc    300

acttctcttt ttttatctta ttttttatt ttcactttta ttctctatcc tattcgagat    360

attatccatc ctcacgcaac tgctgactat cttgaaacaa ttttaccgat tggatttaaa    420

gggctagttg cgatgtttcg ttactggact tttactattt tctatgtgat gtcagaactt    480

tggggaagta ctgttttatt tgtcttattt tggggttttg ctaatcaagt gactaaaatt    540

agtgaggcaa aaagatttta cggtctgttt ggggtaggtg ctaatctttc gggtattttc    600

gcaggacaag cttctgtgta ctgttgtcaa tttaataagc agaacgattt gggaatcctt    660

ggtagtgatc catggtatca atcattagtg atgatggttt ctttaatttt attatcgggt    720

gctttagttt tagctttatt tcgttggatg aatgtagaag tcttaaccga taaacgtttt    780

tatgatcctt cttcggttaa aacagaagga gaagctaaag gtaagctttc tctaaagcaa    840

agcttttcct atcttcttcg ctctaattac ttactttgta ttgctcttat tgttatttct    900

tataacctag ttattaacct cacagaagtt ttatggaaac atcaagtccg agagctatat    960

cctgatccta atgattatac tttatatatg aatcatatcg tatccattat tggggtagta   1020

gcgaccttaa gttccctttt cgtatcagga aatgcgattc gcaaatttgg gtggaccact   1080

actgctttaa ttacacctat cattttagct gtaacaagtt tgggcttttt ctcctttttc   1140

ttccttaaaa aggcatctcc cgaaatttc ttatcttttt ccggagtaac tcctttggtt   1200

ttagtggttt tctttggaac tgctcaaaac atattgagtc gaggagctaa atactctgta   1260

tttgatgcca ctaaagaaat gagttttgtt cctttaaatc ctgaatccaa actcgttgga   1320

aaagcggcga ttgatggagt ttgttctcgc ctcggaaaat cgggtggatc tgtggttcat   1380

cagagccttc tacttttgtt ttctacaatt aatgcaagtg cccttatgt agctatcgtc   1440

ttgttcgccg taattctagt ctgggcaatg gcaattcgcg ttttaggtaa acaatttaat   1500

gaattgacaa gtcaggtaga aaacaatgaa acttctggga cattgatgac tcctattcga   1560

gctgttaata ttctttcaga cacaattttg aaagaacaga aagctgtata a           1611
```

<210> SEQ ID NO 7
<211> LENGTH: 489
<212> TYPE: PRT
<213> ORGANISM: Protochlamydia amoebophila

<400> SEQUENCE: 7

```
Met Lys Asn Gln Gln Asn Ser Val Ser Ser Thr Leu Leu Ile Leu Lys
1               5                   10                  15

Lys Arg Ser Leu Ile Leu Phe Gln Phe Phe Leu Ile Ile Ile Val Tyr
            20                  25                  30

His Thr Leu Lys Asp Leu Lys Asp Thr Ile Val Ile Thr Ala Ser Asp
        35                  40                  45

Ala Gly Ala Glu Ile Ile Pro Phe Ile Lys Ile Trp Gly Met Leu Pro
    50                  55                  60

Leu Ala Ile Cys Ala Ser Tyr Phe Phe Ala Lys Phe Tyr Asn Lys Phe
65                  70                  75                  80

Gly Arg Glu Lys Thr Phe Tyr Ile Phe Ser Ser Phe Leu Leu Val Asn
                85                  90                  95

Tyr Leu Phe Phe Ala Phe Val Leu Tyr Pro Phe Arg Lys Phe Phe Tyr
            100                 105                 110

Leu Glu Asn Val Ala Asp Tyr Leu His Met Ile Leu Pro Val Gly Ala
        115                 120                 125

Lys Gly Phe Val Ala Met Val Ser Tyr Trp His Tyr Thr Leu Phe Tyr
    130                 135                 140

Leu Thr Ala Glu Leu Trp Ser Met Leu Ile Leu Ser Ile Leu Phe Trp
145                 150                 155                 160

Gly Tyr Val Ser Asp Thr Thr Ser Leu Val Glu Ala Lys Lys Phe Tyr
                165                 170                 175

Pro Leu Cys Met Phe Val Gly Asn Met Ala Gly Ile Ile Ser Gly Gln
            180                 185                 190

Leu Ser His Phe Leu Cys Gln His Leu Ser Asp Phe Met Ser Trp Glu
        195                 200                 205

Arg Thr Leu Gln Trp Met Ile Gly Ile Val Cys Val Cys Gly Leu Leu
    210                 215                 220

Ile Met Ile Ile Asn Arg Arg Leu Ala Leu Thr Thr Asp Phe Ser Ala
225                 230                 235                 240

Ile Lys Gln Lys Val Lys Lys Gln Ile Ala Pro Ser Ser Phe Lys Asp
                245                 250                 255

Asn Val Met Asp Val Leu Arg Thr Gly Pro Leu Leu Cys Ile Ala Val
            260                 265                 270

Leu Val Val Gly Phe Gly Leu Thr Thr Asn Leu Ile Glu Val Ile Trp
        275                 280                 285

Lys Glu Asn Ile Arg Gln Leu His Pro Thr Pro Gln Ala Tyr Asn Ala
    290                 295                 300

Tyr Ile Asn Gln Leu Thr Ser Leu Ile Gly Thr Gly Ala Val Cys Ile
305                 310                 315                 320

Ala Leu Leu Ser Ser Trp Ile Phe Arg Lys Phe Thr Trp Thr Gln Ile
                325                 330                 335

Ala Leu Thr Thr Pro Leu Cys Leu Leu Ile Thr Ser Ser Ala Phe Phe
            340                 345                 350

Ser Ser Leu Leu Met Pro Lys Glu Leu Leu Ala Glu Ile Ala Ser Phe
        355                 360                 365

Phe Gln Phe Ser Pro Thr Gln Leu Ile Val Thr Leu Gly Ser Ile Cys
    370                 375                 380

Tyr Val Phe Ser Met Ser Ala Lys Tyr Thr Ile Phe Asp Thr Ser Lys
385                 390                 395                 400

Glu Ile Ala Phe Leu Ser Ile Glu Thr Glu Lys Arg Thr Tyr Ala Lys
                405                 410                 415
```

-continued

```
Ser Val Ile Asp Ser Ile Gly Ser Arg Leu Gly Lys Ser Gly Ala Ser
            420                 425                 430

Cys Phe Tyr Gln Phe Leu Leu Ile Ala Phe Gly Ile Ala Ser Glu His
        435                 440                 445

Ile Leu Leu Ile Gly Val Val Ser Ile Ile Met Ile Gly Ile Ser Ile
    450                 455                 460

Phe Ala Thr Lys Lys Leu Gly Gly Gln Leu Ser Gly Lys Asn Glu Asn
465                 470                 475                 480

His Arg Phe Ile Glu Ala Ser His Gly
                485
```

<210> SEQ ID NO 8
<211> LENGTH: 1470
<212> TYPE: DNA
<213> ORGANISM: Protochlamydia amoebophila

<400> SEQUENCE: 8

```
atgaaaaatc aacaaaattc tgtatcttct accttactaa tcttaaaaaa gcgtagcttg      60

atcctatttc aatttttttct aattatcatt gtttatcata cattaaaaga cctcaaagat    120

acgattgtta tcacagcaag tgatgcaggt gcagagatca ttccttttat taaaatttgg    180

ggaatgcttc ctcttgccat ttgtgctagt tatttttttg ctaaatttta taataaattt    240

ggaagagaaa aaacatttta tatttttagc tctttcttac tagttaacta tcttttcttt    300

gcttttgtat tatatccatt ccgcaagttt ttttatttag aaaatgttgc agattattta    360

catatgattt tacctgttgg agcgaaaggg tttgttgcca tggtaagcta ttggcattac    420

actctatttt atttaacggc agaattatgg tcgatgctca ttctatctat cctttttttgg    480

ggttatgtga gtgatacgac ttctttagta gaagccaaaa aattttaccc cctctgtatg    540

ttcgttggaa atatggcagg aattatttct ggtcagctct ctcatttctt atgtcaacat    600

ttgtctgatt tcatgtcatg ggaaagaacc ctgcaatgga tgattggtat tgtctgtgtt    660

tgcggccttt taattatgat tattaataga cggctggctc ttacaactga tttttcggca    720

attaaacaaa aagtaaaaaa acaaatagct ccctcttctt tcaaagataa tgttatggat    780

gttttaagaa caggtccctt actttgtata gctgtattgg tagtggggtt tggactgaca    840

acgaatctaa ttgaagttat ttggaaagaa aatattaggc aactacaccc gacacctcaa    900

gcctacaatg cttatattaa tcaattgact tctttaattg ggactggtgc tgtttgtata    960

gccttgttat caagctggat ttttagaaag tttacttgga cgcaaattgc cctcacaacc   1020

cctttatgtt tattaatcac aagctctgct ttttttttcat cgcttcttat gcctaaagag   1080

ctgttagcgg aaattgcttc tttttttcag ttttccccaa ctcaattgat agtgacacta   1140

ggatctattt gctatgtttt tagcatgtct gcgaagtaca caatttttga tactagtaaa   1200

gaaatagctt ttctttctat tgaaacagaa aaaagaacgt atgctaaatc tgtaattgat   1260

agcattggct ctcgtttggg aaaatctggc gcttcttgtt tttatcaatt tcttcttatt   1320

gcctttggaa ttgcttccga acatatttta ttaattggag ttgtatccat tataatgatt   1380

ggaatttcga tttttgctac gaaaaaattg ggtgggcagc tgtctggtaa aaatgaaaac   1440

catcgcttta tagaagcttc ccatggataa                                    1470
```

<210> SEQ ID NO 9
<211> LENGTH: 632
<212> TYPE: PRT
<213> ORGANISM: Thalassiosira pseudonana

<400> SEQUENCE: 9

Met Lys Thr Ser Cys Thr Ile Gln Arg Arg Val Lys Ser Ile Ser Ser
1 5 10 15

Lys His Ser Ile Ile Asp Thr His His Ser Thr Ser Arg Arg Leu Ser
20 25 30

Val Ile Leu Leu Phe Phe Leu Leu His Ser Ser Ala Glu Met Leu Phe
35 40 45

Ala Ser Ala Thr Gly Asn His Asn Ala Asn Thr Ser Pro Pro Pro Ala
50 55 60

Asn Ile Pro Met Ile Ser Thr Asn Asn Lys Ser Cys Met Met Arg Arg
65 70 75 80

Thr Arg Ser Gln Ser Arg Arg Asp Ser Ser Arg Ser Pro Asp Ser Val
85 90 95

Ala Ser Ala Asn Val Val Gly Arg Gly Gly Asp Gly Gly Thr Ile Met
100 105 110

Gly Ala Lys Ser Val Phe Gln Thr Ala Ser Lys Ala Leu Pro Pro Asn
115 120 125

Thr Val Ser Ser Thr Ala Ser Gly Ser Val Ser Lys Ala Ser Arg Leu
130 135 140

Arg Thr Val Leu Phe Pro Ile Gln Asn Asp Glu Met Lys Lys Phe Leu
145 150 155 160

Leu Ile Gly Ser Ile Lys Phe Phe Val Ile Leu Ala Leu Thr Leu Thr
165 170 175

Arg Asp Asn Lys Asp Thr Met Val Val Thr Glu Cys Gly Ala Glu Ala
180 185 190

Ile Ala Phe Leu Lys Ile Tyr Gly Val Leu Pro Ser Ala Thr Leu Phe
195 200 205

Ile Ala Leu Tyr Ser Lys Met Ala Thr Ile Phe Asp Lys Lys Thr Leu
210 215 220

Phe Tyr Ala Thr Cys Ile Pro Phe Phe Ala Phe Phe Phe Leu Phe Asp
225 230 235 240

Ala Ile Ile Tyr Pro Asn Arg Asn Val Ile Gln Pro Ser Leu Glu Ser
245 250 255

Val Gln Arg Val Met Arg Ile Thr Ala Asp Ser Ser Gly Ala Met Ser
260 265 270

Ile Phe Ala Lys Leu Phe Ala Asn Trp Thr Ser Ala Leu Phe Tyr Ile
275 280 285

Val Ala Glu Val Tyr Ser Ser Val Ser Val Gly Ile Leu Phe Trp Gln
290 295 300

Tyr Ala Asn Asp Val Val Ser Val Ser Gln Ala Lys Arg Phe Tyr Pro
305 310 315 320

Leu Phe Ala Gln Met Ser Gly Leu Ala Pro Ile Val Ala Gly Gln Tyr
325 330 335

Val Val Arg Tyr Ala Ser Arg Ala Asn Asp Phe Glu Glu Ser Leu His
340 345 350

Arg Leu Thr Trp Met Val Ser Phe Ser Gly Val Met Ile Cys Leu Phe
355 360 365

Tyr Lys Trp Ser Asn Glu Tyr Asn Asp Gln Thr Ser Gly Gly Leu Asn
370 375 380

Gly Gly Ile Glu Asp Gly Val Lys Glu Thr Lys Val Val Lys Lys Lys
385 390 395 400

Lys Ala Lys Met Ser Met Arg Asp Ser Ala Lys Phe Leu Ala Ser Ser
405 410 415

```
Glu Tyr Leu Arg Leu Ile Ala Ala Leu Val Val Gly Tyr Gly Leu Ser
            420                 425                 430

Ile Asn Phe Thr Asp Ile Met Trp Lys Ser Ile Val Lys Arg Gln Tyr
        435                 440                 445

Pro Asp Pro Leu Asp Tyr Gln Arg Phe Met Gly Asn Phe Ser Ser Val
    450                 455                 460

Val Gly Leu Ser Thr Cys Ile Val Ile Phe Leu Gly Val His Ala Ile
465                 470                 475                 480

Arg Ile Leu Gly Trp Arg Met Gly Ala Leu Ala Thr Pro Ala Val Met
                485                 490                 495

Ala Ile Leu Ala Phe Pro Tyr Phe Ser Ser Ile Leu Val Gly Leu Asp
            500                 505                 510

Ser Pro Gly Ser Leu Arg Ile Ala Val Ile Phe Gly Thr Ile Gln Cys
        515                 520                 525

Leu Leu Ser Lys Thr Ala Lys Tyr Ala Leu Phe Asp Pro Thr Thr Gln
    530                 535                 540

Met Ala Tyr Ile Pro Leu Asp Asp Glu Ser Lys Ile Lys Gly Lys Ala
545                 550                 555                 560

Ala Ile Glu Val Leu Gly Ser Arg Ile Gly Lys Ser Gly Gly Ser Leu
                565                 570                 575

Ile Gln Gln Gly Leu Val Leu Val Phe Gly Asn Ile Ile Asn Ala Ala
            580                 585                 590

Pro Ala Leu Val Val Leu Tyr Tyr Ser Val Leu Ala Trp Trp Val Tyr
        595                 600                 605

Ser Ala Asn Arg Leu Gly Ser Leu Phe Leu Ala Lys Thr Ala Met Gln
    610                 615                 620

Glu Glu Thr Lys Glu His Gln Lys
625                 630


<210> SEQ ID NO 10
<211> LENGTH: 1899
<212> TYPE: DNA
<213> ORGANISM: Thalassiosira pseudonana

<400> SEQUENCE: 10

atgaaaacat cttgtacaat ccaacgtcgt gtcaaatcca tctcatccaa acacagtatc      60

atcgacacac accactctac ttctcgccgt ttaagtgtca tcctactctt ctttctacta     120

cactcctcgg cagagatgct atttgcttcc gccacgggca atcacaacgc caatacatca     180

ccaccacctg cgaatattcc catgattagc actaacaaca aatcatgtat gatgcgacga     240

accaggagtc aatcacgacg agatagcagc cgttcgcctg attcggtggc ctcggccaat     300

gttgttggga ggggcggcga tgggggtacc attatgggtg ccaagagtgt cttccagact     360

gcttcgaaag cattacctcc caacactgtg tcgtccacag caagcggcag tgtatccaaa     420

gcatcgcgcc tacgaacggt cctcttcccc attcaaaatg acgagatgaa gaagtttctc     480

ttgattggaa gtatcaagtt ctttgtaatt ctagcgttga cactcacgag agataataag     540

gatacaatgg tggttaccga gtgtggagct gaggccatcg cttttctaaa gatctacgga     600

gtactaccat ccgccacact cttcatagca ctctactcga aaatggccac tatctttgac     660

aaaaagacct tattctacgc cacgtgcatt ccattctttg cattcttctt cttattcgat     720

gcaatcatct atcctaaccg gaatgtcatt cagccttcct tagagagtgt tcagcgtgtc     780

atgagaatca cagccgattc atcgggtgcc atgtccatct ttgcaaagtt gttcgccaat     840

tggacgtcgg ccttgtttta tattgtagca gaggtatact cgtctgtttc agtggggata     900
```

-continued

```
ttgttctggc agtatgccaa tgatgtggtg tctgtctcgc aagcaaaacg attttaccca    960

ctctttgcac agatgagtgg acttgccccc attgtggctg gacagtatgt ggtacgatat   1020

gctagtagag ccaatgactt tgaagaatca ttgcataggt tgacgtggat ggtatccttt   1080

tcgggagtga tgatttgtct gttttacaag tggagcaatg agtacaatga tcagacgtct   1140

ggagggttaa atgggggaat tgaggatgga gtaaaagaga cgaaggtggt gaagaaaaag   1200

aaagccaaaa tgtcaatgag ggattcagcc aagtttttgg cttcatccga gtatttgaga   1260

ctgattgctg ctttggttgt gggatatggt ctgtcgatca actttacaga tataatgtgg   1320

aaatcaatcg tcaagagaca atatcccgat cctctcgact atcaacgttt catggggaac   1380

ttttcatcag tagttggatt gtctacgtgc atcgttatct ttctcggtgt acatgctatt   1440

cgtatactag gctggcgaat gggtgcccta gcgactccag ccgtcatggc aatcttggca   1500

ttcccttact tctcgagcat tctcgttggg ttggacagtc caggtagttt acgaattgca   1560

gtgatctttg gtactattca atgcctgctt agtaagacag caaagtatgc cctgttcgat   1620

ccgacaactc aaatggccta cattcctttg gatgacgaat caaagatcaa gggaaaggca   1680

gcaatagaag tacttggttc tcggattgga aaaagtggtg gttcgttgat acaacaaggt   1740

cttgtgttgg tgtttgggaa cattatcaat gctgctcccg cgttggttgt tctttactac   1800

tcagtgttgg cgtggtgggt gtactcagca aatcggctcg gatcattgtt cttggcaaag   1860

acagctatgc aagaggaaac aaaagagcac cagaagtag                          1899
```

<210> SEQ ID NO 11
<211> LENGTH: 517
<212> TYPE: PRT
<213> ORGANISM: Simkania negevensis

<400> SEQUENCE: 11

```
Met Ser Ser Thr Glu Tyr Glu Lys Ser Thr Trp Thr Gln Lys Ile Trp
1               5                   10                  15

Pro Ile Arg Arg Phe Glu Leu Lys Lys Val Leu Pro Leu Leu Ile Leu
            20                  25                  30

Lys Phe Leu Val Ser Met Val Tyr Ala Thr Leu Thr Leu Ile Lys Asp
        35                  40                  45

Pro Leu Val Val Thr Ala Lys His Ser Gly Ala Glu Val Ile Pro Val
    50                  55                  60

Leu Lys Gly Trp Ile Val Phe Pro Leu Ser Ile Leu Cys Ala Ile Gly
65                  70                  75                  80

Tyr Ser Lys Leu Ser Asn His Phe Lys Arg Ser Thr Leu Phe Tyr Gly
                85                  90                  95

Ile Ile Thr Ala Phe Leu Ala Ile Val Leu Ile Tyr Gly Phe Val Leu
            100                 105                 110

Tyr Pro Asn Met Gly Ile Leu Thr Pro Ser Asp Ser Ala Asn Leu Leu
        115                 120                 125

Thr Ala Lys Phe Gly Glu Lys Tyr Thr His Trp Ile Ala Val Tyr Arg
    130                 135                 140

Asn Trp Ile His Ser Leu Phe Phe Val Thr Thr Glu Leu Trp Gly Gln
145                 150                 155                 160

Val Val Ile Phe Leu Leu Tyr Trp Gly Phe Ala Asn His Ile Cys Gln
                165                 170                 175

Val Lys Glu Ala Lys Arg Ser Tyr Thr Leu Phe Ile Ala Ala Gly Asp
            180                 185                 190
```

```
Leu Ala Thr Ile Leu Ala Gly Pro Leu Thr Tyr Tyr Tyr Gly Lys Lys
        195                 200                 205

Phe Leu Gly Gln Ser Tyr Ala Leu Thr Leu Gln Ser Leu Leu Gly Tyr
    210                 215                 220

Val Leu Val Cys Gly Leu Leu Ile Met Ala Val Tyr Trp Trp Met Asn
225                 230                 235                 240

Arg Tyr Val Leu Thr Asp Lys Arg Tyr Tyr Asp Pro Ser Val Thr Lys
                245                 250                 255

Gln Thr Val Asn Gln Lys Thr Lys Leu Ser Leu Arg Asp Ser Ile Arg
            260                 265                 270

His Ile Phe Ser Ser Lys Tyr Leu Leu Ala Ile Ala Val Leu Val Val
        275                 280                 285

Gly Cys Ala Leu Thr Ile Asn Met Val Glu Val Thr Trp Lys Ala His
    290                 295                 300

Leu Lys Met Gln Tyr Pro Thr Thr Ala Asp Tyr Gln Met Phe Met Gly
305                 310                 315                 320

Arg Val Thr Thr Ile Val Gly Val Val Ala Leu Ile Thr Val Phe Phe
                325                 330                 335

Leu Gly Gly Asn Phe Leu Arg Arg Phe Gly Trp His Phe Ser Ala Gln
            340                 345                 350

Ile Thr Pro Trp Ala Ile Gly Ile Thr Gly Gly Val Phe Phe Leu Leu
        355                 360                 365

Cys Leu Leu Lys Pro Tyr Leu Gly Ser Phe Ala His Tyr Val Gly Leu
    370                 375                 380

Thr Pro Leu Met Met Ile Val Ile Phe Gly Ala Phe Gln Asn Ile Thr
385                 390                 395                 400

Ser Lys Val Val Lys Tyr Ser Phe Phe Asp Ser Thr Lys Glu Met Ala
                405                 410                 415

Tyr Ile Pro Leu Asp Pro Glu Ser Lys Val Lys Gly Lys Ala Ala Ile
            420                 425                 430

Asp Met Val Gly Ser Arg Leu Gly Lys Ser Ser Ser Ser Trp Leu Gln
        435                 440                 445

Ile Gly Leu Ile Glu Leu Val Gly Thr Gly Ser Val Ile Ser Ile Thr
    450                 455                 460

Pro Tyr Leu Leu Pro Ile Val Leu Gly Ala Ala Leu Tyr Trp Ser Tyr
465                 470                 475                 480

Ser Val Arg Tyr Leu Asn Lys Glu Leu Ser Val Arg Glu Glu Thr Leu
                485                 490                 495

Leu Glu Glu Glu Glu Ala Lys Lys Arg Ala Gly Glu Leu Gln Pro Glu
            500                 505                 510

Pro Glu Pro Ala Thr
        515
```

<210> SEQ ID NO 12
<211> LENGTH: 1554
<212> TYPE: DNA
<213> ORGANISM: Simkania negevensis

<400> SEQUENCE: 12

```
atgagtagta ccgaatatga gaagtccaca tggactcaaa aaatctggcc aataaggcgc      60

tttgaactta agaaagtcct tcctctttta atccttaaat ttctagtctc tatggtttat     120

gccactctca ccttaatcaa ggatcccctt gtggtgacgg caaaacattc tggagcagaa     180

gtcattccag ttctaaaagg ttggattgtt ttccccttat cgattctttg tgctattggt     240
```

-continued

```
tactcaaagt taagcaacca cttcaaacgt tccaccctct tttacggaat cattacagct    300

ttcctagcta ttgttcttat ctacggcttc gttttgtatc ccaatatggg aattctcaca    360

ccaagcgact ctgcaaactt gttaacagct aaatttgggg aaaaatacac acactggatt    420

gcagtttatc ggaattggat ccattctctc tttttcgtca ccacagagct ttgggggcaa    480

gttgtcattt tcctcctcta ctggggattt gccaaccaca tttgccaagt gaaagaagct    540

aaaagatctt acactctttt catcgctgca ggcgatttag caacgatctt ggctggtcca    600

cttacctatt actacggaaa aaagtttcta ggacaaagct atgctctcac tcttcaatcc    660

ctactaggat atgtcttagt ctgcgggcta ctcatcatgg cagtctattg gtggatgaat    720

cgatatgtcc taacagacaa acggtactac gatccatcag tgacgaagca aacagtcaac    780

caaaagacca aactctctct gcgtgatagt atccggcata tcttttcatc aaagtatctc    840

cttgctattg cggtcctcgt tgtcggttgc gctctcacca tcaacatggt agaagtcacc    900

tggaaagctc acttaaagat gcaataccca acaactgctg attaccaaat gttcatgggg    960

cgagtcacaa ctattgttgg agttgttgcc ctcatcactg tattcttctt aggaggaaac   1020

ttcctgagac ggtttggatg gcacttcagt gctcaaatca ccccatgggc gattggaatc   1080

acaggtggtg ttttcttttt actctgcctt ttgaagccct atctcgggtc tttcgctcat   1140

tatgttggac tcacccctct tatgatgatt gtcatctttg gagccttcca aaatatcact   1200

agtaaagtcg tcaaatactc gttctttgat tcgacgaaag aaatggctta tattccacta   1260

gaccctgaat ctaaagtgaa aggaaaagca gccatcgaca tggtcggttc aagattgggt   1320

aagtcgagct cctcctggct acaaattggc ttgattgaac tagttgggac tggttcggtg   1380

atctcaatca ctccttatct actgcctatc gttctaggtg ccgccctcta ttggagctac   1440

tctgtacgct acctcaataa agagctttct gtgcgtgaag aaacactcct cgaggaagaa   1500

gaagctaaga aaagagcggg agagcttcag cctgaacctg agcctgccac ttga         1554
```

<210> SEQ ID NO 13
<211> LENGTH: 517
<212> TYPE: PRT
<213> ORGANISM: Simkania negevensis

<400> SEQUENCE: 13

```
Met Ser Ser Thr Glu Tyr Glu Lys Ser Thr Trp Thr Gln Lys Ile Trp
1               5                   10                  15

Pro Ile Arg Arg Phe Glu Leu Lys Lys Val Leu Pro Leu Leu Ile Leu
            20                  25                  30

Lys Phe Leu Val Ser Met Val Tyr Ala Thr Leu Thr Leu Ile Lys Asp
        35                  40                  45

Pro Leu Val Val Thr Ala Lys His Ser Gly Ala Glu Val Ile Pro Val
    50                  55                  60

Leu Lys Gly Trp Ile Val Phe Pro Leu Ser Ile Leu Cys Ala Ile Gly
65                  70                  75                  80

Tyr Ser Lys Leu Ser Asn His Phe Lys Arg Ser Thr Leu Phe Tyr Gly
                85                  90                  95

Ile Ile Thr Ala Phe Leu Ala Ile Val Leu Ile Tyr Gly Phe Val Leu
            100                 105                 110

Tyr Pro Asn Met Gly Ile Leu Thr Pro Ser Asp Ser Ala Asn Leu Leu
        115                 120                 125

Thr Ala Lys Phe Gly Glu Lys Tyr Thr His Trp Ile Ala Val Tyr Arg
    130                 135                 140
```

-continued

```
Asn Trp Ile His Ser Leu Phe Phe Val Thr Thr Glu Leu Trp Gly Gln
145                 150                 155                 160

Val Val Ile Phe Leu Leu Tyr Trp Gly Phe Ala Asn His Ile Cys Gln
                165                 170                 175

Val Lys Glu Ala Lys Arg Ser Tyr Thr Leu Phe Ile Ala Ala Gly Asp
            180                 185                 190

Leu Ala Thr Ile Leu Ala Gly Pro Leu Thr Tyr Tyr Tyr Gly Lys Lys
        195                 200                 205

Phe Leu Gly Gln Ser Tyr Ala Leu Thr Leu Gln Ser Leu Leu Gly Tyr
    210                 215                 220

Val Leu Val Cys Gly Leu Leu Ile Met Ala Val Tyr Trp Trp Met Asn
225                 230                 235                 240

Arg Tyr Val Leu Thr Asp Lys Trp Tyr Tyr Asp Pro Ser Val Thr Lys
                245                 250                 255

Gln Thr Val Asn Gln Lys Thr Lys Leu Ser Leu Arg Asp Ser Ile Arg
            260                 265                 270

His Ile Phe Ser Ser Lys Tyr Leu Leu Ala Ile Ala Val Leu Val Val
        275                 280                 285

Gly Cys Ala Leu Thr Ile Asn Met Val Glu Val Thr Trp Lys Ala His
    290                 295                 300

Leu Lys Met Gln Tyr Pro Thr Thr Ala Asp Tyr Gln Met Phe Met Gly
305                 310                 315                 320

Arg Val Thr Thr Ile Val Gly Val Val Ala Leu Ile Thr Val Phe Phe
                325                 330                 335

Leu Gly Gly Asn Phe Leu Arg Arg Phe Gly Trp His Phe Ser Ala Gln
            340                 345                 350

Ile Thr Pro Trp Ala Ile Gly Ile Thr Gly Gly Val Phe Phe Leu Leu
        355                 360                 365

Cys Leu Leu Lys Pro Tyr Leu Gly Ser Phe Ala His Tyr Val Gly Leu
    370                 375                 380

Thr Pro Leu Met Met Ile Val Ile Phe Gly Ala Phe Gln Asn Ile Thr
385                 390                 395                 400

Ser Lys Val Val Lys Tyr Ser Phe Phe Asp Ser Thr Lys Glu Met Ala
                405                 410                 415

Tyr Ile Pro Leu Asp Pro Glu Ser Lys Val Lys Gly Lys Ala Ala Ile
            420                 425                 430

Asp Met Val Gly Ser Arg Leu Gly Lys Ser Ser Ser Ser Trp Leu Gln
        435                 440                 445

Ile Gly Leu Ile Glu Leu Val Gly Thr Gly Ser Val Ile Ser Ile Thr
    450                 455                 460

Pro Tyr Leu Leu Pro Ile Val Leu Gly Ala Ala Leu Tyr Trp Ser Tyr
465                 470                 475                 480

Ser Val Arg Tyr Leu Asn Lys Glu Leu Ser Val Arg Glu Glu Thr Leu
                485                 490                 495

Leu Glu Glu Glu Glu Ala Lys Lys Arg Ala Gly Glu Leu Gln Pro Glu
            500                 505                 510

Pro Glu Pro Ala Thr
        515
```

<210> SEQ ID NO 14
<211> LENGTH: 526
<212> TYPE: PRT
<213> ORGANISM: Simkania negevensis -continued

<400> SEQUENCE: 14

```
Met Ser Thr Gln Thr Asp Val Ser Phe Ser Lys Trp Arg Ser Phe Leu
1               5                   10                  15

Trp Pro Ile Gln Gly Arg Glu Ile Lys Lys Phe Leu Pro Leu Leu Leu
            20                  25                  30

Ile Tyr Ala Leu Ile Cys Leu Asn Tyr Ser Val Leu Lys Val Ala Lys
        35                  40                  45

Asp Thr Leu Val Ile Thr Ala Pro Gly Ser Gly Ala Glu Ala Ile Pro
    50                  55                  60

Phe Ile Lys Val Trp Val Ile Leu Pro Met Ala Leu Leu Val Thr Tyr
65                  70                  75                  80

Leu Phe Thr Arg Leu Phe Asn Arg Phe Ser Gln Glu Gln Val Phe Tyr
                85                  90                  95

Ile Met Ile Gly Ser Phe Ile Ser Phe Phe Ala Leu Phe Ala Phe Val
            100                 105                 110

Leu Tyr Pro Leu Arg Asp Phe Leu His Pro His Asp Thr Ala Asp Lys
        115                 120                 125

Leu Gln Ala Met Leu Pro Gln Gly Phe Gln Gly Leu Ile Ala Ile Phe
    130                 135                 140

Arg Asn Trp Ser Tyr Thr Leu Phe Tyr Val Met Ser Glu Leu Trp Gly
145                 150                 155                 160

Thr Ala Ile Met Ser Val Leu Phe Trp Gly Phe Thr Asn Glu Ile Ile
                165                 170                 175

Ser Val Gly Glu Ala Lys Arg Tyr Tyr Gly Ile Leu Ser Val Gly Ala
            180                 185                 190

Asn Ile Ala Thr Ile Phe Ser Gly Tyr Ile Thr Thr Phe Leu Ser Leu
        195                 200                 205

Gln Val Ile Asp Met Ser Phe Ile Phe Gly Pro Asp Arg Trp Gly Gln
    210                 215                 220

Ser Leu Gly Leu Val Thr Cys Val Val Val Ala Ala Gly Leu Leu Ile
225                 230                 235                 240

Met Ala Leu Phe Arg Trp Tyr Asn Lys Arg Val Ile Asn Arg Asp Ala
                245                 250                 255

Val Leu Leu Lys Met Lys Gln Asp His Thr Glu Thr Lys Lys Thr Met
            260                 265                 270

Lys Met Gly Met Arg Lys Asn Phe Ala Tyr Leu Ala Lys Ser Lys Tyr
        275                 280                 285

Leu Ile Cys Ile Ala Val Leu Val Val Ala Phe Asn Val Gly Ile Asn
    290                 295                 300

Met Val Glu Ile Ile Trp Lys Asp Gln Ile Lys Glu Leu Tyr Pro Asn
305                 310                 315                 320

Pro Asn Asp Phe Ile Val Tyr Met Gly Lys Val Met Ser Ala Ile Gly
                325                 330                 335

Trp Val Ala Thr Phe Val Gly Leu Phe Leu Ser Ser Asn Leu Ile Arg
            340                 345                 350

Arg Leu Gly Trp Thr Val Ser Ala Leu Ile Thr Pro Val Ala Leu Leu
        355                 360                 365

Val Thr Gly Val Phe Phe Phe Gly Phe Ile Leu Phe Lys Asn Asn Pro
    370                 375                 380

Thr Leu Val Gly Trp Thr Ala Ala Ile Gly Phe Thr Pro Leu Ala Leu
385                 390                 395                 400

Gly Val Leu Phe Gly Thr Ile Gln Asn Val Met Ser Arg Ala Cys Lys
                405                 410                 415
```

-continued

```
Tyr Thr Leu Phe Asp Ser Thr Lys Glu Ile Ala Phe Ile Pro Leu Ser
            420                 425                 430

Pro Glu Ser Lys Leu Lys Gly Lys Ala Ala Ile Asp Gly Val Gly Ser
        435                 440                 445

Arg Val Gly Lys Ser Gly Gly Ser Ile Val His Gly Gly Leu Leu Met
    450                 455                 460

Leu Phe Gly Ser Val Ser Leu Ser Ala Pro Tyr Val Gly Leu Ile Leu
465                 470                 475                 480

Leu Ala Val Val Phe Gly Trp Ile Gly Ala Ala Arg Ser Leu Gly Arg
                485                 490                 495

Gln Phe Asn Leu Leu Thr Thr His His Glu Lys Leu Glu Ile Asn Glu
            500                 505                 510

Glu Ala Gln Pro Ser Glu Lys Lys Pro Leu Leu Glu Ser Val
        515                 520                 525


<210> SEQ ID NO 15
<211> LENGTH: 1581
<212> TYPE: DNA
<213> ORGANISM: Simkania negevensis

<400> SEQUENCE: 15

atgtcaacac agactgatgt gagtttcagt aaatggcgct catttttgtg gccaattcaa      60

ggaagagaaa ttaaaaaatt tcttcctctt ctcctgattt acgctctcat ttgtcttaac     120

tatagcgtct taaaagtcgc aaaagacaca cttgtcatta cagcccctgg atcaggcgca     180

gaagcaatcc cgtttatcaa ggtctgggtc attctcccca tggcactcct cgtaacttat     240

ctctttactc gcctcttcaa tcgatttagc caagaacaag tgttttacat catgatcggg     300

agcttcattt cgtttttcgc tctatttgca tttgtcctct accccttgcg agattttctt     360

catcctcatg acacagctga taaattacaa gccatgcttc cacagggatt ccaagggctc     420

atagccattt tccgtaactg gtcctatacc ctcttttatg tgatgtctga gctatgggga     480

accgctatta tgtctgtcct cttttgggga ttcacaaatg aaattatttc tgtaggtgag     540

gccaaaaggt attatggaat tctcagtgta ggggccaata ttgcaactat tttttcaggg     600

tacatcacca cctttctctc tttgcaagtg attgacatgt cattcatttt tggacctgac     660

cgctggggac aatcattagg tcttgtgaca tgtgttgttg ttgcagcagg tctccttatt     720

atggcccttt tcagatggta caacaagcga gtcattaatc gtgatgcagt actattaaaa     780

atgaaacaag accacacaga aacgaagaag accatgaaaa tgggaatgcg taagaatttt     840

gcttaccttg caaaatcaaa gtatttaatt tgcattgcag ttctggttgt tgcattcaat     900

gttggaatca acatggtcga aattatctgg aaagatcaaa tcaaagaact gtatcccaat     960

cccaacgatt ttattgttta tatggggaag gtcatgagtg caattggttg ggttgcaaca    1020

tttgtcggac tatttctcag tagtaattta atcaggcgct taggatggac tgtcagcgcc    1080

ttaatcactc ctgttgctct cctcgtaaca ggtgttttct ttttcggatt cattctcttt    1140

aaaaacaacc ctacattagt gggttggaca gccgccatag gatttacacc tcttgcacta    1200

ggggttctct ttgggacaat ccaaaatgtg atgtctcgag catgtaaata caccttattt    1260

gactctacaa aagaaatagc gtttatcccc cttagccctg agtccaagct aaaaggaaaa    1320

gctgcaattg atggagtagg ctctcgcgtt ggaaagtccg gagggtcgat tgttcatggt    1380

ggactactga tgctcttcgg ctccgtttct ctcagcgcac cttacgtcgg cttgatctta    1440

ctcgccgttg ttttcggttg gattggtgca gctcgttcac tcgggagaca atttaatctc    1500
```

```
cttacgacgc atcatgaaaa actcgagatt aacgaggagg cacagccctc cgaaaaaaag   1560

cccttacttg aatccgttta a                                             1581


<210> SEQ ID NO 16
<211> LENGTH: 498
<212> TYPE: PRT
<213> ORGANISM: Rickettsia prowazekii

<400> SEQUENCE: 16

Met Ser Thr Ser Lys Ser Glu Asn Tyr Leu Ser Glu Leu Arg Lys Ile
1               5                   10                  15

Ile Trp Pro Ile Glu Gln Tyr Glu Asn Lys Lys Phe Leu Pro Leu Ala
            20                  25                  30

Phe Met Met Phe Cys Ile Leu Leu Asn Tyr Ser Thr Leu Arg Ser Ile
        35                  40                  45

Lys Asp Gly Phe Val Val Thr Asp Ile Gly Thr Glu Ser Ile Ser Phe
    50                  55                  60

Leu Lys Thr Tyr Ile Val Leu Pro Ser Ala Val Ile Ala Met Ile Ile
65                  70                  75                  80

Tyr Val Lys Leu Cys Asp Ile Leu Lys Gln Glu Asn Val Phe Tyr Val
                85                  90                  95

Ile Thr Ser Phe Phe Leu Gly Tyr Phe Ala Leu Phe Ala Phe Val Leu
            100                 105                 110

Tyr Pro Tyr Pro Asp Leu Val His Pro Asp His Lys Thr Ile Glu Ser
        115                 120                 125

Leu Ser Leu Ala Tyr Pro Asn Phe Lys Trp Phe Ile Lys Ile Val Gly
    130                 135                 140

Lys Trp Ser Phe Ala Ser Phe Tyr Thr Ile Ala Glu Leu Trp Gly Thr
145                 150                 155                 160

Met Met Leu Ser Leu Leu Phe Trp Gln Phe Ala Asn Gln Ile Thr Lys
                165                 170                 175

Ile Ala Glu Ala Lys Arg Phe Tyr Ser Met Phe Gly Leu Leu Ala Asn
            180                 185                 190

Leu Ala Leu Pro Val Thr Ser Val Val Ile Gly Tyr Phe Leu His Glu
        195                 200                 205

Lys Thr Gln Ile Val Ala Glu His Leu Lys Phe Val Pro Leu Phe Val
    210                 215                 220

Ile Met Ile Thr Ser Ser Phe Leu Ile Ile Leu Thr Tyr Arg Trp Met
225                 230                 235                 240

Asn Lys Asn Val Leu Thr Asp Pro Arg Leu Tyr Asp Pro Ala Leu Val
                245                 250                 255

Lys Glu Lys Lys Thr Lys Ala Lys Leu Ser Phe Ile Glu Ser Leu Lys
            260                 265                 270

Met Ile Phe Thr Ser Lys Tyr Val Gly Tyr Ile Ala Leu Leu Ile Ile
        275                 280                 285

Ala Tyr Gly Val Ser Val Asn Leu Val Glu Gly Val Trp Lys Ser Lys
    290                 295                 300

Val Lys Glu Leu Tyr Pro Thr Lys Glu Ala Tyr Thr Ile Tyr Met Gly
305                 310                 315                 320

Gln Phe Gln Phe Tyr Gln Gly Trp Val Ala Ile Ala Phe Met Leu Ile
                325                 330                 335

Gly Ser Asn Ile Leu Arg Lys Val Ser Trp Leu Thr Ala Ala Met Ile
            340                 345                 350
```

-continued

Thr Pro Leu Met Met Phe Ile Thr Gly Ala Ala Phe Phe Ser Phe Ile
355 360 365

Phe Phe Asp Ser Val Ile Ala Met Asn Leu Thr Gly Ile Leu Ala Ser
370 375 380

Ser Pro Leu Thr Leu Ala Val Met Ile Gly Met Ile Gln Asn Val Leu
385 390 395 400

Ser Lys Gly Val Lys Tyr Ser Leu Phe Asp Ala Thr Lys Asn Met Ala
405 410 415

Tyr Ile Pro Leu Asp Lys Asp Leu Arg Val Lys Gly Gln Ala Ala Val
420 425 430

Glu Val Ile Gly Gly Arg Leu Gly Lys Ser Gly Gly Ala Ile Ile Gln
435 440 445

Ser Thr Phe Phe Ile Leu Phe Pro Val Phe Gly Phe Ile Glu Ala Thr
450 455 460

Pro Tyr Phe Ala Ser Ile Phe Phe Ile Ile Val Ile Leu Trp Ile Phe
465 470 475 480

Ala Val Lys Gly Leu Asn Lys Glu Tyr Gln Val Leu Val Asn Lys Asn
485 490 495

Glu Lys

<210> SEQ ID NO 17
<211> LENGTH: 1497
<212> TYPE: DNA
<213> ORGANISM: Rickettsia prowazekii

<400> SEQUENCE: 17
atgagtactt ccaaaagtga aaattatctt tcagaactaa gaaagataat ttggcctata 60
gaacaatatg aaaataagaa gtttttgcca cttgcattta tgatgttctg tattttatta 120
aactactcaa ctcttcgttc aattaaagac ggttttgtag taacagatat aggtacagaa 180
tcgataagtt ttttaaaaac atatatagta ctaccttctg ctgtaattgc tatgataatt 240
tatgttaagc tatgtgatat tttaaagcaa gaaaacgtat tttatgttat tacttcattt 300
tttttagggt attttgcatt atttgccttt gttctttacc catatcctga tttagtccac 360
cctgatcata aaactataga atctttaagt ttagcttatc ctaatttcaa atggtttata 420
aaaatagttg gtaaatggag ttttgcatct ttttatacta ttgccgagct ttggggaaca 480
atgatgctta gtttattatt ttggcaattt gctaatcaaa ttactaaaat cgctgaagct 540
aaacgtttct actcaatgtt tggtttactt gcgaatttag cattgcctgt aacatcagtg 600
gttattggat attttctaca cgaaaaaact caaatagttg cagaacattt aaaatttgta 660
cctttatttg ttataatgat aacaagtagt ttcttaataa tattaacata tagatggatg 720
aataaaaatg ttctaactga tcctagacta tatgatccag cattagtaaa agaaaaaaaa 780
actaaagcta aattgtcgtt catagaaagt ttaaaaatga tctttacttc gaaatatgta 840
ggttatattg cattattaat tattgcttat ggtgtttcag taaatttagt tgaaggtgtt 900
tggaaatcca aagtaaaaga attatatccg acaaaggagg cttataccat atatatgggt 960
cagttccaat tttatcaggg ttgggttgca attgctttta tgctgatagg tagtaatatt 1020
ttaagaaaag tatcatggct aactgcagct atgatcactc cattaatgat gttcataaca 1080
ggtgcggcat ttttttcatt tatatttttt gatagcgtta ttgcaatgaa tttaaccggc 1140
atccttgctt caagtccttt aacacttgct gttatgatcg gtatgattca aaatgtttta 1200
agtaaaggtg tgaaatattc tttatttgat gcaactaaaa atatggcgta tattccactt 1260

-continued

```
gataaggatt tacgagtcaa agggcaagct gccgttgaag ttatcggagg aaggctcggt   1320

aaatcaggcg gtgctattat tcaatctaca ttctttattt tatttcctgt atttggtttt   1380

atagaggcga ctccttattt tgcttctata ttctttataa tagtaatatt atggatattt   1440

gcagttaaag gtttaaataa agagtatcaa gttttggtaa ataaaaatga aaaatag      1497


<210> SEQ ID NO 18
<211> LENGTH: 507
<212> TYPE: PRT
<213> ORGANISM: Rickettsia prowazekii

<400> SEQUENCE: 18

Met Asn Ile Val Asp Ser Asn Cys Thr Ile Trp His Lys Ala Arg Asn
1               5                   10                  15

Ser Lys Phe Arg His Ile Val Trp Pro Ile Arg Ser Tyr Glu Leu Thr
            20                  25                  30

Lys Phe Ile Pro Met Thr Leu Leu Met Phe Phe Ile Leu Leu Asn Gln
        35                  40                  45

Asn Leu Val Arg Ser Ile Lys Asp Ser Phe Val Val Thr Leu Ile Ser
    50                  55                  60

Ser Glu Val Leu Ser Phe Ile Lys Leu Trp Gly Glu Met Pro Met Gly
65                  70                  75                  80

Val Leu Phe Val Ile Leu Tyr Ser Lys Leu Cys Asn Ile Met Thr Thr
                85                  90                  95

Glu Gln Val Phe Arg Ile Ile Thr Ser Thr Phe Leu Phe Phe Phe Ala
            100                 105                 110

Ile Phe Gly Phe Ile Leu Phe Pro Tyr Lys Glu Phe Phe His Pro Asn
        115                 120                 125

Pro Glu Leu Ile Asn Gln Tyr Ile Ile Val Leu Pro His Leu Lys Trp
    130                 135                 140

Phe Leu Ile Ile Trp Gly Gln Trp Ser Leu Val Leu Phe Tyr Ile Met
145                 150                 155                 160

Gly Glu Leu Trp Pro Val Ile Val Phe Thr Leu Leu Tyr Trp Gln Leu
                165                 170                 175

Ala Asn Lys Ile Thr Lys Val Glu Glu Ala Pro Arg Phe Tyr Ser Phe
            180                 185                 190

Phe Thr Leu Phe Gly Gln Thr Asn Leu Leu Phe Ser Gly Thr Val Ile
        195                 200                 205

Ile Tyr Phe Ala Lys Ser Glu His Phe Leu Leu Pro Leu Phe Ala His
    210                 215                 220

Leu Asn Asp Thr Asn Glu Ile Leu Leu Lys Ser Phe Ile Thr Val Ile
225                 230                 235                 240

Leu Ile Ser Gly Leu Ile Cys Leu Ala Leu His Lys Leu Ile Asp Lys
                245                 250                 255

Ser Val Val Glu Ala Asp Lys Asn Ile Lys Phe Lys Asn Gln Arg Thr
            260                 265                 270

Asp Ile Leu Lys Leu Ser Leu Leu Glu Ser Ala Lys Ile Ile Leu Thr
        275                 280                 285

Ser Arg Tyr Leu Gly Phe Ile Cys Leu Leu Val Met Ser Tyr Ser Met
    290                 295                 300

Ser Ile Asn Leu Ile Glu Gly Leu Trp Met Ser Lys Val Lys Gln Leu
305                 310                 315                 320

Tyr Pro Ala Thr Lys Asp Phe Ile Ser Tyr His Gly Glu Val Leu Phe
                325                 330                 335
```

-continued

```
Trp Thr Gly Val Leu Thr Leu Val Ser Ala Phe Leu Gly Ser Ser Leu
            340                 345                 350

Ile Arg Ile Tyr Gly Trp Phe Trp Gly Ala Ile Ile Thr Pro Ile Met
        355                 360                 365

Met Phe Val Ala Gly Val Met Phe Phe Ser Phe Thr Ile Phe Glu Gln
    370                 375                 380

His Leu Gly Asn Ile Val Asn Thr Leu Gly Tyr Ser Ser Pro Leu Val
385                 390                 395                 400

Ile Ile Val Phe Ile Gly Gly Leu Trp His Val Phe Ala Lys Ser Val
                405                 410                 415

Lys Tyr Ser Leu Phe Asp Ala Thr Lys Glu Met Val Tyr Ile Pro Leu
            420                 425                 430

Asp Asn Glu Ile Lys Thr Lys Gly Lys Ala Ala Val Asp Val Met Gly
        435                 440                 445

Ala Lys Ile Gly Lys Ser Ile Gly Ala Ile Ile Gln Phe Ile Ser Phe
    450                 455                 460

Ser Ile Phe Pro Asn Ala Val His Asn Asp Ile Ala Gly Leu Leu Met
465                 470                 475                 480

Val Thr Phe Ile Ile Val Cys Ile Leu Trp Leu Tyr Gly Val Lys Val
                485                 490                 495

Leu Ser Gln Asn Tyr Asn Lys Met Ile Lys Arg
            500                 505
```

<210> SEQ ID NO 19
<211> LENGTH: 1524
<212> TYPE: DNA
<213> ORGANISM: Rickettsia prowazekii

<400> SEQUENCE: 19

```
atgaatatag tagattctaa ctgtacaatt tggcataaag caagaaatag taaatttagg     60

catatagtat ggccaattag atcgtatgaa ttaacaaaat tcatcccgat gactttatta    120

atgtttttta ttttacttaa tcaaaattta gtgcgtagta ttaaagatag ttttgttgtt    180

acattaatta gttcagaagt attaagtttt ataaaacttt ggggtgaaat gccgatgggg    240

gttttatttg ttattcttta ttctaaactc tgtaatatta tgaccacaga gcaagttttt    300

aggataatta ccagtacctt tttatttttc tttgcaattt ttggttttat tttattccca    360

tacaaagagt tttttcatcc taaccctgaa ttaattaatc aatatatcat tgttctgcct    420

cacttaaagt ggtttttaat aatttgggga caatggagtt tagtattatt ttatataatg    480

ggtgagttat ggcctgttat agtttttact cttttatatt ggcagcttgc aaataaaatc    540

accaaagtcg aagaagcacc aagattttac tcatttttta ctttatttgg acaaactaat    600

ttgctcttct caggcactgt aattatttat tttgctaaga gcgaacattt tttattacct    660

ttatttgctc atttaaatga cacaaatgaa attcttttaa aatcattcat cacagttatt    720

ttaatatcag gattaatttg tttagctctc cataagctaa ttgataaatc agttgtagaa    780

gctgataaaa atataaaatt taaaaaccaa agaacagata tattaaaatt aagcttgctc    840

gaaagtgcaa aaataatctt aacgtctaga tatcttggtt ttatttgtct tctcgtaatg    900

tcttattcta tgagtattaa cctaatagaa ggattgtgga tgtcaaaagt aaaacaactc    960

tatcctgcta caaaggattt tatatcatat cacggtgaag tattgttttg gactggagtg   1020

ttaactttag ttagtgcatt tttaggcagt agtttaatta gaatttatgg ctggttttgg   1080

ggggctatta taacaccgat tatgatgttt gtagcagggg ttatgttttt ttcattcaca   1140
```

atttttgaac aacacttagg aaatatagta aatactcttg gctatagttc tccacttgtc 1200
attatagttt ttattggtgg actttggcat gtatttgcta aatctgtaaa gtattccctt 1260
ttcgatgcta ctaaagaaat ggtgtatatt ccactagata atgaaattaa gactaaaggt 1320
aaagcagcag ttgatgttat gggtgctaaa attggtaagt caataggtgc tattattcaa 1380
ttcatatcct ttagtatctt tccaaatgct gtacataacg acatagcagg cttattgatg 1440
gttactttta ttatcgtatg tatattatgg ctatatggag tgaaagtttt atcacaaaat 1500
tataataaaa tgataaaacg ttaa 1524

<210> SEQ ID NO 20
<211> LENGTH: 501
<212> TYPE: PRT
<213> ORGANISM: Rickettsia prowazekii

<400> SEQUENCE: 20

Met Leu Pro Pro Lys Ile Phe Phe Glu Lys Val Lys Glu Ile Ile Trp
1 5 10 15

Pro Ile Glu Arg Lys Glu Leu Lys Leu Phe Ile Pro Met Ala Leu Met
20 25 30

Met Leu Cys Ile Leu Phe Asn Phe Gly Ala Leu Arg Ser Ile Lys Asp
35 40 45

Ser Leu Val Val Pro Ser Met Gly Ala Glu Ile Ile Ser Phe Leu Lys
50 55 60

Leu Trp Leu Val Leu Pro Ser Cys Val Ile Phe Thr Ile Leu Tyr Val
65 70 75 80

Lys Leu Ser Asn Lys Leu Asn Phe Glu Tyr Ile Phe Tyr Ser Ile Val
85 90 95

Gly Thr Phe Leu Leu Phe Phe Leu Leu Phe Ala Tyr Ile Ile Tyr Pro
100 105 110

Asn Gln Asp Ile Tyr His Pro Asn Asp Ala Met Ile Asn Asn Leu Ile
115 120 125

Ala Ser Tyr Pro Asn Leu Lys Trp Phe Ile Lys Ile Gly Ser Lys Trp
130 135 140

Ser Tyr Ala Leu Met Tyr Ile Phe Ser Glu Leu Trp Ser Ala Val Val
145 150 155 160

Ile Asn Leu Met Phe Trp Gln Phe Ala Asn His Ile Phe Asp Thr Ala
165 170 175

Lys Ala Lys Arg Phe Tyr Pro Val Leu Gly Met Val Gly Asn Ile Gly
180 185 190

Leu Ile Ile Ala Gly Ser Val Leu Val Phe Phe Ser Ser Gly Gln Tyr
195 200 205

Ile Ile Asp Ser Glu Leu Leu Thr Asp Ser Tyr Asn Ser Ser Ser Asn
210 215 220

Asn Ser Ile Met Leu Gln Pro Ile Ile Ser Ile Ile Val Thr Ala Gly
225 230 235 240

Ile Ile Ala Met Phe Leu Phe Arg Ile Ile Asn Lys Phe Ile Leu Thr
245 250 255

Asn Ser Ile Asn Val Leu Asp Val Lys Lys Val Ala Ala Lys Thr Lys
260 265 270

Thr Lys Leu Ala Leu Ile Glu Ser Ile Lys Leu Ile Ile His Ser Lys
275 280 285

Tyr Ile Gly Arg Ile Ala Leu Leu Ile Ile Cys Tyr Gly Leu Leu Ile
290 295 300

```
Asn Ile Val Glu Gly Pro Trp Lys Ala Lys Ile Lys Glu Leu His Pro
305                 310                 315                 320

Asn Thr Val Asp Tyr Val Asn Phe Met Gly Met Phe Asn Ile Trp Met
                325                 330                 335

Gly Ile Ser Cys Val Thr Phe Met Ile Ile Gly Ser Asn Ile Leu Arg
            340                 345                 350

Arg Leu Gly Trp Leu Ile Ser Ala Leu Leu Thr Pro Ile Met Leu Ser
        355                 360                 365

Ile Thr Gly Phe Met Phe Phe Ile Phe Ile Ile Phe Ile Glu Glu Ile
    370                 375                 380

Gly Thr Cys Phe Gly Asp Phe Asn Leu Leu Tyr Val Ala Ile Ile Val
385                 390                 395                 400

Gly Ala Ile Gln Asn Ile Leu Ser Lys Ser Ser Lys Tyr Ser Leu Phe
                405                 410                 415

Asp Ser Thr Lys Glu Met Ala Tyr Ile Pro Leu Ser Leu Glu Leu Arg
            420                 425                 430

Thr Lys Gly Lys Ala Ala Val Glu Val Ile Gly Thr Lys Phe Gly Lys
        435                 440                 445

Ser Leu Gly Ala Phe Ile Gln Ser Leu Ile Phe Ile Ile Ile Pro Thr
    450                 455                 460

Ala Thr Phe Asp Ser Ile Ile Ile Tyr Leu Leu Val Ile Phe Ile Val
465                 470                 475                 480

Met Met Asn Leu Trp Ile Trp Asn Ile Ile Lys Leu Asn Lys Glu Tyr
                485                 490                 495

Ile Lys Leu Cys Gln
            500
```

<210> SEQ ID NO 21
<211> LENGTH: 1506
<212> TYPE: DNA
<213> ORGANISM: Rickettsia prowazekii

<400> SEQUENCE: 21

```
atgttaccgc ctaaaatttt ctttgaaaaa gttaaagaaa taatttggcc tatagaaagg     60

aaagaattaa agctatttat accaatggct ttaatgatgt tatgtatcct gtttaatttt    120

ggggctttaa gatctattaa agatagttta gtagtaccct ctatgggggc tgaaattatt    180

agtttcttaa aattatggtt agtgctaccc tcgtgcgtaa tttttacgat actttacgtt    240

aaacttagta ataaattaaa ttttgaatat attttctata gtatagtcgg tacttttta     300

ctatttttct tattatttgc ctatattatt tatccaaatc aagatattta tcatcctaat    360

gatgcaatga taaataattt aattgcttca taccctaatt taaagtggtt tattaaaata    420

ggtagtaaat ggagttatgc gctaatgtat attttctcag aattatggag tgcagtagtt    480

ataaacttaa tgttttggca atttgctaat cacattttg atactgctaa agctaaacga     540

ttttatcctg ttcttgggat ggttggtaat atcggtctta taatagcagg cagcgtactt    600

gtttttttt caagtgggca gtacatcatt gattcagaat tattaacgga ttcttataat     660

tcatcttcta acaattctat catgcttcag ccaatcatat caattattgt tactgcagga    720

ataattgcta tgtttttatt tagaataata aataaattta ttttaactaa ttctataaat    780

gttttagatg taaaaaaagt tgctgctaaa acaaaaacaa aacttgcatt aattgaaagt    840

ataaaattaa taattcattc aaaatatata ggtcgtattg cattattaat aatctgttat    900

ggattactaa taaatatagt tgaaggacct tggaaagcga aaataaaaga attacatcca    960
```

```
aatactgtag attatgttaa ttttatgggc atgtttaata tttggatggg gatctcatgt   1020

gttactttca tgataatagg tagtaatatt cttagaaggc ttggttggct catttctgca   1080

ttattaactc ctattatgtt atctattaca ggcttcatgt tttttatctt tataattttt   1140

attgaagaaa taggtacatg ttttggtgat tttaatcttc tatatgtagc gattattgtc   1200

ggagcaattc agaatatact tagtaaatcg tctaaatatt cattattcga ttcaacaaaa   1260

gaaatggcat atattccttt atctttagaa ctgagaacta agggaaaagc cgctgtagag   1320

gtaataggaa cgaaatttgg taaatcactt ggagcattta tccagtcttt gatatttatt   1380

attattccaa cggctacctt tgattctatt ataatatatt tactagtaat ttttatagtg   1440

atgatgaatt tatggatttg gaatattata aaattaaata aggaatatat aaagctgtgt   1500

caataa                                                              1506


<210> SEQ ID NO 22
<211> LENGTH: 512
<212> TYPE: PRT
<213> ORGANISM: Rickettsia prowazekii

<400> SEQUENCE: 22

Met Thr Ile Asn Ala Ser Asn Ile Glu Asn Ser Phe Ser Lys Ile Asn
1               5                   10                  15

Ser His Phe Ser Lys Leu Thr Asp Tyr Ile Trp Pro Ile Lys Arg His
            20                  25                  30

Glu Ile Ser Lys Phe Leu Phe Ile Thr Leu Leu Met Phe Cys Ile Leu
        35                  40                  45

Phe Ile Gln Asn Leu Ile Arg Ala Leu Lys Asp Ser Ile Val Thr Thr
    50                  55                  60

Met Ile Gly Ala Glu Thr Ile Ser Phe Leu Lys Phe Trp Gly Val Met
65                  70                  75                  80

Pro Ser Ala Phe Leu Ile Thr Val Ile Tyr Val Lys Leu Val Asn Arg
                85                  90                  95

Met Lys Ala Glu Asn Ile Phe Tyr Leu Ile Ile Ser Ile Phe Leu Thr
            100                 105                 110

Phe Phe Ala Leu Phe Ala Tyr Val Ile Phe Pro Asn His Glu Met Leu
        115                 120                 125

His Leu Arg Pro Val Thr Val His Asn Leu Thr Ala Ser Leu Pro Asn
    130                 135                 140

Leu Lys Trp Phe Ile Leu Leu Leu Ser Lys Trp Ser Phe Ser Leu Phe
145                 150                 155                 160

Tyr Ile Ile Ala Glu Leu Trp Pro Asn Val Val Phe Ala Leu Leu Phe
                165                 170                 175

Trp Gln Phe Val Asn Asn Ile Thr Thr Val Glu Glu Ser Lys Arg Phe
            180                 185                 190

Tyr Pro Leu Phe Gly Leu Leu Ser Gln Thr Gly Ile Tyr Leu Ala Gly
        195                 200                 205

His Phe Leu Glu Asn Leu Ser Asn Ile Asn Tyr Tyr Val Thr Asn Lys
    210                 215                 220

Phe Ala Leu Gln Ser Ser Phe His Thr Leu Ser Ile Gln Ile Ile Leu
225                 230                 235                 240

Thr Ile Val Leu Ile Leu Gly Ile Val Ser Ile Lys Thr Phe Trp Leu
                245                 250                 255

Leu Asn His Lys Val Leu Asp Lys Lys His Met Ala Leu Leu Arg Phe
            260                 265                 270
```

-continued

```
Lys Thr Lys Asn Lys Ser Ile Thr Ile Ala Lys Ser Phe Gln Met Ile
        275                 280                 285

Leu Ser Ser Arg His Ile Arg Leu Ile Ala Thr Leu Leu Ile Cys Tyr
    290                 295                 300

Gly Ile Ala Ile Asn Leu Val Glu Gly Pro Trp Lys Ala Ala Ala Thr
305                 310                 315                 320

Lys Ile Tyr Lys Thr Pro Thr Glu Tyr Ala Ala Phe Ile Gly Ser Tyr
                325                 330                 335

Leu Ser Tyr Thr Gly Val Phe Thr Ile Phe Phe Val Leu Leu Gly Ser
            340                 345                 350

Asn Ile Val Arg Arg Met Gly Trp Phe Thr Ser Ala Val Ile Thr Pro
        355                 360                 365

Ser Ile Val Phe Ile Thr Gly Ile Leu Phe Phe Ala Val Asn Asn Phe
    370                 375                 380

Glu Gly Phe Ala Gly Leu Ile Ile Ala Asn Phe Ile Leu Thr Asp Pro
385                 390                 395                 400

Ala Leu Val Ala Ile Thr Ile Gly Ala Ile Gln Asn Val Leu Ser Lys
                405                 410                 415

Ser Ser Lys Tyr Thr Leu Phe Asp Ser Thr Lys Glu Met Ala Tyr Val
            420                 425                 430

Pro Leu Glu Pro Glu Ile Lys Ile Ser Gly Lys Ala Ala Asp Val
        435                 440                 445

Ile Gly Thr Lys Leu Gly Lys Ser Gly Ser Ala Phe Leu Gln Ser Leu
    450                 455                 460

Ile Phe Ile Ile Leu Pro Ser Ala Ser Tyr Gln Ser Ile Ser Ile Cys
465                 470                 475                 480

Leu Met Ile Ile Phe Ile Leu Thr Cys Val Thr Trp Ile Trp Ala Thr
                485                 490                 495

Lys Glu Leu Asn Lys Glu Tyr Lys Asn Ser Ile Lys Phe Ser Gln Lys
            500                 505                 510
```

<210> SEQ ID NO 23
<211> LENGTH: 1539
<212> TYPE: DNA
<213> ORGANISM: Rickettsia prowazekii

<400> SEQUENCE: 23

```
atgacgatta acgccagtaa tatagaaaat tctttttcta aaatcaatag ccatttttct      60

aagcttacag attatatctg gcctataaaa cgccacgaaa tttctaagtt tttattcatt     120

acattattaa tgttctgtat tttatttatt caaaatctca tcagagcttt aaaagatagt     180

attgttacta ctatgatagg tgctgagact atatcatttt tgaaattttg gggcgtgatg     240

ccgtcagcat tcttaataac tgttatatat gttaaacttg tcaataggat gaaagcagaa     300

aatatatttt atcttattat atcaattttt ttaacattct ttgctttgtt tgcatacgtt     360

attttcccaa atcatgaaat gctgcattta aggcctgtaa ccgtgcataa tttaacggca     420

agtttaccga atttaaaatg gtttatactt cttttatcaa aatggagttt ttcactattt     480

tatataatag ccgaattatg gccaaatgta gtttttgcat tactgttttg gcagtttgtg     540

aataatatta ctacagtaga agaatcgaaa agattttatc cattatttgg tttacttagt     600

caaacaggta tttatttagc aggacatttt ttagaaaatc taagtaatat aaattattat     660

gtcactaata aatttgcatt gcaatcgtct tttcatacac tttctataca aattatacta     720

actatagtat taattttagg catagtatcg ataaaaactt tttggttact taatcataaa     780
```

-continued

```
gtactagaca aaaagcatat ggcattactc aggttcaaaa caaaaaataa atctattact    840
attgctaaaa gttttcagat gattctatcg tcaagacaca ttagattaat tgcaactttg    900
cttatctgct atggcattgc aattaattta gtagaaggcc cttggaaagc agcagcaact    960
aaaatttata aaactccaac cgaatatgca gcttttatag gaagttattt aagctacact   1020
ggagtattta ctattttctt tgttctactt ggttccaata tagttagaag aatgggctgg   1080
tttacttcag ctgtgatcac accttcaata gtttttatta ccggtatatt attttttgct   1140
gttaataatt ttgaaggctt tgctggctta ataatagcaa attttatttt gaccgatcct   1200
gctttagttg ctataacaat aggtgctatt caaaatgtac ttagtaaatc aagcaaatat   1260
actttatttg attctacaaa agaaatggct tatgttcctt tagaaccaga aatcaaaata   1320
agtggtaagg ctgctgccga cgttataggt acaaaactcg gtaaatccgg tagtgcattt   1380
ttacaatcat taatatttat aatattacct tctgctagtt atcaatctat ttcaatctgt   1440
ttaatgatta tatttatcct cacttgcgta acttggattt gggctactaa agaactaaat   1500
aaagaatata aaaattctat taaattttct caaaaataa                          1539
```

```
<210> SEQ ID NO 24
<211> LENGTH: 500
<212> TYPE: PRT
<213> ORGANISM: Rickettsia prowazekii

<400> SEQUENCE: 24

Met Leu Ser Thr Ser Pro Ser Arg Ser Phe Lys Asn Lys Phe Arg Ala
1               5                   10                  15

Ala Phe Trp Pro Val His Asn Tyr Glu Leu Gly Lys Phe Ile Pro Ile
            20                  25                  30

Ser Ala Leu Met Phe Cys Ile Leu Phe Asn Gln Asn Ile Leu Arg Ile
        35                  40                  45

Leu Lys Asp Ser Ile Leu Ile Ser Glu Ile Ser Ala Glu Ile Ala Gly
    50                  55                  60

Phe Ala Lys Val Tyr Cys Val Thr Pro Val Ala Ala Leu Phe Val Ile
65                  70                  75                  80

Ile Tyr Ala Lys Met Ile Asn His Leu Thr Phe Glu Lys Ile Phe Tyr
                85                  90                  95

Tyr Leu Ser Ala Phe Phe Ile Ser Cys Phe Ile Leu Phe Ala Phe Val
            100                 105                 110

Ile Tyr Pro Asn Ile His Ile Phe His Val His Pro Asp Thr Leu Ser
        115                 120                 125

Asp Trp Met Asn Lys Tyr Pro His Phe Lys Trp Tyr Ile Ser Leu Val
    130                 135                 140

Gly Asn Trp Gly Tyr Ile Val Tyr Tyr Ser Leu Ala Glu Leu Trp Pro
145                 150                 155                 160

Asn Ile Phe Tyr Val Leu Leu Phe Trp Gln Phe Thr Asn Glu Leu Thr
                165                 170                 175

Thr Thr Glu Glu Ala Lys Arg Phe Tyr Thr Leu Phe Ser Leu Phe Gly
            180                 185                 190

Asn Ser Ser Leu Ile Leu Val Gly Phe Leu Met Met Asn Leu Ser Ser
        195                 200                 205

Glu Asp Thr Ile Ile Lys Lys Phe Ile Ser Ile Ser Asp Ser Lys Ile
    210                 215                 220

Thr Leu Val Gln Val Ser Thr Thr Ile Ile Ala Ile Val Ala Ile Ile
225                 230                 235                 240
```

```
Cys Cys Leu Leu Val Arg Phe Ile Ser Lys Tyr Ile Phe Thr Asn Pro
            245                 250                 255

Leu Phe Tyr His Lys Thr Lys Ser Ser Arg Ser Thr Ala Gln Arg Met
            260                 265                 270

Gly Leu Ile Lys Ser Phe Lys Tyr Ile Val Lys Ser Lys Tyr Leu Trp
        275                 280                 285

Leu Leu Leu Ile Cys Ser Ala Ala Phe Gly Phe Ala Ile Asn Leu Val
    290                 295                 300

Glu Ala Val Trp Lys Ala Lys Ile Lys Glu Leu Tyr Pro Thr Val Asn
305                 310                 315                 320

Thr Tyr Ala Glu Phe Asn Ser Leu Tyr Ile Leu Trp Thr Gly Val Ala
            325                 330                 335

Ile Ile Val Met Thr Ile Ile Gly Asn Asn Val Met Arg Met His Asn
            340                 345                 350

Trp Phe Val Ala Ala Val Ile Ser Pro Val Ile Ile Met Val Thr Gly
        355                 360                 365

Val Leu Phe Phe Gly Leu Ile Val Phe Asp Gln Gln Ile Leu Ser Leu
    370                 375                 380

Phe Asp Gly Ala Ile Leu Met Ser Pro Leu Ala Leu Ala Val Ser Ile
385                 390                 395                 400

Gly Gly Ile Gln Asn Ile Leu Ala Lys Gly Thr Lys Tyr Ser Ile Trp
            405                 410                 415

Asp Thr Ser Arg Glu Met Leu Tyr Ile Pro Leu Asp Asp Glu Leu Lys
            420                 425                 430

Thr Lys Gly Lys Ala Ala Val Asp Val Ile Ser Ala Lys Val Gly Lys
        435                 440                 445

Ser Ser Ser Gly Leu Val Gln Ser Ile Ile Phe Thr Leu Val Pro Asn
    450                 455                 460

Ala Thr Phe Thr Ser Ile Ser Pro Ile Leu Met Val Val Phe Thr Phe
465                 470                 475                 480

Val Cys Phe Ala Trp Ile Tyr Ala Val Arg Lys Ile Tyr Phe Glu Tyr
            485                 490                 495

Gln Lys Ile Ala
            500
```

```
<210> SEQ ID NO 25
<211> LENGTH: 1503
<212> TYPE: DNA
<213> ORGANISM: Rickettsia prowazekii

<400> SEQUENCE: 25
atgctaagta cctcaccgtc acgatcgttt aaaaacaaat ttagagcagc attttggcct      60
gtgcataatt atgaacttgg gaaatttatt ccgatcagcg ccttaatgtt ttgtatttta     120
tttaatcaaa atattttgcg aatcttaaag gatagtattt taatctctga gattagtgca     180
gaaatagcag gatttgctaa agtttactgc gttacacctg tagctgcttt gtttgttatt     240
atttatgcta aaatgatcaa tcatttgaca tttgaaaaaa tcttttatta tttaagtgca     300
ttttttataa gctgttttat tttatttgcc tttgtgattt atcctaatat tcatattttt     360
catgtacatc ctgatacact atcagactgg atgaacaaat atcctcattt taagtggtat     420
atctcattag taggtaattg gggttatata gtatattata gtcttgccga gctttggcct     480
aatatttttt acgtattatt attttggcag tttactaatg aacttactac taccgaagaa     540
gcaaaaagat tttatactct cttttcgcta ttcggtaatt cttccttaat attagtcggc     600
```

```
tttttaatga tgaatttatc atcggaagat actattatta agaaatttat aagtatttca    660

gatagtaaaa tcactttagt tcaagtatca acgacgatta tagcaattgt tgcaatcatt    720

tgttgtttgt tagttaggtt tattagcaag tacattttta ctaatccatt attttatcat    780

aaaacaaaaa gcagtagatc aactgcacaa cggatgggac taattaaaag ctttaaatat    840

attgtgaaat caaaatattt atggctactt ttaatttgtt ctgcagcttt cggatttgct    900

ataaacttag tcgaagcagt atggaaagca aaaattaagg aattatatcc gactgtaaat    960

acctacgctg aattcaatag tctgtatata ctttggacag gcgttgcgat aattgttatg   1020

acaattatcg gtaataacgt catgcgtatg cataattggt ttgtagccgc agttatttcc   1080

ccagtgataa taatggtgac aggtgttttg ttctttggac taattgtatt tgatcaacaa   1140

attttatcat tatttgatgg cgcgatttta atgtcacctc ttgcacttgc tgtttctatt   1200

ggcggtattc agaatatttt agccaaaggc actaaatatt ctatatggga tacttcaaga   1260

gaaatgttat atataccact tgatgatgaa cttaaaacaa agggtaaagc agcagttgat   1320

gttataagtg caaaagttgg aaaatcctct agtggtcttg tacaatccat tatttttact   1380

ttagtgccaa atgcgacctt tacctcaatc tcgccgattt taatggtagt atttacgttc   1440

gtatgctttg cttggattta tgcagtaaga aaaatatatt ttgaatatca aaaaatagcc   1500

tga                                                                 1503
```

<210> SEQ ID NO 26
<211> LENGTH: 194
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (69)..(69)
<223> OTHER INFORMATION: dNaM or its biotinylated analog dMMO2^SSBIO

<400> SEQUENCE: 26

```
gcaggcatgc aagcttggcg taatcatggt catagctgtt tcctgtgtga aattgttatc     60

cgctcacant tccacacaac atacgagccg gaagcataaa gtgtaaagcc tggggtgcct    120

aatgagtgag ctaactcaca ttaattgcgt tgcgctcact gcccgctttc cagtcgggaa    180

acctgtcgtg ccag                                                      194
```

<210> SEQ ID NO 27
<211> LENGTH: 304
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (179)..(179)
<223> OTHER INFORMATION: dNaM

<400> SEQUENCE: 27

```
gctgcaaggc gattaagttg ggtaacgcca gggttttccc agtcacgacg ttgtaaaacg     60

acggccagtg aattcgagct cggtacccgg ggatcctcta gagtcgacct gcaggcatgc    120

aagcttggcg taatcatggt catagctgtt tcctgtgtga aattgttatc cgctcacant    180

tccacacaac atacgagccg gaagcataaa gtgtaaagcc tggggtgcct aatgagtgag    240

ctaactcaca ttaattgcgt tgcgctcact gcccgctttc cagtcgggaa acctgtcgtg    300

ccag                                                                 304
```

```
<210> SEQ ID NO 28
<211> LENGTH: 5151
<212> TYPE: DNA
<213> ORGANISM: Artificial Sequence
<220> FEATURE:
<223> OTHER INFORMATION: Synthetic polynucleotide; sequence of the pACS
      plasmid

<400> SEQUENCE: 28

ggggaattgt gagcggataa caattcccct gtagaaataa ttttgtttaa ctttaataag     60

gagatatacc atgagaccat ttccgacgat tgccttgatt tcggtttttc tttcggcggc    120

gactcgcatt tcggcaactt cctctcatca agcaagtgca cttcctctca aaaagggaac    180

gcatgtcccg gactctccga agttgtcaaa gctatatatc atggccaaaa ccaagagtgt    240

atcctcgtcc ttcgaccccc ctcggggagg cagtactgtt gcaccaacta caccgttggc    300

aaccggcggt gcgctccgca aagtgcgaca agccgtcttt cccatctacg gaaaccaaga    360

agtcaccaaa tttctgctca tcggatccat taaattcttt ataatcttgg cactcacgct    420

cacgcgtgat accaaggaca cgttgattgt cacgcaatgt ggtgccgaag cgattgcctt    480

tctcaaaata tacggggtgc tacccgcagc gaccgcattt atcgcgctct attccaaaat    540

gtccaacgcc atgggcaaaa aaatgctatt ttattccact tgcattcctt tctttacctt    600

tttcgggctg tttgatgttt tcatttaccc gaacgcggag cgactgcacc ctagtttgga    660

agccgtgcag gcaattctcc cgggcggtgc cgcatctggc ggcatggcgg ttctggccaa    720

gattgcgaca cactggacat cggccttatt ttacgtcatg gcggaaatat attcttccgt    780

atcggtgggg ctattgtttt ggcagtttgc gaacgacgtc gtcaacgtgg atcaggccaa    840

gcgcttttat ccattatttg ctcaaatgag tggcctcgct ccagttttag cgggccagta    900

tgtggtacgg tttgccagca aagcggtcaa ctttgaggca tccatgcatc gactcacggc    960

ggccgtaaca tttgctggta ttatgatttg catcttttac caactcagtt cgtcatatgt   1020

ggagcgaacg gaatcagcaa agccagcggc agataacgag cagtctatca aaccgaaaaa   1080

gaagaaaccc aaaatgtcca tggttgaatc ggggaaattt ctcgcgtcaa gtcagtacct   1140

gcgtctaatt gccatgctgg tgctgggata cggcctcagt attaacttta ccgaaatcat   1200

gtggaaaagc ttggtgaaga aacaatatcc agacccgcta gattatcaac gatttatggg   1260

taacttctcg tcagcggttg gtttgagcac atgcattgtt attttcttcg gtgtgcacgt   1320

gatccgtttg ttggggtgga aagtcggagc gttggctaca cctgggatca tggccattct   1380

agcgttaccc ttttttgctt gcattttgtt gggtttggat agtccagcac gattggagat   1440

cgccgtaatc tttggaacaa ttcagagttt gctgagcaaa acctccaagt atgccctttt   1500

cgaccctacc acacaaatgg cttatattcc tctggacgac gaatcaaagg tcaaaggaaa   1560

agcggcaatt gatgttttgg gatcgcggat tggcaagagt ggaggctcac tgatccagca   1620

gggcttggtc tttgtttttg gaaatatcat taatgccgca cctgtagtag gggttgtcta   1680

ctacagtgtc cttgttgcgt ggatgagcgc agctggccga ctaagtgggc tttttcaagc   1740

acaaacagaa atggataagg ccgacaaaat ggaggcaaag accaacaaag aaaagtagtt   1800

aacctaggct gctgccaccg ctgagcaata actagcataa ccccttgggg cctctaaacg   1860

ggtcttgagg ggttttttgc tgaaacctca ggcatttgag aagcacacgg tcacactgct   1920

tccggtagtc aataaaccgg taaaccagca atagacataa gcggctattt aacgaccctg   1980

ccctgaaccg acgaccgggt catcgtggcc ggatcttgcg gcccctcggc ttgaacgaat   2040

tgttagacat tatttgccga ctaccttggt gatctcgcct ttcacgtagt ggacaaattc   2100
```

-continued

```
ttccaactga tctgcgcgcg aggccaagcg atcttcttct tgtccaagat aagcctgtct   2160
agcttcaagt atgacgggct gatactgggc cggcaggcgc tccattgccc agtcggcagc   2220
gacatccttc ggcgcgattt tgccggttac tgcgctgtac caaatgcggg acaacgtaag   2280
cactacattt cgctcatcgc cagcccagtc gggcggcgag ttccatagcg ttaaggtttc   2340
atttagcgcc tcaaatagat cctgttcagg aaccggatca aagagttcct ccgccgctgg   2400
acctaccaag gcaacgctat gttctcttgc ttttgtcagc aagatagcca gatcaatgtc   2460
gatcgtggct ggctcgaaga tacctgcaag aatgtcattg cgctgccatt ctccaaattg   2520
cagttcgcgc ttagctggat aacgccacgg aatgatgtcg tcgtgcacaa caatggtgac   2580
ttctacagcg cggagaatct cgctctctcc aggggaagcc gaagtttcca aaaggtcgtt   2640
gatcaaagct cgccgcgttg tttcatcaag ccttacggtc accgtaacca gcaaatcaat   2700
atcactgtgt ggcttcaggc cgccatccac tgcggagccg tacaaatgta cggccagcaa   2760
cgtcggttcg agatggcgct cgatgacgcc aactacctct gatagttgag tcgatacttc   2820
ggcgatcacc gcttccctca tactcttcct ttttcaatat tattgaagca tttatcaggg   2880
ttattgtctc atgagcggat acatatttga atgtatttag aaaaataaac aaatagctag   2940
ctcactcggt cgctacgctc cgggcgtgag actgcggcgg gcgctgcgga cacatacaaa   3000
gttacccaca gattccgtgg ataagcaggg gactaacatg tgaggcaaaa cagcagggcc   3060
gcgccggtgg cgtttttcca taggctccgc cctcctgcca gagttcacat aaacagacgc   3120
ttttccggtg catctgtggg agccgtgagg ctcaaccatg aatctgacag tacgggcgaa   3180
acccgacagg acttaaagat ccccaccgtt tccggcgggt cgctccctct tgcgctctcc   3240
tgttccgacc ctgccgttta ccggatacct gttccgcctt tctcccttac gggaagtgtg   3300
gcgctttctc atagctcaca cactggtatc tcggctcggt gtaggtcgtt cgctccaagc   3360
tgggctgtaa gcaagaactc cccgttcagc ccgactgctg cgccttatcc ggtaactgtt   3420
cacttgagtc caacccggaa aagcacggta aaacgccact ggcagcagcc attggtaact   3480
gggagttcgc agaggatttg tttagctaaa cacgcggttg ctcttgaagt gtgcgccaaa   3540
gtccggctac actggaagga cagatttggt tgctgtgctc tgcgaaagcc agttaccacg   3600
gttaagcagt tccccaactg acttaacctt cgatcaaacc acctccccag gtggtttttt   3660
cgtttacagg gcaaaagatt acgcgcagaa aaaaaggatc tcaagaagat cctttgatct   3720
tttctactga accgctctag atttcagtgc aatttatctc ttcaaatgta gcacctgaag   3780
tcagccccat acgatataag ttgtaattct catgttagtc atgccccgcg cccaccggaa   3840
ggagctgact gggttgaagg ctctcaaggg catcggtcga gatcccggtg cctaatgagt   3900
gagctaactt acattaattg cgttgcgctc actgcccgct ttccagtcgg gaaacctgtc   3960
gtgccagctg cattaatgaa tcggccaacg cgcgggggaga ggcggtttgc gtattgggcg   4020
ccagggtggt ttttcttttc accagtgaga cgggcaacag ctgattgccc ttcaccgcct   4080
ggccctgaga gagttgcagc aagcggtcca cgctggtttg ccccagcagg cgaaaatcct   4140
gtttgatggt ggttaacggc gggatataac atgagctgtc ttcggtatcg tcgtatccca   4200
ctaccgagat gtccgcacca acgcgcagcc cggactcggt aatggcgcgc attgcgccca   4260
gcgccatctg atcgttggca accagcatcg cagtgggaac gatgccctca ttcagcattt   4320
gcatggtttg ttgaaaaccg gacatggcac tccagtcgcc ttcccgttcc gctatcggct   4380
gaatttgatt gcgagtgaga tatttatgcc agccagccag acgcagacgc gccgagacag   4440
aacttaatgg gcccgctaac agcgcgattt gctggtgacc caatgcgacc agatgctcca   4500
```

-continued

```
cgcccagtcg cgtaccgtct tcatgggaga aaataatact gttgatgggt gtctggtcag   4560

agacatcaag aaataacgcc ggaacattag tgcaggcagc ttccacagca atggcatcct   4620

ggtcatccag cggatagtta atgatcagcc cactgacgcg ttgcgcgaga agattgtgca   4680

ccgccgcttt acaggcttcg acgccgcttc gttctaccat cgacaccacc acgctggcac   4740

ccagttgatc ggcgcgagat ttaatcgccg cgacaatttg cgacggcgcg tgcagggcca   4800

gactggaggt ggcaacgcca atcagcaacg actgtttgcc cgccagttgt tgtgccacgc   4860

ggttgggaat gtaattcagc tccgccatcg ccgcttccac tttttcccgc gttttcgcag   4920

aaacgtggct ggcctggttc accacgcggg aaacggtctg ataagagaca ccggcatact   4980

ctgcgacatc gtataacgtt actggtttca cattcaccac cctgaattga ctctcttccg   5040

ggcgctatca tgccataccg cgaaaggttt tgcgccattc gatggtgtcc gggatctcga   5100

cgctctccct tatgcgactc ctgcattagg aaattaatac gactcactat a            5151
```

<210> SEQ ID NO 29
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 29

```
ggtatatctc cttattaaag ttaaacaaaa ttatttctac agggg                     45
```

<210> SEQ ID NO 30
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 30

```
gtttaacttt aataaggaga tataccatga gaccatttcc gac                       43
```

<210> SEQ ID NO 31
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 31

```
gcagcagcct aggttaacta cttttctttg ttggtctttg                           40
```

<210> SEQ ID NO 32
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 32

```
gtttaacttt aataaggaga tataccatga aaaaatcttg tacaatcc                  48
```

<210> SEQ ID NO 33
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 33
gcagcagcct aggttaacta cttctggtgc tcttttg 37

<210> SEQ ID NO 34
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 34
ctatgaccat gattacgcca agcttg 26

<210> SEQ ID NO 35
<211> LENGTH: 75
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (34)..(34)
<223> OTHER INFORMATION: dNaM

<400> SEQUENCE: 35
ctgtttcctg tgtgaaattg ttatccgctc acanttccac acaacatacg agccggaagc 60
ataaagtgta aagcc 75

<210> SEQ ID NO 36
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 36
ctgtttcctg tgtgaaattg ttatccgctc acatttccac acaacatacg agccggaagc 60
ataaagtgta aagcc 75

<210> SEQ ID NO 37
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 37
caagcttggc gtaatcatgg tcatagctgt ttcctgtgtg aaattgttat ccgc 54

<210> SEQ ID NO 38
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 38
gctcactcat taggcacccc aggctttaca ctttatgctt ccggc 45

<210> SEQ ID NO 39
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 39
gcaggcatgc aagcttggcg taatcatgg 29

<210> SEQ ID NO 40
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 40
gctgcaaggc gattaagttg ggtaacgcc 29

<210> SEQ ID NO 41
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 41
ctggcacgac aggtttcccg actgg 25

<210> SEQ ID NO 42
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 42

Asp Tyr Lys Asp Asp Asp Asp Lys Gly
1 5

<210> SEQ ID NO 43
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 43

Gly Lys Pro Ile Pro Asn Pro Leu Leu Gly Leu Asp Ser Thr
1 5 10

<210> SEQ ID NO 44
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 44

Glu Gln Lys Leu Ile Ser Glu Glu Asp Leu
1 5 10

<210> SEQ ID NO 45
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 45

Gln Pro Glu Leu Ala Pro Glu Asp Pro Glu Asp
1 5 10

-continued

```
<210> SEQ ID NO 46
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 46

Tyr Pro Tyr Asp Val Pro Asp Tyr Ala
1               5


<210> SEQ ID NO 47
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 47

Tyr Thr Asp Ile Glu Met Asn Arg Leu Gly Lys
1               5                   10


<210> SEQ ID NO 48
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 48

Cys Cys Pro Gly Cys Cys
1               5


<210> SEQ ID NO 49
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 49

ttaacctagg ctgctgccac cg                                              22


<210> SEQ ID NO 50
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 50

tggggtgcct aatgagtgag c                                               21
```